United States Patent
Grote et al.

Patent Number: 5,994,359
Date of Patent: Nov. 30, 1999

[54] IMINO OXYPHENYL ACETIC ACID DERIVATIVES, METHODS AND INTERMEDIATES FOR THEIR PREPARATION AND USE THEREOF

[75] Inventors: Thomas Grote, Schifferstadt; Hubert Sauter, Mannheim; Reinhard Kirstgen, Neustadt; Herbert Bayer, Mannheim; Ruth Müller, Friedelsheim; Bernd Müller, Frankenthal; Klaus Oberdorf, Heidelberg; Wassilios Grammenos, Ludwigshafen; Norbert Götz, Worms; Michael Rack, Heidelberg; Albrecht Harreus, Ludwigshafen; Franz Röhl, Schifferstadt; Eberhard Ammermann, Heppenheim; Volker Harries, Frankenthal; Gisela Lorenz, Hambach; Siegfried Strathmann, Limburgerhof, all of Germany

[73] Assignee: BASF Aktiengesellschaft, Ludwigshafen, Germany

[21] Appl. No.: 09/091,921
[22] PCT Filed: Dec. 16, 1996
[86] PCT No.: PCT/EP96/05642
    § 371 Date: Jun. 25, 1998
    § 102(e) Date: Jun. 25, 1998
[87] PCT Pub. No.: WO97/24317
    PCT Pub. Date: Jul. 10, 1997

[30] Foreign Application Priority Data

Dec. 27, 1995 [DE] Germany ............ 195 48 370
Feb. 9, 1996 [DE] Germany ............ 196 04 732
Jun. 4, 1996 [DE] Germany ............ 196 22 332
Sep. 9, 1996 [DE] Germany ............ 196 36 512

[51] Int. Cl.[6] ............ C07C 251/60; A01N 37/50
[52] U.S. Cl. ............ 514/255; 514/357; 514/406; 514/438; 514/459; 514/542; 514/538; 514/619; 514/522; 514/508; 564/163; 560/35; 562/869; 558/414; 558/7; 558/391; 549/75; 549/426; 548/247; 548/337.1; 548/375.1; 546/329; 546/330; 546/334; 544/336
[58] Field of Search ............ 564/163; 560/35; 562/869; 558/414, 7, 391; 514/542, 538, 619, 522, 508, 438, 459, 406, 357, 255; 549/75, 426; 548/247, 337.1, 375.1; 546/329, 330, 334; 544/336

[56] References Cited

FOREIGN PATENT DOCUMENTS 2104806 3/1994 Canada.
96/14305 5/1996 WIPO.

*Primary Examiner*—Mukund J. Shah
*Assistant Examiner*—Bruck Kifle
*Attorney, Agent, or Firm*—Keil & Weinkauf

[57] ABSTRACT

2-Iminooxyphenylacetic acid derivatives

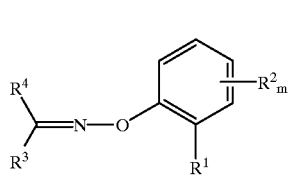

where the substituents and the index have the following meanings:

$R^1$ is $C(CO_2CH_3)=NOCH_3$ (Ia), $C(CONHCH_3)=NOCH_3$ (Ib), $C(CONH_2)=NOCH_3$ (Ic), $C(CO_2CH_3)=CHOCH_3$ (Id) or $C(CO_2CH_3)=CHCH_3$ (Ie);

$R^2$ is cyano, nitro, halogen, alkyl, haloalkyl or alkoxy;

m is 0, 1 or 2;

$R^3$ is hydrogen, cyano, hydroxyl, halogen,
  alkyl, haloalkyl, alkoxyalkyl, alkoxy, haloalkoxy, alkylthio, cyclopropyl, alkenyl,
  unsubstituted or substituted aryloxyalkyl, benzyl or benzyloxy, $R^4$ is hydrogen, cyano,
  unsubstituted or substituted alkyl, alkenyl, alkynyl, cycloalkyl, heterocyclyl, aryl and hetaryl;
  unsubstituted or substituted alkoxy, alkenyloxy, alkynyloxy, cycloalkoxy, heterocyclyloxy, aryloxy and hetaryloxy;
  unsubstituted or substituted arylthio and hetarylthio;
  $-Q-C(R^5)=N-Y^1-R^6$ or $-Q-O-N=CR^7R^8$, $R^3$ and $R^4$ together with the carbon atom to which they are bonded are an unsubstituted or substituted four- to eight-membered ring which, besides carbon atoms, may contain one or two oxygen and/or sulfur atoms and/or NH and/or $N(C_1-C_4$-alkyl) groups;

$R^3$ and $R^4$ not simultaneously being bonded to the carbon atom via hetero atoms;

their salts, processes and intermediates for their preparation, and their use.

16 Claims, No Drawings

IMINO OXYPHENYL ACETIC ACID DERIVATIVES, METHODS AND INTERMEDIATES FOR THEIR PREPARATION AND USE THEREOF

The present invention relates to 2-iminooxyphenylacetic acid derivatives of the formula I

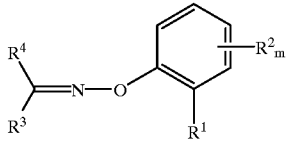

(I)

where the substituents and the index have the following meanings:

$R^1$ is $C(CO_2CH_3)=NOCH_3$ (Ia), $C(CONHCH_3)=NOCH_3$ (Ib), $C(CONH_2)=NOCH_3$ (Ic), $C(CO_2CH_3)=CHOCH_3$ (Id) or $C(CO_2CH_3)=CHCH_3$ (Ie);

$R^2$ is cyano, nitro, halogen, $C_1$–$C_4$-alkyl, $C_1$–$C_4$-haloalkyl or $C_1$–$C_4$-alkoxy;

m is 0, 1 or 2, it being possible for the radicals $R^2$ to be different when m is 2;

$R^3$ is hydrogen, cyano, hydroxyl, halogen,
$C_1$–$C_6$-alkyl, $C_1$–$C_6$-haloalkyl, $C_1$–$C_6$-alkoxy-$C_1$–$C_6$-alkyl, $C_1$–$C_6$-alkoxy, $C_1$–$C_6$-haloalkoxy, $C_1$–$C_6$-alkylthio, cyclopropyl, $C_2$–$C_6$-alkenyl, aryloxy-$C_1$–$C_6$-alkyl, benzyl or benzyloxy, it being possible for the aromatic rings in these radicals to have attached to them one to three of the following groups: cyano, nitro, halogen, $C_1$–$C_6$-alkyl, $C_1$–$C_6$-haloalkyl, $C_1$–$C_6$-alkoxy, $C_1$–$C_6$-haloalkoxy, or $C(CH_3)=N-Y-R^a$ where $R^a$ is $C_1$–$C_6$-alkyl and Y is oxygen or nitrogen, the nitrogen atom having attached to it a hydrogen atom or a $C_1$–$C_6$-alkyl group;

$R^4$ is hydrogen, cyano,
unsubstituted or substituted alkyl, alkenyl, alkynyl, cycloalkyl, heterocyclyl, aryl and hetaryl;
unsubstituted or substituted alkoxy, alkenyloxy, alkynyloxy, cycloalkoxy, heterocyclyloxy, aryloxy and hetaryloxy;
unsubstituted or substituted arylthio and hetarylthio;
$-Q_p-C(R^5)=N-Y^1-R^6$ or $-Q-O-N=CR^7R^8$ where Q is a direct bond, $CH_2$, $CH(CH_3)$, $CH(CH_2CH_3)$ or 1,1-cyclopropyl;

p is 0 or 1;

Y is oxygen or nitrogen, the nitrogen atom having attached to it a hydrogen atom or a $C_1$–$C_4$-alkyl group;

$R^5$ is one of the groups mentioned for $R^3$, or
unsubstituted or substituted cycloalkoxy, heterocyclyloxy, aryloxy, hetaryloxy, arylthio and hetarylthio;

$R^6$ is unsubstituted or substituted $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl;
unsubstituted or substituted aryl, hetaryl, arylcarbonyl, hetarylcarbonyl, arylsulfonyl or hetarylsulfonyl;

$R^7, R^8$ are methyl, ethyl, phenyl and benzyl, it being possible for the aromatic rings to have attached to them one to three of the following substituents: cyano, nitro, halogen, $C_1$–$C_6$-alkyl, $C_1$–$C_6$-haloalkyl, $C_1$–$C_6$-alkoxy and $C_1$–$C_6$-haloalkoxy;

$R^3$ and $R^4$ together with the carbon atom to which they are bonded are a four- to eight-membered ring which, besides carbon atoms, may contain one or two oxygen and/or sulfur atoms and/or NH and/or $N(C_1$–$C_4$-alkyl) groups and whose carbon atoms can have attached to them one of the following substituents: halogen, $C_1$–$C_6$-alkyl or $C_1$–$C_4$-alkoxyimino;

$R^3$ and $R^4$ not simultaneously being bonded to the carbon atom via hetero atoms;

and salts thereof.

Moreover, the invention relates to processes and intermediates for the preparation of the compounds I, to compositions comprising them, and to their use for controlling animal pests and harmful fungi.

Phenylacetic acid derivatives for controlling animal pests and harmful fungi have been disclosed in the literature (EP-A 370 629, EP-A 463 488, EP-A 460 575, WO-A 95/21,154, WO-A 95/21,153, WO-A 95/18,789).

It is an object of the present invention to provide compounds which are more powerful inhibitors of mitochondrial respiration and thus have an improved activity against animal pests and harmful fungi.

We have found that this object is achieved by the compounds I defined at the outset. We have furthermore found processes and intermediates for the preparation of these compounds, and compositions which are suitable for controlling animal pests and harmful fungi.

The compounds I can be prepared by various routes, it generally being irrelevant whether the group $-O-N=CR^3R^4$ (also termed "side chain" hereinbelow) or the radical $R^1$ (also termed "pharmacophore" hereinbelow) is synthesized first, or in which precursor of the "pharmacophore" the "side chain" is coupled with the skeleton.

1. For example, in the preparation of the compounds I where $R_1$ is $C(CO_2CH_3)=NOCH_3$ (Ia), $C(CO_2CH_3)=CHOCH_3$ (Id) or $C(CO_2CH_3)=CHCH_3$ (Ie), a procedure is followed in which a benzoic ester of the formula II is converted with an oxime of the formula III in the presence of a base to give the corresponding derivative of the formula IV, IV is hydrolyzed to give the corresponding carboxylic acid IVa, and IVa is subsequently first reacted to give the chloride Va and then the cyanide Vb, Vb is converted into the corresponding α-ketoester VI via a Pinner reaction, and VI is subsequently converted either a) with O-methylhydroxylamine or a salt thereof (VIIa) to give the corresponding compound Ia [R=C(CO_2CH_3)=NOCH_3], or b) with a Wittig or Wittig-Horner reagent of the formula VIIb to give the corresponding compound Id [R=C(CO_2CH_3)=CHOCH_3], or c) with a Wittig or Wittig-Horner reagent of the formula VIIc to give the corresponding compound Ie [R=C(CO_2CH_3)=CHCH_3].

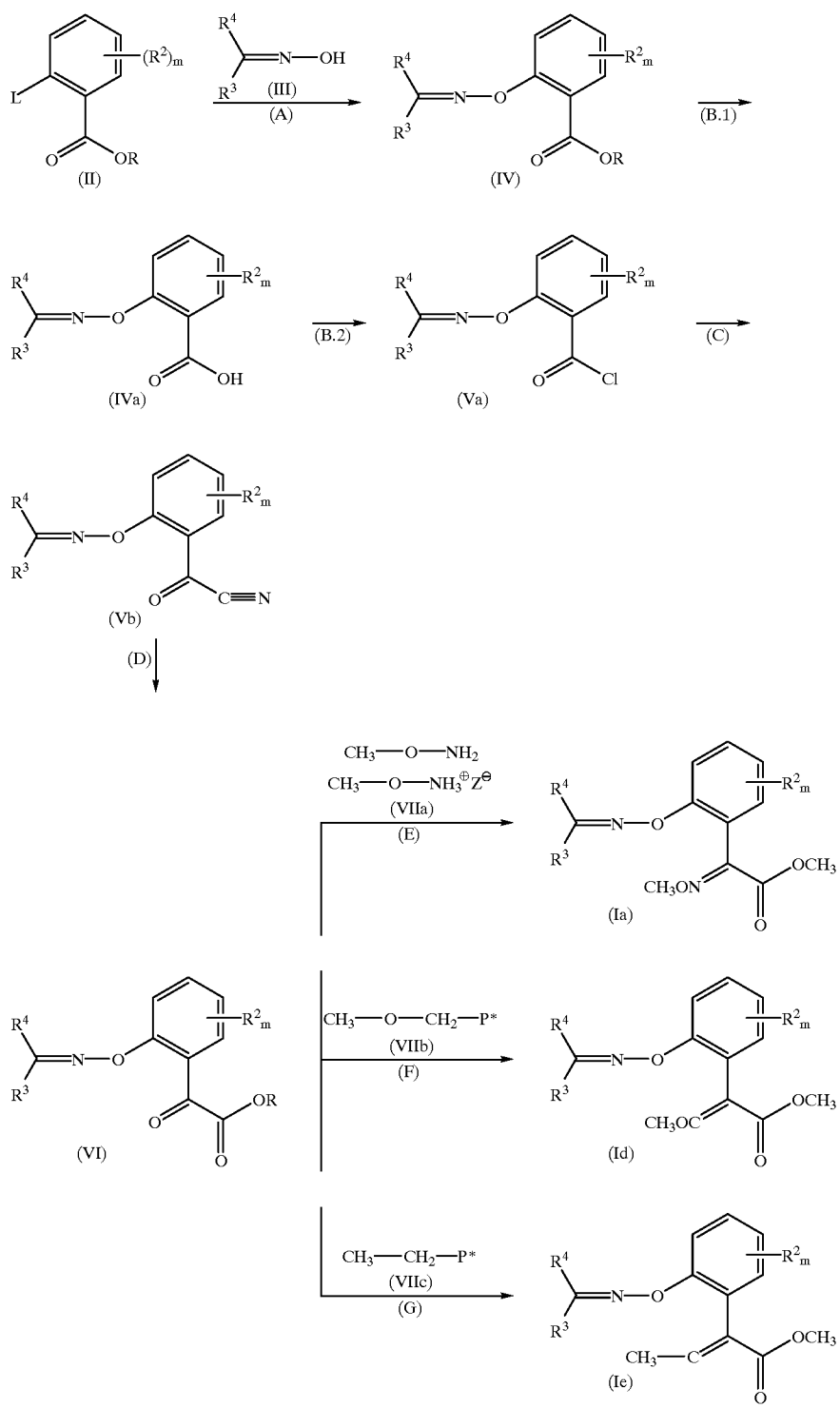

L in formula II is a leaving group conventionally used in nucleophilic aromatic substitution, such as halogen (eg. fluorine, chlorine, bromine), nitro or sulfonate.

R in formula II a $C_1$–$C_4$-alkyl group, in particular methyl.

$Z^-$ in formula VIIa is the anion of an inorganic acid, in particular a halide anion.

P* in formulae VIIb and VIIc is a phosphonate radical or phosphonium halide radical suitable for a Wittig or Wittig-Horner reaction.

1A. The reaction of the benzoic ester (II) with the oxime (III) is normally carried out at from −20° C. to 170° C., preferably 0° C. to 100° C., in an inert organic solvent in the presence of a base [J.Heterocycl.Chem. 4, (1967)

441; J.Org.Chem. 49, (1984) 180; Synthesis 1975, 782; J.Heterocycl.Chem. 26, (1989) 1293].

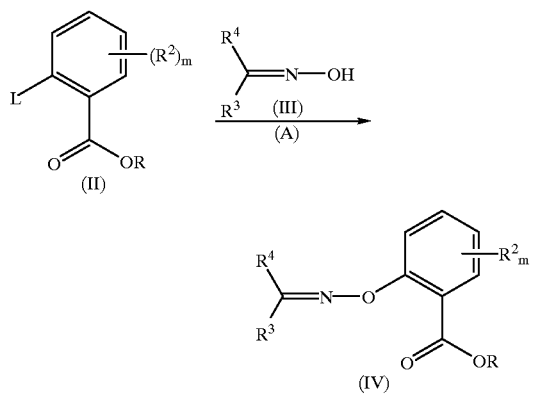

Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide, dimethylacetamide, 1,3-dimethylimidazolidin-2-one, 1,3-dimethyltetrahydro-2(1H)-pyrimidinone and hexamethylphosphoric triamide, especially preferably tetrahydrofuran, dimethyl sulfoxide, dimethylacetamide, dimethylformamide and 1,3-dimethyltetrahydro-2(1H)-pyrimidinone. Mixtures of these may also be used.

Bases which are suitable are, generally, inorganic compounds such as alkali metal hydrides and alkaline earth metal hydrides, such as lithium hydride, sodium hydride, potassium hydride and calcium hydride, alkali metal carbonates and alkaline earth metal carbonates such as lithium carbonate and calcium carbonate, furthermore silver carbonate, alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, and also alkali metal alkoxides and alkaline earth metal alkoxides such as sodium methoxide, sodium ethoxide, potassium methoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Substances which are especially preferred are sodium hydride, potassium carbonate, potasium methoxide, potassium ethoxide, potassium tert-butoxide and sodium methoxide. In general, the bases are employed in equimolar amounts, in excess or, if appropriate, as the solvent.

With a view to completeness of the reaction, it may be advantageous to carry out the reaction in the presence of catalytic amounts of a crown ether, such as 18-crown-6 or 15-crown-5, or of another customary phase-transfer catalyst. Suitable phase-transfer catalysts are ammonium halides and ammonium tetrafluoroborates such as benzyltriethylammonium chloride, benzyltributylammonium chloride, tetrabutylammonium chloride, hexadecyltrimethylammonium bromide and tetrabutylammonium tetrafluoroborate, and also phosphonium halides such as tetrabutylphosphonium chloride and tetraphenylphosphonium bromide.

In general, the starting materials are reacted with each other in equimolar amounts. It may be advantageous for the yield to employ III in an excess based on II.

With a view to the reaction rate and to the completeness of the reaction, it may be advantageous first to treat the compounds III with base and to react the resulting salt with the compound II.

The starting materials II required for the preparation of the compounds I have been disclosed in the literature. Those starting materials III which are not already known from the literature cited at the outset can be obtained by the methods described therein (cf. WO-A 95/21,153).

1B. The reaction of the ester IV to the corresponding acid IVa is carried out in a manner known per se by means of acidic or alkaline hydrolysis at from 0° C. to 100° C., preferably from 0° C. to 50° C., in an inert organic solvent or aqueous/organic solvents in the presence of a base or of an acid [alkaline hydrolysis, cf.: J.Org.Chem. 30, (1965) 3676; acidic hydrolysis, cf.: Chem.Ind. (London) 1964, 193].

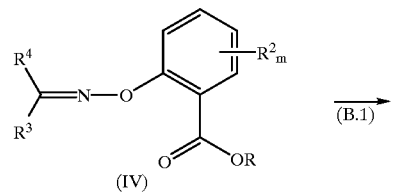

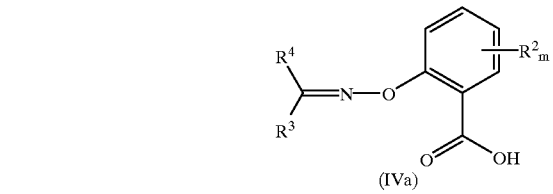

The resulting carboxylic acid IVa is subsequently chlorinated in a manner known per se using customary chlorinating agents at from 0° C. to 150° C., preferably 0° C. to 100° C., in the presence or absence of an inert organic solvent [Houben-Weyl, Supplementary Volume 5, p. 59 et seq., 225 et seq. and 664 et seq.].

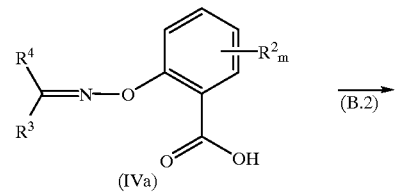

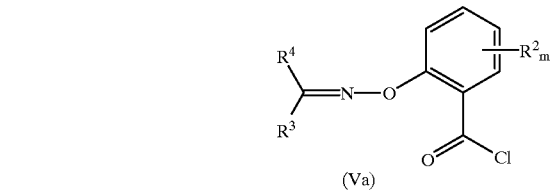

Suitable chlorinating reagents are all reagents conventionally used for this purpose, in particular $SOCl_2$, $(COCl)_2$, $POCl_3$, $AlCl_3$ and $PCl_5$. In general, the chlorinating agents are used in an excess or, if desired, as the solvent.

Suitable solvents are aliphatic hydrocarbons such as pentane, hexane, cyclohexane and petroleum ether, aromatic hydrocarbons such as toluene, o-, m- and p-xylene, and halogenated hydrocarbons such as methylene chloride, chloroform and chlorobenzene. Mixtures of these may also be used.

In general, the starting materials are reacted with each other in at least equimolar amounts. It may be advantageous for the yield to employ the chlorinating agent in an excess based on IVa.

1C. The reaction of benzoyl chloride Va to give the corresponding cyanide Vb is carried out in a manner known per se [DE Appl. No. 19 603 990.8; Bull.Chem.Soc.Jpn. 60, (1987) 1085; Synthesis 1983, 636; J.Org.Chem. 43, (1978) 2280; Tetrahedron.Lett. 1974, 2275] at from 0° C. to 150° C., preferably 10° C. to 100° C., using an inorganic cyanide in an inert organic solvent in the presence or absence of a catalyst.

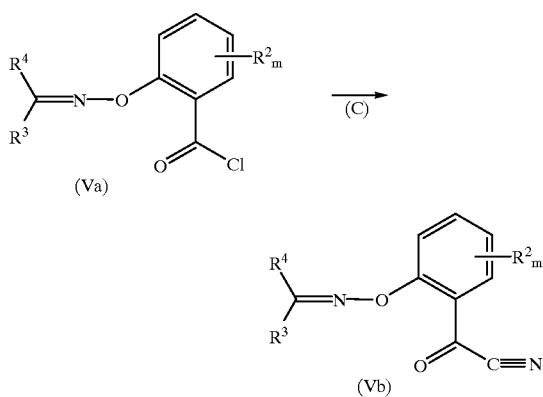

Suitable inorganic cyanides are cyanides of metals of the first main group or the subgroups of the Periodic Table, for example lithium, sodium, potassium, copper and silver, in particular copper, and organic cyanides such as trimethylsilyl cyanide.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tertbutyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol and also dimethyl sulfoxide and dimethylformamide, especially preferably toluene, methylene chloride and tetrahydrofuran. Mixtures of these may also be used.

The use of a catalyst is recommended when carrying out the reaction with the abovementioned cyanide compounds, with the exception of CuCN. Catalysts which are used are customary phase-transfer catalysts, in particular ammonium salts such as tetrabutylammonium bromide.

In general, the starting materials are reacted with each other in equimolar amounts. It may be advantageous for the yield to employ the cyanide in an excess based on Va.

1D. The reaction of the cyanide Vb to give the α-ketoester VI is carried out in a manner known per se by way of a Pinner reaction at from 0° C. to 150° C., preferably 30° C. to 100° C., in an alcohol (R—OH) in the presence of an acid and of a catalyst [Tetrahedron Lett. 21, (1980) 3539; J.Org.Chem. 47, (1982) 2342].

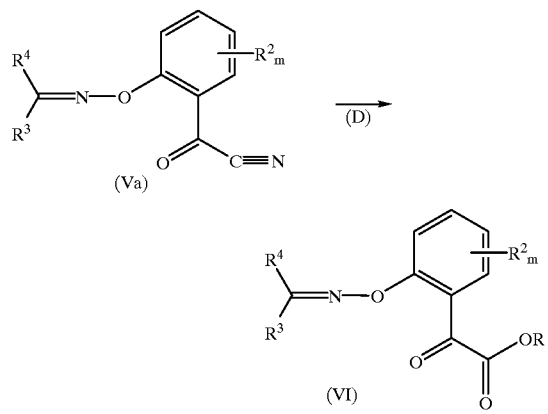

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid.

In general, the acids are used in at least equimolar amounts, but preferably in excess.

1E. The reaction of the α-ketoester VI with O-methylhydroxylamine or a salt thereof (VIIa) to give the compound Ia is carried out in a manner known per se at from 0° C. to 100° C., preferably 20° C. to 70° C., in an inert organic solvent in the presence or absence of a base [U.S. Pat. No. 5,221,762].

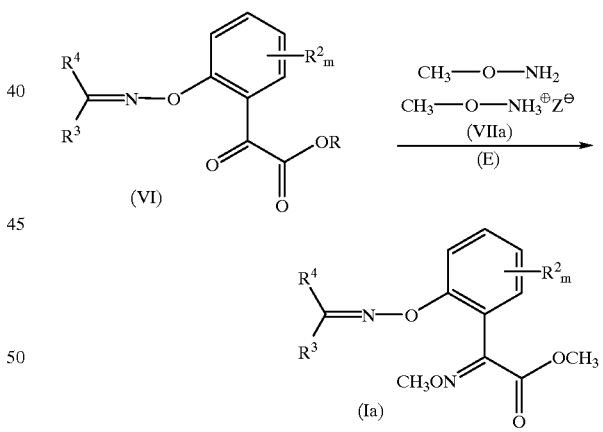

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tertbutyl methyl ether, dioxane, anisole and tetrahydrofuran, nitriles such as acetonitrile and propionitrile, ketones such as acetone, methyl ethyl ketone, diethyl ketone and tertbutyl methyl ketone, alcohols such as methanol, ethanol, n-propanol, isopropanol, n-butanol and tert-butanol and also dimethyl sulfoxide and dimethylformamide, especially preferably dimethylformamide or alcohols. Mixtures of these may also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Tertiary amines are especially preferred.

In general, the bases are employed in catalytic amounts, but they may also be used in equimolar amounts, in an excess or, if desired, as the solvent.

In general, the starting materials are reacted with each other in equimolar amounts. It may be advantageous for the yield to employ VIIa in an excess based on VI.

1F. The reaction of the α-ketoesters VI to give the compound Id is carried out in a manner known per se by way of a Wittig or Wittig-Horner reaction at from 0° C. to 100° C., preferably 0° C. to 50° C., in an inert organic solvent in the presence of a base and of a catalyst [Tetrahedron 44, (1988) 3727].

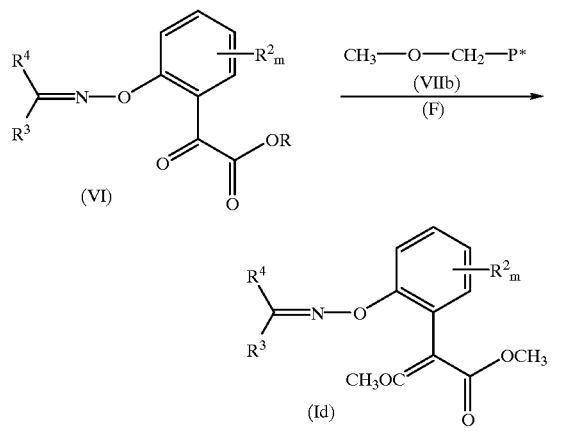

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tertbutyl methyl ether, dioxane, anisole and tetrahydrofuran, nitriles such as acetonitrile and propionitrile, ketones such as acetone, methyl ethyl ketone, diethyl ketone and tertbutyl methyl ketone, alcohols such as methanol, ethanol, n-propanol, isopropanol, n-butanol and tert-butanol and also dimethyl sulfoxide and dimethylformamide, especially preferably dimethylformamide. Mixtures of these may also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Alkoxides are especially preferred.

In general, the bases are employed in catalytic amounts, but they may also be used in equimolar amounts, in an excess or, if desired, as the solvent. In general, the starting materials are reacted with each other in equimolar amounts. It may be advantageous for the yield to employ VIIb in an excess based on VI.

1G. The reaction of the α-ketoesters VI to give the compound Ie is carried out in a manner known per se by way of a Wittig or Wittig-Horner reaction at from 0° C. to 100° C., preferably 0° C. to 50° C., in an inert organic solvent in the presence of a base and of a catalyst [Austr.J.Chem. 34, (1981) 2363; Can.J.Chem. 49, (1971) 2143].

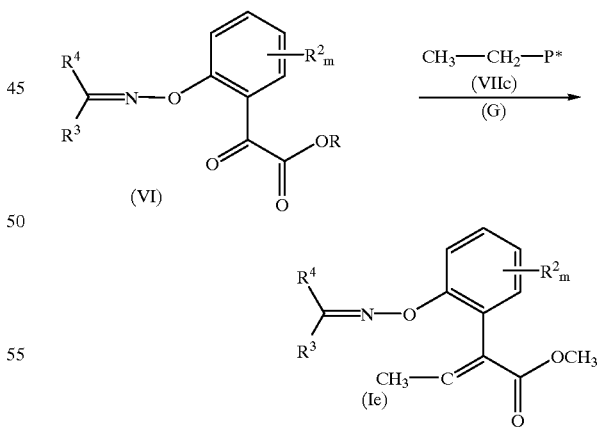

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tertbutyl methyl ether, dioxane, anisole and tetrahydrofuran, nitriles such as acetonitrile and propionitrile, ketones such as acetone, methyl ethyl ketone, diethyl ketone and tertbutyl methyl ketone, alcohols such as methanol, ethanol, n-propanol, isopropanol, n-butanol and tert-butanol and also dimethyl sulfoxide and dimethylformamide, especially preferably dimethylformamide. Mixtures of these may also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Alkoxides are especially preferred.

In general, the bases are employed in catalytic amounts, but they may also be used in equimolar amounts, in an excess or, if desired, as the solvent.

In general, the starting materials are reacted with each other in equimolar amounts. It may be advantageous for the yield to employ VIIc in an excess based on VI.

2. The compounds Vb are also especially preferably obtained by reacting a cyanide of the formula Vc with an oxime of the formula III as described under item 1A.

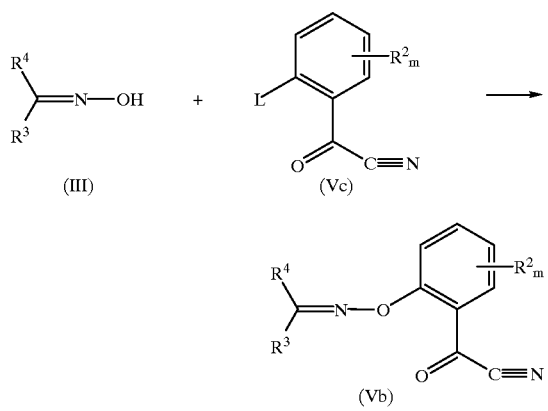

3. Compounds of the formula VI are advantageously also obtained by converting an α-ketoester of the formula VIa into the compound VIb and reacting VIb in situ with a ketone or aldehyde IX to give VI.

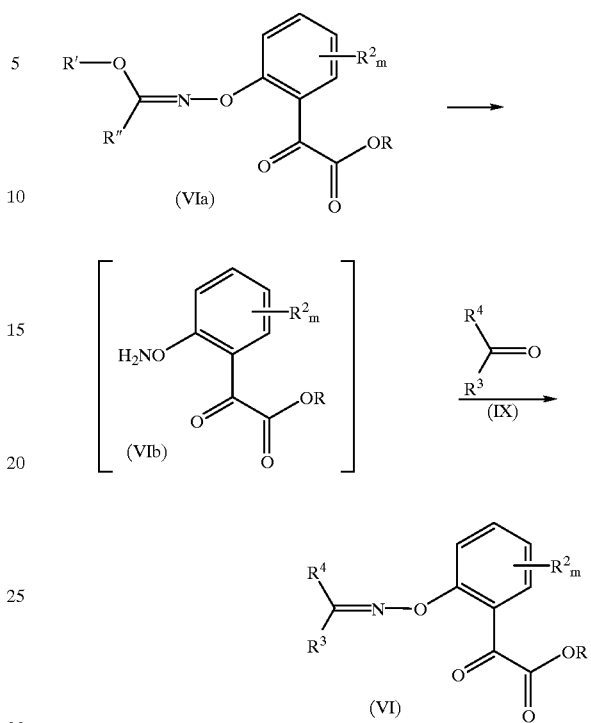

In formula VIa, the groups R' and R" independently of one another are $C_1$–$C_6$-alkyl or aryl.

The hydroxylamine VIb is liberated from the oxime VIa, and the resulting reaction mixture is further reacted with the ketone IX in a manner known per se at from 0° C. to 150° C., preferably 0° C. to 50° C., in an inert organic solvent in the presence of an acid or of a catalyst.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tertbutyl methyl ether, dioxane, anisole and tetrahydrofuran, nitriles such as acetonitrile and propionitrile, ketones such as acetone, methyl ethyl ketone, diethyl ketone and tertbutyl methyl ketone, alcohols such as methanol, ethanol, n-propanol, isopropanol, n-butanol and tert-butanol and also dimethyl sulfoxide and dimethylformamide, especially preferably alcohols. Mixtures of these may also be used.

Acids and acidic catalysts which are used are inorganic acids such as hydrofluoric acid, hydrochloric acid, hydrobromic acid, sulfuric acid and perchloric acid, Lewis acids such as boron trifluoride, aluminum trichloride, iron(III) chloride, tin(IV) chloride, titanium(IV) chloride and zinc(II) chloride, and organic acids such as formic acid, acetic acid, propionic acid, oxalic acid, citric acid and trifluoroacetic acid.

In general, the acids are employed in catalytic amounts, but they may also be used in equimolar amounts, in an excess or, if appropriate, as the solvent.

In general, the starting materials are reacted with each other in equimolar amounts. It may be advantageous for the yield to employ IX in an excess based on VIIb.

4. Compounds I where $R^1$ is $C(CONHCH_3)$=$NOCH_3$ (Ib) or $C(CONH_2)$=$NOCH_3$ (Ic) are obtained, for example, by reacting a compound of the formula Ia in a manner known per se with methylamine or a salt thereof (XIII) or with ammonia or an ammonium salt, eg.

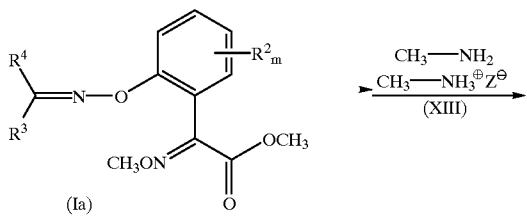

$Z^-$ in formula XIII is the anion of an inorganic acid, in particular a halide anion such as chlorine and bromine.

This reaction is normally carried out at from 0° C. to 150° C., preferably 0° C. to 70° C., in an inert organic solvent in the presence or absence of a base. Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol and also dimethyl sulfoxide and dimethylformamide, especially preferably tetrahydrofuran. Mixtures of these may also be used.

In the event that the ammonium salts are employed as the starting materials, the reaction is advantageously carried out in the presence of a base. Bases which are suitable are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Tertiary amines and potassium carbonate are especially preferred.

The bases are used in at least equimolar amounts, in an excess or, if desired, as the solvent.

In general, the starting materials are reacted with each other in equimolar amounts. It may be advantageous for the yield to employ XIII or ammonia in an excess based on Ia.

5. In an especially preferred process, the compounds Ib are advantageously obtained by first converting an α-ketoamide of the formula VIc with an oxime of the formula III under the conditions described for 1A. to give the corresponding amide of the formula VId and subsequently reacting VId with O-methylhydroxylamine or a salt thereof (VIIa) under the conditions described for 4.

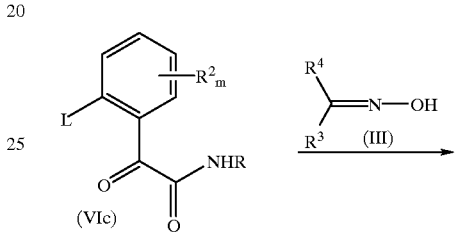

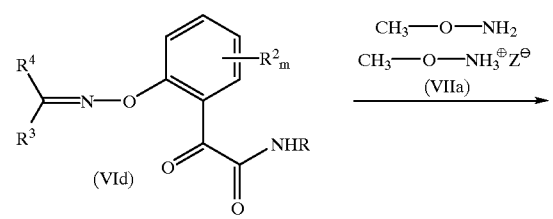

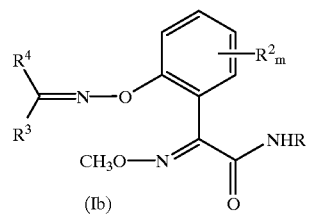

6. In a further process, the compounds I are also obtained by converting an α-ketoester VIe with N-hydroxyphthalimide (XI) to give the corresponding protected oxime of the formula VIf. The α-ketoester function of the oxime VIf can subsequently be converted into the various groups $R^1$ in a manner known per se as specified for the above-described processes (cf. formulae XIIa and XIIb). The phthalimide protective group is subsequently eliminated in a manner known per se using hydrazine in ethanol [Synthesis 23, (1979) 682] or with hydrogen bromide in acetic acid [J.Org.Chem. 28, (1963) 1604], and the resulting O-substituted hydroxylamine (cf. formulae XIIIa and XIIIb) is reacted in situ with the ketone of the formula IX to give I.

The reaction sequence is outlined in the reaction scheme below.

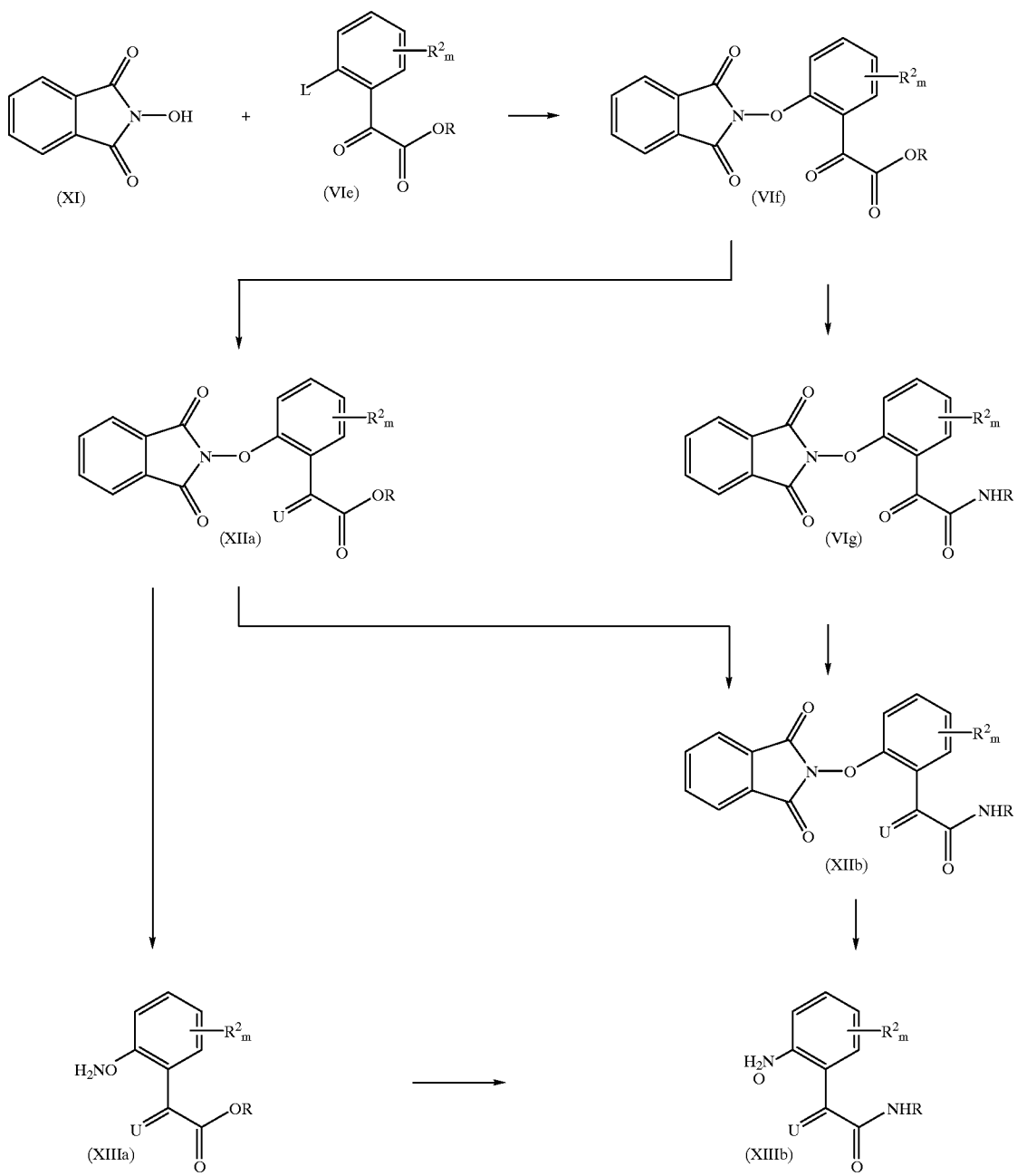

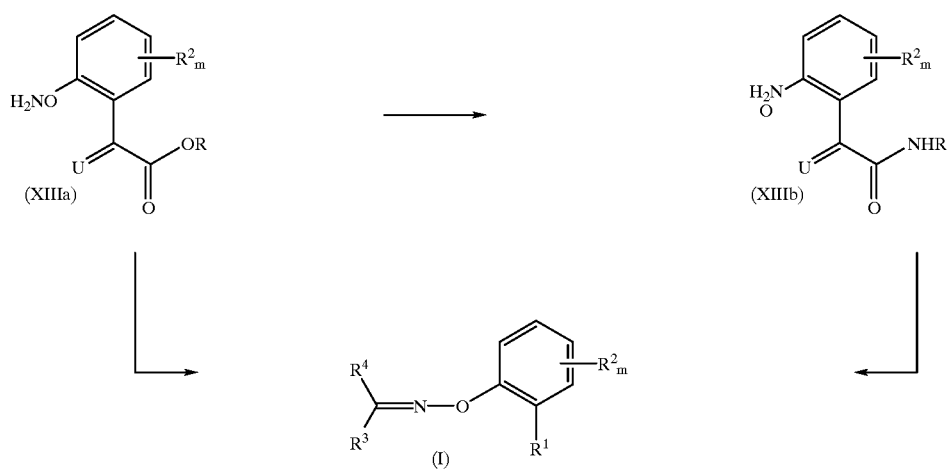

The individual reactions are carried out in general and in particular under the process conditions described at the out-set.

7. In a further especially preferred process, the compounds I are also obtained by first converting the α-ketoester VIe into the corresponding α-ketoester VI by means of reaction with the oxime III. The α-ketoester function of the oxime VI can subsequently be converted in a manner known per se into the various groups $R^1$ as specified in the above-described processes.

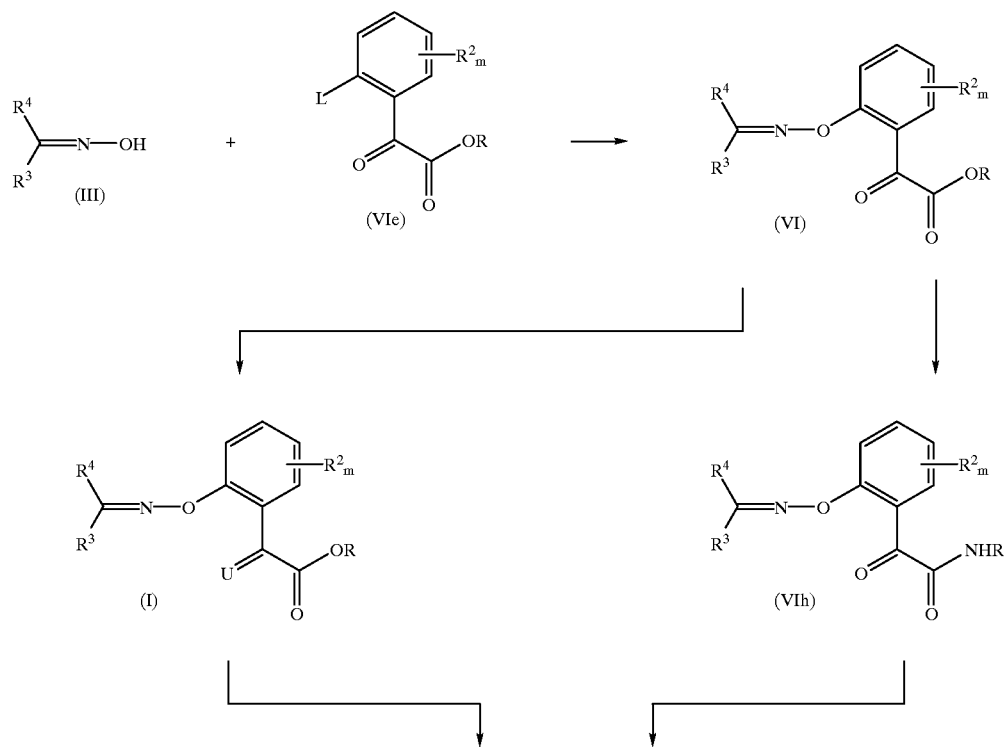

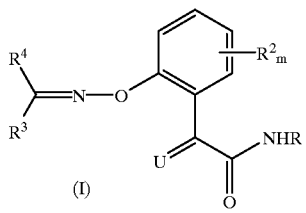

The individual reactions are carried out in general and in particular under the process conditions described at the out-set.

The compounds VIe which are required as starting material for the above reactions are obtained, for example, as shown in the reaction scheme which follows:

In a further process, the compounds I are also obtained as specified in the methods described in EP-A 178 826, EP-A 256 667 and EP-A 468 775 as shown in the reaction scheme which follows, starting from phenyl ketones of the formula VI:

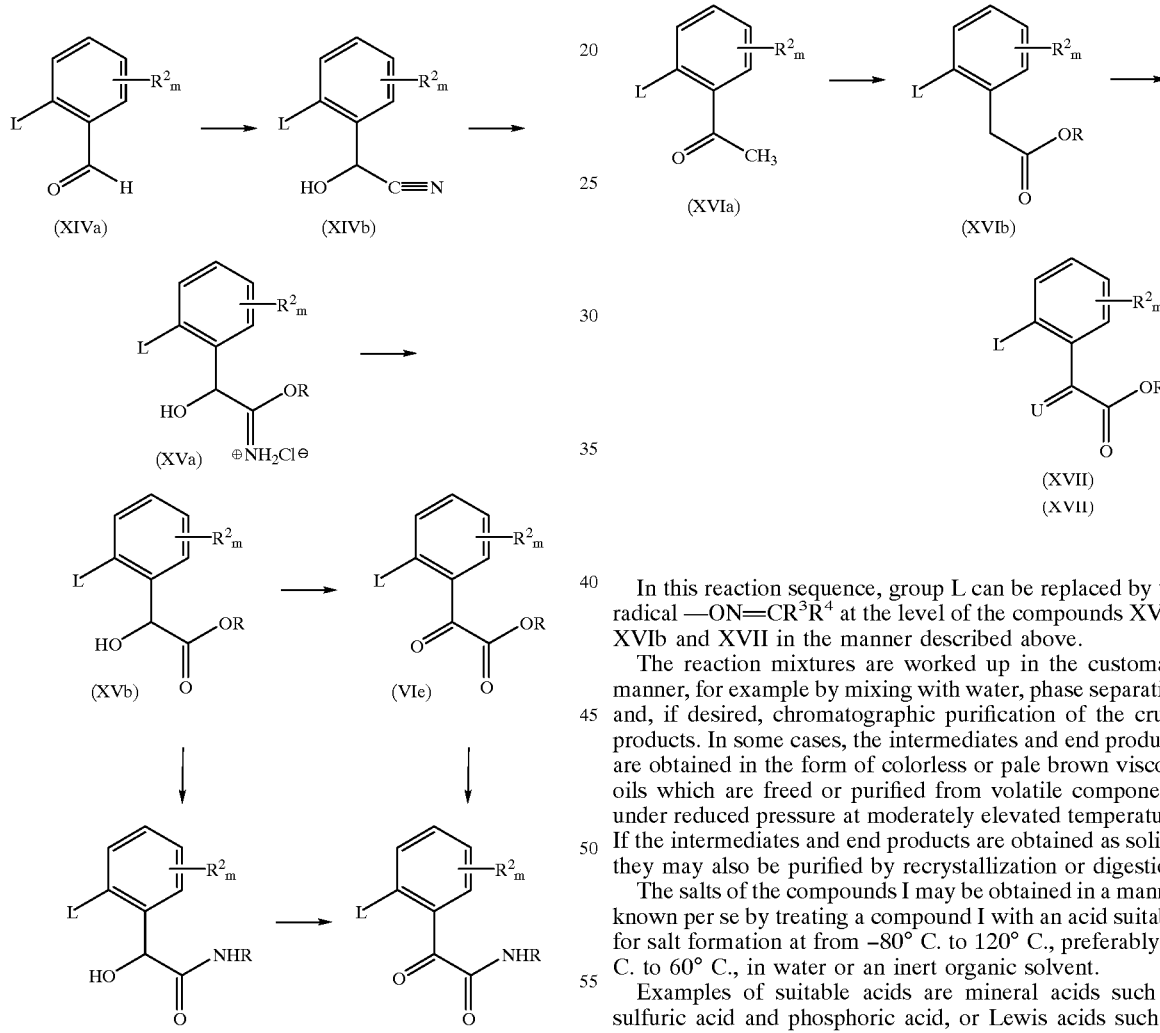

The corresponding reaction sequence gives the α-ketoester of the formula VI or the corresponding α-ketoamide when group L is substituted by group —ON=CR$^3$R$^4$ as specified in the conditions described at the outset by means of a reaction with the oxime III (at the level of the compounds XIVa, XIVb, XVb or VIe).

The process is carried out as specified in the methods described in *Coll. Czech. Chem. Commun.* 29, (1964) 97/119.

In this reaction sequence, group L can be replaced by the radical —ON=CR$^3$R$^4$ at the level of the compounds XVIa, XVIb and XVII in the manner described above.

The reaction mixtures are worked up in the customary manner, for example by mixing with water, phase separation and, if desired, chromatographic purification of the crude products. In some cases, the intermediates and end products are obtained in the form of colorless or pale brown viscous oils which are freed or purified from volatile components under reduced pressure at moderately elevated temperature. If the intermediates and end products are obtained as solids, they may also be purified by recrystallization or digestion.

The salts of the compounds I may be obtained in a manner known per se by treating a compound I with an acid suitable for salt formation at from −80° C. to 120° C., preferably 0° C. to 60° C., in water or an inert organic solvent.

Examples of suitable acids are mineral acids such as sulfuric acid and phosphoric acid, or Lewis acids such as zinc chloride.

In general, the type of salt is not critical with a view to the use of the compounds I against animal pests and harmful fungi. Preferred for the purposes of the invention are those salts which do not adversely affect the plants, areas, materials, seeds and spaces to be kept free from animal pests or harmful fungi.

In relation to their C=N or C=C double bonds, the compounds I can be in the form of E and Z isomers; with a view to the double bond of the radical R$^1$, the E isomers are generally biologically more active and thus preferred.

With a view to the double bond of the O—N=CR³R⁴ group and other double bonds found in the radicals R³ and R⁴, E and Z isomers are also possible. In general, preferred compounds I are those where these double bonds are in the E configuration.

These double bonds are normally formed upon synthesis preferably in the E configuration. The isomer mixtures can either be separated into the individual isomers in the customary manner, for example by fractional crystallization or chromatography, or they may be converted into other isomers when exposed to protonic acids or Lewis acids or light. If isomer mixtures are obtained upon synthesis, however, separation is generally not necessary since in some cases the isomers may be converted into each other during application according to the invention due to exposure to light, formulation medium or else in vivo.

In the definitions of the symbols in the formulae above, collective terms were used which generally represent the following substituents:

Halogen: fluorine, chlorine, bromine and iodine;

Alkyl: saturated straight-chain or branched hydrocarbon radicals having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 4, 6 or 10 carbon atoms (as mentioned above), it being possible for some or all of the hydrogen atoms in these groups to be replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkylcarbonyl: an alkyl group having 1 to 6 or 10 carbon atoms (as mentioned above), which is bonded to the skeleton via a carbonyl group (—CO—);

Alkylsulfonyl: a straight-chain or branched alkyl group having 1 to 6 or 10 carbon atoms (as mentioned above) which is bonded to the skeleton via a sulfonyl group (—SO₂—);

Alkylsulfoxyl: a straight-chain or branched alkyl group having 1 to 6 carbon atoms (as mentioned above) which is bonded to the skeleton via a sulfoxyl group (—SO₃—);

Alkoxy: straight-chain or branched alkyl groups having 1 to 4 or 6 carbon atoms (as mentioned above) which are bonded to the skeleton via an oxygen atom (—O—);

Haloalkoxy: straight-chain or branched haloalkyl groups having 1 to 4, 6 or 10 carbon atoms (as mentioned above) which are bonded to the skeleton via an oxygen atom (—O—);

Alkoxycarbonyl: an alkoxy group having 1 to 6 carbon atoms (as mentioned above) which is bonded to the skeleton via a carbonyl group (—CO—);

Alkoxyimino: straight-chain or branched alkyl groups having 1 to 4 carbon atoms (as mentioned above) which are bonded to the skeleton via an oxyimino group (—ON=);

Alkylthio: straight-chain or branched alkyl groups having 1 to 6 carbon atoms (as mentioned above) which are bonded to the skeleton via a sulfur atom (—S—);

Alkylamino: a straight-chain or branched alkyl group having 1 to 6 carbon atoms (as mentioned above) which is bonded to the skeleton via an amino group (—NH—);

Dialkylamino: two independent straight-chain or branched alkyl groups having in each case 1 to 6 carbon atoms (as mentioned above) which are bonded to the skeleton via a nitrogen atom;

Alkylaminocarbonyl: an alkylamino group having 1 to 6 carbon atoms (as mentioned above) which is bonded to the skeleton via a carbonyl group (—CO—);

Dialkylaminocarbonyl: an dialkylamino group having two independent $C_1$–$C_6$-alkyl groups (as mentioned above) which is bonded to the skeleton via a carbonyl group (—CO—);

Alkylaminothiocarbonyl: an alkylamino group having 1 to 6 carbon atoms (as mentioned above) which is bonded to the skeleton via a thiocarbonyl group (—CS—);

Dialkylaminothiocarbonyl: a dialkylamino group having two independent $C_1$–$C_6$-alkyl group (as mentioned above) which is bonded to the skeleton via a thiocarbonyl group (—CS—);

Alkenyl: unsaturated straight-chain or branched hydrocarbon radicals having 2 to 6 or 10 carbon atoms and a double bond in any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: unsaturated straight-chain or branched hydrocarbon radicals having 3 to 6 or 10 carbon atoms and a double bond in any position which is not adjacent to the hetero atom (as mentioned above) which are bonded to the skeleton via an oxygen atom (—O—);

Alkenylcarbonyl: unsaturated straight-chain or branched hydrocarbon radicals having 2 to 10 carbon atoms and a double bond in any position (as mentioned above) which are bonded to the skeleton via a carbonyl group (—CO—);

Alkynyl: straight-chain or branched hydrocarbon groups having 2 to 4, 6, 8 or 10 carbon atoms and a triple bond in any position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

Alkynyloxy: unsaturated straight-chain or branched hydrocarbon radicals having 3 to 10 carbon atoms and a triple bond in any position which is not adjacent to the hetero atom (as mentioned above) which are bonded to the skeleton via an oxygen atom (—O—);

Alkynylcarbonyl: unsaturated straight-chain or branched hydrocarbon radicals having 2 to 10 carbon atoms and a triple bond in any position (as mentioned above) which are bonded to the skeleton via a carbonyl group (—CO—);

Cycloalkyl: monocyclic saturated hydrocarbon groups having 3 to 6 or 10 carbon ring members, eg. $C_3$–$C_8$-cycloalkyl such as cyclopropyl, cyclobutyl, cyclopentyl, cyclohexyl, cycloheptyl and cyclooctyl;

Cycloalkoxy: monocyclic saturated hydrocarbon groups having 3 to 6 or 10 carbon ring members (as mentioned above) which are bonded to the skeleton via an oxygen group (—O—);

Cycloalkenyl: monocyclic mono unsaturated hydrocarbon groups having 3 to 6 or 10 carbon ring members and a double bond in any position of the ring, eg. $C_5$–$C_8$-cycloalkyl such as cyclopentenyl, cyclohexenyl, cycloheptenyl and cyclooctenyl;

Heterocyclyl: 5- or 6-membered heterocycles containing, besides carbon ring members, one to three nitrogen atoms and/or an oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl;

Heterocyclyloxy: 5- or 6-membered heterocycles (as mentioned above) which are bonded to the skeleton via an oxygen atom (—O—);

Aryl: a mono- to trinuclear aromatic ring system containing 6 to 14 ring members, eg. phenyl, naphthyl and anthracenyl;

Aryloxy: a mono- to trinuclear aromatic ring system (as mentioned above) which is bonded to the skeleton via an oxygen atom (—O—);

Arylthio: a mono- to trinuclear aromatic ring system (as mentioned above) which is bonded to the skeleton via an sulfur atom (—S—);

Arylcarbonyl: a mono- to trinuclear aromatic ring system (as mentioned above) which is bonded to the skeleton via a carbonyl group (—CO—);

Arylsulfonyl: a mono- to trinuclear aromatic ring system (as mentioned above) which is bonded to the skeleton via a sulfonyl group (—$SO_2$—);

Hetaryl: a mono- or binuclear, 5-, 6-, 9- or 10-membered aromatic ring system which, besides carbon ring members, contains hetero atoms from the group consisting of oxygen, sulfur and nitrogen, eg.

5-membered hetaryl containing one to four nitrogen atoms or one to three nitrogen atoms and a sulfur or oxygen atom: 5-membered hetaryl ring group which, besides carbon atoms, may contain one to four nitrogen atoms or one to three nitrogen atoms and a sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered hetaryl, containing one to three nitrogen atoms or a nitrogen atom and an oxygen or sulfur atom: 5-membered hetaryl ring groups which, besides carbon atoms, may contain one to four nitrogen atoms or one to three nitrogen atoms and a sulfur or oxygen atom as ring members, and in which two adjacent carbon ring members or a nitrogen and an adjacent carbon ring member may be bridged by a buta-1,3-diene-1,4-diyl group;

5-membered hetaryl, bonded via nitrogen and containing one to four nitrogen atoms, or benzo-fused 5-membered hetaryl, bonded via nitrogen and containing one to three nitrogen atoms: 5-membered hetaryl ring groups which, besides carbon atoms, may contain one to four nitrogen atoms, or one to three nitrogen atoms, as ring members and in which two adjacent carbon ring members or a nitrogen and an adjacent carbon ring member may be bridged by a buta-1,3-diene-1,4-diyl group, these rings being bonded to the skeleton via one of the nitrogen ring members;

6-membered hetaryl, containing one to three, or one to four, nitrogen atoms: 6-membered hetaryl ring groups which, besides carbon atoms, may contain one to three, or one to four, nitrogen atoms as ring members eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Hetaryloxy: a mono- or binuclear heteroaromatic ring system (as mentioned above) which is bonded to the skeleton via an oxygen atom (—O—);

Hetarylthio: a mono- or binuclear heteroaromatic ring system (as mentioned above) which is bonded to the skeleton via a sulfur atom (—S—);

Hetarylcarbonyl: a mono- or binuclear heteroaromatic ring system (as mentioned above) which is bonded to the skeleton via a carbonyl group (—CO—);

Hetarylsulfonyl: a mono- or binuclear heteroaromatic ring system (as mentioned above) which is bonded to the skeleton via a sulfonyl group (—SO$_2$—).

The addition "unsubstituted or substituted" when relating to alkyl, alkenyl and alkynyl groups is intended to express that these groups may be partially or fully halogenated [ie. some or all of the hydrogen atoms of these groups may be replaced by identical or different halogen atoms as mentioned above (preferably fluorine, chlorine or bromine)] and/or may have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals preferably containing 1 to 6 carbon atoms, in particular 1 to 4 carbon atoms.

The addition "unsubstituted or substituted" when relating to the cyclic (saturated, unsaturated or aromatic) groups is intended to express that these groups may be partially or fully halogenated [ie. some or all of the hydrogen atoms in these groups may be replaced by identical or different halogen atoms as mentioned above (preferably fluorine, chlorine or bromine, in particular fluorine or chlorine)] and/or may have attached to them 1 to 4 (in particular 1 to 3) of the following radicals:

cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino, alkylcarbonyl-N-alkylamino and alkylcarbonyl-N-alkylamino, the alkyl groups in these radicals preferably containing 1 to 6 carbon atoms, in particular 1 to 4 carbon atoms, and the alkenyl or alkynyl groups mentioned in these radicals containing 2 to 8, preferably 2 to 6, in particular 2 to 4 carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members and the alkyl groups in these radicals preferably containing 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing, in particular, 5 or 6 ring members and the alkyl groups in these radicals preferably containing 1 to 6 carbon atoms, in particular 1 to 4 carbon atoms and/or can have attached to them one or two (in particular one) of the following radicals:

formyl,

CR$^v$=NOR$^{vi}$ [where R$^v$ is hydrogen, alkyl, cycloalkyl and aryl and R$^{vi}$ is alkyl, alkenyl, haloalkenyl, alkynyl and arylalkyl (the abovementioned alkyl groups preferably containing 1 to 6 carbon atoms, in particular 1 to 4 carbon atoms, the abovementioned cycloalkyl groups, alkenyl groups and alkynyl groups preferably containing 3 to 8, in particular 3 to 6, carbon atoms) and aryl is, in particular, phenyl which is unsubstituted or may be substituted by customary groups] or NR$^{vii}$—CO—D—R$^{viii}$ [where R$^{vii}$ is hydrogen, hydroxyl, C$_1$–C$_6$-alkyl, C$_2$–C$_6$-alkenyl, C$_2$–C$_6$-alkynyl, C$_1$–C$_6$-alkoxy, C$_2$–C$_6$-alkenyloxy, C$_2$–C$_6$-alkynyloxy, C$_1$–C$_6$-alkoxy-C$_1$–C$_6$-alkyl, C$_1$–C$_6$-alkoxy-C$_1$–C$_6$-alkoxy and C$_1$–C$_6$-alkoxycarbonyl, R$^{viii}$ is hydrogen, C$_1$–C$_6$-alkyl, C$_2$–C$_6$-alkenyl, C$_2$–C$_6$-alkynyl, C$_3$–C$_6$-cycloalkyl, C$_3$–C$_6$-cycloalkenyl, aryl, aryl-C$_1$–C$_6$-alkyl, hetaryl and hetaryl-C$_1$–C$_6$-alkyl and D is a direct bond, oxygen or nitrogen, it being possible for the nitrogen to have attached to it one of the groups mentioned under R$^{vi}$], and/or where two adjacent C atoms of the cyclic systems may have attached to them a C$_3$–C$_5$-alkylene, C$_3$–C$_5$-alkenylene, oxy-C$_2$–C$_4$-alkylene, oxy-C$_1$–C$_3$-alkyleneoxy, oxy-C$_2$–C$_4$-alkenylene, oxy-C$_2$–C$_4$-alkenyleneoxy or butadienediyl group, it being possible for these bridges, in turn, to be partially or fully halogenated and/or to have attached to them one to three, in particular one or two, of the following radicals:

$C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

Customary groups are to be understood as meaning, in particular, the following substituents: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

Preferred compounds with a view to their biological activities are those where $R^4$ has the following meanings:

alkyl, alkenyl, alkynyl, alkoxy, alkenyloxy or alkynyloxy, it being possible for the hydrocarbon groups, in turn, to be partially or fully halogenated and/or to have attached to them one to three of the following radicals:

cyano, nitro, hydroxyl, mercapto, amino, carboxyl, aminocarbonyl, aminothiocarbonyl,
$C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyloxy, benzyloxy, aryl, aryloxy, hetaryl and hetaryloxy, it being possible for the aromatic rings to be substituted by customary groups;

cycloalkyl, cycloalkoxy, heterocyclyl or heterocyclyloxy, it being possible for the cyclic groups, in turn, to be partially or fully halogenated and/or to have attached to them one to three of the following radicals:

cyano, nitro, hydroxyl, mercapto, amino, carboxyl, aminocarbonyl, aminothiocarbonyl,
$C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$_1$–$C_6$-alkylamino, $C_1$–$C_6$-alkylaminocarbonyl, di-$_1$–$C_6$-alkylaminocarbonyl, $C_1$–$C_6$-alkylaminothiocarbonyl, di-$_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy, it being possible for the aromatic rings to be substituted by customary groups;

aryl, hetaryl, aryloxy or hetaryloxy, it being possible for the cyclic groups, in turn, to be partially or fully halogenated and/or to have attached to them one to three of the following radicals:

cyano, nitro, hydroxyl, mercapto, amino, carboxyl, aminocarbonyl, aminothiocarbonyl,
$C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, it being possible for the aromatic rings to be substituted by customary groups, $C(=NOR^i)$—$A_n$—$R^{ii}$ or $NR^{iii}$—CO—D—$R^{iv}$;

A is oxygen, sulfur or nitrogen, the nitrogen having attached to it hydrogen or $C_1$–$C_6$-alkyl;

n is 0 or 1;

$R^i$ is hydrogen, $C_1$–$C_6$-alkyl, $C_3$–$C_6$-alkenyl or $C_3$–$C_6$-alkynyl;

$R^{ii}$ is hydrogen or $C_1$–$C_6$-alkyl;

D is a direct bond, oxygen or $NR^b$ ($R^b$=hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl);

$R^{iii}$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^{iv}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl.

Especially preferred phenyl derivatives of the formula I are those where the substituents have the following meanings:

$R^3$ is hydrogen or cyano,
$C_1$–$C_6$-alkyl, $C_1$–$C_6$-haloalkyl, $C_3$–$C_6$-cycloalkyl, $C_3$–$C_6$-cycloalkyl-$C_1$–$C_4$-alkyl, aryl, aryl-$C_1$–$C_4$-alkyl and aryloxy-$C_1$–$C_4$-alkyl, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(=NOR^i)$—$A_n$—$R^{ii}$;

$R^4$ is unsubstituted or substituted aryl, hetaryl, aryloxy, hetaryloxy, arylthio and hetarylthio;

—$Q_p$—$C(R^5)$=N—$Y^1$—$R^6$ or —Q—O—N=$CR^7R^8$, $R^3$ and $R^4$ together with the carbon atom to which they are bonded are a four- to eight-membered ring which, besides carbon atoms, may contain one or two oxygen and/or sulfur atoms and/or NH and/or N($C_1$–$C_4$-alkyl) groups and whose carbon atoms may have attached to them one of the following substituents: halogen, $C_1$–$C_6$-alkyl or $C_1$–$C_4$-alkoxyimino;

$R^3$ and $R^4$ not simultaneously being bonded to the carbon atom via hetero atoms.

Moreover, preferred phenyl derivatives of the formula I are those where the substituents have the following meanings:

$R^3$ is hydrogen, cyano, halogen,
$C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_3$–$C_6$-cycloalkyl, $C_3$–$C_6$-cycloalkyl-$C_1$–$C_4$-alkyl, aryl, aryl-$C_1$–$C_4$-alkyl, aryloxy-$C_1$–$C_4$-alkyl and aryl-$C_1$–$C_4$-alkoxy, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(=NOR^i)$—$A_n$—$R^{ii}$;

$R^4$ is unsubstituted or substituted aryl and hetaryl;

—$Q_p$—$C(R^5)$=N—$Y^1$—$R^6$ or —Q—O—N=$CR^7R^8$, $R^3$ and $R^4$ not simultaneously being bonded to the carbon atom via hetero atoms.

Furthermore, preferred compounds of the formula I are those where m is 0, $R^1$ is the groups (Ia), (Ib), (Ic) and (Id), $R^1$ is the group (Ib), $R^1$ is the group (Id), $R^3$ is $C_1$–$C_4$-alkyl (in particular methyl), $R^4$ is unsubstituted or substituted $C_1$–$C_6$-alkyl, $R^4$ is unsubstituted or substituted $C_2$–$C_6$-alkenyl, $R^4$ is unsubstituted or substituted aryl (in particular 3-substituted phenyl), $R^3$ is methyl and $R^4$ is unsubstituted or substituted $C_1$–$C_6$-alkyl, $R^3$ is methyl and $R^4$ is unsubstituted or substituted aryl (in particular 3-substituted phenyl), $R^4$ is $C(R^5)=N-Y^1-R^6$, where $y^1$ is, in particular, oxygen and $R^5$ is, in particular, methyl, ethyl, allyl or propargyl.

Furthermore, preferred compounds of the formula I are those where $R^3$ is $C_1$–$C_6$-alkyl, $C_1$–$C_6$-haloalkyl, $C_1$–$C_6$-alkoxy, $C_1$–$C_6$-haloalkoxy, cyclopropyl or $C(CH_3)=NO-C_1$–$C_6$-alkyl, and $R^4$ is aryl, hetaryl or benzyl, it being possible for the aromatic rings in these radicals to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy and $C(=NOR^i)-A_n-R^{ii}$, or $R^4$ is $CR^5=N-Y^l-R^6$.

Furthermore, preferred compounds of the formula I are those where $R^3$ is $C_1$–$C_6$-alkyl, $C_1$–$C_6$-haloalkyl, $C_1$–$C_6$-alkoxy, $C_1$–$C_6$-haloalkoxy, cyclopropyl or $C(CH_3)=NO-C_1$–$C_6$-alkyl, and $R^4$ is $C_1$–$C_6$-alkyl, $C_2$–$C_6$-alkenyl, $C_2$–$C_6$-alkynyl or cyclopropyl, it being possible for these radicals to be partially or fully halogenated and/or to have attached to them one to three of the following groups: aryl and hetaryl, it being possible for the aromatic groups, in turn, to have attached to them one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy.

Furthermore, preferred compounds of the formula I are those where $R^3$ is $C_1$–$C_6$-alkyl, $C_1$–$C_6$-haloalkyl, cyclopropyl or $C(CH_3)=NO-C_1$–$C_6$-alkyl, and $R^4$ is $C_1$–$C_6$-alkoxy, it being possible for this radical to be partially or fully halogenated and/or to have attached to it one to three of the following groups: aryl and hetaryl, it being possible for the aromatic groups, in turn, to have attached to them one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy.

Furthermore, preferred compounds of the formula I are those where $R^3$ is $C_1$–$C_6$-alkyl, $C_1$–$C_6$-haloalkyl, $C_1$–$C_6$-alkoxy, $C_1$–$C_6$-haloalkoxy, cyclopropyl or $C(CH_3)=NO-C_1$–$C_6$-alkyl, and $R^4$ is $C_1$–$C_6$-alkyl, $C_2$–$C_6$-alkenyl, $C_2$–$C_6$-alkenyl or cyclopropyl, it being possible for these radicals to be partially or fully halogenated and/or to have attached to them one to three of the following groups: aryl and hetaryl, it being possible for the aromatic groups, in turn, to have attached to them one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy, or $R^4$ is aryl, hetaryl or benzyl, it being possible for the aromatic rings in these radicals to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy and $C(=NOR^i)-A_n-R^{ii}$, or $R^4$ is $CR^5=N-Y^1-R^6$.

Furthermore, preferred compounds of the formula I are those where $R^3$ is $_1$–$C_6$-alkyl, $C_1$–$C_6$-haloalkoxy, cyclopropyl or $C(CH_3)=NO-C_1$–$C_6$-alkyl, and $R^4$ is $C_1$–$C_6$-alkyloxy, it being possible for this radical to be partially or fully halogenated and/or to have attached to it one to three of the following groups: aryl and hetaryl, it being possible for the aromatic groups, in turn, to have attached to them one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy, or $R^4$ is aryloxy, hetaryloxy or N-aryl-N-methylamino, it being possible for the aromatic rings in these radicals to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy and $C(=NOR^i)-A_n-R^{ii}$, or $R^4$ is $CR^5=N-Y^1-R^6$.

Especially preferred compounds with a view to the use against animal pests and harmful fungi are those of the formula I.1

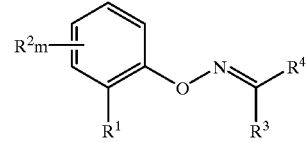

(I.1)

where the substituents and the index have the following meaning:

$R_1$ is $C(CO_2CH_3)=CHCH_3$, $C(CO_2CH_3)=CHOCH_3$, $C(CO_2CH_3)=NOCH_3$ or $C(CONHCH_3)=NOCH_3$;

$R^2$ is cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

m is 0 or 1;

$R^3$ is hydrogen, hydroxyl, cyano,
$C_1$–$C_4$-alkyl, $C_1$–$C_2$-haloalkyl, $C_1$–$C_4$-alkoxy, $C_1$–$C_2$-haloalkoxy, $C_3$–$C_6$-cycloalkyl, $C_3$–$C_6$-cycloalkyl-$C_1$–$C_4$-alkyl, or benzyl which may be substituted by customary groups;

$R^4$ is hydrogen, $C_3$–$C_6$-cycloalkyl,
$C_1$–$C_6$-alkyl or $C_1$–$C_6$-alkoxy which may be partially or fully halogenated and/or may have attached to it one to three (in particular one) of the following groups: cyano, $C_1$–$C_4$-alkoxy, $C_3$–$C_6$-cycloalkyl, or phenyl, naphthyl, pyridinyl, pyrazinyl, thienyl, pyrazolyl or isoxazolyl, each of which is unsubstituted or substituted by customary groups;

phenyl, naphthyl, pyridinyl, pyrazinyl, thienyl, pyrazolyl or isoxazolyl, each of which is unsubstituted or substituted by customary groups;

phenoxy, naphthyloxy, pyridinyloxy, pyrazinyloxy, thienyloxy, pyrazolyloxy or isoxazolyloxy, each of which is unsubstituted or substituted by customary groups; or $R^3$ and $R^4$ together with the carbon atom to which they are bonded are a saturated or partially unsaturated, four- to eight-membered ring which, besides hydrocarbon ring members, may contain a hetero atom from the group consisting of oxygen, sulfur and nitrogen and which may be partially halogenated and/or may have attached to it one to three of the following groups: $C_1$–$C_4$-alkyl, $C_1$–$C_4$-haloalkyl, $C_1$–$C_4$-alkoxy, $C_1$–$C_4$-haloalkoxy, oxo (=O) and $C_1$–$C_4$-alkoxyimino (=N-alkoxy)

$R^3$ and $R^4$ not simultaneously being bonded to the carbon atom via hetero atoms.

Compounds which are furthermore especially preferred with a view to the use against animal pests and harmful fungi are those of the formula I.3

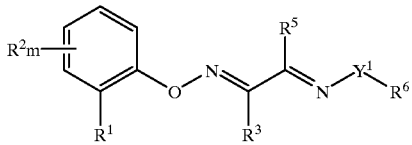

(I.3)

where the substituents and the index have the following meanings:

$R^1$ is $C(CO_2CH_3)$=$CHCH_3$, $C(CO_2CH_3)$=$CHOCH_3$, $C(CO_2CH_3)$=$NOCH_3$ or $C(CONHCH_3)$=$NOCH_3$;

$R^2$ is cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

m is 0 or 1;

$R^3$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^5$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$Y^1$ is O, NH or $N(CH_3)$;

$R^6$ is hydrogen, $C_1$–$C_6$-alkyl which may have attached to it one of the following groups: $C_1$–$C_4$-alkoxy, $C_3$–$C_6$-cycloalkyl which is unsubstituted or substituted by customary groups, or phenyl which is unsubstituted or substituted by customary groups;

$C_3$–$C_6$-alkenyl, $C_3$–$C_6$-haloalkenyl, $C_3$–$C_6$-alkynyl, $C_3$–$C_6$-haloalkynyl, or $C_3$–$C_6$-cycloalkyl which is unsubstituted or substituted by customary groups.

Furthermore, especially preferred compounds with a view to the use against animal pests and harmful fungi are those of the formula 1.5

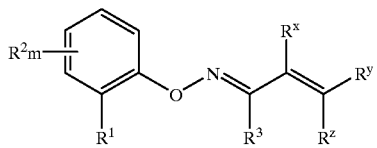

(I.5)

where the substituents and the index have the following meanings:

$R^1$ is $C(CO_2CH_3)$=$CHCH_3$, $C(CO_2CH_3)$=$CHOCH_3$, $C(CO_2CH_3)$=$NOCH_3$ or $C(CONHCH_3)$=$NOCH_3$;

$R^2$ is cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

m is 0 or 1;

$R^3$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^x$ is hydrogen, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^y$ is hydrogen, $C_1$–$C_6$-alkyl, which may be partially or fully halogenated and/or may have attached to it one to three (in particular one) of the following groups: $C_1$–$C_4$-alkoxy, $C_3$–$C_6$-cycloalkyl which is unsubstituted or substituted by customary groups, or phenyl which is unsubstituted or substituted by customary groups;

$C_1$–$C_6$-alkoxy, $C_1$–$C_6$-haloalkoxy, $C_3$–$C_6$-cycloalkyl which is unsubstituted or substituted by customary groups; phenyl which is unsubstituted or substituted by customary groups, pyridyl which is unsubstituted or substituted by customary groups, or pyrimidyl which is unsubstituted or substituted by customary groups;

$R^z$ is hydrogen, cyano, halogen, $C_1$–$C_4$-alkyl, $C_1$–$C_2$-haloalkyl and $C_3$–$C_6$-cycloalkyl, or $R^y$ and $R^x$ together with the double bond to which they are bonded are $C_4$–$C_6$-cycloalkenyl.

Especially preferred compounds I with a view to their use are those compiled in the tables which follow. Moreover, the groups mentioned in the tables for one substituent are, on their own, an especially preferred embodiment of the substituent in question, independently of the combination in which they are mentioned.

Table 1

Compounds of the general formula Ia.1 where $R^2_m$ is hydrogen and the combination of the radicals $R^3$ and $R^4$ for each compound corresponds to one line of Table A

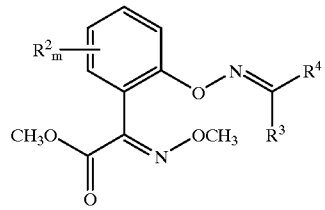

(Ia.1)

Table 2

Compounds of the general formula Ib.1 where $R^2_m$ is hydrogen and the combination of the radicals $R^3$ and $R^4$ for each compound corresponds to one line of Table A

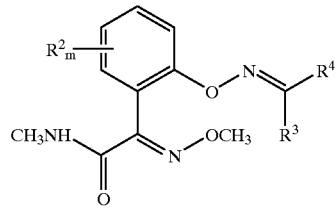

(Ib.1)

Table 3

Compounds of the general formula Ic.1 where $R^2_m$ is hydrogen and the combination of the radicals $R^3$ and $R^4$ for each compound corresponds to one line of Table A

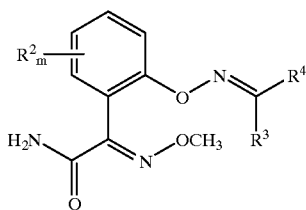

(Ic.1)

Table 4

Compounds of the general formula Id.1 where $R^2_m$ is hydrogen and the combination of the radicals $R^3$ and $R^4$ for each compound corresponds to one line of Table A

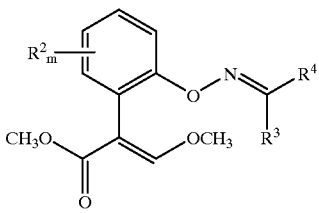

(Id.1)

Table 5

Compounds of the general formula Ie.1 where $R^2_m$ is hydrogen and the combination of the radicals $R^3$ and $R^4$ for each compound corresponds to one line of Table A

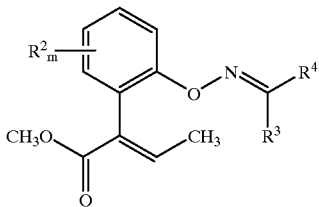

(Ie.1)

Table 6

Compounds of the general formula Ia.2 where $R^2_m$ is hydrogen and the combination of the radicals $R^3$ and $R^4$ for each compound corresponds to one line of Table A

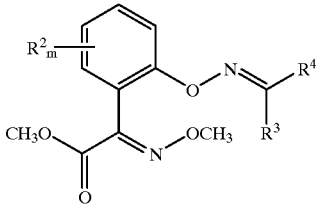

(Ia.2)

Table 7

Compounds of the general formula Ib.2 where $R^2_m$ is hydrogen and the combination of the radicals $R^3$ and $R^4$ for each compound corresponds to one line of Table A

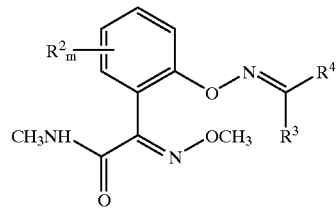

(Ib.2)

Table 8

Compounds of the general formula Ic.2 where $R^2_m$ is hydrogen and the combination of the radicals $R^3$ and $R^4$ for each compound corresponds to one line of Table A

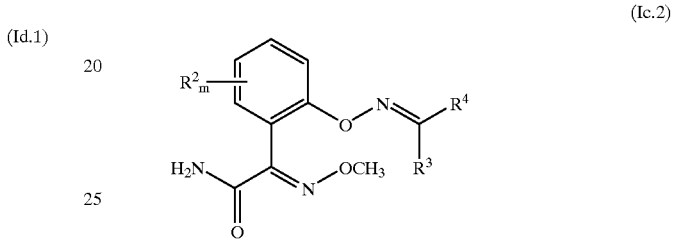

(Ic.2)

Table 9

Compounds of the general formula Id.2 where $R^2_m$ is hydrogen and the combination of the radicals $R^3$ and $R^4$ for each compound corresponds to one line of Table A

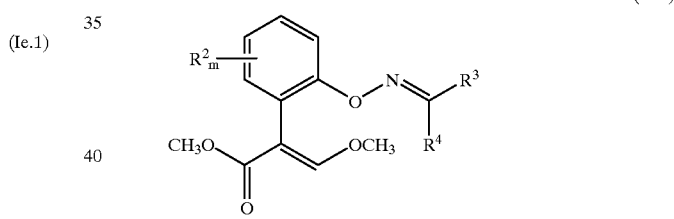

(Id.2)

Table 10

Compounds of the general formula Ie.2 where $R^2_m$ is hydrogen and the combination of the radicals $R^3$ and $R^4$ for each compound corresponds to one line of Table A

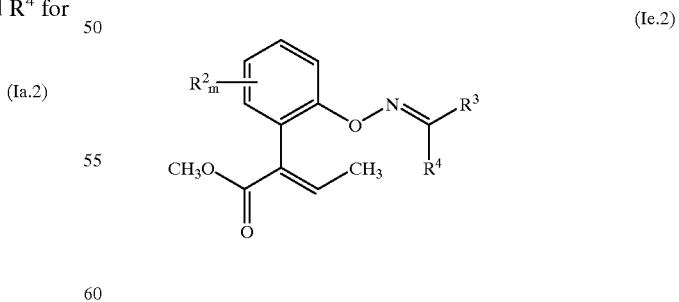

(Ie.2)

TABLE A

| No. | $R^3$ | $R^4$ |
|---|---|---|
| A.1 | H | $CH_3$ |
| A.2 | H | $CH_2CH_3$ |
| A.3 | H | $CH_2CH_2CH_3$ |

TABLE A-continued

| No. | R³ | R⁴ |
|---|---|---|
| A.4 | H | CH(CH₃)₂ |
| A.5 | H | CH₂CH₂CH₂CH₃ |
| A.6 | H | C(CH₃)₃ |
| A.7 | H | CH(CH₃)CH₂CH₃ |
| A.8 | H | C₆H₅ |
| A.9 | H | 2-F—C₆H₄ |
| A.10 | H | 3-F—C₆H₄ |
| A.11 | H | 4-F—C₆H₄ |
| A.12 | H | 3-CH₃—C₆H₄ |
| A.13 | H | 3-OCH₃—C₆H₄ |
| A.14 | H | 3-CF₃—C₆H₄ |
| A.15 | H | 3-Cl—C₆H₄ |
| A.16 | H | 2-CH₃—C₆H₄ |
| A.17 | H | 4-CH₃—C₆H₄ |
| A.18 | H | cyclopropyl |
| A.19 | H | cyclohexyl |
| A.20 | H | CH₂CH₂Cl |
| A.21 | H | CH₂CH₂CH₂CN |
| A.22 | H | CH₂—C₆H₅ |
| A.23 | H | CH₂CH₂CH₂CH₂—OCH₃ |
| A.24 | H | CH₂CH₂—OCH₂CH₃ |
| A.25 | H | CH₂C(CH₃)=NOCH₃ |
| A.26 | H | CH₂-[4-F—C₆H₄] |
| A.27 | H | CH₂-[3-CN—C₆H₄] |
| A.28 | H | 3-CN—C₆H₄ |
| A.29 | H | 3,5-(CH₃)₂—C₆H₃ |
| A.30 | H | 3-COCH₃—C₆H₄ |
| A.31 | H | 3-[C(CH₃)=NOCH₃]—C₆H₄ |
| A.32 | H | 1-naphthyl |
| A.33 | H | CH₂CH₂—O—C₆H₅ |
| A.34 | H | CH₂-[3-Cl-pyridin-5-yl] |
| A.35 | H | 4-OCH₃-pyridin-2-yl |
| A.36 | H | CH₂-[5-Cl-pyrazin-2-yl] |
| A.37 | H | 2-thienyl |
| A.38 | H | 3-CH(CH₃)₂-isoxazol-5-yl |
| A.39 | H | 3-C₆H₅-pyrazol-1-yl |
| A.40 | H | OCH(CH₃)₂ |
| A.41 | H | OCH₂CH₂CH₂CH₂CH₃ |
| A.42 | H | O-[4-F—C₆H₄] |
| A.43 | H | OCH₂-[4-F—C₆H₄] |
| A.44 | H | O-[6-CH₃-pyridin-2-yl] |
| A.45 | H | O—CO-[4-Cl—C₆H₄] |
| A.46 | H | NH-[4-Cl—C₆H₄] |
| A.47 | CH₃ | CH₃ |
| A.48 | CH₃ | CH₂CH₃ |
| A.49 | CH₃ | CH₂CH₂CH₃ |
| A.50 | CH₃ | CH(CH₃)₂ |
| A.51 | CH₃ | CH₂CH₂CH₂CH₃ |
| A.52 | CH₃ | C(CH₃)₃ |
| A.53 | CH₃ | CH(CH₃)CH₂CH₃ |
| A.54 | CH₃ | C₆H₅ |
| A.55 | CH₃ | 2-F—C₆H₄ |
| A.56 | CH₃ | 3-F—C₆H₄ |
| A.57 | CH₃ | 4-F—C₆H₄ |
| A.58 | CH₃ | 3-CH₃—C₆H₄ |
| A.59 | CH₃ | 3-OCH₃—C₆H₄ |
| A.60 | CH₃ | 3-CF₃—C₆H₄ |
| A.61 | CH₃ | 3-Cl—C₆H₄ |
| A.62 | CH₃ | 2-CH₃—C₆H₄ |
| A.63 | CH₃ | 4-CH₃—C₆H₄ |
| A.64 | CH₃ | cyclopropyl |
| A.65 | CH₃ | cyclohexyl |
| A.66 | CH₃ | CH₂CH₂Cl |
| A.67 | CH₃ | CH₂CH₂CH₂CN |
| A.68 | CH₃ | CH₂—C₆H₅ |
| A.69 | CH₃ | CH₂CH₂CH₂CH₂—OCH₃ |
| A.70 | CH₃ | CH₂CH₂—OCH₂CH₃ |
| A.71 | CH₃ | CH₂C(CH₃)=NOCH₃ |
| A.72 | CH₃ | CH₂-[4-F—C₆H₄] |
| A.73 | CH₃ | CH₂-(3-CN-C₆H₄) |
| A.74 | CH₃ | 3-CN—C₆H₄ |
| A.75 | CH₃ | 3,5-(CH₃)₂—C₆H₃ |
| A.76 | CH₃ | 3-COCH₃—C₆H₄ |
| A.77 | CH₃ | 3-[C(CH₃)=NOCH₃]—C₆H₄ |
| A.78 | CH₃ | 1-naphthyl |
| A.79 | CH₃ | CH₂CH₂—O—C₆H₅ |
| A.80 | CH₃ | CH₂-[3-Cl-pyridin-5-yl] |
| A.81 | CH₃ | 4-OCH₃-pyridin-2-yl |
| A.82 | CH₃ | CH₂-[5-Cl-pyrazin-2-yl] |
| A.83 | CH₃ | 2-thienyl |
| A.84 | CH₃ | 3-CH(CH₃)₂-isoxazol-5-yl |
| A.85 | CH₃ | 3-C₆H₅-pyrazol-1-yl |
| A.86 | CH₃ | OCH(CH₃)₂ |
| A.87 | CH₃ | OCH₂CH₂CH₂CH₂CH₃ |
| A.88 | CH₃ | 0-[4-F—C₆H₄] |
| A.89 | CH₃ | OCH₂-[4-F—C₆H₄] |
| A.90 | CH₃ | O-[6-CH₃-pyridin-2-yl] |
| A.91 | CH₃ | O—CO-[4-Cl—C₆H₄] |
| A.92 | CH₃ | NH-[4-Cl—C₆H₄] |
| A.93 | OH | CH₃ |
| A.94 | OH | CH₂CH₂CH₂CH₃ |
| A.95 | OH | CH(CH₃)₂ |
| A.96 | OH | 3-CH₃—C₆H₄ |
| A.97 | OH | CH₂—C₆H₅ |
| A.98 | OH | 3,5-Cl₂—C₆H₃ |
| A.99 | OCH₃ | CH₃ |
| A.100 | OCH₃ | CH₂CH₂CH₂CH₃ |
| A.101 | OCH₃ | CH(CH₃)₂ |
| A.102 | OCH₃ | CH₂CH₂CH₂CH₂CH₂CH₃ |
| A.103 | OCH₃ | 3-CH₃—C₆H₄ |
| A.104 | OCH₃ | CH₂—C₆H₅ |
| A.105 | OCH₃ | 3,5-Cl₂—C₆H₃ |
| A.106 | OCH₂CH₃ | CH₃ |
| A.107 | OCH₂CH₃ | CH₂CH₂CH₃ |
| A.108 | OCH₂CH₃ | CH(CH₃)₂ |
| A.109 | OCH₂CH₃ | CH₂CH₂CH₂CH₂CH₃ |
| A.110 | OCH₂CH₃ | 3-CH₃—C₆H₄ |
| A.111 | OCH₂CH₃ | CH₂-[4-F—C₆H₄] |
| A.112 | OCH₂CH₃ | 2,4-F₂—C₆H₃ |
| A.113 | cyclopropyl | CH₃ |
| A.114 | cyclopropyl | CH₂CH₂CH₃ |
| A.115 | cyclopropyl | OCH₂CH₃ |
| A.116 | cyclopropyl | C₆H₅ |
| A.117 | Cl | C₆H₅ |
| A.118 | Cl | CH₃ |
| A.119 | Cl | CH(CH₃)₂ |
| A.120 | Cl | 3-CH₃—C₆H₄ |
| A.121 | Cl | 3-CN—C₆H₄ |
| A.122 | Cl | CH₂CH₂—O—C₆H₅ |
| A.123 | Cl | CH₂CH₂—OCH₂CH₃ |
| A.124 | Cl | CH₂-[4-F—C₆H₄] |
| A.125 | SCH₃ | CH₃ |
| A.126 | SCH₃ | C₆H₅ |
| A.127 | SCH₃ | CH(CH₃)₂ |
| A.128 | CH(CH₃)₂ | CH₃ |
| A.129 | CH(CH₃)₂ | CH₂CH₃ |
| A.130 | CH(CH₃)₂ | C₆H₅ |
| A.131 | CH(CH₃)₂ | OCH₃ |
| A.132 | CH(CH₃)₂ | OCH(CH₃)₂ |
| A.133 | CH(CH₃)₂ | 3-CH₃—C₆H₄ |
| A.134 | CN | CH₃ |
| A.135 | CN | 3-CH₃—C₆H₄ |
| A.136 | CN | CH₂-[2,4-Cl₂—C₆H₃] |
| A.137 | CN | CH₂CH₂CH₂CH₃ |
| A.138 | CN | CH(CH₃)₂ |
| A.139 | CH₂CH₃ | CH₃ |
| A.140 | CH₂CH₃ | CH₂CH₃ |
| A.141 | CH₂CH₃ | CH₂CH₂CH₃ |
| A.142 | CH₂CH₃ | CH(CH₃)₂ |
| A.143 | CH₂CH₃ | CH₂CH₂CH₂CH₃ |
| A.144 | CH₂CH₃ | C(CH₃)₃ |
| A.145 | CH₂CH₃ | CH(CH₃)CH₂CH₃ |
| A.146 | CH₂CH₃ | C₆H₅ |
| A.147 | CH₂CH₃ | 2-F—C₆H₄ |
| A.148 | CH₂CH₃ | 3-F—C₆H₄ |
| A.149 | CH₂CH₃ | 4-F—C₆H₄ |
| A.150 | CH₂CH₃ | 3-CH₃—C₆H₄ |
| A.151 | CH₂CH₃ | 3-OCH₃—C₆H₄ |
| A.152 | CH₂CH₃ | 3-CF₃—C₆H₄ |
| A.153 | CH₂CH₃ | 3-Cl—C₆H₄ |
| A.154 | CH₂CH₃ | 2-CH₃—C₆H₄ |
| A.155 | CH₂CH₃ | 4-CH₃—C₆H₄ |
| A.156 | CH₂CH₃ | cyclopropyl |
| A.157 | CH₂CH₃ | cyclohexyl |

TABLE A-continued

| No. | R³ | R⁴ |
|---|---|---|
| A.158 | $CH_2CH_3$ | $CH_2CH_2Cl$ |
| A.159 | $CH_2CH_3$ | $CH_2CH_2CH_2CN$ |
| A.160 | $CH_2CH_3$ | $CH_2$—$C_6H_5$ |
| A.161 | $CH_2CH_3$ | $CH_2CH_2CH_2CH_2$—$OCH_3$ |
| A.162 | $CH_2CH_3$ | $CH_2CH_2$—$OCH_2CH_3$ |
| A.163 | $CH_2CH_3$ | $CH_2C(CH_3)$=$NOCH_3$ |
| A.164 | $CH_2CH_3$ | $CH_2$-[4-F—$C_6H_4$] |
| A.165 | $CH_2CH_3$ | $CH_2$-[3-CN—$C_6H_4$] |
| A.166 | $CH_2CH_3$ | 3-CN—$C_6H_4$ |
| A.167 | $CH_2CH_3$ | 3,5-$(CH_3)_2$—$C_6H_3$ |
| A.168 | $CH_2CH_3$ | 3-$COCH_3$—$C_6H_4$ |
| A.169 | $CH_2CH_3$ | 3-[$C(CH_3)$=$NOCH_3$]—$C_6H_4$ |
| A.170 | $CH_2CH_3$ | 1-naphthyl |
| A.171 | $CH_2CH_3$ | $CH_2CH_2$—O—$C_6H_5$ |
| A.172 | $CH_2CH_3$ | $CH_2$-[3-Cl-pyridin-5-yl] |
| A.173 | $CH_2CH_3$ | 4-$OCH_3$-pyridin-2-yl |
| A.174 | $CH_2CH_3$ | $CH_2$-[5-Cl-pyrazin-2-yl] |
| A.175 | $CH_2CH_3$ | 2-thienyl |
| A.176 | $CH_2CH_3$ | 3-$CH(CH_3)_2$-isoxazol-5-yl |
| A.177 | $CH_2CH_3$ | 3-$C_6H_5$-pyrazol-1-yl |
| A.178 | $CH_2CH_3$ | $OCH(CH_3)_2$ |
| A.179 | $CH_2CH_3$ | $OCH_2CH_2CH_2CH_3$ |
| A.180 | $CH_2CH_3$ | O-[4-F—$C_6H_4$] |
| A.181 | $CH_2CH_3$ | $OCH_2$-[4-F—$C_6H_4$] |
| A.182 | $CH_2CH_3$ | O-[6-$CH_3$-pyridin-2-yl] |
| A.183 | $CH_2CH_3$ | O—CO-[4-Cl—$C_6H_4$] |
| A.184 | $CH_2CH_3$ | NH-[4-Cl—$C_6H_4$] |
| A.185 | $CH_3$ | $CH_2ON$=$C(CH_3)_2$ |
| A.186 | $CH_3$ | $CH_2ON$=$C(CH_3)$—$CH_2CH_3$ |
| A.187 | $CH_3$ | $CH_2ON$=$C(CH_3)$—$C_6H_5$ |
| A.188 | $CH_3$ | $CH_2ON$=$C(CH_3)$-[4-Cl—$C_6H_4$] |
| A.189 | $CH_2CH_3$ | $CH_2ON$=$C(CH_3)_2$ |
| A.190 | $CH_2CH_3$ | $CH_2ON$=$C(CH_3)$—$CH_2CH_3$ |
| A.191 | $CH_2CH_3$ | $CH_2ON$=$C(CH_3)$—$C_6H_5$ |
| A.192 | $CH_2CH_3$ | $CH_2ON$=$C(CH_3)$-[4-Cl—$C_6H_4$] |
| A.193 | $CH_2$—$C_6H_5$ | $CH_2ON$=$C(CH_3)_2$ |
| A.194 | $CH_2$—$C_6H_5$ | $CH_2ON$=$C(CH_3)$—$CH_2CH_3$ |
| A.195 | $CH_2$—$C_6H_5$ | $CH_2ON$=$C(CH_3)$—$C_6H_5$ |
| A.196 | $CH_2$—$C_6H_5$ | $CH_2ON$=$C(CH_3)$-[4-Cl—$C_6H_4$] |
| A.197 | H | CH=CH—$C_6H_5$ |
| A.198 | H | CH=$C(CH_3)$—$C_6H_5$ |
| A.199 | H | CH=CCl—$C_6H_5$ |
| A.200 | H | $C(CH_3)$=CH—$C_6H_5$ |
| A.201 | H | CCl=CH—$C_6H_5$ |
| A.202 | H | CH=CH-[4-F—$C_6H_4$] |
| A.203 | H | CH=$C(CH_3)$-[4-F—$C_6H_4$] |
| A.204 | H | CH=CCl-[4-F—$C_6H_4$] |
| A.205 | H | CCl=CH-[4-F—$C_6H_4$] |
| A.206 | H | $C(CH_3)$=CH-[4-F—$C_6H_4$] |
| A.207 | $CH_3$ | CH=CH—$C_6H_5$ |
| A.208 | $CH_3$ | CH=$C(CH_3)$—$C_6H_5$ |
| A.209 | $CH_3$ | CH=CCl—$C_6H_5$ |
| A.210 | $CH_3$ | $C(CH_3)$=CH—$C_6H_5$ |
| A.211 | $CH_3$ | CCl=CH—$C_6H_5$ |
| A.212 | $CH_3$ | CH=CH-[4-F—$C_6H_4$] |
| A.213 | $CH_3$ | CH=$C(CH_3)$-[4-F—$C_6H_4$] |
| A.214 | $CH_3$ | CH=CCl-[4-F—$C_6H_4$] |
| A.215 | $CH_3$ | CCl=CH-[4-F—$C_6H_4$] |
| A.216 | $CH_3$ | $C(CH_3)$=CH-[4-F—$C_6H_4$] |
| A.217 | $CH_2CH_3$ | CH=CH—$C_6H_5$ |
| A.218 | $CH_2CH_3$ | CH=$C(CH_3)$—$C_6H_5$ |
| A.219 | $CH_2CH_3$ | CH=CCl—$C_6H_5$ |
| A.220 | $CH_2CH_3$ | $C(CH_3)$=CH—$C_6H_5$ |
| A.221 | $CH_2CH_3$ | CCl=CH—$C_6H_5$ |
| A.222 | $CH_2CH_3$ | CH=CH-[4-F—$C_6H_4$] |
| A.223 | $CH_2CH_3$ | CH=$C(CH_3)$-[4-F—$C_6H_4$] |
| A.224 | $CH_2CH_3$ | CH=CCl-[4-F—$C_6H_4$] |
| A.225 | $CH_2CH_3$ | CCl=CH-[4-F—$C_6H_4$] |
| A.226 | $CH_2CH_3$ | $C(CH_3)$=CH-[4-F—$C_6H_4$] |
| A.227 | $CH_2$—$C_6H_5$ | CH=CH—$C_6H_5$ |
| A.228 | $CH_2$—$C_6H_5$ | CH=$C(CH_3)$—$C_6H_5$ |
| A.229 | $CH_2$—$C_6H_5$ | CH=CCl—$C_6H_5$ |
| A.230 | $CH_2$—$C_6H_5$ | $C(CH_3)$=CH—$C_6H_5$ |
| A.231 | $CH_2$—$C_6H_5$ | CCl=CH—$C_6H_5$ |
| A.232 | $CH_2$—$C_6H_5$ | CH=CH-[4-F—$C_6H_4$] |
| A.233 | $CH_2$—$C_6H_5$ | CH=$C(CH_3)$-[4-F—$C_6H_4$] |
| A.234 | $CH_2$—$C_6H_5$ | CH=CCl-[4-F—$C_6H_4$] |
| A.235 | $CH_2$—$C_6H_5$ | CCl=CH-[4-F—$C_6H_4$] |
| A.236 | $CH_2$—$C_6H_5$ | $C(CH_3)$=CH-[4-F—$C_6H_4$] |
| A.237 | H | $CH(CH_3)$—$C(CH_3)$=$NOCH_3$ |
| A.238 | H | $CH(CH_3)$—$C(CH_3)$=$NOCH_2CH_3$ |
| A.239 | H | $CH(CH_3)$—$C_6H_5$ |
| A.240 | H | $CH(CH_3)$-[4-F—$C_6H_4$] |
| A.241 | H | 1-$C_6H_5$-cyclopropyl |
| A.242 | H | 1-[4-Cl—$C_6H_4$]-cyclopropyl |
| A.243 | H | $CH_2C(CH_3)$=$NOCH_3$ |
| A.244 | H | $CH_2C(CH_3)$=$NOCH_2CH_3$ |
| A.245 | H | 1-[$C(CH_3)$=$NOCH_3$]-cyclopropyl |
| A.246 | $CH_3$ | $CH(CH_3)$—$C(CH_3)$=$NOCH_3$ |
| A.247 | $CH_3$ | $CH(CH_3)$—$C(CH_3)$=$NOCH_2CH_3$ |
| A.248 | $CH_3$ | $CH(CH_3)$—$C_6H_5$ |
| A.249 | $CH_3$ | $CH(CH_3)$-[4-F—$C_6H_4$] |
| A.250 | $CH_3$ | 1-$C_6H_5$-cyclopropyl |
| A.251 | $CH_3$ | 1-[4-Cl—$C_6H_4$]-cyclopropyl |
| A.252 | $CH_3$ | $CH_2C(CH_3)$=$NOCH_3$ |
| A.253 | $CH_3$ | $CH_2C(CH_3)$=$NOCH_2CH_3$ |
| A.254 | $CH_3$ | 1-[$C(CH_3)$=$NOCH_3$]-cyclopropyl |
| A.255 | $CH_2CH_3$ | $CH(CH_3)$—$C(CH_3)$=$NOCH_3$ |
| A.256 | $CH_2CH_3$ | $CH(CH_3)$—$C(CH_3)$=$NOCH_2CH_3$ |
| A.257 | $CH_2CH_3$ | $CH(CH_3)$—$C_6H_5$ |
| A.258 | $CH_2CH_3$ | $CH(CH_3)$-[4-F—$C_6H_4$] |
| A.259 | $CH_2CH_3$ | 1-$C_6H_5$-cyclopropyl |
| A.260 | $CH_2CH_3$ | 1-[4-Cl-$C_6H_4$]-cyclopropyl |
| A.261 | $CH_2CH_3$ | $CH_2C(CH_3)$=$NOCH_3$ |
| A.262 | $CH_2CH_3$ | $CH_2C(CH_3)$=$NOCH_2CH_3$ |
| A.263 | $CH_2CH_3$ | 1-[$C(CH_3)$=$NOCH_3$]-cyclopropyl |
| A.264 | $CH_2$—$C_6H_5$ | $CH(CH_3)$—$C(CH_3)$=$NOCH_3$ |
| A.265 | $CH_2$—$C_6H_5$ | $CH(CH_3)$—$C(CH_3)$=$NOCH_2CH_3$ |
| A.266 | $CH_2$—$C_6H_5$ | $CH(CH_3)$—$C_6H_5$ |
| A.267 | $CH_2$—$C_6H_5$ | $CH(CH_3)$-[4-F—$C_6H_4$] |
| A.268 | $CH_2$—$C_6H_5$ | 1-$C_6H_5$-cyclopropyl |
| A.269 | $CH_2$—$C_6H_5$ | 1-[4-Cl—$C_6H_4$]-cyclopropyl |
| A.270 | $CH_2$—$C_6H_5$ | $CH_2C(CH_3)$=$NOCH_3$ |
| A.271 | $CH_2$—$C_6H_5$ | $CH_2C(CH_3)$=$NOCH_2CH_3$ |
| A.272 | $CH_2$—$C_6H_5$ | 1-[$C(CH_3)$=$NOCH_3$]-cyclopropyl |
| A.273 | | —$(CH_2)4$— |
| A.274 | | —$(CH_2)5$— |
| A.275 | | —$(CH_2)_2$—O—$(CH_2)_2$— |
| A.276 | | —$(CH_2)_2$—S—$(CH_2)_2$— |
| A.277 | | —$(CH_2)_2$—$CH(CH_3)$—$(CH_2)_2$— |
| A.278 | | —$(CH_2)_2$—$C(=O)$—$(CH_2)_2$— |
| A.279 | | —$(CH_2)_2$—$C(=NOCH_3)$—$(CH_2)_2$— |
| A.280 | | —$(CH_2)_2$—$C(OCH_3)_2$—$(CH_2)_2$— |
| A.281 | | —$CH_2$—$CH(CH_3)$—$CH_2$—$CH(CH_3)$—$CH_2$— |
| A.282 | | —$(CH_2)_3$—$CH(CH_3)$—$CH_2$— |
| A.283 | | —CH=CH—$C(=NOCH_3)$—CH=CH— |
| A.284 | | —$CH_2$—$C(=NOCH_3)$—$(CH_2)_3$— |

Table 11

Compounds of the general formula Ia.3 where $R^2_m$ is hydrogen, Y is oxygen, and the combination of the radicals $R^3$, $R^4$, $R^5$ and $R^6$ for each compound corresponds to one line of Table B

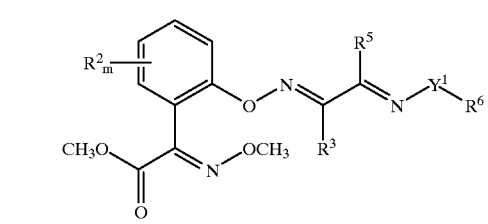

(Ia.3)

Table 12

Compounds of the general formula Ia.3 where $R^2_m$ is hydrogen, Y is NH, and the combination of the radicals $R^3$, $R^4$, $R^5$ and $R^6$ for each compound corresponds to one line of Table B

Table 13

Compounds of the general formula Ia.3 where $R^2_m$ is hydrogen, Y is N(CH$_3$), and the combination of the radicals $R^3$, $R^4$, $R^5$ and $R^6$ for each compound corresponds to one line of Table B

Table 14

Compounds of the general formula Ib.3 where $R^2_m$ is hydrogen, Y is oxygen, and the combination of the radicals $R^3$, $R^4$, $R^5$ and $R^6$ for each compound corresponds to one line of Table B (Ib.3)

Table 15

Compounds of the general formula Ib.3 where $R^2_m$ is hydrogen, Y is NH, and the combination of the radicals $R^3$, $R^4$, $R^5$ and $R^6$ for each compound corresponds to one line of Table B

Table 16

Compounds of the general formula Ib.3 where $R^2_m$ is hydrogen, Y is N(CH$_3$), and the combination of the radicals $R^3$, $R^4$, $R^5$ and $R^6$ for each compound corresponds to one line of Table B

Table 17

Compounds of the general formula Ic.3 where $R^2_m$ is hydrogen, Y is oxygen, and the combination of the radicals $R^3$, $R^4$, $R^5$ and $R^6$ for each compound corresponds to one line of Table B (Ic.3)

Table 18

Compounds of the general formula Ic.3 where $R^2_m$ is hydrogen, Y is NH, and the combination of the radicals $R^3$, $R^4$, $R^5$ and $R^6$ for each compound corresponds to one line of Table B

Table 19

Compounds of the general formula Ic.3 where $R^2_m$ is hydrogen, Y is N(CH$_3$), and the combination of the radicals $R^3$, $R^4$, $R^5$ and $R^6$ for each compound corresponds to one line of Table B

Table 20

Compounds of the general formula Id.3 where $R^2_m$ is hydrogen, Y is oxygen, and the combination of the radicals $R^3$, $R^4$, $R^5$ and $R^6$ for each compound corresponds to one line of Table B (Id.3)

Table 21

Compounds of the general formula Id.3 where $R^2_m$ is hydrogen, Y is NH, and the combination of the radicals $R^3$, $R^4$, $R^5$ and $R^6$ for each compound corresponds to one line of Table B

Table 22

Compounds of the general formula Id.3 where $R^2_m$ is hydrogen, Y is N(CH$_3$), and the combination of the radicals $R^3$, $R^4$, $R^5$ and $R^6$ for each compound corresponds to one line of Table B

Table 23

Compounds of the general formula Ie.3 where $R^2_m$ is hydrogen, Y is oxygen, and the combination of the radicals $R^3$, $R^4$, $R^5$ and $R^6$ for each compound corresponds to one line of Table B (Ie.3)

Table 24

Compounds of the general formula Ie.3 where $R^2_m$ is hydrogen, Y is NH, and the combination of the radicals $R^3$, $R^4$, $R^5$ and $R^6$ for each compound corresponds to one line of Table B

Table 25

Compounds of the general formula Ie.3 where $R^2_m$ is hydrogen, Y is N(CH$_3$), and the combination of the radicals $R^3$, $R^4$, $R^5$ and $R^6$ for each compound corresponds to one line of Table B

Table 26

Compounds of the general formula Ia.4 where $R^2_m$ is hydrogen, Y is oxygen, and the combination of the radicals $R^3$, $R^4$, $R^5$ and $R^6$ for each compound corresponds to one line of Table B (Ia.4)

Table 27

Compounds of the general formula Ia.4 where $R^2_m$ is hydrogen, Y is NH, and the combination of the radicals $R^3$, $R^4$, $R^5$ and $R^6$ for each compound corresponds to one line of Table B Table 28

Compounds of the general formula Ia.4 where $R^2_m$ is hydrogen, Y is N(CH$_3$), and the combination of the radicals $R^3$, $R^4$, $R^5$ and $R^6$ for each compound corresponds to one line of Table B Table 29

Compounds of the general formula Ib.4 where $R^2_m$ is hydrogen, Y is oxygen, and the combination of the radicals $R^3$, $R^4$, $R^5$ and $R^6$ for each compound corresponds to one line of Table B

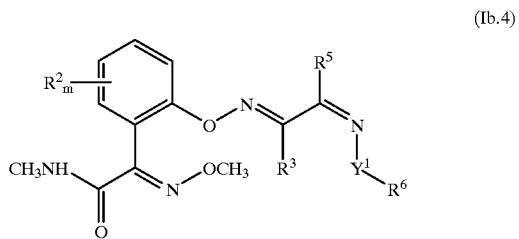
(Ib.4)

Table 30

Compounds of the general formula Ib.4 where $R^2_m$ is hydrogen, Y is NH, and the combination of the radicals $R^3$, $R^4$, $R^5$ and $R^6$ for each compound corresponds to one line of Table B Table 31

Compounds of the general formula Ib.4 where $R^2_m$ is hydrogen, Y is N(CH$_3$), and the combination of the radicals $R^3$, $R^4$, $R^5$ and $R^6$ for each compound corresponds to one line of Table B Table 32

Compounds of the general formula Ic.4 where $R^2_m$ is hydrogen, Y is oxygen, and the combination of the radicals $R^3$, $R^4$, $R^5$ and $R^6$ for each compound corresponds to one line of Table B

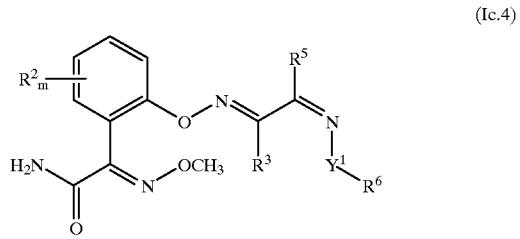
(Ic.4)

Table 33

Compounds of the general formula Ic.4 where $R^2_m$ is hydrogen, Y is NH, and the combination of the radicals $R^3$, $R^4$, $R^5$ and $R^6$ for each compound corresponds to one line of Table B Table 34

Compounds of the general formula Ic.4 where $R^2_m$ is hydrogen, Y is N(CH$_3$), and the combination of the radicals $R^3$, $R^4$, $R^5$ and $R^6$ for each compound corresponds to one line of Table B Table 35

Compounds of the general formula Id.4 where $R^2$, is hydrogen, Y is oxygen, and the combination of the radicals $R^3$, $R^4$, $R^5$ and $R^6$ for each compound corresponds to one line of Table B

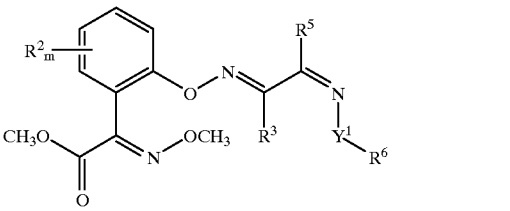
(Id.4)

Table 36

Compounds of the general formula Id.4 where $R^2_m$ is hydrogen, Y is NH, and the combination of the radicals $R^3$, $R^4$, $R^5$ and $R^6$ for each compound corresponds to one line of Table B Table 37

Compounds of the general formula Id.4 where $R^2_m$ is hydrogen, Y is N(CH$_3$), and the combination of the radicals $R^3$, $R^4$, $R^5$ and $R^6$ for each compound corresponds to one line of Table B Table 38

Compounds of the general formula Ie.4 where $R^2_m$ is hydrogen, Y is oxygen, and the combination of the radicals $R^3$, $R^4$, $R^5$ and $R^6$ for each compound corresponds to one line of Table B

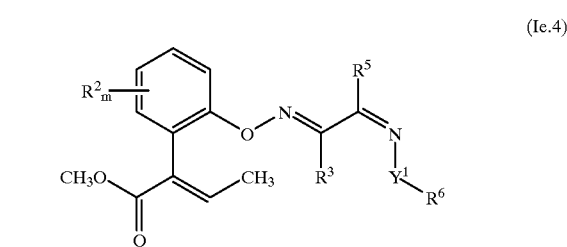
(Ie.4)

Table 39

Compounds of the general formula Ie.4 where $R^2_m$ is hydrogen, Y is NH, and the combination of the radicals $R^3$, $R^4$, $R^5$ and $R^6$ for each compound corresponds to one line of Table B Table 40

Compounds of the general formula Ie.4 where $R^2_m$ is hydrogen, Y is N(CH$_3$), and the combination of the radicals $R^3$, $R^4$, $R^5$ and $R^6$ for each compound corresponds to one line of Table B

TABLE B

| No. | $R_3$ | $R_5$ | $R_6$ |
|---|---|---|---|
| B. 1 | Cl | H | H |
| B. 2 | Cl | CH$_3$ | H |
| B. 3 | Cl | CH$_2$CH$_3$ | H |
| B. 4 | Cl | CF$_3$ | H |
| B. 5 | Cl | CHF$_2$ | H |
| B. 6 | Cl | CH$_2$F | H |
| B. 7 | Cl | Cl | H |
| B. 8 | Cl | OCH3 | H |
| B. 9 | Cl | OCH$_2$CH$_3$ | H |
| B. 10 | Cl | CN | H |
| B. 11 | CH$_3$ | H | H |
| B. 12 | CH$_3$ | CH$_3$ | H |
| B. 13 | CH$_3$ | CH$_2$CH$_3$ | H |
| B. 14 | CH$_3$ | CF$_3$ | H |
| B. 15 | CH$_3$ | CHF$_2$ | H |
| B. 16 | CH$_3$ | CH$_2$F | H |

TABLE B-continued

| No. | R₃ | R₅ | R₆ |
|---|---|---|---|
| B. 17 | CH₃ | Cl | H |
| B. 18 | CH₃ | OCH₃ | H |
| B. 19 | CH₃ | OCH₂CH₃ | H |
| B. 20 | CH₃ | CN | H |
| B. 21 | CF₃ | H | H |
| B. 22 | CF₃ | CH₃ | H |
| B. 23 | CF₃ | CH₂CH₃ | H |
| B. 24 | CF₃ | CF₃ | H |
| B. 25 | CF₃ | CHF₂ | H |
| B. 26 | CF₃ | CH₂F | H |
| B. 27 | CF₃ | Cl | H |
| B. 28 | CF₃ | OCH₃ | H |
| B. 29 | CF₃ | OCH₂CH₃ | H |
| B. 30 | CF₃ | CN | H |
| B. 31 | Cl | H | CH₃ |
| B. 32 | Cl | CH₃ | CH₃ |
| B. 33 | Cl | CH₂CH₃ | CH₃ |
| B. 34 | Cl | CF₃ | CH₃ |
| B. 35 | Cl | CHF₂ | CH₃ |
| B. 36 | Cl | CH₂F | CH₃ |
| B. 37 | Cl | Cl | CH₃ |
| B. 38 | Cl | OCH₃ | CH₃ |
| B. 39 | Cl | OCH₂CH₃ | CH₃ |
| B. 40 | Cl | CN | CH₃ |
| B. 41 | CH₃ | H | CH₃ |
| B. 42 | CH₃ | CH₃ | CH₃ |
| B. 43 | CH₃ | CH₂CH₃ | CH₃ |
| B. 44 | CH₃ | CF₃ | CH₃ |
| B. 45 | CH₃ | CHF₂ | CH₃ |
| B. 46 | CH₃ | CH₂F | CH₃ |
| B. 47 | CH₃ | Cl | CH₃ |
| B. 48 | CH₃ | OCH₃ | CH₃ |
| B. 49 | CH₃ | OCH₂CH₃ | CH₃ |
| B. 50 | CH₃ | CN | CH₃ |
| B. 51 | CF₃ | H | CH₃ |
| B. 52 | CF₃ | CH₃ | CH₃ |
| B. 53 | CF₃ | CH₂CH₃ | CH₃ |
| B. 54 | CF₃ | CF₃ | CH₃ |
| B. 55 | CF₃ | CHF₂ | CH₃ |
| B. 56 | CF₃ | CH₂F | CH₃ |
| B. 57 | CF₃ | Cl | CH₃ |
| B. 58 | CF₃ | OCH₃ | CH₃ |
| B. 59 | CF₃ | OCH₂CH₃ | CH₃ |
| B. 60 | CF₃ | CN | CH₃ |
| B. 61 | Cl | H | CH₂CH₃ |
| B. 62 | Cl | CH₃ | CH₂CH₃ |
| B. 63 | Cl | CH₂CH₃ | CH₂CH₃ |
| B. 64 | Cl | CF₃ | CH₂CH₃ |
| B. 65 | Cl | CHF₂ | CH₂CH₃ |
| B. 66 | Cl | CH₂F | CH₂CH₃ |
| B. 67 | Cl | Cl | CH₂CH₃ |
| B. 68 | Cl | OCH₃ | CH₂CH₃ |
| B. 69 | Cl | OCH₂CH₃ | CH₂CH₃ |
| B. 70 | Cl | CN | CH₂CH₃ |
| B. 71 | CH₃ | H | CH₂CH₃ |
| B. 72 | CH₃ | CH₃ | CH₂CH₃ |
| B. 73 | CH₃ | CH₂CH₃ | CH₂CH₃ |
| B. 74 | CH₃ | CF₃ | CH₂CH₃ |
| B. 75 | CH₃ | CHF₂ | CH₂CH₃ |
| B. 76 | CH₃ | CH₂F | CH₂CH₃ |
| B. 77 | CH₃ | Cl | CH₂CH₃ |
| B. 78 | CH₃ | OCH₃ | CH₂CH₃ |
| B. 79 | CH₃ | OCH₂CH₃ | CH₂CH₃ |
| B. 80 | CH₃ | CN | CH₂CH₃ |
| B. 81 | CF₃ | H | CH₂CH₃ |
| B. 82 | CF₃ | CH₃ | CH₂CH₃ |
| B. 83 | CF₃ | CH₂CH₃ | CH₂CH₃ |
| B. 84 | CF₃ | CF₃ | CH₂CH₃ |
| B. 85 | CF₃ | CHF₂ | CH₂H₃ |
| B. 86 | CF₃ | CH₂F | CH₂CH₃ |
| B. 87 | CF₃ | Cl | CH₂CH₃ |
| B. 88 | CF₃ | OCH₃ | CH₂CH₃ |
| B. 89 | CF₃ | OCH₂CH₃ | CH₂CH₃ |
| B. 90 | CF₃ | CN | CH₂CH₃ |
| B. 91 | Cl | H | CH₂CH₂CH₃ |
| B. 92 | Cl | CH₃ | CH₂CH₂CH₃ |
| B. 93 | Cl | CH₂CH₃ | CH₂CH₂CH₃ |
| B. 94 | Cl | CF₃ | CH₂CH₂CH₃ |
| B. 95 | Cl | CHF₂ | CH₂CH₂CH₃ |
| B. 96 | Cl | CH₂F | CH₂CH₂CH₃ |
| B. 97 | Cl | Cl | CH₂CH₂CH₃ |
| B. 98 | Cl | OCH₃ | CH₂CH₂CH₃ |
| B. 99 | Cl | OCH₂CH₃ | CH₂CH₂CH₃ |
| B. 100 | Cl | CN | CH₂CH₂CH₃ |
| B. 101 | CH₃ | H | CH₂CH₂CH₃ |
| B. 102 | CH₃ | CH₃ | CH₂CH₂CH₃ |
| B. 103 | CH₃ | CH₂CH₃ | CH₂CH₂CH₃ |
| B. 104 | CH₃ | CF₃ | CH₂CH₂CH₃ |
| B. 105 | CH₃ | CHF₂ | CH₂CH₂CH₃ |
| B. 106 | CH₃ | CH₂F | CH₂CH₂CH₃ |
| B. 107 | CH₃ | Cl | CH₂CH₂CH₃ |
| B. 108 | CH₃ | OCH₃ | CH₂CH₂CH₃ |
| B. 109 | CH₃ | OCH₂CH₃ | CH₂CH₂CH₃ |
| B. 110 | CH₃ | CN | CH₂CH₂CH₃ |
| B. 111 | CF₃ | H | CH₂CH₂CH₃ |
| B. 112 | CF₃ | CH₃ | CH₂CH₂CH₃ |
| B. 113 | CF₃ | CH₂CH₃ | CH₂CH₂CH₃ |
| B. 114 | CF₃ | CF₃ | CH₂CH₂CH₃ |
| B. 115 | CF₃ | CHF₂ | CH₂CH₂CH₃ |
| B. 116 | CF₃ | CH₂F | CH₂CH₂CH₃ |
| B. 117 | CF₃ | Cl | CH2CH2CH₃ |
| B. 118 | CF₃ | OCH₃ | CH₂CH₂CH₃ |
| B. 119 | CF₃ | OCH₂CH₃ | CH₂CH₂CH₃ |
| B. 120 | CF₃ | CN | CA₂CH₂CH₃ |
| B. 121 | Cl | H | CH(CH₃)₂ |
| B. 122 | Cl | CH₃ | CH(CH₃)₂ |
| B. 123 | Cl | CH₂CH₃ | CH(CH₃)₂ |
| B. 124 | Cl | CF₃ | CH(CH₃)₂ |
| B. 125 | Cl | CHF₂ | CH(CH₃)₂ |
| B. 126 | Cl | CH₂F | CH(CH₃)₂ |
| B. 127 | Cl | Cl | CH(CH₃)₂ |
| B. 128 | Cl | OCH₃ | CH(CH₃)₂ |
| B. 129 | Cl | OCH₂CH₃ | CH(CH₃)₂ |
| B. 130 | Cl | CN | CH(CH₃)₂ |
| B. 131 | CH₃ | H | CH(CH₃)₂ |
| B. 132 | CH₃ | CH₃ | CH(CH₃)₂ |
| B. 133 | CH₃ | CH₂CH₃ | CH(CH₃)₂ |
| B. 134 | CH₃ | CF₃ | CH(CH₃)₂ |
| B. 135 | CH₃ | CHF₂ | CH(CH₃)₂ |
| B. 136 | CH₃ | CH₂F | CH(CH₃)₂ |
| B. 137 | CH₃ | Cl | CH(CH₃)₂ |
| B. 138 | CH₃ | OCH₃ | CH(CH₃)₂ |
| B. 139 | CH₃ | OCH₂CH₃ | CH(CH₃)₂ |
| B. 140 | CH₃ | CN | CH(CH₃)₂ |
| B. 141 | CF₃ | H | CH(CH₃)₂ |
| B. 142 | CF₃ | CH₃ | CH(CH₃)₂ |
| B. 143 | CF₃ | CH₂CH₃ | CH(CH₃)₂ |
| B. 144 | CF₃ | CF₃ | CH(CH₃)₂ |
| B. 145 | CF₃ | CHF₂ | CH(CH₃)₂ |
| B. 146 | CF₃ | CH₂F | CH(CH₃)₂ |
| B. 147 | CF₃ | Cl | CH(CH₃)₂ |
| B. 148 | CF₃ | OCH₃ | CH(CH₃)₂ |
| B. 149 | CF₃ | OCH₂CH₃ | CH(CH₃)₂ |
| B. 150 | CF₃ | CN | CH(CH₃)₂ |
| B. 151 | Cl | H | CH₂CH=CH₂ |
| B. 152 | Cl | CH₃ | CH₂CH=CH₂ |
| B. 153 | Cl | CH₂CH₃ | CH₂CH=CH₂ |
| B. 154 | Cl | CF₃ | CH₂CH=CH₂ |
| B. 155 | Cl | CHF₂ | CH₂CH=CH₂ |
| B. 156 | Cl | CH₂F | CH₂CH=CH₂ |
| B. 157 | Cl | Cl | CH₂CH=CH₂ |
| B. 158 | Cl | OCH₃ | CH₂CH=CH₂ |
| B. 159 | Cl | OCH₂CH₃ | CH₂CH=CH₂ |
| B. 160 | Cl | CN | CH₂CH=CH₂ |
| B. 161 | CH₃ | H | CH₂CH=CH₂ |
| B. 162 | CH₃ | CH₃ | CH₂CH=CH₂ |
| B. 163 | CH₃ | CH₂CH₃ | CH₂CH=CH₂ |
| B. 164 | CH₃ | CF₃ | CH₂CH=CH₂ |
| B. 165 | CH₃ | CHF₂ | CH₂CH=CH₂ |
| B. 166 | CH₃ | CH₂F | CH₂CH=CH₂ |
| B. 167 | CH₃ | Cl | CH₂CH=CH₂ |
| B. 168 | CH₃ | OCH₃ | CH₂CH=CH₂ |
| B. 169 | CH₃ | OCH₂CH₃ | CH₂CH=CH₂ |
| B. 170 | CH₃ | CN | CH₂CH=CH₂ |

TABLE B-continued

| No. | R₃ | R₅ | R₆ |
|---|---|---|---|
| B. 171 | CF₃ | H | CH₂CH=CH₂ |
| B. 172 | CF₃ | CH₃ | CH₂CH=CH₂ |
| B. 173 | CF₃ | CH₂CH₃ | CH₂CH=CH₂ |
| B. 174 | CF₃ | CF₃ | CH₂CH=CH₂ |
| B. 175 | CF₃ | CHF₂ | CH₂CH=CH₂ |
| B. 176 | CF₃ | CH₂F | CH₂CH=CH₂ |
| B. 177 | CF₃ | Cl | CH₂CH=CH₂ |
| B. 178 | CF₃ | OCH₃ | CH₂CH=CH₂ |
| B. 179 | CF₃ | OCH₂CH₃ | CH₂CH=CH₂ |
| B. 180 | CF₃ | CN | CH₂CH=CH₂ |
| B. 181 | Cl | H | CH₂CH=CH—Cl (trans) |
| B. 182 | Cl | CH₃ | CH₂CH=CH—Cl (trans) |
| B. 183 | Cl | CH₂CH₃ | CH₂CH=CH—Cl (trans) |
| B. 184 | Cl | CF₃ | CH₂CH=CH—Cl (trans) |
| B. 185 | Cl | CHF₂ | CH₂CH=CH—Cl (trans) |
| B. 186 | Cl | CH₂F | CH₂CH=CH—Cl (trans) |
| B. 187 | Cl | Cl | CH₂CH=CH—Cl (trans) |
| B. 188 | Cl | OCH₃ | CH₂CH=CH—Cl (trans) |
| B. 189 | Cl | OCH₂CH₃ | CH₂CH=CH—Cl (trans) |
| B. 190 | Cl | CN | CH₂CH=CH—Cl (trans) |
| B. 191 | CH₃ | H | CH₂CH=CH—Cl (trans) |
| B. 192 | CH₃ | CH₃ | CH₂CH=CH—Cl (trans) |
| B. 193 | CH₃ | CH₂CH₃ | CH₂CH=CH—Cl (trans) |
| B. 194 | CH₃ | CF₃ | CH₂CH=CH—Cl (trans) |
| B. 195 | CH₃ | CHF₂ | CH₂CH=CH—Cl (trans) |
| B. 196 | CH₃ | CH₂F | CH₂CH=CH—Cl (trans) |
| B. 197 | CH₃ | Cl | CH₂CH=CH—Cl (trans) |
| B. 198 | CH₃ | OCH₃ | CH₂CH=CH—Cl (trans) |
| B. 199 | CH₃ | OCH₂CH₃ | CH₂CH=CH—Cl (trans) |
| B. 200 | CH₃ | CN | CH₂CH=CH—Cl (trans) |
| B. 201 | CF₃ | H | CH₂CH=CH—Cl (trans) |
| B. 202 | CF₃ | CH₃ | CH₂CH=CH—Cl (trans) |
| B. 203 | CF₃ | CH₂CH₃ | CH₂CH=CH—Cl (trans) |
| B. 204 | CF₃ | CF₃ | CH₂CH=CH—Cl (trans) |
| B. 205 | CF₃ | CHF₂ | CH₂CH=CH—Cl (trans) |
| B. 206 | CF₃ | CH₂F | CH₂CH=CH—Cl (trans) |
| B. 207 | CF₃ | Cl | CH₂CH=CH—Cl (trans) |
| B. 208 | CF₃ | OCH₃ | CH₂CH=CH—Cl (trans) |
| B. 209 | CF₃ | OCH₂CH₃ | CH₂CH=CH—Cl (trans) |
| B. 210 | CF₃ | CN | CH₂CH=CH—Cl (trans) |
| B. 211 | Cl | H | CH₂CCl=CH₂ |
| B. 212 | Cl | CH₃ | CH₂CCl=CH₂ |
| B. 213 | Cl | CH₂CH₃ | CH₂CCl=CH₂ |
| B. 214 | Cl | CF₃ | CH₂CCl=CH₂ |
| B. 215 | Cl | CHF₂ | CH₂CCl=CH₂ |
| B. 216 | Cl | CH₂F | CH₂CCl=CH₂ |
| B. 217 | Cl | Cl | CH₂CCl=CH₂ |
| B. 218 | Cl | OCH₃ | CH₂CCl=CH₂ |
| B. 219 | Cl | OCH₂CH₃ | CH₂CCl=CH₂ |
| B. 220 | Cl | CN | CH₂CCl=CH₂ |
| B. 221 | CH₃ | H | CH₂CCl=CH₂ |
| B. 222 | CH₃ | CH₃ | CH₂CCl=CH₂ |
| B. 223 | CH₃ | CH₂CH₃ | CH₂CCl=CH₂ |
| B. 224 | CH₃ | CF₃ | CH₂CCl=CH₂ |
| B. 225 | CH₃ | CHF₂ | CH₂CCl=CH₂ |
| B. 226 | CH₃ | CH₂F | CH₂CCl=CH₂ |
| B. 227 | CH₃ | Cl | CH₂CCl=CH₂ |
| B. 228 | CH₃ | OCH₃ | CH₂CCl=CH₂ |
| B. 229 | CH₃ | OCH₂CH₃ | CH₂CCl=CH₂ |
| B. 230 | CH₃ | CN | CH₂CCl=CH₂ |
| B. 231 | CF₃ | H | CH₂CCl=CH₂ |
| B. 232 | CF₃ | CH₃ | CH₂CCl=CH₂ |
| B. 233 | CF₃ | CH₂CH₃ | CH₂CCl=CH₂ |
| B. 234 | CF₃ | CF₃ | CH₂CCl=CH₂ |
| B. 235 | CF₃ | CHF₂ | CH₂CCl=CH₂ |
| B. 236 | CF₃ | CH₂F | CH₂CCl=CH₂ |
| B. 237 | CF₃ | Cl | CH₂CCl=CH₂ |
| B. 238 | CF₃ | OCH₃ | CH₂CCl=CH₂ |
| B. 239 | CF₃ | OCH₂CH₃ | CH₂CCl=CH₂ |
| B. 240 | CF₃ | CN | CH₂CCl=CH₂ |
| B. 241 | Cl | H | CH₂C≡CH |
| B. 242 | Cl | CH₃ | CH₂C≡CH |
| B. 243 | Cl | OH₂CH₃ | CH₂C≡CH |
| B. 244 | Cl | CF₃ | CH₂C≡CH |
| B. 245 | Cl | CHF₂ | CH₂C≡CH |
| B. 246 | Cl | CH₂F | CH₂C≡CH |
| B. 247 | Cl | Cl | CH₂C≡CH |
| B. 248 | Cl | OCH₃ | CH₂C≡CH |
| B. 249 | Cl | OCH₂CH₃ | CH₂C≡CH |
| B. 250 | Cl | CN | CH₂C≡CH |
| B. 251 | CH₃ | H | CH₂C≡CH |
| B. 252 | CH₃ | CH₃ | CH₂C≡CH |
| B. 253 | CH₃ | CH₂CH₃ | CH₂C≡CH |
| B. 254 | CH₃ | CF₃ | CH₂C≡CH |
| B. 255 | CH₃ | CHF₂ | CH₂C≡CH |
| B. 256 | CH₃ | CH₂F | CH₂C≡CH |
| B. 257 | CH₃ | Cl | CH₂C≡CH |
| B. 258 | CH₃ | OCH₃ | CH₂C≡CH |
| B. 259 | CH₃ | OCH₂CH₃ | CH₂C≡CH |
| B. 260 | CH₃ | CN | CH₂C≡CH |
| B. 261 | CF₃ | H | CH₂C≡CH |
| B. 262 | CF₃ | CH₃ | CH₂C≡CH |
| B. 263 | CF₃ | CH₂CH₃ | CH₂C≡CH |
| B. 264 | CF₃ | CF₃ | CH₂C≡CH |
| B. 265 | CF₃ | CHF₂ | CH₂C≡CH |
| B. 266 | CF₃ | CH₂F | CH₂C≡CH |
| B. 267 | CF₃ | Cl | CH₂C≡CH |
| B. 268 | CF₃ | OCH₃ | CH₂C≡CH |
| B. 269 | CF₃ | OCH₂CH₃ | CH₂C≡CH |
| B. 270 | CF₃ | CN | CH₂C≡CH |
| B. 271 | Cl | H | CH₂C≡CCH₃ |
| B. 272 | Cl | CH₃ | CH₂C≡CCH₃ |
| B. 273 | Cl | CH₂CH₃ | CH₂C≡CCH₃ |
| B. 274 | Cl | CF₃ | CH₂C≡CCH₃ |
| B. 275 | Cl | CHF₂ | CH₂C≡CCH₃ |
| B. 276 | Cl | CH₂F | CH₂C≡CCH₃ |
| B. 277 | Cl | Cl | CH₂C≡CCH₃ |
| B. 278 | Cl | OCH₃ | CH₂C≡CCH₃ |
| B. 279 | Cl | OCH₂CH₃ | CH₂C≡CCH₃ |
| B. 280 | Cl | CN | CH₂C≡CCH₃ |
| B. 281 | CH₃ | H | CH₂C≡CCH₃ |
| B. 282 | CH₃ | CH₃ | CH₂C≡CCH₃ |
| B. 283 | CH₃ | CH₂CH₃ | CH₂C≡CCH₃ |
| B. 284 | CH₃ | CF₃ | CH₂C≡CCH₃ |
| B. 285 | CH₃ | CHF₂ | CH₂C≡CCH₃ |
| B. 286 | CH₃ | CH₂F | CH₂C≡CCH₃ |
| B. 287 | CH₃ | Cl | CH₂C≡CCH₃ |
| B. 288 | CH₃ | OCH₃ | CH₂C≡CCH₃ |
| B. 289 | CH₃ | OCH₂CH₃ | CH₂C≡CCH₃ |
| B. 290 | CH₃ | CN | CH₂C≡CCH₃ |
| B. 291 | CF₃ | H | CH₂C≡CCH₃ |
| B. 292 | CF₃ | CH₃ | CH₂C≡CCH₃ |
| B. 293 | CF₃ | CH₂CH₃ | CH₂C≡CCH₃ |
| B. 294 | CF₃ | CF₃ | CH₂C≡CCH₃ |
| B. 295 | CF₃ | CHF₂ | CH₂C≡CCH₃ |
| B. 296 | CF₃ | CH₂F | CH₂C≡CCH₃ |
| B. 297 | CF₃ | Cl | CH₂C≡CCH₃ |
| B. 298 | CF₃ | OCH₃ | CH₂C≡CCH₃ |
| B. 299 | CF₃ | OCH₂CH₃ | CH₂C≡CCH₃ |
| B. 300 | CF₃ | CN | CH₂C≡CCH₃ |
| B. 301 | Cl | H | CH₂C≡C—I |
| B. 302 | Cl | CH₃ | CH₂C≡C—I |
| B. 303 | Cl | CH₂CH₃ | CH₂C≡C—I |
| B. 304 | Cl | CF₃ | CH₂C≡C—I |
| B. 305 | Cl | CHF₂ | CH₂C≡C—I |
| B. 306 | Cl | CH₂F | CH₂C≡C—I |
| B. 307 | Cl | Cl | CH₂C≡C—I |
| B. 308 | Cl | OCH₃ | CH₂C≡C—I |
| B. 309 | Cl | OCH₂CH₃ | CH₂C≡C—I |
| B. 310 | Cl | CN | CH₂C≡C—I |
| B. 311 | CH₃ | H | CH₂C≡C—I |
| B. 312 | CH₃ | CH₃ | CH₂C≡C—I |
| B. 313 | CH₃ | CH₂CH₃ | CH₂C≡C—I |
| B. 314 | CH₃ | CF₃ | CH₂C≡C—I |
| B. 315 | CH₃ | CHF₂ | CH₂C≡C—I |
| B. 316 | CH₃ | CH₂F | CH₂C≡C—I |
| B. 317 | CH₃ | Cl | CH₂C≡C—I |
| B. 318 | CH₃ | OCH₃ | CH₂C≡C—I |
| B. 319 | CH₃ | OCH₂CH₃ | CH₂C≡C—I |
| B. 320 | CH₃ | CN | CH₂C≡C—I |
| B. 321 | CF₃ | H | CH₂C≡C—I |
| B. 322 | CF₃ | CH₃ | CH₂C≡C—I |
| B. 323 | CF₃ | CH₂CH₃ | CH₂C≡C—I |
| B. 324 | CF₃ | CF₃ | CH₂C≡C—I |

TABLE B-continued

| No. | R₃ | R₅ | R₆ |
|---|---|---|---|
| B. 325 | CF₃ | CHF₂ | CH₂C≡C—I |
| B. 326 | CF₃ | CH₂F | CH₂C≡C—I |
| B. 327 | CF₃ | Cl | CH₂C≡C—I |
| B. 328 | CF₃ | OCH₃ | CH₂C≡C—I |
| B. 329 | CF₃ | OCH₂CH₃ | CH₂C≡C—I |
| B. 330 | CF₃ | CN | CH₂C≡C—I |
| B. 331 | Cl | H | CH(CH₃)C≡CH |
| B. 332 | Cl | CH₃ | CH(CH₃)C≡CH |
| B. 333 | Cl | CH₂CH₃ | CH(CH₃)C≡CH |
| B. 334 | Cl | CF₃ | CH(CH₃)C≡CH |
| B. 335 | Cl | CHF₂ | CH(CH₃)C≡CH |
| B. 336 | Cl | CH₂F | CH(CH₃)C≡CH |
| B. 337 | Cl | Cl | CH(CH₃)C≡CH |
| B. 338 | Cl | OCH₃ | CH(CH₃)C≡CH |
| B. 339 | Cl | OCH₂CH₃ | CH(CH₃)C≡CH |
| B. 340 | Cl | CN | CH(CH₃)C≡CH |
| B. 341 | CH₃ | H | CH(CH₃)C≡CH |
| B. 342 | CH₃ | CH₃ | CH(CH₃)C≡CH |
| B. 343 | CH₃ | CH₂CH₃ | CH(CH₃)C≡CH |
| B. 344 | CH₃ | CF₃ | CH(CH₃)C≡CH |
| B. 345 | CH₃ | CHF₂ | CH(CH₃)C≡CH |
| B. 346 | CH₃ | CH₂F | CH(CH₃)C≡CH |
| B. 347 | CH₃ | Cl | CH(CH₃)C≡CH |
| B. 348 | CH₃ | OCH₃ | CH(CH₃)C≡CH |
| B. 349 | CH₃ | OCH₂CH₃ | CH(CH₃)C≡CH |
| B. 350 | CH₃ | CN | CH(CH₃)C≡CH |
| B. 351 | CF₃ | H | CH(CH₃)C≡CH |
| B. 352 | CF₃ | CH₃ | CH(CH₃)C≡CH |
| B. 353 | CF₃ | CH₂CH₃ | CH(CH₃)C≡CH |
| B. 354 | CF₃ | CF₃ | CH(CH₃)C≡CH |
| B. 355 | CF₃ | CHF₂ | CH(CH₃)C≡CH |
| B. 356 | CF₃ | CH₂F | CH(CH₃)C≡CH |
| B. 357 | CF₃ | Cl | CH(CH₃)C≡CH |
| B. 358 | CF₃ | OC₂H₃ | CH(CH₃)C≡CH |
| B. 359 | CF₃ | OCH₂CH₃ | CH(CH₃)C≡CH |
| B. 360 | CF₃ | CN | CH(CH₃)C≡CH |
| B. 361 | Cl | H | CH₂CH₂—O—CH₂CH₃ |
| B. 362 | Cl | CH₃ | CH₂CH₂—O—CH₂CH₃ |
| B. 363 | Cl | CH₂CH₃ | CH₂CH₂—O—CH₂CH₃ |
| B. 364 | Cl | CF₃ | CH₂CH₂—O—CH₂CH₃ |
| B. 365 | Cl | CHF₂ | CH₂CH₂—O—CH₂CH₃ |
| B. 366 | Cl | CH₂F | CH₂CH₂—O—CH₂CH₃ |
| B. 367 | Cl | Cl | CH₂CH₂—O—CH₂CH₃ |
| B. 368 | Cl | OCH₃ | CH₂CH₂—O—CH₂CH₃ |
| B. 369 | Cl | OCH₂CH₃ | CH₂CH₂—O—CH₂CH₃ |
| B. 370 | Cl | CN | CH₂CH₂—O—CH₂CH₃ |
| B. 371 | CH₃ | H | CH₂CH₂—O—CH₂CH₃ |
| B. 372 | CH₃ | CH₃ | CH₂CH₂—O—CH₂CH₃ |
| B. 373 | CH₃ | CH₂CH₃ | CH₂CH₂—O—CH₂CH₃ |
| B. 374 | CH₃ | CF₃ | CH₂CH₂—O—CH₂CH₃ |
| B. 375 | CH₃ | CHF₂ | CH₂CH₂—O—CH₂CH₃ |
| B. 376 | CH₃ | CH₂F | CH₂CH₂—O—CH₂CH₃ |
| B. 377 | CH₃ | Cl | CH₂CH₂—O—CH₂CH₃ |
| B. 378 | CH₃ | OCH₃ | CH₂CH₂—O—CH₂CH₃ |
| B. 379 | CH₃ | OCH₂CH₃ | CH₂CH₂—O—CH₂CH₃ |
| B. 380 | CH₃ | CN | CH₂CH₂—O—CH₂CH₃ |
| B. 381 | CF₃ | H | CH₂CH₂—O—CH₂CH₃ |
| B. 382 | CF₃ | CH₃ | CH₂CH₂—O—CH₂CH₃ |
| B. 383 | CF₃ | CH₂CH₃ | CH₂CH₂—O—CH₂CH₃ |
| B. 384 | CF₃ | CF₃ | CH₂CH₂—O—CH₂CH₃ |
| B. 385 | CF₃ | CHF₂ | CH₂CH₂—O—CH₂CH₃ |
| B. 386 | CF₃ | CH₂F | CH₂CH₂—O—CH₂CH₃ |
| B. 387 | CF₃ | Cl | CH₂CH₂—O—CH₂CH₃ |
| B. 388 | CF₃ | OCH₃ | CH₂CH₂—O—CH₂CH₃ |
| B. 389 | CF₃ | OCH₂CH₃ | CH₂CH₂—O—CH₂CH₃ |
| B. 390 | CF₃ | CN | CH₂CH₂—O—CH₂CH₃ |
| B. 391 | Cl | H | CH₂—C₆H₅ |
| B. 392 | Cl | CH₃ | CH₂—C₆H₅ |
| B. 393 | Cl | CH₂CH₃ | CH₂—C₆H₅ |
| B. 394 | Cl | CF₃ | CH₂—C₆H₅ |
| B. 395 | Cl | CHF₂ | CH₂—C₆H₅ |
| B. 396 | Cl | CH₂F | CH₂—C₆H₅ |
| B. 397 | Cl | Cl | CH₂—C₆H₅ |
| B. 398 | Cl | OCH₃ | CH₂—C₆H₅ |
| B. 399 | Cl | OCH₂CH₃ | CH₂—C₆H₅ |
| B. 400 | Cl | CN | CH₂—C₆H₅ |
| B. 401 | CH₃ | H | CH₂—C₆H₅ |
| B. 402 | CH₃ | CH₃ | CH₂—C₆H₅ |
| B. 403 | CH₃ | CH₂CH₃ | CH₂—C₆H₅ |
| B. 404 | CH₃ | CF₃ | CH₂—C₆H₅ |
| B. 405 | CH₃ | CHF₂ | CH₂—C₆H₅ |
| B. 406 | CH₃ | CH₂F | CH₂—C₆H₅ |
| B. 407 | CH₃ | Cl | CH₂—C₆H₅ |
| B. 408 | CH₃ | OCH₃ | CH₂—C₆H₅ |
| B. 409 | CH₃ | OCH₂CH₃ | CH₂—C₆H₅ |
| B. 410 | CH₃ | CN | CH₂—C₆H₅ |
| B. 411 | CF₃ | H | CH₂—C₆H₅ |
| B. 412 | CF₃ | CH₃ | CH₂—C₆H₅ |
| B. 413 | CF₃ | CH₂CH₃ | CH₂—C₆H₅ |
| B. 414 | CF₃ | CF₃ | CH₂—C₆H₅ |
| B. 415 | CF₃ | CHF₂ | CH₂—C₆H₅ |
| B. 416 | CF₃ | CH₂F | CH₂—C₆H₅ |
| B. 417 | CF₃ | Cl | CH₂—C₆H₅ |
| B. 418 | CF₃ | OCH₃ | CH₂—C₆H₅ |
| B. 419 | CF₃ | OCH₂CH₃ | CH₂—C₆H₅ |
| B. 420 | CF₃ | CN | CH₂—C₆H₅ |
| B. 421 | Cl | H | cyclopropyl |
| B. 422 | Cl | CH₃ | cyclopropyl |
| B. 423 | Cl | CH₂CH₃ | cyclopropyl |
| B. 424 | Cl | CF₃ | cyclopropyl |
| B. 425 | Cl | CHF₂ | cyclopropyl |
| B. 426 | Cl | CH₂F | cyclopropyl |
| B. 427 | Cl | Cl | cyclopropyl |
| B. 428 | Cl | OCH₃ | cyclopropyl |
| B. 429 | Cl | OCH₂CH₃ | cyclopropyl |
| B. 430 | Cl | CN | cyclopropyl |
| B. 431 | CH₃ | H | cyclopropyl |
| B. 432 | CH₃ | CH₃ | cyclopropyl |
| B. 433 | CH₃ | CH₂CH₃ | cyclopropyl |
| B. 434 | CH₃ | CF₃ | cyclopropyl |
| B. 435 | CH₃ | CHF₂ | cyclopropyl |
| B. 436 | CH₃ | CH₂F | cyclopropyl |
| B. 437 | CH₃ | Cl | cyclopropyl |
| B. 438 | CH₃ | OCH₃ | cyclopropyl |
| B. 439 | CH₃ | OCH₂CH₃ | cyclopropyl |
| B. 440 | CH₃ | CN | cyclopropyl |
| B. 441 | CF₃ | H | cyclopropyl |
| B. 442 | CF₃ | CH₃ | cyclopropyl |
| B. 443 | CF₃ | CH₂CH₃ | cyclopropyl |
| B. 444 | CF₃ | CF₃ | cyclopropyl |
| B. 445 | CF₃ | CHF₂ | cyclopropyl |
| B. 446 | CF₃ | CH₂F | cyclopropyl |
| B. 447 | CF₃ | Cl | cyclopropyl |
| B. 448 | CF₃ | OCH₃ | cyclopropyl |
| B. 449 | CF₃ | OCH₂CH₃ | cyclopropyl |
| B. 450 | CF₃ | CN | cyclopropyl |
| B. 451 | Cl | H | CH₂-(2,2-Cl₂-cyclopropyl) |
| B. 452 | Cl | CH₃ | CH₂-(2,2-Cl₂-cyclopropyl) |
| B. 453 | Cl | CH₂CH₃ | CH₂-(2,2-Cl₂-cyclopropyl) |
| B. 454 | Cl | CF₃ | CH₂-(2,2-Cl₂-cyclopropyl) |
| B. 455 | Cl | CHF₂ | CH₂-(2,2-Cl₂-cyclopropyl) |
| B. 456 | Cl | CH₂F | CH₂-(2,2-Cl₂-cyclopropyl) |
| B. 457 | Cl | Cl | CH₂-(2,2-Cl₂-cyclopropyl) |
| B. 458 | Cl | OCH₃ | CH₂-(2,2-Cl₂-cyclopropyl) |
| B. 459 | Cl | OCH₂CH₃ | CH₂-(2,2-Cl₂-cyclopropyl) |
| B. 460 | Cl | CN | CH₂-(2,2-Cl₂-cyclopropyl) |
| B. 461 | CH₃ | H | CH₂-(2,2-Cl₂-cyclopropyl) |
| B. 462 | CH₃ | CH₃ | CH₂-(2,2-Cl₂-cyclopropyl) |
| B. 463 | CH₃ | CH₂CH₃ | CH₂-(2,2-Cl₂-cyclopropyl) |
| B. 464 | CH₃ | CF₃ | CH₂-(2,2-Cl₂-cyclopropyl) |
| B. 465 | CH₃ | CHF₂ | CH₂-(2,2-Cl₂-cyclopropyl) |
| B. 466 | CH₃ | CH₂F | CH₂-(2,2-Cl₂-cyclopropyl) |
| B. 467 | CH₃ | Cl | CH₂-(2,2-Cl₂-cyclopropyl) |
| B. 468 | CH₃ | OCH₃ | CH₂-(2,2-Cl₂-cyclopropyl) |
| B. 469 | CH₃ | OCH₂CH₃ | CH₂-(2,2-Cl₂-cyclopropyl) |
| B. 470 | CH₃ | CN | CH₂-(2,2-Cl₂-cyclopropyl) |
| B. 471 | CF₃ | H | CH₂-(2,2-Cl₂-cyclopropyl) |
| B. 472 | CF₃ | CH₃ | CH₂-(2,2-Cl₂-cyclopropyl) |
| B. 473 | CF₃ | CH₂CH₃ | CH₂-(2,2-Cl₂-cyclopropyl) |
| B. 474 | CF₃ | CF₃ | CH₂-(2,2-Cl₂-cyclopropyl) |
| B. 475 | CF₃ | CHF₂ | CH₂-(2,2-Cl₂-cyclopropyl) |
| B. 476 | CF₃ | CH₂F | CH₂-(2,2-Cl₂-cyclopropyl) |
| B. 477 | CF₃ | Cl | CH₂-(2,2-Cl₂-cyclopropyl) |
| B. 478 | CF₃ | OCH₃ | CH₂-(2,2-Cl₂-cyclopropyl) |

TABLE B-continued

| No. | R₃ | R₅ | R₆ |
|---|---|---|---|
| B. 479 | CF₃ | OCH₂CH₃ | CH₂-(2,2-Cl₂-cyclopropyl) |
| B. 480 | CF₃ | CN | CH₂-(2,2-Cl₂-cyclopropyl) |
| B. 481 | H | CH₃ | H |
| B. 482 | H | CH₂CH₃ | H |
| B. 483 | H | CF₃ | H |
| B. 484 | H | Cl | H |
| B. 485 | H | OCH₃ | H |
| B. 486 | CH₂CH₃ | CH₃ | H |
| B. 487 | CH₂CH₃ | CH₂CH₃ | H |
| B. 488 | CH₂CH₃ | CF₃ | H |
| B. 489 | CH₂CH₃ | Cl | H |
| B. 490 | CH₂CH₃ | OCH₃ | H |
| B. 491 | CHF₂ | CH₃ | H |
| B. 492 | CHF₂ | CH₂CH₃ | H |
| B. 493 | CHF₂ | CF₃ | H |
| B. 494 | CHF₂ | Cl | H |
| B. 495 | CHF₂ | OCH₃ | H |
| B. 496 | CH2F | CH₃ | H |
| B. 497 | CH2F | CH₂CH₃ | H |
| B. 498 | CH2F | CF₃ | H |
| B. 499 | CH2F | Cl | H |
| B. 500 | CH2F | OCH₃ | H |
| B. 501 | OCH₃ | CH₃ | H |
| B. 502 | OCH₃ | CH₂CH3 | H |
| B. 503 | OCH₃ | CF₃ | H |
| B. 504 | OCH₃ | Cl | H |
| B. 505 | OCH₃ | OCH₃ | H |
| B. 506 | OCH₂CH₃ | CH₃ | H |
| B. 507 | OCH₂CH₃ | CH₂CH₃ | H |
| B. 508 | OCH₂CH₃ | CF₃ | H |
| B. 509 | OCH₂CH₃ | Cl | H |
| B. 510 | OCH₂CH₃ | OCH₃ | H |
| B. 511 | CN | CH₃ | H |
| B. 512 | CN | CH₂CH₃ | H |
| B. 513 | CN | CF₃ | H |
| B. 514 | CN | Cl | H |
| B. 515 | CN | OCH₃ | H |
| B. 516 | H | CH₃ | CH₃ |
| B. 517 | H | CH₂CH₃ | CH₃ |
| B. 518 | H | CF₃ | CH₃ |
| B. 519 | H | Cl | CH₃ |
| B. 520 | H | OCH₃ | CH₃ |
| B. 521 | CH₂CH₃ | CH₃ | CH₃ |
| B. 522 | CH₂CH₃ | CH₂CH₃ | CH₃ |
| B. 523 | CH₂CH₃ | CF₃ | CH₃ |
| B. 524 | CH₂CH₃ | Cl | CH₃ |
| B. 525 | CH₂CH₃ | OCH₃ | CH₃ |
| B. 526 | CHF₂ | CH₃ | CH₃ |
| B. 527 | CHF₂ | CH₂CH₃ | CH₃ |
| B. 528 | CHF₂ | CF₃ | CH₃ |
| B. 529 | CHF₂ | Cl | CH₃ |
| B. 530 | CHF₂ | OCH₃ | CH₃ |
| B. 531 | CH₂F | CH₃ | CH₃ |
| B. 532 | CH₂F | CH₂CH₃ | CH₃ |
| B. 533 | CH₂F | CF₃ | CH₃ |
| B. 534 | CH₂F | Cl | CH₃ |
| B. 535 | CH₂F | OCH₃ | CH₃ |
| B. 536 | OCH₃ | CH₃ | CH₃ |
| B. 537 | OCH₃ | CH₂CH₃ | CH₃ |
| B. 538 | OCH₃ | CF₃ | CH₃ |
| B. 539 | OCH₃ | Cl | CH₃ |
| B. 540 | OCH₃ | OCH₃ | CH₃ |
| B. 541 | OCH₂CH₃ | CH₃ | CH₃ |
| B. 542 | OCH₂CH₃ | CH₂CH₃ | CH₃ |
| B. 543 | OCH₂CH₃ | CF₃ | CH₃ |
| B. 544 | OCH₂CH₃ | Cl | CH₃ |
| B. 545 | OCH₂CH₃ | OCH₃ | CH₃ |
| B. 546 | CN | CH₃ | CH₃ |
| B. 547 | CN | CH₂CH₃ | CH₃ |
| B. 548 | CN | CF₃ | CH₃ |
| B. 549 | CN | Cl | CH₃ |
| B. 550 | CN | OCH₃ | CH₃ |
| B. 551 | H | CH₃ | CH₂CH₃ |
| B. 552 | H | CH₂CH₃ | CH₂CH₃ |
| B. 553 | H | CF₃ | CH₂CH₃ |
| B. 554 | H | Cl | CH₂CH₃ |
| B. 555 | H | OCH₃ | CH₂CH₃ |
| B. 556 | CH₂CH₃ | CH₃ | CH₂CH₃ |
| B. 557 | CH₂CH₃ | CH₂CH₃ | CH₂CH₃ |
| B. 558 | CH₂CH₃ | CF₃ | CH₂CH₃ |
| B. 559 | CH₂CH₃ | Cl | CH₂CH₃ |
| B. 560 | CH₂CH₃ | OCH₃ | CH₂CH₃ |
| B. 561 | CHF₂ | CH₃ | CH₂CH₃ |
| B. 562 | CHF₂ | CH₂CH₃ | CH₂CH₃ |
| B. 563 | CHF₂ | CF₃ | CH₂CH₃ |
| B. 564 | CHF₂ | Cl | CH₂CH₃ |
| B. 565 | CHF₂ | OCH₃ | CH₂CH₃ |
| B. 566 | CH₂F | CH₃ | CH₂CH₃ |
| B. 567 | CH₂F | CH₂CH₃ | CH₂CH₃ |
| B. 568 | CH₂F | CF₃ | CH₂CH₃ |
| B. 569 | CH₂F | Cl | CH₂CH₃ |
| B. 570 | CH₂F | OCH₃ | CH₂CH₃ |
| B. 571 | OCH₃ | CH₃ | CH₂CH₃ |
| B. 572 | OCH₃ | CH₂CH₃ | CH₂CH₃ |
| B. 573 | OCH₃ | CF₃ | CH₂CH₃ |
| B. 574 | OCH₃ | Cl | CH₂CH₃ |
| B. 575 | OCH₃ | OCH₃ | CH₂CH₃ |
| B. 576 | OCH₂CH₃ | CH₃ | CH₂CH₃ |
| B. 577 | OCH₂CH₃ | CH₂CH₃ | CH₂CH₃ |
| B. 578 | OCH₂CH₃ | CF₃ | CH₂CH₃ |
| B. 579 | OCH₂CH₃ | Cl | CH₂CH₃ |
| B. 580 | OCH₂CH₃ | OCH₃ | CH₂CH₃ |
| B. 581 | CN | CH₃ | CH₂CH₃ |
| B. 582 | CN | CH₂CH₃ | CH₂CH₃ |
| B. 583 | CN | CF₃ | CH₂CH₃ |
| B. 584 | CN | Cl | CH₂CH₃ |
| B. 585 | CN | OCH₃ | CH₂CH₃ |
| B. 586 | H | CH₃ | CH₂CH₂CH₃ |
| B. 587 | H | CH₂CH₃ | CH₂CH₂CH₃ |
| B. 588 | H | CF₃ | CH₂CH₂CH₃ |
| B. 589 | H | Cl | CH₂CH₂CH₃ |
| B. 590 | H | OCH₃ | CH₂CH₂CH₃ |
| B. 591 | CH₂CH₃ | CH₃ | CH₂CH₂CH₃ |
| B 592 | CH₂CH₃ | CH₂CH₃ | CH₂CH₂CH₃ |
| B. 593 | CH₂CH₃ | CF₃ | CH₂CH₂CH₃ |
| B. 594 | CH₂CH₃ | Cl | CH₂CH₂CH₃ |
| B. 595 | CH₂CH₃ | OCH₃ | CH₂CH₂CH₃ |
| B. 596 | CHF₂ | CH₃ | CH₂CH₂CH₃ |
| B. 597 | CHF₂ | CH₂CH₃ | CH₂CH₂CH₃ |
| B. 598 | CHF₂ | CF₃ | CH₂CH₂CH₃ |
| B. 599 | CHF₂ | Cl | CH₂CH₂CH₃ |
| B. 600 | CHF₂ | OCH₃ | CH₂CH₂CH₃ |
| B. 601 | CH₂F | CH₃ | CH₂CH₂CH₃ |
| B. 602 | CH₂F | CH₂CH₃ | CH₂CH₂CH₃ |
| B. 603 | CH₂F | CF₃ | CH₂CH₂CH₃ |
| B. 604 | CH₂F | Cl | CH₂CH₂CH₃ |
| B. 605 | CH₂F | OCH₃ | CH₂CH₂CH₃ |
| B. 606 | OCH₃ | CH₃ | CH₂CH₂CH₃ |
| B. 607 | OCH₃ | CH₂CH₃ | CH₂CH₂CH₃ |
| B. 608 | OCH₃ | CF₃ | CH₂CH₂CH₃ |
| B. 609 | OCH₃ | Cl | CH₂CH₂CH₃ |
| B. 610 | OCH₃ | OCH₃ | CH₂CH₂CH₃ |
| B. 611 | OCH₂CH₃ | CH₃ | CH₂CH₂CH₃ |
| B. 612 | OCH₂CH₃ | CH₂CH₃ | CH₂CH₂CH₃ |
| B. 613 | OCH₂CH₃ | CF₃ | CH₂CH₂CH₃ |
| B. 614 | OCH₂CH₃ | Cl | CH₂CH₂CH₃ |
| B. 615 | OCH₂CH₃ | OCH₃ | CH₂CH₂CH₃ |
| B. 616 | CN | CH₃ | CH₂CH₂CH₃ |
| B. 617 | CN | CH₂CH₃ | CH₂CH₂CH₃ |
| B. 618 | CN | CF₃ | CH₂CH₂CH₃ |
| B. 619 | CN | Cl | CH₂CH₂CH₃ |
| B. 620 | CN | OCH₃ | CH₂CH₂CH₃ |
| B. 621 | H | CH₃ | CH(CH₃)₂ |
| B. 622 | H | CH₂CH₃ | CH(CH₃)₂ |
| B. 623 | H | CF₃ | CH(CH₃)₂ |
| B. 624 | H | Cl | CH(CH₃)₂ |
| B. 625 | H | OCH₃ | CH(CH₃)₂ |
| B. 626 | CH₂CH₃ | CH₃ | CH(CH₃)₂ |
| B. 627 | CH₂CH₃ | CH₂CH₃ | CH(CH₃)₂ |
| B. 628 | CH₂CH₃ | CF₃ | CH(CH₃)₂ |
| B. 629 | CH₂CH₃ | Cl | CH(CH₃)₂ |
| B. 630 | CH₂CH₃ | OCH₃ | CH(CH₃)₂ |
| B. 631 | CHF₂ | CH₃ | CH(CH₃)₂ |
| B. 632 | CHF₂ | CH₂CH₃ | CH(CH₃)₂ |

TABLE B-continued

| No. | R₃ | R₅ | R₆ |
|---|---|---|---|
| B. 633 | CHF₂ | CF₃ | CH(CH₃)₂ |
| B. 634 | CHF₂ | Cl | CH(CH₃)₂ |
| B. 635 | CHF₂ | OCH₃ | CH(CH₃)₂ |
| B. 636 | CH₂F | CH₃ | CH(CH₃)₂ |
| B. 637 | CH₂F | CH₂CH₃ | CH(CH₃)₂ |
| B. 638 | CH₂F | CF₃ | CH(CH₃)₂ |
| B. 639 | CH₂F | Cl | CH(CH₃)₂ |
| B. 640 | CH₂F | OCH₃ | CH(CH₃)₂ |
| B. 641 | OCH₃ | CH₃ | CH(CH₃)₂ |
| B. 642 | OCH₃ | CH₂CH₃ | CH(CH₃)₂ |
| B. 643 | OCH₃ | CF₃ | CH(CH₃)₂ |
| B. 644 | OCH₃ | Cl | CH(CH₃)₂ |
| B. 645 | OCH₃ | OCH₃ | CH(CH₃)₂ |
| B. 646 | OCH₂CH₃ | CH₃ | CH(CH₃)₂ |
| B. 647 | OCH₂CH₃ | CH₂CH₃ | CH(CH₃)₂ |
| B. 648 | OCH₂CH₃ | CF₃ | CH(CH₃)₂ |
| B. 649 | OCH₂CH₃ | Cl | CH(CH₃)₂ |
| B. 650 | OCH₂CH₃ | OCH₃ | CH(CH₃)₂ |
| B. 651 | CN | CH₃ | CH(CH₃)₂ |
| B. 652 | CN | CH₂CH₃ | CH(CH₃)₂ |
| B. 653 | CN | CF₃ | CH(CH₃)₂ |
| B. 654 | CN | Cl | CH(CH₃)₂ |
| B. 655 | CN | OCH₃ | CH(CH₃)₂ |
| B. 656 | H | CH₃ | CH₂CH=CH₂ |
| B. 657 | H | CH₂CH₃ | CH₂CH=CH₂ |
| B. 658 | H | CF₃ | CH₂CH=CH₂ |
| B. 659 | H | Cl | CH₂CH=CH₂ |
| B. 660 | H | OCH₃ | CH₂CH=CH₂ |
| B. 661 | CH₂CH₃ | CH₃ | CH₂CH=CH₂ |
| B. 662 | CH₂CH₃ | CH₂CH₃ | CH₂CH=CH₂ |
| B. 663 | CH₂CH₃ | CF₃ | CH₂CH=CH₂ |
| B. 664 | CH₂CH₃ | Cl | CH₂CH=CH₂ |
| B. 665 | CH₂CH₃ | OCH₃ | CH₂CH=CH₂ |
| B. 666 | CHF₂ | CH₃ | CH₂CH=CH₂ |
| B. 667 | CHF₂ | CH₂CH₃ | CH₂CH=CH₂ |
| B. 668 | CHF₂ | CF₃ | CH₂CH=CH₂ |
| B. 669 | CHF₂ | Cl | CH₂CH=CH₂ |
| B. 670 | CHF₂ | OCH₃ | CH₂CH=CH₂ |
| B. 671 | CH₂F | CH₃ | CH₂CH=CH₂ |
| B. 672 | CH₂F | CH₂CH₃ | CH₂CH=CH₂ |
| B. 673 | CH₂F | CF₃ | CH₂CH=CH₂ |
| B. 674 | CH₂F | Cl | CH₂CH=CH₂ |
| B. 675 | CH₂F | OCH₃ | CH₂CH=CH₂ |
| B. 676 | OCH₃ | CH₃ | CH₂CH=CH₂ |
| B. 677 | OCH₃ | CH₂CH₃ | CH₂CH=CH₂ |
| B. 678 | OCH₃ | CF₃ | CH₂CH=CH₂ |
| B. 679 | OCH₃ | Cl | CH₂CH=CH₂ |
| B. 680 | OCH₃ | OCH₃ | CH₂CH=CH₂ |
| B. 681 | OCH₂CH₃ | CH₃ | CH₂CH=CH₂ |
| B. 682 | OCH₂CH₃ | CH₂CH₃ | CH₂CH=CH₂ |
| B. 683 | OCH₂CH₃ | CF₃ | CH₂CH=CH₂ |
| B. 684 | OCH₂CH₃ | Cl | CH₂CH=CH₂ |
| B. 685 | OCH₂CH₃ | OCH₃ | CH₂CH=CH₂ |
| B. 686 | CN | CH₃ | CH₂CH=CH₂ |
| B. 687 | CN | CH₂CH₃ | CH₂CH=CH₂ |
| B. 688 | CN | CF₃ | CH₂CH=CH₂ |
| B. 689 | CN | Cl | CH₂CH=CH₂ |
| B. 690 | CN | OCH₃ | CH₂CH=CH₂ |
| B. 691 | H | CH₃ | CH₂CH=CH—Cl (trans) |
| B. 692 | H | CH₂CH₃ | CH₂CH=CH—Cl (trans) |
| B. 693 | H | CF₃ | CH₂CH=CH—Cl (trans) |
| B. 694 | H | Cl | CH₂CH=CH—Cl (trans) |
| B. 695 | H | OCH₃ | CH₂CH=CH—Cl (trans) |
| B. 696 | CH₂CH₃ | CH₃ | CH₂CH=CH—Cl (trans) |
| B. 697 | CH₂CH₃ | CH₂CH₃ | CH₂CH=CH—Cl (trans) |
| B. 698 | CH₂CH₃ | CF₃ | CH₂CH=CH—Cl (trans) |
| B. 699 | CH₂CH₃ | Cl | CH₂CH=CH—Cl (trans) |
| B. 700 | CH₂CH₃ | OCH₃ | CH₂CH=CH—Cl (trans) |
| B. 701 | CHF₂ | CH₃ | CH₂CH=CH—Cl (trans) |
| B. 702 | CHF₂ | CH₂CH₃ | CH₂CH=CH—Cl (trans) |
| B. 703 | CHF₂ | CF₃ | CH₂CH=CH—Cl (trans) |
| B. 704 | CHF₂ | Cl | CH₂CH=CH—Cl (trans) |
| B. 705 | CHF₂ | OCH₃ | CH₂CH=CH—Cl (trans) |
| B. 706 | CH₂F | CH₃ | CH₂CH=CH—Cl (trans) |
| B. 707 | CH₂F | CH₂CH₃ | CH₂CH=CH—Cl (trans) |
| B. 708 | CH₂F | CF₃ | CH₂CH=CH—Cl (trans) |
| B. 709 | CH₂F | Cl | CH₂CH=CH—Cl (trans) |

TABLE B-continued

| No. | R₃ | R₅ | R₆ |
|---|---|---|---|
| B. 710 | CH₂F | OCH₃ | CH₂CH=CH—Cl (trans) |
| B. 711 | OCH₃ | CH₃ | CH₂CH=CH—Cl (trans) |
| B. 712 | OCH₃ | CH₂CH₃ | CH₂CH=CH—Cl (trans) |
| B. 713 | OCH₃ | CF₃ | CH₂CH=CH—Cl (trans) |
| B. 714 | OCH₃ | Cl | CH₂CH=CH—Cl (trans) |
| B. 715 | OCH₃ | OCH₃ | CH₂CH=CH—Cl (trans) |
| B. 716 | OCH₂CH₃ | CH₃ | CH₂CH=CH—Cl (trans) |
| B. 717 | OCH₂CH₃ | CH₂CH₃ | CH₂CH=CH—Cl (trans) |
| B. 718 | OCH₂CH₃ | CF₃ | CH₂CH=CH—Cl (trans) |
| B. 719 | OCH₂CH₃ | Cl | CH₂CH=CH—Cl (trans) |
| B. 720 | OCH₂CH₃ | OCH₃ | CH₂CH=CH—Cl (trans) |
| B. 721 | CN | CH₃ | CH₂CH=CH—Cl (trans) |
| B. 722 | CN | CH₂CH₃ | CH₂CH=CH—Cl (trans) |
| B. 723 | CN | CF₃ | CH₂CH=CH—Cl (trans) |
| B. 724 | CN | Cl | CH₂CH=CH—Cl (trans) |
| B. 725 | CN | OCH₃ | CH₂CH=CH—Cl (trans) |
| B. 726 | H | CH₃ | CH₂CCl=CH₂ |
| B. 727 | H | CH₂CH₃ | CH₂CCl=CH₂ |
| B. 728 | H | CF₃ | CH₂CCl=CH₂ |
| B. 729 | H | Cl | CH₂CCl=CH₂ |
| B. 730 | H | OCH₃ | CH₂CCl=CH₂ |
| B. 731 | CH₂CH₃ | CH₃ | CH₂CCl=CH₂ |
| B. 732 | CH₂CH₃ | CH₂CH₃ | CH₂CCl=CH₂ |
| B. 733 | CH₂CH₃ | CF₃ | CH₂CCl=CH₂ |
| B. 734 | CH₂CH₃ | Cl | CH₂CCl=CH₂ |
| B. 735 | CH₂CH₃ | OCH₃ | CH₂CCl=CH₂ |
| B. 736 | CHF₂ | CH₃ | CH₂CCl=CH₂ |
| B. 737 | CHF₂ | CH₂CH₃ | CH₂CCl=CH₂ |
| B. 738 | CHF₂ | CF₃ | CH₂CCl=CH₂ |
| B. 739 | CHF₂ | Cl | CH₂CCl=CH₂ |
| B. 740 | CHF₂ | OCH₃ | CH₂CCl=CH₂ |
| B. 741 | CH₂F | CH₃ | CH₂CCl=CH₂ |
| B. 742 | CH₂F | CH₂CH₃ | CH₂CCl=CH₂ |
| B. 743 | CH₂F | CF₃ | CH₂CCl=CH₂ |
| B. 744 | CH₂F | Cl | CH₂CCl=CH₂ |
| B. 745 | CH₂F | OCH₃ | CH₂CCl=CH₂ |
| B. 746 | OCH₃ | CH₃ | CH₂CCl=CH₂ |
| B. 747 | OCH₃ | CH₂CH₃ | CH₂CCl=CH₂ |
| B. 746 | OCH₃ | CF₃ | CH₂Cdl=CH₂ |
| B. 749 | OCH₃ | Cl | CH₂CCl=CH₂ |
| B. 750 | OCH₃ | OCH₃ | CH₂CCl=CH₂ |
| B. 751 | OCH₂CH₃ | CH₃ | CH₂CCl=CH₂ |
| B. 752 | OCH₂CH₃ | CH₂CH₃ | CH₂CCl=CH₂ |
| B. 753 | OCH₂CH₃ | CF₃ | CH₂CCl=CH₂ |
| B. 754 | OCH₂CH₃ | Cl | CH₂CCl=CH₂ |
| B. 755 | OCH₂CH₃ | OCH₃ | CH₂CCl=CH₂ |
| B. 756 | CN | CH₃ | CH₂CCl=CH₂ |
| B. 757 | CN | CH₂CH₃ | CH₂CCl=CH₂ |
| B. 758 | CN | CF₃ | CH₂CCl=CH₂ |
| B. 759 | CN | Cl | CH₂CCl=CH₂ |
| B. 760 | CN | OCH₃ | CH₂CCl=CH₂ |
| B. 761 | H | CH₃ | CH₂C≡CH |
| B. 762 | H | CH₂CH₃ | CH₂C≡CH |
| B. 763 | H | CF₃ | CH₂C≡CH |
| B. 764 | H | Cl | CH₂C≡CH |
| B. 765 | H | OCH₃ | CH₂C≡CH |
| B. 766 | CH₂CH₃ | CH₃ | CH₂C≡CH |
| B. 767 | CH₂CH₃ | CH₂CH₃ | CH₂C≡CH |
| B. 768 | CH₂CH₃ | CF₃ | CH₂C≡CH |
| B. 769 | CH₂CH₃ | Cl | CH₂C≡CH |
| B. 770 | CH₂CH₃ | OCH₃ | CH₂C≡CH |
| B. 771 | CHF₂ | CH₃ | CH₂C≡CH |
| B. 772 | CHF₂ | CH₂CH₃ | CH₂C≡CH |
| B. 773 | CHF₂ | CF₃ | CH₂C≡CH |
| B. 774 | CHF₂ | Cl | CH₂C≡CH |
| B. 775 | CHF₂ | OCH₃ | CH₂C≡CH |
| B. 776 | CH₂F | CH₃ | CH₂C≡CH |
| B. 777 | CH₂F | CH₂CH₃ | CH₂C≡CH |
| B. 778 | CH₂F | CF₃ | CH₂C≡CH |
| B. 779 | CH₂F | Cl | CH₂C≡CH |
| B. 780 | CH₂F | OCH₃ | CH₂C≡CH |
| B. 781 | OCH₃ | CH₃ | CH₂C≡CH |
| B. 782 | OCH₃ | CH₂CH₃ | CH₂C≡CH |
| B. 783 | OCH₃ | CF₃ | CH₂C≡CH |
| B. 784 | OCH₃ | Cl | CH₂C≡CH |
| B. 785 | OCH₃ | OCH₃ | CH₂C≡CH |
| B. 786 | OCH₂CH₃ | CH₃ | CH₂C≡CH |

TABLE B-continued

| No. | $R_3$ | $R_5$ | $R_6$ |
|---|---|---|---|
| B. 787 | $OCH_2CH_3$ | $CH_2CH_3$ | $CH_2C\equiv CH$ |
| B. 788 | $OCH_2CH_3$ | $CF_3$ | $CH_2C\equiv CH$ |
| B. 789 | $OCH_2CH_3$ | Cl | $CH_2C\equiv CH$ |
| B. 790 | $OCH_2CH_3$ | $OCH_3$ | $CH_2C\equiv CH$ |
| B. 791 | CN | $CH_3$ | $CH_2C\equiv CH$ |
| B. 792 | CN | $CH_2CH_3$ | $CH_2C\equiv CH$ |
| B. 793 | CN | $CF_3$ | $CH_2C\equiv CH$ |
| B. 794 | CN | Cl | $CH_2C\equiv CH$ |
| B. 795 | CN | $OCH_3$ | $CH_2C\equiv CH$ |
| B. 796 | H | $CH_3$ | $CH_2C\equiv CCH_3$ |
| B. 797 | H | $CH_2CH_3$ | $CH_2C\equiv CCH_3$ |
| B. 798 | H | $CF_3$ | $CH_2C\equiv CCH_3$ |
| B. 799 | H | Cl | $CH_2C\equiv CCH_3$ |
| B. 800 | H | $OCH_3$ | $CH_2C\equiv CCH_3$ |
| B. 801 | $CH_2CH_3$ | $CH_3$ | $CH_2C\equiv CCH_3$ |
| B. 802 | $CH_2CH_3$ | $CH_2CH_3$ | $CH_2C\equiv CCH_3$ |
| B. 803 | $CH_2CH_3$ | $CF_3$ | $CH_2C\equiv CCH_3$ |
| B. 804 | $CH_2CH_3$ | Cl | $CH_2C\equiv CCH_3$ |
| B. 805 | $CH_2CH_3$ | $OCH_3$ | $CH_2C\equiv CCH_3$ |
| B. 806 | $CHF_2$ | $CH_3$ | $CH_2C\equiv CCH_3$ |
| B. 807 | $CHF_2$ | $CH_2CH_3$ | $CH_2C\equiv CCH_3$ |
| B. 808 | $CHF_2$ | $CF_3$ | $CH_2C\equiv CCH_3$ |
| B. 809 | $CHF_2$ | Cl | $CH_2C\equiv CCH_3$ |
| B. 810 | $CHF_2$ | $OCH_3$ | $CH_2C\equiv CCH_3$ |
| B. 811 | $CH_2F$ | $CH_3$ | $CH_2C\equiv CCH_3$ |
| B. 812 | $CH_2F$ | $CH_2CH_3$ | $CH_2C\equiv CCH_3$ |
| B. 813 | $CH_2F$ | $CF_3$ | $CH_2C\equiv CCH_3$ |
| B. 814 | $CH_2F$ | Cl | $CH_2C\equiv CCH_3$ |
| B. 815 | $CH_2F$ | $OCH_3$ | $CH_2C\equiv CCH_3$ |
| B. 816 | $OCH_3$ | $CH_3$ | $CH_2C\equiv CCH_3$ |
| B. 817 | $OCH_3$ | $CH_2CH_3$ | $CH_2C\equiv CCH_3$ |
| B. 818 | $OCH_3$ | $CF_3$ | $CH_2C\equiv CCH_3$ |
| B. 819 | $OCH_3$ | Cl | $CH_2C\equiv CCH_3$ |
| B. 820 | $OCH_3$ | OCH3 | $CH_2C\equiv CCH_3$ |
| B. 821 | $OCH_2CH_3$ | CH3 | $CH_2C\equiv CCH_3$ |
| B. 822 | $OCH_2CH_3$ | $CH_2CH_3$ | $CH_2C\equiv CCH_3$ |
| B. 823 | $OCH_2CH_3$ | CF3 | $CH_2C\equiv CCH_3$ |
| B. 824 | $OCH_2CH_3$ | Cl | $CH_2C\equiv CCH_3$ |
| B. 825 | $OCH_2CH_3$ | OCH3 | $CH_2C\equiv CCH_3$ |
| B. 826 | CN | CH3 | $CH_2C\equiv CCH_3$ |
| B. 827 | CN | $CH_2CH_3$ | $CH_2C\equiv CCH_3$ |
| B. 828 | CN | $CF_3$ | $CH_2C\equiv CCH_3$ |
| B. 829 | CN | Cl | $CH_2C\equiv CCH_3$ |
| B. 830 | CN | $OCH_3$ | $CH_2C\equiv CCH_3$ |
| B. 831 | H | $CH_3$ | $CH_2C\equiv C-I$ |
| B. 832 | H | $CH_2CH_3$ | $CH_2C\equiv C-I$ |
| B. 833 | H | $CF_3$ | $CH_2C\equiv C-I$ |
| B. 834 | H | Cl | $CH_2C\equiv C-I$ |
| B. 835 | H | $OCH_3$ | $CH_2C\equiv C-I$ |
| B. 836 | $CH_2CH_3$ | $CH_3$ | $CH_2C\equiv C-I$ |
| B. 837 | $CH_2CH_3$ | $CH_2CH_3$ | $CH_2C\equiv C-I$ |
| B. 838 | $CH_2CH_3$ | $CF_3$ | $CH_2C\equiv C-I$ |
| B. 839 | $CH_2CH_3$ | Cl | $CH_2C\equiv C-I$ |
| B. 840 | $CH_2CH_3$ | $OCH_3$ | $CH_2C\equiv C-I$ |
| B. 841 | $CHF_2$ | $CH_3$ | $CH_2C\equiv C-I$ |
| B. 842 | $CHF_2$ | $CH_2CH_3$ | $CH_2C\equiv C-I$ |
| B. 843 | $CHF_2$ | $CF_3$ | $CH_2C\equiv C-I$ |
| B. 844 | $CHF_2$ | Cl | $CH_2C\equiv C-I$ |
| B. 845 | $CHF_2$ | $OCH_3$ | $CH_2C\equiv C-I$ |
| B. 846 | $CH_2F$ | $CH_3$ | $CH_2C\equiv C-I$ |
| B. 847 | $CH_2F$ | $CH_2CH_3$ | $CH_2C\equiv C-I$ |
| B. 848 | $CH_2F$ | $CF_3$ | $CH_2C\equiv C-I$ |
| B. 849 | $CH_2F$ | Cl | $CH_2C\equiv C-I$ |
| B. 850 | $CH_2F$ | $OCH_3$ | $CH_2C\equiv C-I$ |
| B. 851 | $OCH_3$ | $CH_3$ | $CH_2C\equiv C-I$ |
| B. 852 | $OCH_3$ | $CH_2CH_3$ | $CH_2C\equiv C-I$ |
| B. 853 | $OCH_3$ | $CF_3$ | $CH_2C\equiv C-I$ |
| B. 854 | $OCH_3$ | Cl | $CH_2C\equiv C-I$ |
| B. 855 | $OCH_3$ | $OCH_3$ | $CH_2C\equiv C-I$ |
| B. 856 | $OCH_2CH_3$ | $CH_3$ | $CH_2C\equiv C-I$ |
| B. 857 | $OCH_2CH_3$ | $CH_2CH_3$ | $CH_2C\equiv C-I$ |
| B. 858 | $OCH_2CH_3$ | $CF_3$ | $CH_2C\equiv C-I$ |
| B. 859 | $OCH_2CH_3$ | Cl | $CH_2C\equiv C-I$ |
| B. 860 | $OCH_2CH_3$ | $OCH_3$ | $CH_2C\equiv C-I$ |
| B. 861 | CN | $CH_3$ | $CH_2C\equiv C-I$ |
| B. 862 | CN | $CH_2CH_3$ | $CH_2C\equiv C-I$ |
| B. 863 | CN | $CF_3$ | $CH_2C\equiv C-I$ |
| B. 864 | CN | Cl | $CH_2C\equiv C-I$ |
| B. 865 | CN | $OCH_3$ | $CH_2C\equiv C-I$ |
| B. 866 | H | $CH_3$ | $CH(CH_3)C\equiv CH$ |
| B. 867 | H | $CH_2CH_3$ | $CH(CH_3)C\equiv CH$ |
| B. 868 | H | $CF_3$ | $CH(CH_3)C\equiv CH$ |
| B. 869 | H | Cl | $CH(CH_3)C\equiv CH$ |
| B. 870 | H | $OCH_3$ | $CH(CH_3)C\equiv CH$ |
| B. 871 | $CH_2CH_3$ | $CH_3$ | $CH(CH_3)C\equiv CH$ |
| B. 872 | $CH_2CH_3$ | $CH_2CH_3$ | $CH(CH_3)C\equiv CH$ |
| B. 873 | $CH_2CH_3$ | $CF_3$ | $CH(CH_3)C\equiv CH$ |
| B. 874 | $CH_2CH_3$ | Cl | $CH(CH_3)C\equiv CH$ |
| B. 875 | $CH_2CH_3$ | $OCH_3$ | $CH(CH_3)C\equiv CH$ |
| B. 876 | $CHF_2$ | $CH_3$ | $CH(CH_3)C\equiv CH$ |
| B. 877 | $CHF_2$ | $CH_2CH_3$ | $CH(CH_3)C\equiv CH$ |
| B. 878 | $CHF_2$ | $CF_3$ | $CH(CH_3)C\equiv CH$ |
| B. 879 | $CHF_2$ | Cl | $CH(CH_3)C\equiv CH$ |
| B. 880 | $CHF_2$ | $OCH_3$ | $CH(CH_3)C\equiv CH$ |
| B. 881 | $CH_2F$ | $CH_3$ | $CH(CH_3)C\equiv CH$ |
| B. 882 | $CH_2F$ | $CH_2CH_3$ | $CH(CH_3)C\equiv CH$ |
| B. 883 | $CH_2F$ | $CF_3$ | $CH(CH_3)C\equiv CH$ |
| B. 884 | $CH_2F$ | Cl | $CH(CH_3)C\equiv CH$ |
| B. 885 | $CH_2F$ | $OCH_3$ | $CH(CH_3)C\equiv CH$ |
| B. 886 | $OCH_3$ | $CH_3$ | $CH(CH_3)C\equiv CH$ |
| B. 887 | $OCH_3$ | $CH_2CH_3$ | $CH(CH_3)C\equiv CH$ |
| B. 888 | $OCH_3$ | $CF_3$ | $CH(CH_3)C\equiv CH$ |
| B. 889 | $OCH_3$ | Cl | $CH(CH_3)C\equiv CH$ |
| B. 890 | $OCH_3$ | $OCH_3$ | $CH(CH_3)C\equiv CH$ |
| B. 891 | $OCH_{2CH3}$ | $CH_3$ | $CH(CH_3)C\equiv CH$ |
| B. 892 | $OCH_2CH_3$ | $CH_2CH_3$ | $CH(CH_3)C\equiv CH$ |
| B. 893 | $OCH_2CH_3$ | $CF_3$ | $CH(CH_3)C\equiv CH$ |
| B. 894 | $OCH_2CH_3$ | Cl | $CH(CH_3)C\equiv CH$ |
| B. 895 | $OCH_2CH_3$ | $OCH_3$ | $CH(CH_3)C\equiv CH$ |
| B. 896 | CN | $CH_3$ | $CH(CH_3)C\equiv CH$ |
| B. 897 | CN | $CH_2CH_3$ | $CH(CH_3)C\equiv CH$ |
| B. 898 | CN | $CF_3$ | $CH(CH_3)C\equiv CH$ |
| B. 899 | CN | Cl | $CH(CH_3)C\equiv CH$ |
| B. 900 | CN | $OCH_3$ | $CH(CH_3)C\equiv CH$ |
| B. 901 | H | $CH_3$ | $CH_2CH_2-O-CH_2CH_3$ |
| B. 902 | H | $CH_2CH_3$ | $CH_2CH_2-O-CH_2CH_3$ |
| B. 903 | H | $CF_3$ | $CH_2CH_2-O-CH_2CH_3$ |
| B. 904 | H | Cl | $CH_2CH_2-O-CH_2CH_3$ |
| B. 905 | H | $OCH_3$ | $CH_2CH_2-O-CH_2CH_3$ |
| B. 906 | $CH_2CH_3$ | $CH_3$ | $CH_2CH_2-O-CH_2CH_3$ |
| B. 907 | $CH_2CH_3$ | $CH_2CH_3$ | $CH_2CH_2-O-CH_2CH_3$ |
| B. 908 | $CH_2CH_3$ | $CF_3$ | $CH_2CH_2-O-CH_2CH_3$ |
| B. 909 | $CH_2CH_3$ | Cl | $CH_2CH_2-O-CH_2CH_3$ |
| B. 910 | $CH_2CH_3$ | $OCH_3$ | $CH_2CH_2-O-CH_2CH_3$ |
| B. 911 | $CHF_2$ | $CH_3$ | $CH_2CH_2-O-CH_2CH_3$ |
| B. 912 | $CHF_2$ | $CH_2CH_3$ | $CH_2CH_2-O-CH_2CH_3$ |
| B. 913 | $CHF_2$ | $CF_3$ | $CH_2CH_2-O-CH_2CH_3$ |
| B. 914 | $CHF_2$ | Cl | $CH_2CH_2-O-CH_2CH_3$ |
| B. 915 | $CHF_2$ | $OCH_3$ | $CH_2CH_2-O-CH_2CH_3$ |
| B. 916 | $CH_2F$ | $CH_3$ | $CH_2CH_2-O-CH_2CH_3$ |
| B. 917 | $CH_2F$ | $CH_2CH_3$ | $CH_2CH_2-O-CH_2CH_3$ |
| B. 918 | $CH_2F$ | $CF_3$ | $CH_2CH_2-O-CH_2CH_3$ |
| B. 919 | $CH_2F$ | Cl | $CH_2CH_2-O-CH_2CH_3$ |
| B. 920 | $CH_2F$ | $OCH_3$ | $CH_2CH_2-O-CH_2CH_3$ |
| B. 921 | $OCH_3$ | $CH_3$ | $CH_2CH_2-O-CH_2CH_3$ |
| B. 922 | $OCH_3$ | $CH_2CH_3$ | $CH_2CH_2-O-CH_2CH_3$ |
| B. 923 | $OCH_3$ | $CF_3$ | $CH_2CH_2-O-CH_2CH_3$ |
| B. 924 | $OCH_3$ | Cl | $CH_2CH_2-O-CH_2CH_3$ |
| B. 925 | $OCH_3$ | $OCH_3$ | $CH_2CH_2-O-CH_2CH_3$ |
| B. 926 | $OCH_2CH_3$ | $CH_3$ | $CH_2CH_2-O-CH_2CH_3$ |
| B. 927 | $OCH_2CH_3$ | $CH_2CH_3$ | $CH_2CH_2-O-CH_2CH_3$ |
| B. 928 | $OCH_2CH_3$ | $CF_3$ | $CH_2CH_2-O-CH_2CH_3$ |
| B. 929 | $OCH_2CH_3$ | Cl | $CH_2CH_2-O-CH_2CH_3$ |
| B. 930 | $OCH_2CH_3$ | $OCH_3$ | $CH_2CH_2-O-CH_2CH_3$ |
| B. 931 | CN | $CH_3$ | $CH_2CH_2-O-CH_2CH_3$ |
| B. 932 | CN | $CH_2CH_3$ | $CH_2CH_2-O-CH_2CH_3$ |
| B. 933 | CN | $CF_3$ | $CH_2CH_2-O-CH_2CH_3$ |
| B. 934 | CN | Cl | $CH_2CH_2-O-CH_2CH_3$ |
| B. 935 | CN | $OCH_3$ | $CH_2CH_2-O-CH_2CH_3$ |
| B. 936 | H | $CH_3$ | $CH_2-C_6H_5$ |
| B. 937 | H | $CH_2CH_3$ | $CH_2-C_6H_5$ |
| B. 938 | H | $CF_3$ | $CH_2-C_6H_5$ |
| B. 939 | H | Cl | $CH_2-C_6H_5$ |
| B. 940 | H | $OCH_3$ | $CH_2-C_6H_5$ |

TABLE B-continued

| No. | R₃ | R₅ | R₆ |
|---|---|---|---|
| B. 941 | CH₂CH₃ | CH₃ | CH₂—C₆H₅ |
| B. 942 | CH₂CH₃ | CH₂CH₃ | CH₂—C₆H₅ |
| B. 943 | CH₂CH₃ | CF₃ | CH₂—C₆H₅ |
| B. 944 | CH₂CH₃ | Cl | CH₂—C₆H₅ |
| B. 945 | CH₂CH₃ | OCH₃ | CH₂—C₆H₅ |
| B. 946 | CHF₂ | CH₃ | CH₂—C₆H₅ |
| B. 947 | CHF₂ | CH₂CH₃ | CH₂—C₆H₅ |
| B. 948 | CHF₂ | CF₃ | CH₂—C₆H₅ |
| B. 949 | CHF₂ | Cl | CH₂—C₆H₅ |
| B. 950 | CHF₂ | OCH₃ | CH₂—C₆H₅ |
| B. 951 | CH₂F | CH₃ | CH₂—C₆H₅ |
| B. 952 | CH₂F | CH₂CH₃ | CH₂—C₆H₅ |
| B. 953 | CH₂F | CF₃ | CH₂—C₆H₅ |
| B. 954 | CH₂F | Cl | CH₂—C₆H₅ |
| B. 955 | CH₂F | OCH₃ | CH₂—C₆H₅ |
| B. 956 | OCH₃ | CH₃ | CH₂—C₆H₅ |
| B. 957 | OCH₃ | CH₂CH₃ | CH₂—C₆H₅ |
| B. 958 | OCH₃ | CF₃ | CH₂—C₆H₅ |
| B. 959 | OCH₃ | Cl | CH₂—C₆H₅ |
| B. 960 | OCH₃ | OCH₃ | CH₂—C₆H₅ |
| B. 961 | OCH₂CH₃ | CH₃ | CH₂—C₆H₅ |
| B. 962 | OCH₂CH₃ | CH₂CH₃ | CH₂—C₆H₅ |
| B. 963 | OCH₂CH₃ | CF₃ | CH₂—C₆H₅ |
| B. 964 | OCH₂CH₃ | Cl | CH₂—C₆H₅ |
| B. 965 | OCH₂CH₃ | OCH₃ | CH₂—C₆H₅ |
| B. 966 | CN | CH₃ | CH₂—C₆H₅ |
| B. 967 | CN | CH₂CH₃ | CH₂—C₆H₅ |
| B. 968 | CN | CF₃ | CH₂—C₆H₅ |
| B. 969 | CN | Cl | CH₂—C₆H₅ |
| B. 970 | CN | OCH₃ | CH₂—C₆H₅ |
| B. 971 | H | CH₃ | cyclopropyl |
| B. 972 | H | CH₂CH₃ | cyclopropyl |
| B. 973 | H | CF₃ | cyclopropyl |
| B. 974 | H | Cl | cyclopropyl |
| B. 975 | H | OCH₃ | cyclopropyl |
| B. 976 | CH₂CH₃ | CH₃ | cyclopropyl |
| B. 977 | CH₂CH₃ | CH₂CH₃ | cyclopropyl |
| B. 978 | CH₂CH₃ | CF₃ | cyclopropyl |
| B. 979 | CH₂CH₃ | Cl | cyclopropyl |
| B. 980 | CH₂CH₃ | OCH₃ | cyclopropyl |
| B. 981 | CHF₂ | CH₃ | cyclopropyl |
| B. 982 | CHF₂ | CH₂CH₃ | cyclopropyl |
| B. 983 | CHF₂ | CF₃ | cyclopropyl |
| B. 984 | CHF₂ | Cl | cyclopropyl |
| B. 985 | CHF₂ | OCH₃ | cyclopropyl |
| B. 986 | CH₂F | CH₃ | cyclopropyl |
| B. 987 | CH₂F | CH₂CH₃ | cyclopropyl |
| B. 988 | CH₂F | CF₃ | cyclopropyl |
| B. 989 | CH₂F | Cl | cyclopropyl |
| B. 990 | CH₂F | OCH₃ | cyclopropyl |
| B. 991 | OCH₃ | CH₃ | cyclopropyl |
| B. 992 | OCH₃ | CH₂CH₃ | cyclopropyl |
| B. 993 | OCH₃ | CF₃ | cyclopropyl |
| B. 994 | OCH₃ | Cl | cyclopropyl |
| B. 995 | OCH₃ | OCH₃ | cyclopropyl |
| B. 996 | OCH₂CH₃ | CH₃ | cyclopropyl |
| B. 997 | OCH₂CH₃ | CH₂CH₃ | cyclopropyl |
| B. 998 | OCH₂CH₃ | CF₃ | cyclopropyl |
| B. 999 | OCH₂CH₃ | Cl | cyclopropyl |
| B. 1000 | OCH₂CH₃ | OCH₃ | cyclopropyl |
| B. 1001 | CN | CH₃ | cyclopropyl |
| B. 1002 | CN | CH₂CH₃ | cyclopropyl |
| B. 1003 | CN | CF₃ | cyclopropyl |
| B. 1004 | CN | Cl | cyclopropyl |
| B. 1005 | CN | OCH₃ | cyclopropyl |
| B. 1006 | H | CH₃ | CH₂-(2,2-Cl₂-cyclopropyl) |
| B. 1007 | H | CH₂CH₃ | CH₂-(2,2-Cl₂-cyclopropyl) |
| B. 1008 | H | CF₃ | CH₂-(2,2-Cl₂-cyclopropyl) |
| B. 1009 | H | Cl | CH₂-(2,2-Cl₂-cyclopropyl) |
| B. 1010 | H | OCH₃ | CH₂-(2,2-Cl₂-cyclopropyl) |
| B. 1011 | CH₂CH₃ | CH₃ | CH₂-(2,2-Cl₂-cyclopropyl) |
| B. 1012 | CH₂CH₃ | CH₂CH₃ | CH₂-(2,2-Cl₂-cyclopropyl) |
| B. 1013 | CH₂CH₃ | CF₃ | CH₂-(2,2-Cl₂-cyclopropyl) |
| B. 1014 | CH₂CH₃ | Cl | CH₂-(2,2-Cl₂-cyclopropyl) |
| B. 1015 | CH₂CH₃ | OCH₃ | CH₂-(2,2-Cl₂-cyclopropyl) |
| B. 1016 | CHF₂ | CH₃ | CH₂-(2,2-Cl₂-cyclopropyl) |
| B. 1017 | CHF₂ | CH₂CH₃ | CH₂-(2,2-Cl₂-cyclopropyl) |
| B. 1018 | CHF₂ | CF₃ | CH₂-(2,2-Cl₂-cyclopropyl) |
| B. 1019 | CHF₂ | Cl | CH₂-(2,2-Cl₂-cyclopropyl) |
| B. 1020 | CHF₂ | OCH₃ | CH₂-(2,2-Cl₂-cyclopropyl) |
| B. 1021 | CH₂F | CH₃ | CH₂-(2,2-Cl₂-cyclopropyl) |
| B. 1022 | CH₂F | CH₂CH₃ | CH₂-(2,2-Cl₂-cyclopropyl) |
| B. 1023 | CH₂F | CF₃ | CH₂-(2,2-Cl₂-cyclopropyl) |
| B. 1024 | CH₂F | Cl | CH₂-(2,2-Cl₂-cyclopropyl) |
| B. 1025 | CH₂F | OCH₃ | CH₂-(2,2-Cl₂-cyclopropyl) |
| B. 1026 | OCH₃ | CH₃ | CH₂-(2,2-Cl₂-cyclopropyl) |
| B. 1027 | OCH₃ | CH₂CH₃ | CH₂-(2,2-Cl₂-cyclopropyl) |
| B. 1028 | OCH₃ | CF₃ | CH₂-(2,2-Cl₂-cyclopropyl) |
| B. 1029 | OCH₃ | Cl | CH₂-(2,2-Cl₂-cyclopropyl) |
| B. 1030 | OCH₃ | OCH₃ | CH₂-(2,2-Cl₂-cyclopropyl) |
| B. 1031 | OCH₂CH₃ | CH₃ | CH₂-(2,2-Cl₂-cyclopropyl) |
| B. 1032 | OCH₂CH₃ | CH₂CH₃ | CH₂-(2,2-Cl₂-cyclopropyl) |
| B. 1033 | OCH₂CH₃ | CF₃ | CH₂-(2,2-Cl₂-cyclopropyl) |
| B. 1034 | OCH₂CH₃ | Cl | CH₂-(2,2-Cl₂-cyclopropyl) |
| B. 1035 | OCH₂CH₃ | OCH₃ | CH₂-(2,2-Cl₂-cyclopropyl) |
| B. 1036 | CN | CH₃ | CH₂-(2,2-Cl₂-cyclopropyl) |
| B. 1037 | CN | CH₂CH₃ | CH₂-(2,2-Cl₂-cyclopropyl) |
| B. 1038 | CN | CF₃ | CH₂-(2,2-Cl₂-cyclopropyl) |
| B. 1039 | CN | Cl | CH₂-(2,2-Cl₂-cyclopropyl) |
| B. 1040 | CN | OCH₃ | CH₂-(2,2-Cl₂-cyclopropyl) |
| B. 1041 | Cl | H | CH₂C≡C—Cl |
| B. 1042 | Cl | CH₃ | CH₂C≡C—Cl |
| B. 1043 | Cl | CH₂CH₃ | CH₂C≡C—Cl |
| B. 1044 | Cl | CF₃ | CH₂C≡C—Cl |
| B. 1045 | Cl | CHF₂ | CH₂C≡C—Cl |
| B. 1046 | Cl | CH₂F | CH₂C≡C—Cl |
| B. 1047 | Cl | Cl | CH₂C≡C—Cl |
| B. 1048 | Cl | OCH₃ | CH₂C≡C—Cl |
| B. 1049 | Cl | OCH₂CH₃ | CH₂C≡C—Cl |
| B. 1050 | Cl | CN | CH₂C≡C—Cl |
| B. 1051 | CH₃ | H | CH₂C≡C—Cl |
| B. 1052 | CH₃ | CH₃ | CH₂C≡C—Cl |
| B. 1053 | CH₃ | CH₂CH3 | CH₂C≡C—Cl |
| B. 1054 | CH₃ | CF₃ | CH₂C≡C—Cl |
| B. 1055 | CH₃ | CHF₂ | CH₂C≡C—Cl |
| B. 1056 | CH₃ | CH₂F | CH₂C≡C—Cl |
| B. 1057 | CH₃ | Cl | CH₂C≡C—Cl |
| B. 1058 | CH₃ | OCH₃ | CH₂C≡C—Cl |
| B. 1059 | CH₃ | OCH₂CH₃ | CH₂C≡C—Cl |
| B. 1060 | CH₃ | CN | CH₂C≡C—Cl |
| B. 1061 | CF₃ | H | CH₂C≡C—Cl |
| B. 1062 | CF₃ | CH₃ | CH₂C≡C—Cl |
| B. 1063 | CF₃ | CH₂CH3 | CH₂C≡C—Cl |
| B. 1064 | CF₃ | CF₃ | CH₂C≡C—Cl |
| B. 1065 | CF₃ | CHF₂ | CH₂C≡C—Cl |
| B. 1066 | CF₃ | CH₂F | CH₂C≡C—Cl |
| B. 1067 | CF₃ | Cl | CH₂C≡C—Cl |
| B. 1068 | CF₃ | OCH₃ | CH₂C≡C—Cl |
| B. 1069 | CF₃ | OCH₂CH₃ | CH₂C≡C—Cl |
| B. 1070 | CF₃ | CN | CH₂C≡C—Cl |
| B. 1071 | H | CH₃ | CH₂C≡C—Cl |
| B. 1072 | H | CH₂CH₃ | CH₂C≡C—Cl |
| B. 1073 | H | CF₃ | CH₂C≡C—Cl |
| B. 1074 | H | Cl | CH₂C≡C—Cl |
| B. 1075 | H | OCH₃ | CH₂C≡C—Cl |
| B. 1076 | CH₂CH₃ | CH₃ | CH₂C≡C—Cl |
| B. 1077 | CH₂CH₃ | CH₂CH₃ | CH₂C≡C—Cl |
| B. 1078 | CH₂CH₃ | CF₃ | CH₂C≡C—Cl |
| B. 1079 | CH₂CH₃ | Cl | CH₂C≡C—Cl |
| B. 1080 | CH₂CH₃ | OCH₃ | CH₂C≡C—Cl |
| B. 1081 | CHF₂ | CH₃ | CH₂C≡C—Cl |
| B. 1082 | CHF₂ | CH₂CH₃ | CH₂C≡C—Cl |
| B. 1083 | CHF₂ | CF₃ | CH₂C≡C—Cl |
| B. 1084 | CHF₂ | Cl | CH₂C≡C—Cl |
| B. 1085 | CHF₂ | OCH₃ | CH₂C≡C—Cl |
| B. 1086 | CH₂F | CH₃ | CH₂C≡C—Cl |
| B. 1087 | CH₂F | CH₂CH₃ | CH₂C≡C—Cl |
| B. 1088 | CH₂F | CF₃ | CH₂C≡C—Cl |
| B. 1089 | CH₂F | Cl | CH₂C≡C—Cl |
| B. 1090 | CH₂F | OCH₃ | CH₂C≡C—Cl |
| B. 1091 | OCH₃ | CH₃ | CH₂C≡C—Cl |
| B. 1092 | OCH₃ | CH₂CH₃ | CH₂C≡C—Cl |
| B. 1093 | OCH₃ | CF₃ | CH₂C≡C—Cl |
| B. 1094 | OCH₃ | Cl | CH₂C≡C—Cl |

TABLE B-continued

| No. | R₃ | R₅ | R₆ |
|---|---|---|---|
| B. 1095 | OCH₃ | OCH₃ | CH₂C≡C—Cl |
| B. 1096 | OCH₂CH₃ | CH₃ | CH₂C≡C—Cl |
| B. 1097 | OCH₂CH₃ | CH₂CH₃ | CH₂C≡C—Cl |
| B. 1098 | OCH₂CH₃ | CF₃ | CH₂C≡C—Cl |
| B. 1099 | OCH₂CH₃ | Cl | CH₂C≡C—Cl |
| B. 1100 | OCH₂CH₃ | OCH₃ | CH₂C≡C—Cl |
| B. 1101 | CN | CH₃ | CH₂C≡C—Cl |
| B. 1102 | CN | CH₂CH₃ | CH₂C≡C—Cl |
| B. 1103 | CN | CF₃ | CH₂C≡C—Cl |
| B. 1104 | CN | Cl | CH₂C≡C—Cl |
| B. 1105 | CN | OCH₃ | CH₂C≡C—Cl |
| B. 1106 | Cl | H | CH₂C≡C—CH₂CH₃ |
| B. 1107 | Cl | CH₃ | CH₂C≡C—CH₂CH₃ |
| B. 1108 | Cl | CH₂CH₃ | CH₂C≡C—CH₂CH₃ |
| B. 1109 | Cl | CF₃ | CH₂C≡C—CH₂CH₃ |
| B. 1110 | Cl | CHF₂ | CH₂C≡C—CH₂CH₃ |
| B. 1111 | Cl | CH₂F | CH₂C≡C—CH₂CH₃ |
| B. 1112 | Cl | Cl | CH₂C≡C—CH₂CH₃ |
| B. 1113 | Cl | OCH₃ | CH₂C≡C—CH₂CH₃ |
| B. 1114 | Cl | OCH₂CH₃ | CH₂C≡C—CH₂CH₃ |
| B. 1115 | Cl | CN | CH₂C≡C—CH₂CH₃ |
| B. 1116 | CH₃ | H | CH₂C≡C—CH₂CH₃ |
| B. 1117 | CH₃ | CH₃ | CH₂C≡C—CH₂CH₃ |
| B. 1118 | CH₃ | CH₂CH₃ | CH₂C≡C—CH₂CH₃ |
| B. 1119 | CH₃ | CF₃ | CH₂C≡C—CH₂CH₃ |
| B. 1120 | CH₃ | CHF₂ | CH₂C≡C—CH₂CH₃ |
| B. 1121 | CH₃ | CH₂F | CH₂C≡C—CH₂CH₃ |
| B. 1122 | CH₃ | Cl | CH₂C≡C—CH₂CH₃ |
| B. 1123 | CH₃ | OCH₃ | CH₂C≡C—CH₂CH₃ |
| B. 1124 | CH₃ | OCH₂CH₃ | CH₂C≡C—CH₂CH₃ |
| B. 1125 | CH₃ | CN | CH₂C≡C—CH₂CH₃ |
| B. 1126 | CF₃ | H | CH₂C≡C—CH₂CH₃ |
| B. 1127 | CF₃ | CH₃ | CH₂C≡C—CH₂CH₃ |
| B. 1128 | CF₃ | CH₂CH₃ | CH₂C≡C—CH₂CH₃ |
| B. 1129 | CF₃ | CF₃ | CH₂C≡C—CH₂CH₃ |
| B. 1130 | CF₃ | CHF₂ | CH₂C≡C—CH₂CH₃ |
| B. 1131 | CF₃ | CH₂F | CH₂C≡C—CH₂CH₃ |
| B. 1132 | CF₃ | Cl | CH₂C≡C—CH₂CH₃ |
| B. 1133 | CF₃ | OCH₃ | CH₂C≡C—CH₂CH₃ |
| B. 1134 | CF₃ | OCH₂CH₃ | CH₂C≡C—CH₂CH₃ |
| B. 1135 | CF₃ | CN | CH₂C≡C—CH₂CH₃ |
| B. 1136 | H | CH₃ | CH₂C≡C—CH₂CH₃ |
| B. 1137 | H | CH₂CH₃ | CH₂C≡C—CH₂CH₃ |
| B. 1138 | H | CF₃ | CH₂C≡C—CH₂CH₃ |
| B. 1139 | H | Cl | CH₂C≡C—CH₂CH₃ |
| B. 1140 | H | OCH₃ | CH₂C≡C—CH₂CH₃ |
| B. 1141 | CH₂F | CH₃ | CH₂C≡C—CH₂CH₃ |
| B. 1142 | CH₂F | CH₂CH₃ | CH₂C≡C—CH₂CH₃ |
| B. 1143 | CH₂F | CF₃ | CH₂C≡C—CH₂CH₃ |
| B. 1144 | CH₂F | Cl | CH₂C≡C—CH₂CH₃ |
| B. 1145 | CH₂F | OCH₃ | CH₂C≡C—CH₂CH₃ |
| B. 1146 | CHF₂ | CH₃ | CH₂C≡C—CH₂CH₃ |
| B. 1147 | CHF₂ | CH₂CH₃ | CH₂C≡C—CH₂CH₃ |
| B. 1148 | CHF₂ | CF₃ | CH₂C≡C—CH₂CH₃ |
| B. 1149 | CHF₂ | Cl | CH₂C≡C—CH₂CH₃ |
| B. 1150 | CHF₂ | OCH₃ | CH₂C≡C—CH₂CH₃ |
| B. 1151 | CH2_F | CH₃ | CH₂C≡C—CH₂CH₃ |
| B. 1152 | CH2_F | CH₂CH₃ | CH₂C≡C—CH₂CH₃ |
| B. 1153 | CH2_F | CF₃ | CH₂C≡C—CH₂CH₃ |
| B. 1154 | CH2_F | Cl | CH₂C≡C—CH₂CH₃ |
| B. 1155 | CH2_F | OCH₃ | CH₂C≡C—CH₂CH₃ |
| B. 1156 | OCH₃ | CH₃ | CH₂C≡C—CH₂CH₃ |
| B. 1157 | OCH₃ | CH₂CH₃ | CH₂C≡C—CH₂CH₃ |
| B. 1158 | OCH₃ | CF₃ | CH₂C≡C—CH₂CH₃ |
| B. 1159 | OCH₃ | Cl | CH₂C≡C—CH₂CH₃ |
| B. 1160 | OCH₃ | OCH₃ | CH₂C≡C—CH₂CH₃ |
| B. 1161 | OCH₂CH₃ | CH₃ | CH₂C≡C—CH₂CH₃ |
| B. 1162 | OCH₂CH₃ | CH₂CH₃ | CH₂C≡C—CH₂CH₃ |
| B. 1163 | OCH₂CH₃ | CF₃ | CH₂C≡C—CH₂CH₃ |
| B. 1164 | OCH₂CH₃ | Cl | CH₂C≡C—CH₂CH₃ |
| B. 1165 | OCH₂CH₃ | OCH₃ | CH₂C≡C—CH₂CH₃ |
| B. 1166 | CN | CH₃ | CH₂C≡C—CH₂CH₃ |
| B. 1167 | CN | CH₂CH₃ | CH₂C≡C—CH₂CH₃ |
| B. 1168 | CN | CF₃ | CH₂C≡C—CH₂CH₃ |
| B. 1169 | CN | Cl | CH₂C≡C—CH₂CH₃ |
| B. 1170 | CN | OCH₃ | CH₂C≡C—CH₂CH₃ |
| B. 1171 | Cl | H | CH₂C≡C—CF₃ |
| B. 1172 | Cl | CH₃ | CH₂C≡C—CF₃ |
| B. 1173 | Cl | CH₂CH₃ | CH₂C≡C—CF₃ |
| B. 1174 | Cl | CF₃ | CH₂C≡C—CF₃ |
| B. 1175 | Cl | CHF₂ | CH₂C≡C—CF₃ |
| B. 1176 | Cl | CH₂F | CH₂C≡C—CF₃ |
| B. 1177 | Cl | Cl | CH₂C≡C—CF₃ |
| B. 1178 | Cl | OCH₃ | CH₂C≡C—CF₃ |
| B. 1179 | Cl | OCH₂CH₃ | CH₂C≡C—CF₃ |
| B. 1180 | Cl | CN | CH₂C≡C—CF₃ |
| B. 1181 | CH₃ | H | CH₂C≡C—CF₃ |
| B. 1182 | CH₃ | CH₃ | CH₂C≡C—CF₃ |
| B. 1183 | CH₃ | CH₂CH₃ | CH₂C≡C—CF₃ |
| B. 1184 | CH₃ | CF₃ | CH₂C≡C—CF₃ |
| B. 1185 | CH₃ | CHF₂ | CH₂C≡C—CF₃ |
| B. 1186 | CH₃ | CH₂F | CH₂C≡C—CF₃ |
| B. 1187 | CH₃ | Cl | CH₂C≡C—CF₃ |
| B. 1188 | CH₃ | OCH₃ | CH₂C≡C—CF₃ |
| B. 1189 | CH₃ | OCH₂CH₃ | CH₂C≡C—CF₃ |
| B. 1190 | CH₃ | CN | CH₂C≡C—CF₃ |
| B. 1191 | CF₃ | H | CH₂C≡C—CF₃ |
| B. 1192 | CF₃ | CH3 | CH₂C≡C—CF₃ |
| B. 1193 | CF₃ | CH₂CH₃ | CH₂C≡C—CF₃ |
| B. 1194 | CF₃ | CF₃ | CH₂C≡C—CF₃ |
| B. 1195 | CF₃ | CHF₂ | CH₂C≡C—CF₃ |
| B. 1196 | CF₃ | CH₂F | CH₂C≡C—CF₃ |
| B. 1197 | CF₃ | Cl | CH₂C≡C—CF₃ |
| B. 1198 | CF₃ | OCH₃ | CH₂C≡C—CF₃ |
| B. 1199 | CF₃ | OCH₂CH₃ | CH₂C≡C—CF₃ |
| B. 1200 | CF₃ | CN | CH₂C≡C—CF₃ |
| B. 1201 | H | CH₃ | CH₂C≡C—CF₃ |
| B. 1202 | H | CH₂CH₃ | CH₂C≡C—CF₃ |
| B. 1203 | H | CF₃ | CH₂C≡C—CF₃ |
| B. 1204 | H | Cl | CH₂C≡C—CF₃ |
| B. 1205 | H | OCH₃ | CH₂C≡C—CF₃ |
| B. 1206 | CH₂CH₃ | CH₃ | CH₂C≡C—CF₃ |
| B. 1207 | CH₂CH₃ | CH₂CH₃ | CH₂C≡C—CF₃ |
| B. 1208 | CH₂CH₃ | CF₃ | CH₂C≡C—CF₃ |
| B. 1209 | CH₂CH₃ | Cl | CH₂C≡C—CF₃ |
| B. 1210 | CH₂CH₃ | OCH₃ | CH₂C≡C—CF₃ |
| B. 1211 | CHF₂ | CH₃ | CH₂C≡C—CF₃ |
| B. 1212 | CHF₂ | CH₂CH₃ | CH₂C≡C—CF₃ |
| B. 1213 | CHF₂ | CF3 | CH₂C≡C—CF₃ |
| B. 1214 | CHF₂ | Cl | CH₂C≡C—CF₃ |
| B. 1215 | CHF₂ | OCH₃ | CH₂C≡C—CF₃ |
| B. 1216 | CH₂F | CH₃ | CH₂C≡C—CF₃ |
| B. 1217 | CH₂F | CH₂CH₃ | CH₂C≡C—CF₃ |
| B. 1218 | CH₂F | CF₃ | CH₂C≡C—CF₃ |
| B. 1219 | CH₂F | Cl | CH₂C≡C—CF₃ |
| B. 1220 | CH₂F | OCH₃ | CH₂C≡C—CF₃ |
| B. 1221 | OCH₃ | CH₃ | CH₂C≡C—CF₃ |
| B. 1222 | OCH₃ | CH₂CH₃ | CH₂C≡C—CF₃ |
| B. 1223 | OCH₃ | CF₃ | CH₂C≡C—CF₃ |
| B. 1224 | OCH₃ | Cl | CH₂C≡C—CF₃ |
| B. 1225 | OCH₃ | OCH₃ | CH₂C≡C—CF₃ |
| B. 1226 | OCH₂CH₃ | CH₃ | CH₂C≡C—CF₃ |
| B. 1227 | OCH₂CH₃ | CH₂CH₃ | CH₂C≡C—CF₃ |
| B. 1228 | OCH₂CH₃ | CF₃ | CH₂C≡C—CF₃ |
| B. 1229 | OCH₂CH₃ | Cl | CH₂C≡C—CF₃ |
| B. 1230 | OCH₂CH₃ | OCH₃ | CH₂C≡C—CF₃ |
| B. 1231 | CN | CH₃ | CH₂C≡C—CF₃ |
| B. 1232 | CN | CH₂CH₃ | CH₂C≡C—CF₃ |
| B. 1233 | CN | CF₃ | CH₂C≡C—CF₃ |
| B. 1234 | CN | Cl | CH₂C≡C—CF₃ |
| B. 1235 | CN | OCH₃ | CH₂C≡C—CF₃ |
| B. 1236 | Cl | H | CH₂C≡C—C(CH₃)₃ |
| B. 1237 | Cl | CH₃ | CH₂C≡C—C(CH₃)₃ |
| B. 1238 | Cl | CH₂CH₃ | CH₂C≡C—C(CH₃)₃ |
| B. 1239 | Cl | CF₃ | CH₂C≡C—C(CH₃)₃ |
| B. 1240 | Cl | CHF₂ | CH₂C≡C—C(CH₃)₃ |
| B. 1241 | Cl | CH₂F | CH₂C≡C—C(CH₃)₃ |
| B. 1242 | Cl | Cl | CH₂C≡C—C(CH₃)₃ |
| B. 1243 | Cl | OCH₃ | CH₂C≡C—C(CH₃)₃ |
| B. 1244 | Cl | OCH₂CH₃ | CH₂C≡C—C(CH₃)₃ |
| B. 1245 | Cl | CN | CH₂C≡C—C(CH₃)₃ |
| B. 1246 | CH₃ | H | CH₂C≡C—C(CH₃)₃ |
| B. 1247 | CH₃ | CH₃ | CH₂C≡C—C(CH₃)₃ |
| B. 1248 | CH₃ | CH₂CH₃ | CH₂C≡C—C(CH₃)₃ |

TABLE B-continued

| No. | R₃ | R₅ | R₆ |
|---|---|---|---|
| B. 1249 | CH₃ | CF₃ | CH₂C≡C—C(CH₃)₃ |
| B. 1250 | CH₃ | CHF₂ | CH₂C≡C—C(CH₃)₃ |
| B. 1251 | CH₃ | CH₂F | CH₂C≡C—C(CH₃)₃ |
| B. 1252 | CH₃ | Cl | CH₂C≡C—C(CH₃)₃ |
| B. 1253 | CH₃ | OCH₃ | CH₂C≡C—C(CH₃)₃ |
| B. 1254 | CH₃ | OCH₂CH₃ | CH₂C≡C—C(CH₃)₃ |
| B. 1255 | CH₃ | CN | CH₂C≡C—C(CH₃)₃ |
| B. 1256 | CF₃ | H | CH₂C≡C—C(CH₃)₃ |
| B. 1257 | CF₃ | CH₃ | CH₂C≡C—C(CH₃)₃ |
| B. 1258 | CF₃ | CH₂CH₃ | CH₂C≡C—C(CH₃)₃ |
| B. 1259 | CF₃ | CF₃ | CH₂C≡C—C(CH₃)₃ |
| B. 1260 | CF₃ | CHF₂ | CH₂C≡C—C(CH₃)₃ |
| B. 1261 | CF₃ | CH₂F | CH₂C≡C—C(CH₃)₃ |
| B. 1262 | CF₃ | Cl | CH₂C≡C—C(CH₃)₃ |
| B. 1263 | CF₃ | OCH₃ | CH₂C≡C—C(CH₃)₃ |
| B. 1264 | CF₃ | OCH₂CH₃ | CH₂C≡C—C(CH₃)₃ |
| B. 1265 | CF₃ | CN | CH₂C≡C—C(CH₃)₃ |
| B. 1266 | H | CH₃ | CH₂C≡C—C(CH₃)₃ |
| B. 1267 | H | CH₂CH₃ | CH₂C≡C—C(CH₃)₃ |
| B. 1268 | H | CF₃ | CH₂C≡C—C(CH₃)₃ |
| B. 1269 | H | Cl | CH₂C≡C—C(CH₃)₃ |
| B. 1270 | H | OCH₃ | CH₂C≡C—C(CH₃)₃ |
| B. 1271 | CH₂CH₃ | CH₃ | CH₂C≡C—C(CH₃)₃ |
| B. 1272 | CH₂CH₃ | CH₂CH₃ | CH₂C≡C—C(CH₃)₃ |
| B. 1273 | CH₂CH₃ | CF₃ | CH₂C≡C—C(CH₃)₃ |
| B. 1274 | CH₂CH₃ | Cl | CH₂C≡C—C(CH₃)₃ |
| B. 1275 | CH₂CH₃ | OCH₃ | CH₂C≡C—C(CH₃)₃ |
| B. 1276 | CHF₂ | CH₃ | CH₂C≡C—C(CH₃)₃ |
| B. 1277 | CHF₂ | CH₂CH₃ | CH₂C≡C—C(CH₃)₃ |
| B. 1278 | CHF₂ | CF₃ | CH₂C≡C—C(CH₃)₃ |
| B. 1279 | CHF₂ | Cl | CH₂C≡C—C(CH₃)₃ |
| B. 1280 | CHF₂ | OCH₃ | CH₂C≡C—C(CH₃)₃ |
| B. 1281 | CH₂F | CH₃ | CH₂C≡C—C(CH₃)₃ |
| B. 1282 | CH₂F | CH₂CH₃ | CH₂C≡C—C(CH₃)₃ |
| B. 1283 | CH₂F | CF₃ | CH₂C≡C—C(CH₃)₃ |
| B. 1284 | CH₂F | Cl | CH₂C≡C—C(CH₃)₃ |
| B. 1285 | CH₂F | OCH₃ | CH₂C≡C—C(CH₃)₃ |
| B. 1286 | OCH₃ | CH₃ | CH₂C≡C—C(CH₃)₃ |
| B. 1287 | OCH₃ | CH₂CH₃ | CH₂C≡C—C(CH₃)₃ |
| B. 1288 | OCH₃ | CF₃ | CH₂C≡C—C(CH₃)₃ |
| B. 1289 | OCH₃ | Cl | CH₂C≡C—C(CH₃)₃ |
| B. 1290 | OCH₃ | OCH₃ | CH₂C≡C—C(CH₃)₃ |
| B. 1291 | OCH₂CH₃ | CH₃ | CH₂C≡C—C(CH₃)₃ |
| B. 1292 | OCH₂CH₃ | CH₂CH₃ | CH₂C≡C—C(CH₃)₃ |
| B. 1293 | OCH₂CH₃ | CF₃ | CH₂C≡C—C(CH₃)₃ |
| B. 1294 | OCH₂CH₃ | Cl | CH₂C≡C—C(CH₃)₃ |
| B. 1295 | OCH₂CH₃ | OCH₃ | CH₂C≡C—C(CH₃)₃ |
| B. 1296 | CN | CH₃ | CH₂C≡C—C(CH₃)₃ |
| B. 1297 | CN | CH₂CH₃ | CH₂C≡C—C(CH₃)₃ |
| B. 1298 | CN | CF₃ | CH₂C≡C—C(CH₃)₃ |
| B. 1299 | CN | Cl | CH₂C≡C—C(CH₃)₃ |
| B. 1300 | CN | OCH₃ | CH₂C≡C—C(CH₃)₃ |
| B. 1301 | Cl | H | CH₂C≡C—C₆H₅ |
| B. 1302 | Cl | CH₃ | CH₂C≡C—C₆H₅ |
| B. 1303 | Cl | CH₂CH₃ | CH₂C≡C—C₆H₅ |
| B. 1304 | Cl | CF₃ | CH₂C≡C—C₆H₅ |
| B. 1305 | Cl | CHF₂ | CH₂C≡C—C₆H₅ |
| B. 1306 | Cl | CH₂F | CH₂C≡C—C₆H₅ |
| B. 1307 | Cl | Cl | CH₂C≡C—C₆H₅ |
| B. 1308 | Cl | OCH₃ | CH₂C≡C—C₆H₅ |
| B. 1309 | Cl | OCH₂CH₃ | CH₂C≡C—C₆H₅ |
| B. 1310 | Cl | CN | CH₂C≡C—C₆H₅ |
| B. 1311 | CH₃ | H | CH₂C≡C—C₆H₅ |
| B. 1312 | CH₃ | CH₃ | CH₂C≡C—C₆H₅ |
| B. 1313 | CH₃ | CH₂CH₃ | CH₂C≡C—C₆H₅ |
| B. 1314 | CH₃ | CF₃ | CH₂C≡C—C₆H₅ |
| B. 1315 | CH₃ | CHF₂ | CH₂C≡C—C₆H₅ |
| B. 1316 | CH₃ | CH₂F | CH₂C≡C—C₆H₅ |
| B. 1317 | CH₃ | Cl | CH₂C≡C—C₆H₅ |
| B. 1318 | CH₃ | OCH₃ | CH₂C≡C—C₆H₅ |
| B. 1319 | CH₃ | OCH₂CH₃ | CH₂C≡C—C₆H₅ |
| B. 1320 | CH₃ | CN | CH₂C≡C—C₆H₅ |
| B. 1321 | CF₃ | H | CH₂C≡C—C₆H₅ |
| B. 1322 | CF₃ | CH₃ | CH₂C≡C—C₆H₅ |
| B. 1323 | CF₃ | CH₂CH₃ | CH₂C≡C—C₆H₅ |
| B. 1324 | CF₃ | CF₃ | CH₂C≡C—C₆H₅ |
| B. 1325 | CF₃ | CHF₂ | CH₂C≡C—C₆H₅ |
| B. 1326 | CF₃ | CH₂F | CH₂C≡C—C₆H₅ |
| B. 1327 | CF₃ | Cl | CH₂C≡C—C₆H₅ |
| B. 1328 | CF₃ | OCH₃ | CH₂C≡C—C₆H₅ |
| B. 1329 | CF₃ | OCH₂CH₃ | CH₂C≡C—C₆H₅ |
| B. 1330 | CF₃ | CN | CH₂C≡C—C₆H₅ |
| B. 1331 | H | CH₃ | CH₂C≡C—C₆H₅ |
| B. 1332 | H | CH₂CH₃ | CH₂C≡C—C₆H₅ |
| B. 1333 | H | CF₃ | CH₂C≡C—C₆H₅ |
| B. 1334 | H | Cl | CH₂C≡C—C₆H₅ |
| B. 1335 | H | OCH₃ | CH₂C≡C—C₆H₅ |
| B. 1336 | CH₂CH₃ | CH₃ | CH₂C≡C—C₆H₅ |
| B. 1337 | CH₂CH₃ | CH₂CH₃ | CH₂C≡C—C₆H₅ |
| B. 1338 | CH₂CH₃ | CF₃ | CH₂C≡C—C₆H₅ |
| B. 1339 | CH₂CH₃ | Cl | CH₂C≡C—C₆H₅ |
| B. 1340 | CH₂CH₃ | OCH₃ | CH₂C≡C—C₆H₅ |
| B. 1341 | CHF₂ | CH₃ | CH₂C≡C—C₆H₅ |
| B. 1342 | CHF₂ | CH₂CH₃ | CH₂C≡C—C₆H₅ |
| B. 1343 | CHF₂ | CF₃ | CH₂C≡C—C₆H₅ |
| B. 1344 | CHF₂ | Cl | CH₂C≡C—C₆H₅ |
| B. 1345 | CHF₂ | OCH₃ | CH₂C≡C—C₆H₅ |
| B. 1346 | CH₂F | CH₃ | CH₂C≡C—C₆H₅ |
| B. 1347 | CH₂F | CH₂CH₃ | CH₂C≡C—C₆H₅ |
| B. 1348 | CH₂F | CF₃ | CH₂C≡C—C₆H₅ |
| B. 1349 | CH₂F | Cl | CH₂C≡C—C₆H₅ |
| B. 1350 | CH₂F | OCH₃ | CH₂C≡C—C₆H₅ |
| B. 1351 | OCH₃ | CH₃ | CH₂C≡C—C₆H₅ |
| B. 1352 | OCH₃ | CH₂CH₃ | CH₂C≡C—C₆H₅ |
| B. 1353 | OCH₃ | CF₃ | CH₂C≡C—C₆H₅ |
| B. 1354 | OCH₃ | Cl | CH₂C≡C—C₆H₅ |
| B. 1355 | OCH₃ | OCH₃ | CH₂C≡C—C₆H₅ |
| B. 1356 | OCH₂CH₃ | CH₃ | CH₂C≡C—C₆H₅ |
| B. 1357 | OCH₂CH₃ | CH₂CH₃ | CH₂C≡C—C₆H₅ |
| B. 1358 | OCH₂CH₃ | CF₃ | CH₂C≡C—C₆H₅ |
| B. 1359 | OCH₂CH₃ | Cl | CH₂C≡C—C₆H₅ |
| B. 1360 | OCH₂CH₃ | OCH₃ | CH₂C≡C—C₆H₅ |
| B. 1361 | CN | CH₃ | CH₂C≡C—C₆H₅ |
| B. 1362 | CN | CH₂CH₃ | CH₂C≡C—C₆H₅ |
| B. 1363 | CN | CF₃ | CH₂C≡C—C₆H₅ |
| B. 1364 | CN | Cl | CH₂C≡C—C₆H₅ |
| B. 1365 | CN | OCH₃ | CH₂C≡C—C₆H₅ |
| B. 1366 | Cl | H | CH₂C≡C-(2-Cl-C₆H₄) |
| B. 1367 | Cl | CH₃ | CH₂C≡C-(2-Cl-C₆H₄) |
| B. 1368 | Cl | CH₂CH₃ | CH₂C≡C-(2-Cl-C₆H₄) |
| B. 1369 | Cl | CF₃ | CH₂C≡C-(2-Cl-C₆H₄) |
| B. 1370 | Cl | CHF₂ | CH₂C≡C-(2-Cl-C₆H₄) |
| B. 1371 | Cl | CH₂F | CH₂C≡C-(2-Cl-C₆H₄) |
| B. 1372 | Cl | Cl | CH₂C≡C-(2-Cl-C₆H₄) |
| B. 1373 | Cl | OCH₃ | CH₂C≡C-(2-Cl-C₆H₄) |
| B. 1374 | Cl | OCH₂CH₃ | CH₂C≡C-(2-Cl-C₆H₄) |
| B. 1375 | Cl | CN | CH₂C≡C-(2-Cl-C₆H₄) |
| B. 1376 | CH₃ | H | CH₂C≡C-(2-Cl-C₆H₄) |
| B. 1377 | CH₃ | CH₃ | CH₂C≡C-(2-Cl-C₆H₄) |
| B. 1378 | CH₃ | CH₂CH₃ | CH₂C≡C-(2-Cl-C₆H₄) |
| B. 1379 | CH₃ | CF₃ | CH₂C≡C-(2-Cl-C₆H₄) |
| B. 1380 | CH₃ | CHF₂ | CH₂C≡C-(2-Cl-C₆H₄) |
| B. 1381 | CH₃ | CH₂F | CH₂C≡C-(2-Cl-C₆H₄) |
| B. 1382 | CH₃ | Cl | CH₂C≡C-(2-Cl-C₆H₄) |
| B. 1383 | CH₃ | OCH₃ | CH₂C≡C-(2-Cl-C₆H₄) |
| B. 1384 | CH₃ | OCH₂CH₃ | CH₂C≡C-(2-Cl-C₆H₄) |
| B. 1385 | CH₃ | CN | CH₂C≡C-(2-Cl-C₆H₄) |
| B. 1386 | CF₃ | H | CH₂C≡C-(2-Cl-C₆H₄) |
| B. 1387 | CF₃ | CH₃ | CH₂C≡C-(2-Cl-C₆H₄) |
| B. 1388 | CF₃ | CH₂CH₃ | CH₂C≡C-(2-Cl-C₆H₄) |
| B. 1389 | CF₃ | CF₃ | CH₂C≡C-(2-Cl-C₆H₄) |
| B. 1390 | CF₃ | CHF₂ | CH₂C≡C-(2-Cl-C₆H₄) |
| B. 1391 | CF₃ | CH₂F | CH₂C≡C-(2-Cl-C₆H₄) |
| B. 1392 | CF₃ | Cl | CH₂C≡C-(2-Cl-C₆H₄) |
| B. 1393 | CF₃ | OCH₃ | CH₂C≡C-(2-Cl-C₆H₄) |
| B. 1394 | CF₃ | OCH₂CH₃ | CH₂C≡C-(2-Cl-C₆H₄) |
| B. 1395 | CF₃ | CN | CH₂C≡C-(2-Cl-C₆H₄) |
| B. 1396 | H | CH₃ | CH₂C≡C-(2-Cl-C₆H₄) |
| B. 1397 | H | CH₂CH₃ | CH₂C≡C-(2-Cl-C₆H₄) |
| B. 1398 | H | CF₃ | CH₂C≡C-(2-Cl-C₆H₄) |
| B. 1399 | H | Cl | CH₂C≡C-(2-Cl-C₆H₄) |
| B. 1400 | H | OCH₃ | CH₂C≡C-(2-Cl-C₆H₄) |
| B. 1401 | CH₂CH₃ | CH₃ | CH₂C≡C-(2-Cl-C₆H₄) |
| B. 1402 | CH₂CH₃ | CH₂CH₃ | CH₂C≡C-(2-Cl-C₆H₄) |

TABLE B-continued

| No. | R$_3$ | R$_5$ | R$_6$ |
|---|---|---|---|
| B. 1403 | CH$_2$CH$_3$ | CF$_3$ | CH$_2$C≡C-(2-Cl-C$_6$H$_4$) |
| B. 1404 | CH$_2$CH$_3$ | Cl | CH$_2$C≡C-(2-Cl-C$_6$H$_4$) |
| B. 1405 | CH$_2$CH$_3$ | OCH$_3$ | CH$_2$C≡C-(2-Cl-C$_6$H$_4$) |
| B. 1406 | CHF$_2$ | CH$_3$ | CH$_2$C≡C-(2-Cl-C$_6$H$_4$) |
| B. 1407 | CHF$_2$ | CH$_2$CH$_3$ | CH$_2$C≡C-(2-Cl-C$_6$H$_4$) |
| B. 1408 | CHF$_2$ | CF$_3$ | CH$_2$C≡C-(2-Cl-C$_6$H$_4$) |
| B. 1409 | CHF$_2$ | Cl | CH$_2$C≡C-(2-Cl-C$_6$H$_4$) |
| B. 1410 | CHF$_2$ | OCH$_3$ | CH$_2$C≡C-(2-Cl-C$_6$H$_4$) |
| B. 1411 | CH$_2$F | CH$_3$ | CH$_2$C≡C-(2-Cl-C$_6$H$_4$) |
| B. 1412 | CH$_2$F | CH$_2$CH$_3$ | CH$_2$C≡C-(2-Cl-C$_6$H$_4$) |
| B. 1413 | CH$_2$F | CF$_3$ | CH$_2$C≡C-(2-Cl-C$_6$H$_4$) |
| B. 1414 | CH$_2$F | Cl | CH$_2$C≡C-(2-Cl-C$_6$H$_4$) |
| B. 1415 | CH$_2$F | OCH$_3$ | CH$_2$C≡C-(2-Cl-C$_6$H$_4$) |
| B. 1416 | OCH$_3$ | CH$_3$ | CH$_2$C≡C-(2-Cl-C$_6$H$_4$) |
| B. 1417 | OCH$_3$ | CH$_2$CH$_3$ | CH$_2$C≡C-(2-Cl-C$_6$H$_4$) |
| B. 1418 | OCH$_3$ | CF$_3$ | CH$_2$C≡C-(2-Cl-C$_6$H$_4$) |
| B. 1419 | OCH$_3$ | Cl | CH$_2$C≡C-(2-Cl-C$_6$H$_4$) |
| B. 1420 | OCH$_3$ | OCH$_3$ | CH$_2$C≡C-(2-Cl-C$_6$H$_4$) |
| B. 1421 | OCH$_2$CH$_3$ | CH$_3$ | CH$_2$C≡C-(2-Cl-C$_6$H$_4$) |
| B. 1422 | OCH$_2$CH$_3$ | CH$_2$CH$_3$ | CH$_2$C≡C-(2-Cl-C$_6$H$_4$) |
| B. 1423 | OCH$_2$CH$_3$ | CF$_3$ | CH$_2$C≡C-(2-Cl-C$_6$H$_4$) |
| B. 1424 | OCH$_2$CH$_3$ | Cl | CH$_2$C≡C-(2-Cl-C$_6$H$_4$) |
| B. 1425 | OCH$_2$CH$_3$ | OCH$_3$ | CH$_2$C≡C-(2-Cl-C$_6$H$_4$) |
| B. 1426 | CN | CH$_3$ | CH$_2$C≡C-(2-Cl-C$_6$H$_4$) |
| B. 1427 | CN | CH$_2$CH$_3$ | CH$_2$C≡C-(2-Cl-C$_6$H$_4$) |
| B. 1428 | CN | CF$_3$ | CH$_2$C≡C-(2-Cl-C$_6$H$_4$) |
| B. 1429 | CN | Cl | CH$_2$C≡C-(2-Cl-C$_6$H$_4$) |
| B. 1430 | CN | OCH$_3$ | CH$_2$C≡C-(2-Cl-C$_6$H$_4$) |

Table 41

Compounds of the general formula Ia.5 where $R^2_m$ is hydrogen and the combination of the radicals $R^3$, $R^x$, $R^y$ and $R^z$ for each compound corresponds to one line of Table C

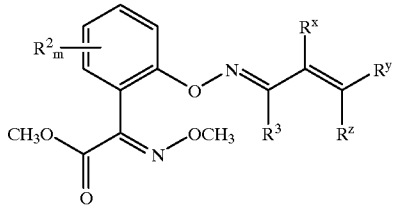
(Ia.5)

Table 42

Compounds of the general formula Ib.5 where $R^2_m$ is hydrogen and the combination of the radicals $R^3$, $R^x$, $R^y$ and $R^z$ for each compound corresponds to one line of Table C

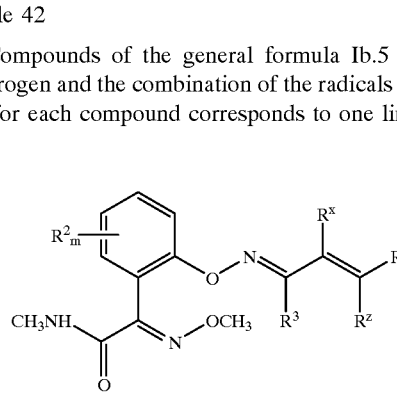
(Ib.5)

Table 43

Compounds of the general formula Ic.5 where $R^2_m$ is hydrogen and the combination of the radicals $R^3$, $R^x$, $R^y$ and $R^z$ for each compound corresponds to one line of Table C

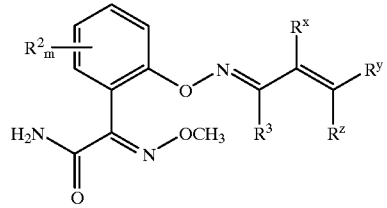
(Ic.5)

Table 44

Compounds of the general formula Id.5 where $R^2_m$ is hydrogen and the combination of the radicals $R^3$, $R^x$, $R^y$ and $R^z$ for each compound corresponds to one line of Table C

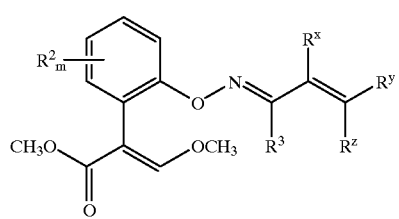
(Id.5)

Table 45

Compounds of the general formula Ie.5 where $R^2_m$ is hydrogen and the combination of the radicals $R^3$, $R^x$, $R^y$ and $R^z$ for each compound corresponds to one line of Table C

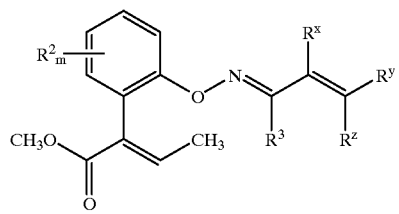
(Ie.5)

Table 46

Compounds of the general formula Ia.6 where $R^2_m$ is hydrogen and the combination of the radicals $R^3$, $R^x$, $R^y$ and $R^z$ for each compound corresponds to one line of Table C

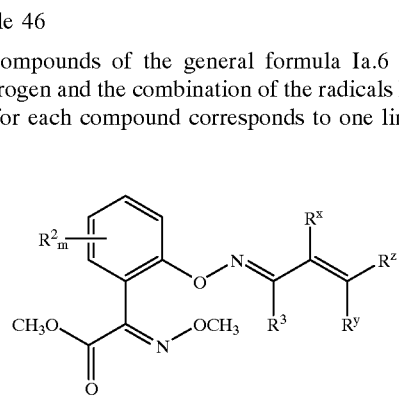
(Ia.6)

Table 47

Compounds of the general formula Ib.6 where $R^2_m$ is hydrogen and the combination of the radicals $R^3$, $R^x$, $R^y$ and $R^z$ for each compound corresponds to one line of Table C

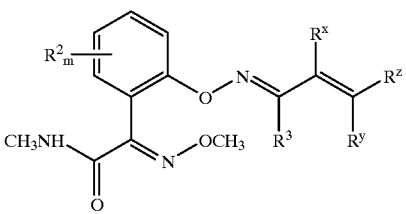

Table 48

Compounds of the general formula Ic.6 where $R^2_m$ is hydrogen and the combination of the radicals $R^3$, $R^x$, $R^y$ and $R^z$ for each compound corresponds to one line of Table C

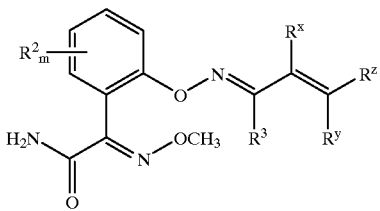

Table 49

Compounds of the general formula Id.6 where $R^2_m$ is hydrogen and the combination of the radicals $R^3$, $R^x$, $R^y$ and $R^z$ for each compound corresponds to one line of Table C

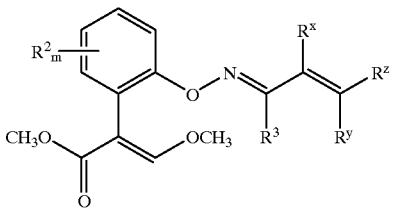

Table 50

Compounds of the general formula Ie.6 where $R^2_m$ is hydrogen and the combination of the radicals $R^3$, $R^x$, $R^y$ and $R^z$ for each compound corresponds to one line of Table C

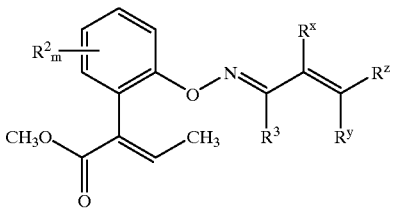

TABLE C

| No. | $R^3$ | $R^x$ | $R^y$ | $R^z$ |
|---|---|---|---|---|
| C.1 | $CH_3$ | H | H | H |
| C.2 | $CH_3$ | H | $CH_3$ | H |
| C.3 | $CH_3$ | H | $C_2H_5$ | H |
| C.4 | $CH_3$ | H | $C_3H_7$ | H |
| C.5 | $CH_3$ | H | $C_4H_9$ | H |
| C.6 | $CH_3$ | H | $CH(CH_3)_2$ | H |
| C.7 | $CH_3$ | H | cyclopropyl | H |
| C.8 | $CH_3$ | H | $CF_3$ | H |
| C.9 | $CH_3$ | H | $OCH_3$ | H |
| C.10 | $CH_3$ | H | $OC_2H_5$ | H |
| C.11 | $CH_3$ | H | $CH_2-C_6H_5$ | H |
| C.12 | $CH_3$ | H | $CH(CH_3)C_6H_5$ | H |
| C.13 | $CH_3$ | H | $C_6H_5$ | H |
| C.14 | $CH_3$ | H | 4-F—$C_6H_5$ | H |
| C.15 | $CH_3$ | H | 4-Cl-2-pyridyl | H |
| C.16 | $CH_3$ | H | F | H |
| C.17 | $CH_3$ | H | CN | H |
| C.18 | $CH_3$ | $CH_3$ | H | H |
| C.19 | $CH_3$ | $CH_3$ | $CH_3$ | H |
| C.20 | $CH_3$ | $CH_3$ | $C_2H_5$ | H |
| C.21 | $CH_3$ | $CH_3$ | $C_3H_7$ | H |
| C.22 | $CH_3$ | $CH_3$ | $C_4H_9$ | H |
| C.23 | $CH_3$ | $CH_3$ | $CH(CH_3)_2$ | H |
| C.24 | $CH_3$ | $CH_3$ | cyclopropyl | H |
| C.25 | $CH_3$ | $CH_3$ | $CF_3$ | H |
| C.26 | $CH_3$ | $CH_3$ | $OCH_3$ | H |
| C.27 | $CH_3$ | $CH_3$ | $OC_2H_5$ | H |
| C.28 | $CH_3$ | $CH_3$ | $CH_2-C_6H_5$ | H |
| C.29 | $CH_3$ | $CH_3$ | $CH(CH_3)C_6H_5$ | H |
| C.30 | $CH_3$ | $CH_3$ | $C_6H_5$ | H |
| C.31 | $CH_3$ | $CH_3$ | 4-F—$C_6H_5$ | H |
| C.32 | $CH_3$ | $CH_3$ | 4-Cl-2-pyridyl | H |
| C.33 | $CH_3$ | $CH_3$ | F | H |
| C.34 | $CH_3$ | $CH_3$ | CN | H |
| C.35 | $CH_3$ | $C_2H_5$ | H | H |
| C.36 | $CH_3$ | $C_2H_5$ | $CH_3$ | H |
| C.37 | $CH_3$ | $C_2H_5$ | $C_2H_5$ | H |
| C.38 | $CH_3$ | $C_2H_5$ | $C_3H_7$ | H |
| C.39 | $CH_3$ | $C_2H_5$ | $C_4H_9$ | H |
| C.40 | $CH_3$ | $C_2H_5$ | $CH(CH_3)_2$ | H |
| C.41 | $CH_3$ | $C_2H_5$ | cyclopropyl | H |
| C.42 | $CH_3$ | $C_2H_5$ | $CF_3$ | H |
| C.43 | $CH_3$ | $C_2H_5$ | $OCH_3$ | H |
| C.44 | $CH_3$ | $C_2H_5$ | $OC_2H_5$ | H |
| C.45 | $CH_3$ | $C_2H_5$ | $CH_2-C_6H_5$ | H |
| C.46 | $CH_3$ | $C_2H_5$ | $CH(CH_3)C_6H_5$ | H |
| C.47 | $CH_3$ | $C_2H_5$ | $C_6H_5$ | H |
| C.48 | $CH_3$ | $C_2H_5$ | 4-F—$C_6H_5$ | H |
| C.49 | $CH_3$ | $C_2H_5$ | 4-Cl-2-pyridyl | H |
| C.50 | $CH_3$ | $C_2H_5$ | F | H |
| C.51 | $CH_3$ | $C_2H_5$ | CN | H |
| C.52 | $CH_3$ | cyclopropyl | H | H |
| C.53 | $CH_3$ | cyclopropyl | $CH_3$ | H |
| C.54 | $CH_3$ | cyclopropyl | $C_2H_5$ | H |
| C.55 | $CH_3$ | cyclopropyl | $C_3H_7$ | H |
| C.56 | $CH_3$ | cyclopropyl | $C_4H_9$ | H |
| C.57 | $CH_3$ | cyclopropyl | $CH(CH_3)_2$ | H |
| C.58 | $CH_3$ | cyclopropyl | cyclopropyl | H |
| C.59 | $CH_3$ | cyclopropyl | $CF_3$ | H |
| C.60 | $CH_3$ | cyclopropyl | $OCH_3$ | H |
| C.61 | $CH_3$ | cyclopropyl | $OC_2H_5$ | H |
| C.62 | $CH_3$ | cyclopropyl | $CH_2-C_6H_5$ | H |
| C.63 | $CH_3$ | cyclopropyl | $CH(CH_3)C_6H_5$ | H |
| C.64 | $CH_3$ | cyclopropyl | $C_6H_5$ | H |
| C.65 | $CH_3$ | cyclopropyl | 4-F—$C_6H_5$ | H |
| C.66 | $CH_3$ | cyclopropyl | 4-Cl-2-pyridyl | H |
| C.67 | $CH_3$ | cyclopropyl | F | H |
| C.68 | $CH_3$ | cyclopropyl | CN | H |
| C.69 | $CH_3$ | $CF_3$ | H | H |
| C.70 | $CH_3$ | $CF_3$ | $CH_3$ | H |
| C.71 | $CH_3$ | $CF_3$ | $C_2H_5$ | H |
| C.72 | $CH_3$ | $CF_3$ | $C_3H_7$ | H |
| C.73 | $CH_3$ | $CF_3$ | $C_4H_9$ | H |
| C.74 | $CH_3$ | $CF_3$ | $CH(CH_3)_2$ | H |
| C.75 | $CH_3$ | $CF_3$ | cyclopropyl | H |
| C.76 | $CH_3$ | $CF_3$ | $CF_3$ | H |
| C.77 | $CH_3$ | $CF_3$ | $OCH_3$ | H |
| C.78 | $CH_3$ | $CF_3$ | $OC_2H_5$ | H |
| C.79 | $CH_3$ | $CF_3$ | $CH_2-C_6H_5$ | H |
| C.80 | $CH_3$ | $CF_3$ | $CH(CH_3)C_6H_5$ | H |

TABLE C-continued

| No. | $R^3$ | $R^x$ | $R^y$ | $R^z$ |
|---|---|---|---|---|
| C.81 | $CH_3$ | $CF_3$ | $C_6H_5$ | H |
| C.82 | $CH_3$ | $CF_3$ | $4\text{-}F\text{—}C_6H_5$ | H |
| C.83 | $CH_3$ | $CF_3$ | 4-Cl-2-pyridyl | H |
| C.84 | $CH_3$ | $CF_3$ | F | H |
| C.85 | $CH_3$ | $CF_3$ | CN | H |
| C.86 | $CH_3$ | Cl | H | H |
| C.87 | $CH_3$ | Cl | $CH_3$ | H |
| C.88 | $CH_3$ | Cl | $C_2H_5$ | H |
| C.89 | $CH_3$ | Cl | $C_3H_7$ | H |
| C.90 | $CH_3$ | Cl | $C_4H_9$ | H |
| C.91 | $CH_3$ | Cl | $CH(CH_3)_2$ | H |
| C.92 | $CH_3$ | Cl | cyclopropyl | H |
| C.93 | $CH_3$ | Cl | $CF_3$ | H |
| C.94 | $CH_3$ | Cl | $OCH_3$ | H |
| C.95 | $CH_3$ | Cl | $OC_2H_5$ | H |
| C.96 | $CH_3$ | Cl | $CH_2\text{—}C_6H_5$ | H |
| C.97 | $CH_3$ | Cl | $CH(CH_3)C_6H_5$ | H |
| C.98 | $CH_3$ | Cl | $C_6H_5$ | H |
| C.99 | $CH_3$ | Cl | $4\text{-}F\text{—}C_6H_5$ | H |
| C.100 | $CH_3$ | Cl | 4-Cl-2-pyridyl | H |
| C.101 | $CH_3$ | Cl | F | H |
| C.102 | $CH_3$ | Cl | CN | H |
| C.103 | $CH_3$ | F | H | H |
| C.104 | $CH_3$ | F | $CH_3$ | H |
| C.105 | $CH_3$ | F | $C_2H_5$ | H |
| C.106 | $CH_3$ | F | $C_3H_7$ | H |
| C.107 | $CH_3$ | F | $C_4H_9$ | H |
| C.108 | $CH_3$ | F | $CH(CH_3)_2$ | H |
| C.109 | $CH_3$ | F | cyclopropyl | H |
| C.110 | $CH_3$ | F | $CF_3$ | H |
| C.111 | $CH_3$ | F | $OCH_3$ | H |
| C.112 | $CH_3$ | F | $OC_2H_5$ | H |
| C.113 | $CH_3$ | F | $CH_2\text{—}C_6H_5$ | H |
| C.114 | $CH_3$ | F | $CH(CH_3)C_6H_5$ | H |
| C.115 | $CH_3$ | F | $C_6H_5$ | H |
| C.116 | $CH_3$ | F | $4\text{-}F\text{—}C_6H_5$ | H |
| C.117 | $CH_3$ | F | 4-Cl-2-pyridyl | H |
| C.118 | $CH_3$ | F | F | H |
| C.119 | $CH_3$ | F | CN | H |
| C.120 | $CH_3$ | $OCH_3$ | H | H |
| C.121 | $CH_3$ | $OCH_3$ | $CH_3$ | H |
| C.122 | $CH_3$ | $OCH_3$ | $C_2H_5$ | H |
| C.123 | $CH_3$ | $OCH_3$ | $C_3H_7$ | H |
| C.124 | $CH_3$ | $OCH_3$ | $C_4H_9$ | H |
| C.125 | $CH_3$ | $OCH_3$ | $CH(CH_3)_2$ | H |
| C.126 | $CH_3$ | $OCH_3$ | cyclopropyl | H |
| C.127 | $CH_3$ | $OCH_3$ | $CF_3$ | H |
| C.128 | $CH_3$ | $OCH_3$ | $OCH_3$ | H |
| C.129 | $CH_3$ | $OCH_3$ | $OC_2H_5$ | H |
| C.130 | $CH_3$ | $OCH_3$ | $CH_2\text{—}C_6H_5$ | H |
| C.131 | $CH_3$ | $OCH_3$ | $CH(CH_3)C_6H_5$ | H |
| C.132 | $CH_3$ | $OCH_3$ | $C_6H_5$ | H |
| C.133 | $CH_3$ | $OCH_3$ | $4\text{-}F\text{—}C_6H_5$ | H |
| C.134 | $CH_3$ | $OCH_3$ | 4-Cl-2-pyridyl | H |
| C.135 | $CH_3$ | $OCH_3$ | F | H |
| C.136 | $CH_3$ | $OCH_3$ | CN | H |
| C.137 | $CH_3$ | H | H | $CH_3$ |
| C.138 | $CH_3$ | H | $CH_3$ | $CH_3$ |
| C.139 | $CH_3$ | H | $C_2H_5$ | $CH_3$ |
| C.140 | $CH_3$ | H | $C_3H_7$ | $CH_3$ |
| C.141 | $CH_3$ | H | $C_4H_9$ | $CH_3$ |
| C.142 | $CH_3$ | H | $CH(CH_3)_2$ | $CH_3$ |
| C.143 | $CH_3$ | H | cyclopropyl | $CH_3$ |
| C.144 | $CH_3$ | H | $CF_3$ | $CH_3$ |
| C.145 | $CH_3$ | H | $OCH_3$ | $CH_3$ |
| C.146 | $CH_3$ | H | $OC_2H_5$ | $CH_3$ |
| C.147 | $CH_3$ | H | $CH_2\text{—}C_6H_5$ | $CH_3$ |
| C.148 | $CH_3$ | H | $CH(CH_3)C_6H_5$ | $CH_3$ |
| C.149 | $CH_3$ | H | $C_6H_5$ | $CH_3$ |
| C.150 | $CH_3$ | H | $4\text{-}F\text{—}C_6H_5$ | $CH_3$ |
| C.151 | $CH_3$ | H | 4-Cl-2-pyridyl | $CH_3$ |
| C.152 | $CH_3$ | H | F | $CH_3$ |
| C.153 | $CH_3$ | H | CN | $CH_3$ |
| C.154 | $CH_3$ | $CH_3$ | H | $CH_3$ |
| C.155 | $CH_3$ | $CH_3$ | $CH_3$ | $CH_3$ |
| C.156 | $CH_3$ | $CH_3$ | $C_2H_5$ | $CH_3$ |
| C.157 | $CH_3$ | $CH_3$ | $C_3H_7$ | $CH_3$ |
| C.158 | $CH_3$ | $CH_3$ | $C_4H_9$ | $CH_3$ |
| C.159 | $CH_3$ | $CH_3$ | $CH(CH_3)_2$ | $CH_3$ |
| C.160 | $CH_3$ | $CH_3$ | cyclopropyl | $CH_3$ |
| C.161 | $CH_3$ | $CH_3$ | $CF_3$ | $CH_3$ |
| C.162 | $CH_3$ | $CH_3$ | $OCH_3$ | $CH_3$ |
| C.163 | $CH_3$ | $CH_3$ | $OC_2H_5$ | $CH_3$ |
| C.164 | $CH_3$ | $CH_3$ | $CH_2\text{—}C_6H_5$ | $CH_3$ |
| C.165 | $CH_3$ | $CH_3$ | $CH(CH_3)C_6H_5$ | $CH_3$ |
| C.166 | $CH_3$ | $CH_3$ | $C_6H_5$ | $CH_3$ |
| C.167 | $CH_3$ | $CH_3$ | $4\text{-}F\text{—}C_6H_5$ | $CH_3$ |
| C.168 | $CH_3$ | $CH_3$ | 4-Cl-2-pyridyl | $CH_3$ |
| C.169 | $CH_3$ | $CH_3$ | F | $CH_3$ |
| C.170 | $CH_3$ | $CH_3$ | CN | $CH_3$ |
| C.171 | $CH_3$ | $C_2H_5$ | H | $CH_3$ |
| C.172 | $CH_3$ | $C_2H_5$ | $CH_3$ | $CH_3$ |
| C.173 | $CH_3$ | $C_2H_5$ | $C_2H_5$ | $CH_3$ |
| C.174 | $CH_3$ | $C_2H_5$ | $C_3H_7$ | $CH_3$ |
| C.175 | $CH_3$ | $C_2H_5$ | $C_4H_9$ | $CH_3$ |
| C.176 | $CH_3$ | $C_2H_5$ | $CH(CH_3)_2$ | $CH_3$ |
| C.177 | $CH_3$ | $C_2H_5$ | cyclopropyl | $CH_3$ |
| C.178 | $CH_3$ | $C_2H_5$ | $CF_3$ | $CH_3$ |
| C.179 | $CH_3$ | $C_2H_5$ | $OCH_3$ | $CH_3$ |
| C.180 | $CH_3$ | $C_2H_5$ | $OC_2H_5$ | $CH_3$ |
| C.181 | $CH_3$ | $C_2H_5$ | $CH_2\text{—}C_6H_5$ | $CH_3$ |
| C.182 | $CH_3$ | $C_2H_5$ | $CH(CH_3)C_6H_5$ | $CH_3$ |
| C.183 | $CH_3$ | $C_2H_5$ | $C_6H_5$ | $CH_3$ |
| C.184 | $CH_3$ | $C_2H_5$ | $4\text{-}F\text{—}C_6H_5$ | $CH_3$ |
| C.185 | $CH_3$ | $C_2H_5$ | 4-Cl-2-pyridyl | $CH_3$ |
| C.186 | $CH_3$ | $C_2H_5$ | F | $CH_3$ |
| C.187 | $CH_3$ | $C_2H_5$ | CN | $CH_3$ |
| C.188 | $CH_3$ | cyclopropyl | H | $CH_3$ |
| C.189 | $CH_3$ | cyclopropyl | $CH_3$ | $CH_3$ |
| C.190 | $CH_3$ | cyclopropyl | $C_2H_5$ | $CH_3$ |
| C.191 | $CH_3$ | cyclopropyl | $C_3H_7$ | $CH_3$ |
| C.192 | $CH_3$ | cyclopropyl | $C_4H_9$ | $CH_3$ |
| C.193 | $CH_3$ | cyclopropyl | $CH(CH_3)_2$ | $CH_3$ |
| C.194 | $CH_3$ | cyclopropyl | cyclopropyl | $CH_3$ |
| C.195 | $CH_3$ | cyclopropyl | $CF_3$ | $CH_3$ |
| C.196 | $CH_3$ | cyclopropyl | $OCH_3$ | $CH_3$ |
| C.197 | $CH_3$ | cyclopropyl | $OC_2H_5$ | $CH_3$ |
| C.198 | $CH_3$ | cyclopropyl | $CH_2\text{—}C_6H_5$ | $CH_3$ |
| C.199 | $CH_3$ | cyclopropyl | $CH(CH_3)C_6H_5$ | $CH_3$ |
| C.200 | $CH_3$ | cyclopropyl | $C_6H_5$ | $CH_3$ |
| C.201 | $CH_3$ | cyclopropyl | $4\text{-}F\text{—}C_6H_5$ | $CH_3$ |
| C.202 | $CH_3$ | cyclopropyl | 4-Cl-2-pyridyl | $CH_3$ |
| C.203 | $CH_3$ | cyclopropyl | F | $CH_3$ |
| C.204 | $CH_3$ | cyclopropyl | CN | $CH_3$ |
| C.205 | $CH_3$ | $CF_3$ | H | $CH_3$ |
| C.206 | $CH_3$ | $CF_3$ | $CH_3$ | $CH_3$ |
| C.207 | $CH_3$ | $CF_3$ | $C_2H_5$ | $CH_3$ |
| C.208 | $CH_3$ | $CF_3$ | $C_3H_7$ | $CH_3$ |
| C.209 | $CH_3$ | $CF_3$ | $C_4H_9$ | $CH_3$ |
| C.210 | $CH_3$ | $CF_3$ | $CH(CH_3)_2$ | $CH_3$ |
| C.211 | $CH_3$ | $CF_3$ | cyclopropyl | $CH_3$ |
| C.212 | $CH_3$ | $CF_3$ | $CF_3$ | $CH_3$ |
| C.213 | $CH_3$ | $CF_3$ | $OCH_3$ | $CH_3$ |
| C.214 | $CH_3$ | $CF_3$ | $OC_2H_5$ | $CH_3$ |
| C.215 | $CH_3$ | $CF_3$ | $CH_2\text{—}C_6H_5$ | $CH_3$ |
| C.216 | $CH_3$ | $CF_3$ | $CH(CH_3)C_6H_5$ | $CH_3$ |
| C.217 | $CH_3$ | $CF_3$ | $C_6H_5$ | $CH_3$ |
| C.218 | $CH_3$ | $CF_3$ | $4\text{-}F\text{—}C_6H_5$ | $CH_3$ |
| C.219 | $CH_3$ | $CF_3$ | 4-Cl-2-pyridyl | $CH_3$ |
| C.220 | $CH_3$ | $CF_3$ | F | $CH_3$ |
| C.221 | $CH_3$ | $CF_3$ | CN | $CH_3$ |
| C.222 | $CH_3$ | Cl | H | $CH_3$ |
| C.223 | $CH_3$ | Cl | $CH_3$ | $CH_3$ |
| C.224 | $CH_3$ | Cl | $C_2H_5$ | $CH_3$ |
| C.225 | $CH_3$ | Cl | $C_3H_7$ | $CH_3$ |
| C.226 | $CH_3$ | Cl | $C_4H_9$ | $CH_3$ |
| C.227 | $CH_3$ | Cl | $CH(CH_3)_2$ | $CH_3$ |
| C.228 | $CH_3$ | Cl | cyclopropyl | $CH_3$ |
| C.229 | $CH_3$ | Cl | $CF_3$ | $CH_3$ |
| C.230 | $CH_3$ | Cl | $OCH_3$ | $CH_3$ |
| C.231 | $CH_3$ | Cl | $OC_2H_5$ | $CH_3$ |
| C.232 | $CH_3$ | Cl | $CH_2\text{—}C_6H_5$ | $CH_3$ |
| C.233 | $CH_3$ | Cl | $CH(CH_3)C_6H_5$ | $CH_3$ |
| C.234 | $CH_3$ | Cl | $C_6H_5$ | $CH_3$ |

TABLE C-continued

| No. | $R^3$ | $R^x$ | $R^y$ | $R^z$ |
|---|---|---|---|---|
| C.235 | $CH_3$ | Cl | 4-F—$C_6H_5$ | $CH_3$ |
| C.236 | $CH_3$ | Cl | 4-Cl-2-pyridyl | $CH_3$ |
| C.237 | $CH_3$ | Cl | F | $CH_3$ |
| C.238 | $CH_3$ | Cl | CN | $CH_3$ |
| C.239 | $CH_3$ | F | H | $CH_3$ |
| C.240 | $CH_3$ | F | $CH_3$ | $CH_3$ |
| C.241 | $CH_3$ | F | $C_2H_5$ | $CH_3$ |
| C.242 | $CH_3$ | F | $C_3H_7$ | $CH_3$ |
| C.243 | $CH_3$ | F | $C_4H_9$ | $CH_3$ |
| C.244 | $CH_3$ | F | $CH(CH_3)_2$ | $CH_3$ |
| C.245 | $CH_3$ | F | cyclopropyl | $CH_3$ |
| C.246 | $CH_3$ | F | $CF_3$ | $CH_3$ |
| C.247 | $CH_3$ | F | $OCH_3$ | $CH_3$ |
| C.248 | $CH_3$ | F | $OC_2H_5$ | $CH_3$ |
| C.249 | $CH_3$ | F | $CH_2$—$C_6H_5$ | $CH_3$ |
| C.250 | $CH_3$ | F | $CH(CH_3)C_6H_5$ | $CH_3$ |
| C.251 | $CH_3$ | F | $C_6H_5$ | $CH_3$ |
| C.252 | $CH_3$ | F | 4-F—$C_6H_5$ | $CH_3$ |
| C.253 | $CH_3$ | F | 4-Cl-2-pyridyl | $CH_3$ |
| C.254 | $CH_3$ | F | F | $CH_3$ |
| C.255 | $CH_3$ | F | CN | $CH_3$ |
| C.256 | $CH_3$ | $OCH_3$ | H | $CH_3$ |
| C.257 | $CH_3$ | $OCH_3$ | $CH_3$ | $CH_3$ |
| C.258 | $CH_3$ | $OCH_3$ | $C_2H_5$ | $CH_3$ |
| C.259 | $CH_3$ | $OCH_3$ | $C_3H_7$ | $CH_3$ |
| C.260 | $CH_3$ | $OCH_3$ | $C_4H_9$ | $CH_3$ |
| C.261 | $CH_3$ | $OCH_3$ | $CH(CH_3)_2$ | $CH_3$ |
| C.262 | $CH_3$ | $OCH_3$ | cyclopropyl | $CH_3$ |
| C.263 | $CH_3$ | $OCH_3$ | $CF_3$ | $CH_3$ |
| C.264 | $CH_3$ | $OCH_3$ | $OCH_3$ | $CH_3$ |
| C.265 | $CH_3$ | $OCH_3$ | $OC_2H_5$ | $CH_3$ |
| C.266 | $CH_3$ | $OCH_3$ | $CH_2$—$C_6H_5$ | $CH_3$ |
| C.267 | $CH_3$ | $OCH_3$ | $CH(CH_3)C_6H_5$ | $CH_3$ |
| C.268 | $CH_3$ | $OCH_3$ | $C_6H_5$ | $CH_3$ |
| C.269 | $CH_3$ | $OCH_3$ | 4-F—$C_6H_5$ | $CH_3$ |
| C.270 | $CH_3$ | $OCH_3$ | 4-Cl-2-pyridyl | $CH_3$ |
| C.271 | $CH_3$ | $OCH_3$ | F | $CH_3$ |
| C.272 | $CH_3$ | $OCH_3$ | CN | $CH_3$ |
| C.273 | H | $CH_3$ | H | H |
| C.274 | H | $CH_3$ | $CH_3$ | H |
| C.275 | H | $CH_3$ | $C_2H_5$ | H |
| C.276 | H | $CH_3$ | $C_3H_7$ | H |
| C.277 | H | $CH_3$ | $C_4H_9$ | H |
| C.278 | H | $CH_3$ | $CH(CH_3)_2$ | H |
| C.279 | H | $CH_3$ | cyclopropyl | H |
| C.280 | H | $CH_3$ | $CF_3$ | H |
| C.281 | H | $CH_3$ | $OCH_3$ | H |
| C.282 | H | $CH_3$ | $OC_2H_5$ | H |
| C.283 | H | $CH_3$ | $CH_2$—$C_6H_5$ | H |
| C.284 | H | $CH_3$ | $CH(CH_3)C_6H_5$ | H |
| C.285 | H | $CH_3$ | $C_6H_5$ | H |
| C.286 | H | $CH_3$ | 4-F—$C_6H_5$ | H |
| C.287 | H | $CH_3$ | 4-Cl-2-pyridyl | H |
| C.288 | H | $CH_3$ | F | H |
| C.289 | H | $CH_3$ | CN | H |
| C.290 | H | $CH_3$ | H | $CH_3$ |
| C.291 | H | $CH_3$ | $CH_3$ | $CH_3$ |
| C.292 | H | $CH_3$ | $C_2H_5$ | $CH_3$ |
| C.293 | H | $CH_3$ | $C_3H_7$ | $CH_3$ |
| C.294 | H | $CH_3$ | $C_4H_9$ | $CH_3$ |
| C.295 | H | $CH_3$ | $CH(CH_3)_2$ | $CH_3$ |
| C.296 | H | $CH_3$ | cyclopropyl | $CH_3$ |
| C.297 | H | $CH_3$ | $CF_3$ | $CH_3$ |
| C.298 | H | $CH_3$ | $OCH_3$ | $CH_3$ |
| C.299 | H | $CH_3$ | $OC_2H_5$ | $CH_3$ |
| C.300 | H | $CH_3$ | $CH_2$—$C_6H_5$ | $CH_3$ |
| C.301 | H | $CH_3$ | $CH(CH_3)C_6H_5$ | $CH_3$ |
| C.302 | H | $CH_3$ | $C_6H_5$ | $CH_3$ |
| C.303 | H | $CH_3$ | 4-F—$C_6H_5$ | $CH_3$ |
| C.304 | H | $CH_3$ | 4-Cl-2-pyridyl | $CH_3$ |
| C.305 | H | $CH_3$ | F | $CH_3$ |
| C.306 | H | $CH_3$ | CN | $CH_3$ |
| C.307 | H | $CF_3$ | H | H |
| C.308 | H | $CF_3$ | $CH_3$ | H |
| C.309 | H | $CF_3$ | $C_2H_5$ | H |
| C.310 | H | $CF_3$ | $C_3H_7$ | H |
| C.311 | H | $CF_3$ | $C_4H_9$ | H |
| C.312 | H | $CF_3$ | $CH(CH_3)_2$ | H |
| C.313 | H | $CF_3$ | cyclopropyl | H |
| C.314 | H | $CF_3$ | $CF_3$ | H |
| C.315 | H | $CF_3$ | $OCH_3$ | H |
| C.316 | H | $CF_3$ | $OC_2H_5$ | H |
| C.317 | H | $CF_3$ | $CH_2$—$C_6H_5$ | H |
| C.318 | H | $CF_3$ | $CH(CH_3)C_6H_5$ | H |
| C.319 | H | $CF_3$ | $C_6H_5$ | H |
| C.320 | H | $CF_3$ | 4-F—$C_6H_5$ | H |
| C.321 | H | $CF_3$ | 4-Cl-2-pyridyl | H |
| C.322 | H | $CF_3$ | F | H |
| C.323 | H | $CF_3$ | CN | H |
| C.324 | H | $CF_3$ | H | $CH_3$ |
| C.325 | H | $CF_3$ | $CH_3$ | $CH_3$ |
| C.326 | H | $CF_3$ | $C_2H_5$ | $CH_3$ |
| C.327 | H | $CF_3$ | $C_3H_7$ | $CH_3$ |
| C.328 | H | $CF_3$ | $C_4H_9$ | $CH_3$ |
| C.329 | H | $CF_3$ | $CH(CH_3)_2$ | $CH_3$ |
| C.330 | H | $CF_3$ | cyclopropyl | $CH_3$ |
| C.331 | H | $CF_3$ | $CF_3$ | $CH_3$ |
| C.332 | H | $CF_3$ | $OCH_3$ | $CH_3$ |
| C.333 | H | $CF_3$ | $OC_2H_5$ | $CH_3$ |
| C.334 | H | $CF_3$ | $CH_2$—$C_6H_5$ | $CH_3$ |
| C.335 | H | $CF_3$ | $CH(CH_3)C_6H_5$ | $CH_3$ |
| C.336 | H | $CF_3$ | $C_6H_5$ | $CH_3$ |
| C.337 | H | $CF_3$ | 4-F—$C_6H_5$ | $CH_3$ |
| C.338 | H | $CF_3$ | 4-Cl-2-pyridyl | $CH_3$ |
| C.339 | H | $CF_3$ | F | $CH_3$ |
| C.340 | H | $CF_3$ | CN | $CH_3$ |
| C.341 | $CF_3$ | $CH_3$ | H | H |
| C.342 | $CF_3$ | $CH_3$ | $CH_3$ | H |
| C.343 | $CF_3$ | $CH_3$ | $C_2H_5$ | H |
| C.344 | $CF_3$ | $CH_3$ | $C_3H_7$ | H |
| C.345 | $CF_3$ | $CH_3$ | $C_4H_9$ | H |
| C.346 | $CF_3$ | $CH_3$ | $CH(CH_3)_2$ | H |
| C.347 | $CF_3$ | $CH_3$ | cyclopropyl | H |
| C.348 | $CF_3$ | $CH_3$ | $CF_3$ | H |
| C.349 | $CF_3$ | $CH_3$ | $OCH_3$ | H |
| C.350 | $CF_3$ | $CH_3$ | $OC_2H_5$ | H |
| C.351 | $CF_3$ | $CH_3$ | $CH_2$—$C_6H_5$ | H |
| C.352 | $CF_3$ | $CH_3$ | $CH(CH_3)C_6H_5$ | H |
| C.353 | $CF_3$ | $CH_3$ | $C_6H_5$ | H |
| C.354 | $CF_3$ | $CH_3$ | 4-F—$C_6H_5$ | H |
| C.355 | $CF_3$ | $CH_3$ | 4-Cl-2-pyridyl | H |
| C.356 | $CF_3$ | $CH_3$ | F | H |
| C.357 | $CF_3$ | $CH_3$ | CN | H |
| C.358 | $CF_3$ | $CH_3$ | H | $CH_3$ |
| C.359 | $CF_3$ | $CH_3$ | $CH_3$ | $CH_3$ |
| C.360 | $CF_3$ | $CH_3$ | $C_2H_5$ | $CH_3$ |
| C.361 | $CF_3$ | $CH_3$ | $C_3H_7$ | $CH_3$ |
| C.362 | $CF_3$ | $CH_3$ | $C_4H_9$ | $CH_3$ |
| C.363 | $CF_3$ | $CH_3$ | $CH(CH_3)_2$ | $CH_3$ |
| C.364 | $CF_3$ | $CH_3$ | cyclopropyl | $CH_3$ |
| C.365 | $CF_3$ | $CH_3$ | $CF_3$ | $CH_3$ |
| C.366 | $CF_3$ | $CH_3$ | $OCH_3$ | $CH_3$ |
| C.367 | $CF_3$ | $CH_3$ | $OC_2H_5$ | $CH_3$ |
| C.368 | $CF_3$ | $CH_3$ | $CH_2$—$C_6H_5$ | $CH_3$ |
| C.369 | $CF_3$ | $CH_3$ | $CH(CH_3)C_6H_5$ | $CH_3$ |
| C.370 | $CF_3$ | $CH_3$ | $C_6H_5$ | $CH_3$ |
| C.371 | $CF_3$ | $CH_3$ | 4-F—$C_6H_5$ | $CH_3$ |
| C.372 | $CF_3$ | $CH_3$ | 4-Cl-2-pyridyl | $CH_3$ |
| C.373 | $CF_3$ | $CH_3$ | F | $CH_3$ |
| C.374 | $CF_3$ | $CH_3$ | CN | $CH_3$ |
| C.375 | $CF_3$ | $CF_3$ | H | H |
| C.376 | $CF_3$ | $CF_3$ | $CH_3$ | H |
| C.377 | $CF_3$ | $CF_3$ | $C_2H_5$ | H |
| C.378 | $CF_3$ | $CF_3$ | $C_3H_7$ | H |
| C.379 | $CF_3$ | $CF_3$ | $C_4H_9$ | H |
| C.380 | $CF_3$ | $CF_3$ | $CH(CH_3)_2$ | H |
| C.381 | $CF_3$ | $CF_3$ | cyclopropyl | H |
| C.382 | $CF_3$ | $CF_3$ | $CF_3$ | H |
| C.383 | $CF_3$ | $CF_3$ | $OCH_3$ | H |
| C.384 | $CF_3$ | $CF_3$ | $OC_2H_5$ | H |
| C.385 | $CF_3$ | $CF_3$ | $CH_2$—$C_6H_5$ | H |
| C.386 | $CF_3$ | $CF_3$ | $CH(CH_3)C_6H_5$ | H |
| C.387 | $CF_3$ | $CF_3$ | $C_6H_5$ | H |
| C.388 | $CF_3$ | $CF_3$ | 4-F—$C_6H_5$ | H |

TABLE C-continued

| No. | $R^3$ | $R^x$ | $R^y$ | $R^z$ |
|---|---|---|---|---|
| C.389 | $CF_3$ | $CF_3$ | 4-Cl-2-pyridyl | H |
| C.390 | $CF_3$ | $CF_3$ | F | H |
| C.391 | $CF_3$ | $CF_3$ | CN | H |
| C.392 | $CF_3$ | $CF_3$ | H | $CH_3$ |
| C.393 | $CF_3$ | $CF_3$ | $CH_3$ | $CH_3$ |
| C.394 | $CF_3$ | $CF_3$ | $C_2H_5$ | $CH_3$ |
| C.395 | $CF_3$ | $CF_3$ | $C_3H_7$ | $CH_3$ |
| C.396 | $CF_3$ | $CF_3$ | $C_4H_9$ | $CH_3$ |
| C.397 | $CF_3$ | $CF_3$ | $CH(CH_3)_2$ | $CH_3$ |
| C.398 | $CF_3$ | $CF_3$ | cyclopropyl | $CH_3$ |
| C.399 | $CF_3$ | $CF_3$ | $CF_3$ | $CH_3$ |
| C.400 | $CF_3$ | $CF_3$ | $OCH_3$ | $CH_3$ |
| C.401 | $CF_3$ | $CF_3$ | $OC_2H_5$ | $CH_3$ |
| C.402 | $CF_3$ | $CF_3$ | $CH_2$—$C_6H_5$ | $CH_3$ |
| C.403 | $CF_3$ | $CF_3$ | $CH(CH_3)C_6H_5$ | $CH_3$ |
| C.404 | $CF_3$ | $CF_3$ | $C_6H_5$ | $CH_3$ |
| C.405 | $CF_3$ | $CF_3$ | 4-F—$C_6H_5$ | $CH_3$ |
| C.406 | $CF_3$ | $CF_3$ | 4-Cl-2-pyridyl | $CH_3$ |
| C.407 | $CF_3$ | $CF_3$ | F | $CH_3$ |
| C.408 | $CF_3$ | $CF_3$ | CN | $CH_3$ |
| C.409 | Cl | $CH_3$ | H | H |
| C.410 | Cl | $CH_3$ | $CH_3$ | H |
| C.411 | Cl | $CH_3$ | $C_2H_5$ | H |
| C.412 | Cl | $CH_3$ | $C_3H_7$ | H |
| C.413 | Cl | $CH_3$ | $C_4H_9$ | H |
| C.414 | Cl | $CH_3$ | $CH(CH_3)_2$ | H |
| C.415 | Cl | $CH_3$ | cyclopropyl | H |
| C.416 | Cl | $CH_3$ | $CF_3$ | H |
| C.417 | Cl | $CH_3$ | $OCH_3$ | H |
| C.418 | Cl | $CH_3$ | $OC_2H_5$ | H |
| C.419 | Cl | $CH_3$ | $CH_2$—$C_6H_5$ | H |
| C.420 | Cl | $CH_3$ | $CH(CH_3)C_6H_5$ | H |
| C.421 | Cl | $CH_3$ | $C_6H_5$ | H |
| C.422 | Cl | $CH_3$ | 4-F—$C_6H_5$ | H |
| C.423 | Cl | $CH_3$ | 4-Cl-2-pyridyl | H |
| C.424 | Cl | $CH_3$ | F | H |
| C.425 | Cl | $CH_3$ | CN | H |
| C.426 | Cl | $CH_3$ | H | $CH_3$ |
| C.427 | Cl | $CH_3$ | $CH_3$ | $CH_3$ |
| C.428 | Cl | $CH_3$ | $C_2H_5$ | $CH_3$ |
| C.429 | Cl | $CH_3$ | $C_3H_7$ | $CH_3$ |
| C.430 | Cl | $CH_3$ | $C_4H_9$ | $CH_3$ |
| C.431 | Cl | $CH_3$ | $CH(CH_3)_2$ | $CH_3$ |
| C.432 | Cl | $CH_3$ | cyclopropyl | $CH_3$ |
| C.433 | Cl | $CH_3$ | $CF_3$ | $CH_3$ |
| C.434 | Cl | $CH_3$ | $OCH_3$ | $CH_3$ |
| C.435 | Cl | $CH_3$ | $OC_2H_5$ | $CH_3$ |
| C.436 | Cl | $CH_3$ | $CH_2$—$C_6H_5$ | $CH_3$ |
| C.437 | Cl | $CH_3$ | $CH(CH_3)C_6H_5$ | $CH_3$ |
| C.438 | Cl | $CH_3$ | $C_6H_5$ | $CH_3$ |
| C.439 | Cl | $CH_3$ | 4-F—$C_6H_5$ | $CH_3$ |
| C.440 | Cl | $CH_3$ | 4-Cl-2-pyridyl | $CH_3$ |
| C.441 | Cl | $CH_3$ | F | $CH_3$ |
| C.442 | Cl | $CH_3$ | CN | $CH_3$ |
| C.443 | Cl | $CF_3$ | H | H |
| C.444 | Cl | $CF_3$ | $CH_3$ | H |
| C.445 | Cl | $CF_3$ | $C_2H_5$ | H |
| C.446 | Cl | $CF_3$ | $C_3H_7$ | H |
| C.447 | Cl | $CF_3$ | $C_4H_9$ | H |
| C.448 | Cl | $CF_3$ | $CH(CH_3)_2$ | H |
| C.449 | Cl | $CF_3$ | cyclopropyl | H |
| C.450 | Cl | $CF_3$ | $CF_3$ | H |
| C.451 | Cl | $CF_3$ | $OCH_3$ | H |
| C.452 | Cl | $CF_3$ | $OC_2H_5$ | H |
| C.453 | Cl | $CF_3$ | $CH_2$—$C_6H_5$ | H |
| C.454 | Cl | $CF_3$ | $CH(CH_3)C_6H_5$ | H |
| C.455 | Cl | $CF_3$ | $C_6H_5$ | H |
| C.456 | Cl | $CF_3$ | 4-F—$C_6H_5$ | H |
| C.457 | Cl | $CF_3$ | 4-Cl-2-pyridyl | H |
| C.458 | Cl | $CF_3$ | F | H |
| C.459 | Cl | $CF_3$ | CN | H |
| C.460 | Cl | $CF_3$ | H | $CH_3$ |
| C.461 | Cl | $CF_3$ | $CH_3$ | $CH_3$ |
| C.462 | Cl | $CF_3$ | $C_2H_5$ | $CH_3$ |
| C.463 | Cl | $CF_3$ | $C_3H_7$ | $CH_3$ |
| C.464 | Cl | $CF_3$ | $C_4H_9$ | $CH_3$ |
| C.465 | Cl | $CF_3$ | $CH(CH_3)_2$ | $CH_3$ |
| C.466 | Cl | $CF_3$ | cyclopropyl | $CH_3$ |
| C.467 | Cl | $CF_3$ | $CF_3$ | $CH_3$ |
| C.468 | Cl | $CF_3$ | $OCH_3$ | $CH_3$ |
| C.469 | Cl | $CF_3$ | $OC_2H_5$ | $CH_3$ |
| C.470 | Cl | $CF_3$ | $CH_2$—$C_6H_5$ | $CH_3$ |
| C.471 | Cl | $CF_3$ | $CH(CH_3)C_6H_5$ | $CH_3$ |
| C.472 | Cl | $CF_3$ | $C_6H_5$ | $CH_3$ |
| C.473 | Cl | $CF_3$ | 4-F—$C_6H_5$ | $CH_3$ |
| C.474 | Cl | $CF_3$ | 4-Cl-2-pyridyl | $CH_3$ |
| C.475 | Cl | $CF_3$ | F | $CH_3$ |
| C.476 | Cl | $CF_3$ | CN | $CH_3$ |
| C.477 | H | $CH_3$ | H | F |
| C.478 | H | $CH_3$ | $CH_3$ | F |
| C.479 | H | $CH_3$ | $C_2H_5$ | F |
| C.480 | H | $CH_3$ | $C_3H_7$ | F |
| C.481 | H | $CH_3$ | $CH(CH_3)_2$ | F |
| C.482 | H | $CH_3$ | cyclopropyl | F |
| C.483 | H | $CH_3$ | $CF_3$ | F |
| C.484 | H | $CH_3$ | $OCH_3$ | F |
| C.485 | H | $CH_3$ | $C_6H_5$ | F |
| C.486 | H | $CH_3$ | 4-F—$C_6H_5$ | F |
| C.487 | H | $CH_3$ | H | $C_2H_5$ |
| C.488 | H | $CH_3$ | $CH_3$ | $C_2H_5$ |
| C.489 | H | $CH_3$ | $C_2H_5$ | $C_2H_5$ |
| C.490 | H | $CH_3$ | $C_3H_7$ | $C_2H_5$ |
| C.491 | H | $CH_3$ | $CH(CH_3)_2$ | $C_2H_5$ |
| C.492 | H | $CH_3$ | cyclopropyl | $C_2H_5$ |
| C.493 | H | $CH_3$ | $CF_3$ | $C_2H_5$ |
| C.494 | H | $CH_3$ | $OCH_3$ | $C_2H_5$ |
| C.495 | H | $CH_3$ | $C_6H_5$ | $C_2H_5$ |
| C.496 | H | $CH_3$ | 4-F—$C_6H_5$ | $C_2H_5$ |
| C.497 | H | $CH_3$ | H | $CF_3$ |
| C.498 | H | $CH_3$ | $CH_3$ | $CF_3$ |
| C.499 | H | $CH_3$ | $C_2H_5$ | $CF_3$ |
| C.500 | H | $CH_3$ | $C_3H_7$ | $CF_3$ |
| C.501 | H | $CH_3$ | $CH(CH_3)_2$ | $CF_3$ |
| C.502 | H | $CH_3$ | cyclopropyl | $CF_3$ |
| C.503 | H | $CH_3$ | $CF_3$ | $CF_3$ |
| C.504 | H | $CH_3$ | $OCH_3$ | $CF_3$ |
| C.505 | H | $CH_3$ | $C_6H_5$ | $CF_3$ |
| C.506 | H | $CH_3$ | 4-F—$C_6H_5$ | $CF_3$ |
| C.507 | H | $CH_3$ | H | CN |
| C.508 | H | $CH_3$ | $CH_3$ | CN |
| C.509 | H | $CH_3$ | $C_2H_5$ | CN |
| C.510 | H | $CH_3$ | $C_3H_7$ | CN |
| C.511 | H | $CH_3$ | $CH(CH_3)_2$ | CN |
| C.512 | H | $CH_3$ | cyclopropyl | CN |
| C.513 | H | $CH_3$ | $CF_3$ | CN |
| C.514 | H | $CH_3$ | $OCH_3$ | CN |
| C.515 | H | $CH_3$ | $C_6H_5$ | CN |
| C.516 | H | $CH_3$ | 4-F—$C_6H_5$ | CN |
| C.517 | H | $CH_3$ | H | Cl |
| C.518 | H | $CH_3$ | $CH_3$ | Cl |
| C.519 | H | $CH_3$ | $C_2H_5$ | Cl |
| C.520 | H | $CH_3$ | $C_3H_7$ | Cl |
| C.521 | H | $CH_3$ | $CH(CH_3)_2$ | Cl |
| C.522 | H | $CH_3$ | cyclopropyl | Cl |
| C.523 | H | $CH_3$ | $CF_3$ | Cl |
| C.524 | H | $CH_3$ | $OCH_3$ | Cl |
| C.525 | H | $CH_3$ | $C_6H_5$ | Cl |
| C.526 | H | $CH_3$ | 4-F—$C_6H_5$ | Cl |
| C.527 | H | $CF_3$ | H | F |
| C.528 | H | $CF_3$ | $CH_3$ | F |
| C.529 | H | $CF_3$ | $C_2H_5$ | F |
| C.530 | H | $CF_3$ | $C_3H_7$ | F |
| C.531 | H | $CF_3$ | $CH(CH_3)_2$ | F |
| C.532 | H | $CF_3$ | cyclopropyl | F |
| C.533 | H | $CF_3$ | $CF_3$ | F |
| C.534 | H | $CF_3$ | $OCH_3$ | F |
| C.535 | H | $CF_3$ | $C_6H_5$ | F |
| C.536 | H | $CF_3$ | 4-F—$C_6H_5$ | F |
| C.537 | H | $CF_3$ | H | $C_2H_5$ |
| C.538 | H | $CF_3$ | $CH_3$ | $C_2H_5$ |
| C.539 | H | $CF_3$ | $C_2H_5$ | $C_2H_5$ |
| C.540 | H | $CF_3$ | $C_3H_7$ | $C_2H_5$ |
| C.541 | H | $CF_3$ | $CH(CH_3)_2$ | $C_2H_5$ |
| C.542 | H | $CF_3$ | cyclopropyl | $C_2H_5$ |

TABLE C-continued

| No. | R³ | Rˣ | Rʸ | Rᶻ |
|---|---|---|---|---|
| C.543 | H | CF₃ | CF₃ | C₂H₅ |
| C.544 | H | CF₃ | OCH₃ | C₂H₅ |
| C.545 | H | CF₃ | C₆H₅ | C₂H₅ |
| C.546 | H | CF₃ | 4-F—C₆H₅ | C₂H₅ |
| C.547 | H | CF₃ | H | CF₃ |
| C.548 | H | CF₃ | CH₃ | CF₃ |
| C.549 | H | CF₃ | C₂H₅ | CF₃ |
| C.550 | H | CF₃ | C₃H₇ | CF₃ |
| C.551 | H | CF₃ | CH(CH₃)₂ | CF₃ |
| C.552 | H | CF₃ | cyclopropyl | CF₃ |
| C.553 | H | CF₃ | CF₃ | CF₃ |
| C.554 | H | CF₃ | OCH₃ | CF₃ |
| C.555 | H | CF₃ | C₆H₅ | CF₃ |
| C.556 | H | CF₃ | 4-F—C₆H₅ | CF₃ |
| C.557 | H | CF₃ | H | CN |
| C.558 | H | CF₃ | CH₃ | CN |
| C.559 | H | CF₃ | C₂H₅ | CN |
| C.560 | H | CF₃ | C₃H₇ | CN |
| C.561 | H | CF₃ | CH(CH₃)₂ | CN |
| C.562 | H | CF₃ | cyclopropyl | CN |
| C.563 | H | CF₃ | CF₃ | CN |
| C.564 | H | CF₃ | OCH₃ | CN |
| C.565 | H | CF₃ | C₆H₅ | CN |
| C.566 | H | CF₃ | 4-F—C₆H₅ | CN |
| C.567 | H | CF₃ | H | Cl |
| C.568 | H | CF₃ | CH₃ | Cl |
| C.569 | H | CF₃ | C₂H₅ | Cl |
| C.570 | H | CF₃ | C₃H₇ | Cl |
| C.571 | H | CF₃ | CH(CH₃)₂ | Cl |
| C.572 | H | CF₃ | cyclopropyl | Cl |
| C.573 | H | CF₃ | CF₃ | Cl |
| C.574 | H | CF₃ | OCH₃ | Cl |
| C.575 | H | CF₃ | C₆H₅ | Cl |
| C.576 | H | CF₃ | 4-F—C₆H₅ | Cl |
| C.577 | CF₃ | CH₃ | H | F |
| C.578 | CF₃ | CH₃ | CH₃ | F |
| C.579 | CF₃ | CH₃ | C₂H₅ | F |
| C.580 | CF₃ | CH₃ | C₃H₇ | F |
| C.581 | CF₃ | CH₃ | CH(CH₃)₂ | F |
| C.582 | CF₃ | CH₃ | cyclopropyl | F |
| C.583 | CF₃ | CH₃ | CF₃ | F |
| C.584 | CF₃ | CH₃ | OCH₃ | F |
| C.585 | CF₃ | CH₃ | C₆H₅ | F |
| C.586 | CF₃ | CH₃ | 4-F—C₆H₅ | F |
| C.587 | CF₃ | CH₃ | H | C₂H₅ |
| C.588 | CF₃ | CH₃ | CH₃ | C₂H₅ |
| C.589 | CF₃ | CH₃ | C₂H₅ | C₂H₅ |
| C.590 | CF₃ | CH₃ | C₃H₇ | C₂H₅ |
| C.591 | CF₃ | CH₃ | CH(CH₃)₂ | C₂H₅ |
| C.592 | CF₃ | CH₃ | cyclopropyl | C₂H₅ |
| C.593 | CF₃ | CH₃ | CF₃ | C₂H₅ |
| C.594 | CF₃ | CH₃ | OCH₃ | C₂H₅ |
| C.595 | CF₃ | CH₃ | C₆H₅ | C₂H₅ |
| C.596 | CF₃ | CH₃ | 4-F—C₆H₅ | C₂H₅ |
| C.597 | CF₃ | CH₃ | H | CF₃ |
| C.598 | CF₃ | CH₃ | CH₃ | CF₃ |
| C.599 | CF₃ | CH₃ | C₂H₅ | CF₃ |
| C.600 | CF₃ | CH₃ | C₃H₇ | CF₃ |
| C.601 | CF₃ | CH₃ | CH(CH₃)₂ | CF₃ |
| C.602 | CF₃ | CH₃ | cyclopropyl | CF₃ |
| C.603 | CF₃ | CH₃ | CF₃ | CF₃ |
| C.604 | CF₃ | CH₃ | OCH₃ | CF₃ |
| C.605 | CF₃ | CH₃ | C₆H₅ | CF₃ |
| C.606 | CF₃ | CH₃ | 4-F—C₆H₅ | CF₃ |
| C.607 | CF₃ | CH₃ | H | CN |
| C.608 | CF₃ | CH₃ | CH₃ | CN |
| C.609 | CF₃ | CH₃ | C₂H₅ | CN |
| C.610 | CF₃ | CH₃ | C₃H₇ | CN |
| C.611 | CF₃ | CH₃ | CH(CH₃)₂ | CN |
| C.612 | CF₃ | CH₃ | cyclopropyl | CN |
| C.613 | CF₃ | CH₃ | CF₃ | CN |
| C.614 | CF₃ | CH₃ | OCH₃ | CN |
| C.615 | CF₃ | CH₃ | C₆H₅ | CN |
| C.616 | CF₃ | CH₃ | 4-F—C₆H₅ | CN |
| C.617 | CF₃ | CH₃ | H | Cl |
| C.618 | CF₃ | CH₃ | CH₃ | Cl |
| C.619 | CF₃ | CH₃ | C₂H₅ | Cl |
| C.620 | CF₃ | CH₃ | C₃H₇ | Cl |
| C.621 | CF₃ | CH₃ | CH(CH₃)₂ | Cl |
| C.622 | CF₃ | CH₃ | cyclopropyl | Cl |
| C.623 | CF₃ | CH₃ | CF₃ | Cl |
| C.624 | CF₃ | CH₃ | OCH₃ | Cl |
| C.625 | CF₃ | CH₃ | C₆H₅ | Cl |
| C.626 | CF₃ | CH₃ | 4-F—C₆H₅ | Cl |
| C.627 | CF₃ | CF₃ | H | F |
| C.628 | CF₃ | CF₃ | CH₃ | F |
| C.629 | CF₃ | CF₃ | C₂H₅ | F |
| C.630 | CF₃ | CF₃ | C₃H₇ | F |
| C.631 | CF₃ | CF₃ | CH(CH₃)₂ | F |
| C.632 | CF₃ | CF₃ | cyclopropyl | F |
| C.633 | CF₃ | CF₃ | CF₃ | F |
| C.634 | CF₃ | CF₃ | OCH₃ | F |
| C.635 | CF₃ | CF₃ | C₆H₅ | F |
| C.636 | CF₃ | CF₃ | 4-F—C₆H₅ | F |
| C.637 | CF₃ | CF₃ | H | C₂H₅ |
| C.638 | CF₃ | CF₃ | CH₃ | C₂H₅ |
| C.639 | CF₃ | CF₃ | C₂H₅ | C₂H₅ |
| C.640 | CF₃ | CF₃ | C₃H₇ | C₂H₅ |
| C.641 | CF₃ | CF₃ | CH(CH₃)₂ | C₂H₅ |
| C.642 | CF₃ | CF₃ | cyclopropyl | C₂H₅ |
| C.643 | CF₃ | CF₃ | CF₃ | C₂H₅ |
| C.644 | CF₃ | CF₃ | OCH₃ | C₂H₅ |
| C.645 | CF₃ | CF₃ | C₆H₅ | C₂H₅ |
| C.646 | CF₃ | CF₃ | 4-F—C₆H₅ | C₂H₅ |
| C.647 | CF₃ | CF₃ | H | CF₃ |
| C.648 | CF₃ | CF₃ | CH₃ | CF₃ |
| C.649 | CF₃ | CF₃ | C₂H₅ | CF₃ |
| C.650 | CF₃ | CF₃ | C₃H₇ | CF₃ |
| C.651 | CF₃ | CF₃ | CH(CH₃)₂ | CF₃ |
| C.652 | CF₃ | CF₃ | cyclopropyl | CF₃ |
| C.653 | CF₃ | CF₃ | CF₃ | CF₃ |
| C.654 | CF₃ | CF₃ | OCH₃ | CF₃ |
| C.655 | CF₃ | CF₃ | C₆H₅ | CF₃ |
| C.656 | CF₃ | CF₃ | 4-F—C₆H₅ | CF₃ |
| C.657 | CF₃ | CF₃ | H | CN |
| C.658 | CF₃ | CF₃ | CH₃ | CN |
| C.659 | CF₃ | CF₃ | C₂H₅ | CN |
| C.660 | CF₃ | CF₃ | C₃H₇ | CN |
| C.661 | CF₃ | CF₃ | CH(CH₃)₂ | CN |
| C.662 | CF₃ | CF₃ | cyclopropyl | CN |
| C.663 | CF₃ | CF₃ | CF₃ | CN |
| C.664 | CF₃ | CF₃ | OCH₃ | CN |
| C.665 | CF₃ | CF₃ | C₆H₅ | CN |
| C.666 | CF₃ | CF₃ | 4-F—C₆H₅ | CN |
| C.667 | CF₃ | CF₃ | H | Cl |
| C.668 | CF₃ | CF₃ | CH₃ | Cl |
| C.669 | CF₃ | CF₃ | C₂H₅ | Cl |
| C.670 | CF₃ | CF₃ | C₃H₇ | Cl |
| C.671 | CF₃ | CF₃ | CH(CH₃)₂ | Cl |
| C.672 | CF₃ | CF₃ | cyclopropyl | Cl |
| C.673 | CF₃ | CF₃ | CF₃ | Cl |
| C.674 | CF₃ | CF₃ | OCH₃ | Cl |
| C.675 | CF₃ | CF₃ | C₆H₅ | Cl |
| C.676 | CF₃ | CF₃ | 4-F—C₆H₅ | Cl |
| C.677 | Cl | CH₃ | H | F |
| C.678 | Cl | CH₃ | CH₃ | F |
| C.679 | Cl | CH₃ | C₂H₅ | F |
| C.680 | Cl | CH₃ | C₃H₇ | F |
| C.681 | Cl | CH₃ | CH(CH₃)₂ | F |
| C.682 | Cl | CH₃ | cyclopropyl | F |
| C.683 | Cl | CH₃ | CF₃ | F |
| C.684 | Cl | CH₃ | OCH₃ | F |
| C.685 | Cl | CH₃ | C₆H₅ | F |
| C.686 | Cl | CH₃ | 4-F—C₆H₅ | F |
| C.687 | Cl | CH₃ | H | C₂H₅ |
| C.688 | Cl | CH₃ | CH₃ | C₂H₅ |
| C.689 | Cl | CH₃ | C₂H₅ | C₂H₅ |
| C.690 | Cl | CH₃ | C₃H₇ | C₂H₅ |
| C.691 | Cl | CH₃ | CH(CH₃)₂ | C₂H₅ |
| C.692 | Cl | CH₃ | cyclopropyl | C₂H₅ |
| C.693 | Cl | CH₃ | CF₃ | C₂H₅ |
| C.694 | Cl | CH₃ | OCH₃ | C₂H₅ |
| C.695 | Cl | CH₃ | C₆H₅ | C₂H₅ |
| C.696 | Cl | CH₃ | 4-F—C₆H₅ | C₂H₅ |

TABLE C-continued

| No. | $R^3$ | $R^x$ | $R^y$ | $R^z$ |
|---|---|---|---|---|
| C.697 | Cl | $CH_3$ | H | $CF_3$ |
| C.698 | Cl | $CH_3$ | $CH_3$ | $CF_3$ |
| C.699 | Cl | $CH_3$ | $C_2H_5$ | $CF_3$ |
| C.700 | Cl | $CH_3$ | $C_3H_7$ | $CF_3$ |
| C.701 | Cl | $CH_3$ | $CH(CH_3)_2$ | $CF_3$ |
| C.702 | Cl | $CH_3$ | cyclopropyl | $CF_3$ |
| C.703 | Cl | $CH_3$ | $CF_3$ | $CF_3$ |
| C.704 | Cl | $CH_3$ | $OCH_3$ | $CF_3$ |
| C.705 | Cl | $CH_3$ | $C_6H_5$ | $CF_3$ |
| C.706 | Cl | $CH_3$ | 4-F—$C_6H_5$ | $CF_3$ |
| C.707 | Cl | $CH_3$ | H | CN |
| C.708 | Cl | $CH_3$ | $CH_3$ | CN |
| C.709 | Cl | $CH_3$ | $C_2H_5$ | CN |
| C.710 | Cl | $CH_3$ | $C_3H_7$ | CN |
| C.711 | Cl | $CH_3$ | $CH(CH_3)_2$ | CN |
| C.712 | Cl | $CH_3$ | cyclopropyl | CN |
| C.713 | Cl | $CH_3$ | $CF_3$ | CN |
| C.714 | Cl | $CH_3$ | $OCH_3$ | CN |
| C.715 | Cl | $CH_3$ | $C_6H_5$ | CN |
| C.716 | Cl | $CH_3$ | 4-F—$C_6H_5$ | CN |
| C.717 | Cl | $CH_3$ | H | Cl |
| C.718 | Cl | $CH_3$ | $CH_3$ | Cl |
| C.719 | Cl | $CH_3$ | $C_2H_5$ | Cl |
| C.720 | Cl | $CH_3$ | $C_3H_7$ | Cl |
| C.721 | Cl | $CH_3$ | $CH(CH_3)_2$ | Cl |
| C.722 | Cl | $CH_3$ | cyclopropyl | Cl |
| C.723 | Cl | $CH_3$ | $CF_3$ | Cl |
| C.724 | Cl | $CH_3$ | $OCH_3$ | Cl |
| C.725 | Cl | $CH_3$ | $C_6H_5$ | Cl |
| C.726 | Cl | $CH_3$ | 4-F—$C_6H_5$ | Cl |
| C.727 | Cl | $CF_3$ | H | F |
| C.728 | Cl | $CF_3$ | $CH_3$ | F |
| C.729 | Cl | $CF_3$ | $C_2H_5$ | F |
| C.730 | Cl | $CF_3$ | $C_3H_7$ | F |
| C.731 | Cl | $CF_3$ | $CH(CH_3)_2$ | F |
| C.732 | Cl | $CF_3$ | cyclopropyl | F |
| C.733 | Cl | $CF_3$ | $CF_3$ | F |
| C.734 | Cl | $CF_3$ | $OCH_3$ | F |
| C.735 | Cl | $CF_3$ | $C_6H_5$ | F |
| C.736 | Cl | $CF_3$ | 4-F—$C_6H_5$ | F |
| C.737 | Cl | $CF_3$ | H | $C_2H_5$ |
| C.738 | Cl | $CF_3$ | $CH_3$ | $C_2H_5$ |
| C.739 | Cl | $CF_3$ | $C_2H_5$ | $C_2H_5$ |
| C.740 | Cl | $CF_3$ | $C_3H_7$ | $C_2H_5$ |
| C.741 | Cl | $CF_3$ | $CH(CH_3)_2$ | $C_2H_5$ |
| C.742 | Cl | $CF_3$ | cyclopropyl | $C_2H_5$ |
| C.743 | Cl | $CF_3$ | $CF_3$ | $C_2H_5$ |
| C.744 | Cl | $CF_3$ | $OCH_3$ | $C_2H_5$ |
| C.745 | Cl | $CF_3$ | $C_6H_5$ | $C_2H_5$ |
| C.746 | Cl | $CF_3$ | 4-F—$C_6H_5$ | $C_2H_5$ |
| C.747 | Cl | $CF_3$ | H | $CF_3$ |
| C.748 | Cl | $CF_3$ | $CH_3$ | $CF_3$ |
| C.749 | Cl | $CF_3$ | $C_2H_5$ | $CF_3$ |
| C.750 | Cl | $CF_3$ | $C_3H_7$ | $CF_3$ |
| C.751 | Cl | $CF_3$ | $CH(CH_3)_2$ | $CF_3$ |
| C.752 | Cl | $CF_3$ | cyclopropyl | $CF_3$ |
| C.753 | Cl | $CF_3$ | $CF_3$ | $CF_3$ |
| C.754 | Cl | $CF_3$ | $OCH_3$ | $CF_3$ |
| C.755 | Cl | $CF_3$ | $C_6H_5$ | $CF_3$ |
| C.756 | Cl | $CF_3$ | 4-F—$C_6H_5$ | $CF_3$ |
| C.757 | Cl | $CF_3$ | H | CN |
| C.758 | Cl | $CF_3$ | $CH_3$ | CN |
| C.759 | Cl | $CF_3$ | $C_2H_5$ | CN |
| C.760 | Cl | $CF_3$ | $C_3H_7$ | CN |
| C.761 | Cl | $CF_3$ | $CH(CH_3)_2$ | CN |
| C.762 | Cl | $CF_3$ | cyclopropyl | CN |
| C.763 | Cl | $CF_3$ | $CF_3$ | CN |
| C.764 | Cl | $CF_3$ | $OCH_3$ | CN |
| C.765 | Cl | $CF_3$ | $C_6H_5$ | CN |
| C.766 | Cl | $CF_3$ | 4-F—$C_6H_5$ | CN |
| C.767 | Cl | $CF_3$ | H | Cl |
| C.768 | Cl | $CF_3$ | $CH_3$ | Cl |
| C.769 | Cl | $CF_3$ | $C_2H_5$ | Cl |
| C.770 | Cl | $CF_3$ | $C_3H_7$ | Cl |
| C.771 | Cl | $CF_3$ | $CH(CH_3)_2$ | Cl |
| C.772 | Cl | $CF_3$ | cyclopropyl | Cl |
| C.773 | Cl | $CF_3$ | $CF_3$ | Cl |
| C.774 | Cl | $CF_3$ | $OCH_3$ | Cl |
| C.775 | Cl | $CF_3$ | $C_6H_5$ | Cl |
| C.776 | Cl | $CF_3$ | 4-F—$C_6H_5$ | Cl |
| C.777 | $CH_3$ | H | H | F |
| C.778 | $CH_3$ | H | $CH_3$ | F |
| C.779 | $CH_3$ | H | $C_2H_5$ | F |
| C.780 | $CH_3$ | H | $C_3H_7$ | F |
| C.781 | $CH_3$ | H | $CH(CH_3)_2$ | F |
| C.782 | $CH_3$ | H | cyclopropyl | F |
| C.783 | $CH_3$ | H | $CF_3$ | F |
| C.784 | $CH_3$ | H | $OCH_3$ | F |
| C.785 | $CH_3$ | H | $C_6H_5$ | F |
| C.786 | $CH_3$ | H | 4-F—$C_6H_5$ | F |
| C.787 | $CH_3$ | $CH_3$ | H | F |
| C.788 | $CH_3$ | $CH_3$ | $CH_3$ | F |
| C.789 | $CH_3$ | $CH_3$ | $C_2H_5$ | F |
| C.790 | $CH_3$ | $CH_3$ | $C_3H_7$ | F |
| C.791 | $CH_3$ | $CH_3$ | $CH(CH_3)_2$ | F |
| C.792 | $CH_3$ | $CH_3$ | cyclopropyl | F |
| C.793 | $CH_3$ | $CH_3$ | $CF_3$ | F |
| C.794 | $CH_3$ | $CH_3$ | $OCH_3$ | F |
| C.795 | $CH_3$ | $CH_3$ | $C_6H_5$ | F |
| C.796 | $CH_3$ | $CH_3$ | 4-F—$C_6H_5$ | F |
| C.797 | $CH_3$ | $C_2H_5$ | H | F |
| C.798 | $CH_3$ | $C_2H_5$ | $CH_3$ | F |
| C.799 | $CH_3$ | $C_2H_5$ | $C_2H_5$ | F |
| C.800 | $CH_3$ | $C_2H_5$ | $C_3H_7$ | F |
| C.801 | $CH_3$ | $C_2H_5$ | $CH(CH_3)_2$ | F |
| C.802 | $CH_3$ | $C_2H_5$ | cyclopropyl | F |
| C.803 | $CH_3$ | $C_2H_5$ | $CF_3$ | F |
| C.804 | $CH_3$ | $C_2H_5$ | $OCH_3$ | F |
| C.805 | $CH_3$ | $C_2H_5$ | $C_6H_5$ | F |
| C.806 | $CH_3$ | $C_2H_5$ | 4-F—$C_6H_5$ | F |
| C.807 | $CH_3$ | cyclopropyl | H | F |
| C.808 | $CH_3$ | cyclopropyl | $CH_3$ | F |
| C.809 | $CH_3$ | cyclopropyl | $C_2H_5$ | F |
| C.810 | $CH_3$ | cyclopropyl | $C_3H_7$ | F |
| C.811 | $CH_3$ | cyclopropyl | $CH(CH_3)_2$ | F |
| C.812 | $CH_3$ | cyclopropyl | cyclopropyl | F |
| C.813 | $CH_3$ | cyclopropyl | $CF_3$ | F |
| C.814 | $CH_3$ | cyclopropyl | $OCH_3$ | F |
| C.815 | $CH_3$ | cyclopropyl | $C_6H_5$ | F |
| C.816 | $CH_3$ | cyclopropyl | 4-F—$C_6H_5$ | F |
| C.817 | $CH_3$ | $CF_3$ | H | F |
| C.818 | $CH_3$ | $CF_3$ | $CH_3$ | F |
| C.819 | $CH_3$ | $CF_3$ | $C_2H_5$ | F |
| C.820 | $CH_3$ | $CF_3$ | $C_3H_7$ | F |
| C.821 | $CH_3$ | $CF_3$ | $CH(CH_3)_2$ | F |
| C.822 | $CH_3$ | $CF_3$ | cyclopropyl | F |
| C.823 | $CH_3$ | $CF_3$ | $CF_3$ | F |
| C.824 | $CH_3$ | $CF_3$ | $OCH_3$ | F |
| C.825 | $CH_3$ | $CF_3$ | $C_6H_5$ | F |
| C.826 | $CH_3$ | $CF_3$ | 4-F—$C_6H_5$ | F |
| C.827 | $CH_3$ | Cl | H | F |
| C.828 | $CH_3$ | Cl | $CH_3$ | F |
| C.829 | $CH_3$ | Cl | $C_2H_5$ | F |
| C.830 | $CH_3$ | Cl | $C_3H_7$ | F |
| C.831 | $CH_3$ | Cl | $CH(CH_3)_2$ | F |
| C.832 | $CH_3$ | Cl | cyclopropyl | F |
| C.833 | $CH_3$ | Cl | $CF_3$ | F |
| C.834 | $CH_3$ | Cl | $OCH_3$ | F |
| C.835 | $CH_3$ | Cl | $C_6H_5$ | F |
| C.836 | $CH_3$ | Cl | 4-F—$C_6H_5$ | F |
| C.837 | $CH_3$ | F | H | F |
| C.838 | $CH_3$ | F | $CH_3$ | F |
| C.839 | $CH_3$ | F | $C_2H_5$ | F |
| C.840 | $CH_3$ | F | $C_3H_7$ | F |
| C.841 | $CH_3$ | F | $CH(CH_3)_2$ | F |
| C.842 | $CH_3$ | F | cyclopropyl | F |
| C.843 | $CH_3$ | F | $CF_3$ | F |
| C.844 | $CH_3$ | F | $OCH_3$ | F |
| C.845 | $CH_3$ | F | $C_6H_5$ | F |
| C.846 | $CH_3$ | F | 4-F—$C_6H_5$ | F |
| C.847 | $CH_3$ | $OCH_3$ | H | F |
| C.848 | $CH_3$ | $OCH_3$ | $CH_3$ | F |
| C.849 | $CH_3$ | $OCH_3$ | $C_2H_5$ | F |
| C.850 | $CH_3$ | $OCH_3$ | $C_3H_7$ | F |

TABLE C-continued

| No. | R³ | Rˣ | Rʸ | Rᶻ |
|---|---|---|---|---|
| C.851 | CH₃ | OCH₃ | CH(CH₃)₂ | F |
| C.852 | CH₃ | OCH₃ | cyclopropyl | F |
| C.853 | CH₃ | OCH₃ | CF₃ | F |
| C.854 | CH₃ | OCH₃ | OCH₃ | F |
| C.855 | CH₃ | OCH₃ | C₆H₅ | F |
| C.856 | CH₃ | OCH₃ | 4-F—C₆H₅ | F |
| C.857 | CH₃ | H | H | C₂H₅ |
| C.858 | CH₃ | H | CH₃ | C₂H₅ |
| C.859 | CH₃ | H | C₂H₅ | C₂H₅ |
| C.860 | CH₃ | H | C₃H₇ | C₂H₅ |
| C.861 | CH₃ | H | CH(CH₃)₂ | C₂H₅ |
| C.862 | CH₃ | H | cyclopropyl | C₂H₅ |
| C.863 | CH₃ | H | CF₃ | C₂H₅ |
| C.864 | CH₃ | H | OCH₃ | C₂H₅ |
| C.865 | CH₃ | H | C₆H₅ | C₂H₅ |
| C.866 | CH₃ | H | 4-F—C₆H₅ | C₂H₅ |
| C.867 | CH₃ | CH₃ | H | C₂H₅ |
| C.868 | CH₃ | CH₃ | CH₃ | C₂H₅ |
| C.869 | CH₃ | CH₃ | C₂H₅ | C₂H₅ |
| C.870 | CH₃ | CH₃ | C₃H₇ | C₂H₅ |
| C.871 | CH₃ | CH₃ | CH(CH₃)₂ | C₂H₅ |
| C.872 | CH₃ | CH₃ | cyclopropyl | C₂H₅ |
| C.873 | CH₃ | CH₃ | CF₃ | C₂H₅ |
| C.874 | CH₃ | CH₃ | OCH₃ | C₂H₅ |
| C.875 | CH₃ | CH₃ | C₆H₅ | C₂H₅ |
| C.876 | CH₃ | CH₃ | 4-F—C₆H₅ | C₂H₅ |
| C.877 | CH₃ | C₂H₅ | H | C₂H₅ |
| C.878 | CH₃ | C₂H₅ | CH₃ | C₂H₅ |
| C.879 | CH₃ | C₂H₅ | C₂H₅ | C₂H₅ |
| C.880 | CH₃ | C₂H₅ | C₃H₇ | C₂H₅ |
| C.881 | CH₃ | C₂H₅ | CH(CH₃)₂ | C₂H₅ |
| C.882 | CH₃ | C₂H₅ | cyclopropyl | C₂H₅ |
| C.883 | CH₃ | C₂H₅ | CF₃ | C₂H₅ |
| C.884 | CH₃ | C₂H₅ | OCH₃ | C₂H₅ |
| C.885 | CH₃ | C₂H₅ | C₆H₅ | C₂H₅ |
| C.886 | CH₃ | C₂H₅ | 4-F—C₆H₅ | C₂H₅ |
| C.887 | CH₃ | cyclopropyl | H | C₂H₅ |
| C.888 | CH₃ | cyclopropyl | CH₃ | C₂H₅ |
| C.889 | CH₃ | cyclopropyl | C₂H₅ | C₂H₅ |
| C.890 | CH₃ | cyclopropyl | C₃H₇ | C₂H₅ |
| C.891 | CH₃ | cyclopropyl | CH(CH₃)₂ | C₂H₅ |
| C.892 | CH₃ | cyclopropyl | cyclopropyl | C₂H₅ |
| C.893 | CH₃ | cyclopropyl | CF₃ | C₂H₅ |
| C.894 | CH₃ | cyclopropyl | OCH₃ | C₂H₅ |
| C.895 | CH₃ | cyclopropyl | C₆H₅ | C₂H₅ |
| C.896 | CH₃ | cyclopropyl | 4-F—C₆H₅ | C₂H₅ |
| C.897 | CH₃ | CF₃ | H | C₂H₅ |
| C.898 | CH₃ | CF₃ | CH₃ | C₂H₅ |
| C.899 | CH₃ | CF₃ | C₂H₅ | C₂H₅ |
| C.900 | CH₃ | CF₃ | C₃H₇ | C₂H₅ |
| C.901 | CH₃ | CF₃ | CH(CH₃)₂ | C₂H₅ |
| C.902 | CH₃ | CF₃ | cyclopropyl | C₂H₅ |
| C.903 | CH₃ | CF₃ | CF₃ | C₂H₅ |
| C.904 | CH₃ | CF₃ | OCH₃ | C₂H₅ |
| C.905 | CH₃ | CF₃ | C₆H₅ | C₂H₅ |
| C.906 | CH₃ | CF₃ | 4-F—C₆H₅ | C₂H₅ |
| C.907 | CH₃ | Cl | H | C₂H₅ |
| C.908 | CH₃ | Cl | CH₃ | C₂H₅ |
| C.909 | CH₃ | Cl | C₂H₅ | C₂H₅ |
| C.910 | CH₃ | Cl | C₃H₇ | C₂H₅ |
| C.911 | CH₃ | Cl | CH(CH₃)₂ | C₂H₅ |
| C.912 | CH₃ | Cl | cyclopropyl | C₂H₅ |
| C.913 | CH₃ | Cl | CF₃ | C₂H₅ |
| C.914 | CH₃ | Cl | OCH₃ | C₂H₅ |
| C.915 | CH₃ | Cl | C₆H₅ | C₂H₅ |
| C.916 | CH₃ | Cl | 4-F—C₆H₅ | C₂H₅ |
| C.917 | CH₃ | F | H | C₂H₅ |
| C.918 | CH₃ | F | CH₃ | C₂H₅ |
| C.919 | CH₃ | F | C₂H₅ | C₂H₅ |
| C.920 | CH₃ | F | C₃H₇ | C₂H₅ |
| C.921 | CH₃ | F | CH(CH₃)₂ | C₂H₅ |
| C.922 | CH₃ | F | cyclopropyl | C₂H₅ |
| C.923 | CH₃ | F | CF₃ | C₂H₅ |
| C.924 | CH₃ | F | OCH₃ | C₂H₅ |
| C.925 | CH₃ | F | C₆H₅ | C₂H₅ |
| C.926 | CH₃ | F | 4-F—C₆H₅ | C₂H₅ |
| C.927 | CH₃ | OCH₃ | H | C₂H₅ |
| C.928 | CH₃ | OCH₃ | CH₃ | C₂H₅ |
| C.929 | CH₃ | OCH₃ | C₂H₅ | C₂H₅ |
| C.930 | CH₃ | OCH₃ | C₃H₇ | C₂H₅ |
| C.931 | CH₃ | OCH₃ | CH(CH₃)₂ | C₂H₅ |
| C.932 | CH₃ | OCH₃ | cyclopropyl | C₂H₅ |
| C.933 | CH₃ | OCH₃ | CF₃ | C₂H₅ |
| C.934 | CH₃ | OCH₃ | OCH₃ | C₂H₅ |
| C.935 | CH₃ | OCH₃ | C₆H₅ | C₂H₅ |
| C.936 | CH₃ | OCH₃ | 4-F—C₆H₅ | C₂H₅ |
| C.937 | CH₃ | H | H | CF₃ |
| C.938 | CH₃ | H | CH₃ | CF₃ |
| C.939 | CH₃ | H | C₂H₅ | CF₃ |
| C.940 | CH₃ | H | C₃H₇ | CF₃ |
| C.941 | CH₃ | H | CH(CH₃)₂ | CF₃ |
| C.942 | CH₃ | H | cyclopropyl | CF₃ |
| C.943 | CH₃ | H | CF₃ | CF₃ |
| C.944 | CH₃ | H | OCH₃ | CF₃ |
| C.945 | CH₃ | H | C₆H₅ | CF₃ |
| C.946 | CH₃ | H | 4-F—C₆H₅ | CF₃ |
| C.947 | CH₃ | CH₃ | H | CF₃ |
| C.948 | CH₃ | CH₃ | CH₃ | CF₃ |
| C.949 | CH₃ | CH₃ | C₂H₅ | CF₃ |
| C.950 | CH₃ | CH₃ | C₃H₇ | CF₃ |
| C.951 | CH₃ | CH₃ | CH(CH₃)₂ | CF₃ |
| C.952 | CH₃ | CH₃ | cyclopropyl | CF₃ |
| C.953 | CH₃ | CH₃ | CF₃ | CF₃ |
| C.954 | CH₃ | CH₃ | OCH₃ | CF₃ |
| C.955 | CH₃ | CH₃ | C₆H₅ | CF₃ |
| C.956 | CH₃ | CH₃ | 4-F—C₆H₅ | CF₃ |
| C.957 | CH₃ | C₂H₅ | H | CF₃ |
| C.958 | CH₃ | C₂H₅ | CH₃ | CF₃ |
| C.959 | CH₃ | C₂H₅ | C₂H₅ | CF₃ |
| C.960 | CH₃ | C₂H₅ | C₃H₇ | CF₃ |
| C.961 | CH₃ | C₂H₅ | CH(CH₃)₂ | CF₃ |
| C.962 | CH₃ | C₂H₅ | cyclopropyl | CF₃ |
| C.963 | CH₃ | C₂H₅ | CF₃ | CF₃ |
| C.964 | CH₃ | C₂H₅ | OCH₃ | CF₃ |
| C.965 | CH₃ | C₂H₅ | C₆H₅ | CF₃ |
| C.966 | CH₃ | C₂H₅ | 4-F—C₆H₅ | CF₃ |
| C.967 | CH₃ | cyclopropyl | H | CF₃ |
| C.968 | CH₃ | cyclopropyl | CH₃ | CF₃ |
| C.969 | CH₃ | cyclopropyl | C₂H₅ | CF₃ |
| C.970 | CH₃ | cyclopropyl | C₃H₇ | CF₃ |
| C.971 | CH₃ | cyclopropyl | CH(CH₃)₂ | CF₃ |
| C.972 | CH₃ | cyclopropyl | cyclopropyl | CF₃ |
| C.973 | CH₃ | cyclopropyl | CF₃ | CF₃ |
| C.974 | CH₃ | cyclopropyl | OCH₃ | CF₃ |
| C.975 | CH₃ | cyclopropyl | C₆H₅ | CF₃ |
| C.976 | CH₃ | cyclopropyl | 4-F—C₆H₅ | CF₃ |
| C.977 | CH₃ | CF₃ | H | CF₃ |
| C.978 | CH₃ | CF₃ | CH₃ | CF₃ |
| C.979 | CH₃ | CF₃ | C₂H₅ | CF₃ |
| C.980 | CH₃ | CF₃ | C₃H₇ | CF₃ |
| C.981 | CH₃ | CF₃ | CH(CH₃)₂ | CF₃ |
| C.982 | CH₃ | CF₃ | cyclopropyl | CF₃ |
| C.983 | CH₃ | CF₃ | CF₃ | CF₃ |
| C.984 | CH₃ | CF₃ | OCH₃ | CF₃ |
| C.985 | CH₃ | CF₃ | C₆H₅ | CF₃ |
| C.986 | CH₃ | CF₃ | 4-F—C₆H₅ | CF₃ |
| C.987 | CH₃ | Cl | H | CF₃ |
| C.988 | CH₃ | Cl | CH₃ | CF₃ |
| C.989 | CH₃ | Cl | C₂H₅ | CF₃ |
| C.990 | CH₃ | Cl | C₃H₇ | CF₃ |
| C.991 | CH₃ | Cl | CH(CH₃)₂ | CF₃ |
| C.992 | CH₃ | Cl | cyclopropyl | CF₃ |
| C.993 | CH₃ | Cl | CF₃ | CF₃ |
| C.994 | CH₃ | Cl | OCH₃ | CF₃ |
| C.995 | CH₃ | Cl | C₆H₅ | CF₃ |
| C.996 | CH₃ | Cl | 4-F—C₆H₅ | CF₃ |
| C.997 | CH₃ | F | H | CF₃ |
| C.998 | CH₃ | F | CH₃ | CF₃ |
| C.999 | CH₃ | F | C₂H₅ | CF₃ |
| C.1000 | CH₃ | F | C₃H₇ | CF₃ |
| C.1001 | CH₃ | F | CH(CH₃)₂ | CF₃ |
| C.1002 | CH₃ | F | cyclopropyl | CF₃ |
| C.1003 | CH₃ | F | CF₃ | CF₃ |
| C.1004 | CH₃ | F | OCH₃ | CF₃ |

TABLE C-continued

| No. | $R^3$ | $R^x$ | $R^y$ | $R^z$ |
|---|---|---|---|---|
| C.1005 | $CH_3$ | F | $C_6H_5$ | $CF_3$ |
| C.1006 | $CH_3$ | F | 4-F—$C_6H_5$ | $CF_3$ |
| C.1007 | $CH_3$ | $OCH_3$ | H | $CF_3$ |
| C.1008 | $CH_3$ | $OCH_3$ | $CH_3$ | $CF_3$ |
| C.1009 | $CH_3$ | $OCH_3$ | $C_2H_5$ | $CF_3$ |
| C.1010 | $CH_3$ | $OCH_3$ | $C_3H_7$ | $CF_3$ |
| C.1011 | $CH_3$ | $OCH_3$ | $CH(CH_3)_2$ | $CF_3$ |
| C.1012 | $CH_3$ | $OCH_3$ | cyclopropyl | $CF_3$ |
| C.1013 | $CH_3$ | $OCH_3$ | $CF_3$ | $CF_3$ |
| C.1014 | $CH_3$ | $OCH_3$ | $OCH_3$ | $CF_3$ |
| C.1015 | $CH_3$ | $OCH_3$ | $C_6H_5$ | $CF_3$ |
| C.1016 | $CH_3$ | $OCH_3$ | 4-F—$C_6H_5$ | $CF_3$ |
| C.1017 | $CH_3$ | H | H | CN |
| C.1018 | $CH_3$ | H | $CH_3$ | CN |
| C.1019 | $CH_3$ | H | $C_2H_5$ | CN |
| C.1020 | $CH_3$ | H | $C_3H_7$ | CN |
| C.1021 | $CH_3$ | H | $CH(CH_3)_2$ | CN |
| C.1022 | $CH_3$ | H | cyclopropyl | CN |
| C.1023 | $CH_3$ | H | $CF_3$ | CN |
| C.1024 | $CH_3$ | H | $OCH_3$ | CN |
| C.1025 | $CH_3$ | H | $C_6H_5$ | CN |
| C.1026 | $CH_3$ | H | 4-F—$C_6H_5$ | CN |
| C.1027 | $CH_3$ | $CH_3$ | H | CN |
| C.1028 | $CH_3$ | $CH_3$ | $CH_3$ | CN |
| C.1029 | $CH_3$ | $CH_3$ | $C_2H_5$ | CN |
| C.1030 | $CH_3$ | $CH_3$ | $C_3H_7$ | CN |
| C.1031 | $CH_3$ | $CH_3$ | $CH(CH_3)_2$ | CN |
| C.1032 | $CH_3$ | $CH_3$ | cyclopropyl | CN |
| C.1033 | $CH_3$ | $CH_3$ | $CF_3$ | CN |
| C.1034 | $CH_3$ | $CH_3$ | $OCH_3$ | CN |
| C.1035 | $CH_3$ | $CH_3$ | $C_6H_5$ | CN |
| C.1036 | $CH_3$ | $CH_3$ | 4-F—$C_6H_5$ | CN |
| C.1037 | $CH_3$ | $C_2H_5$ | H | CN |
| C.1038 | $CH_3$ | $C_2H_5$ | $CH_3$ | CN |
| C.1039 | $CH_3$ | $C_2H_5$ | $C_2H_5$ | CN |
| C.1040 | $CH_3$ | $C_2H_5$ | $C_3H_7$ | CN |
| C.1041 | $CH_3$ | $C_2H_5$ | $CH(CH_3)_2$ | CN |
| C.1042 | $CH_3$ | $C_2H_5$ | cyclopropyl | CN |
| C.1043 | $CH_3$ | $C_2H_5$ | $CF_3$ | CN |
| C.1044 | $CH_3$ | $C_2H_5$ | $OCH_3$ | CN |
| C.1045 | $CH_3$ | $C_2H_5$ | $C_6H_5$ | CN |
| C.1046 | $CH_3$ | $C_2H_5$ | 4-F—$C_6H_5$ | CN |
| C.1047 | $CH_3$ | cyclopropyl | H | CN |
| C.1048 | $CH_3$ | cyclopropyl | $CH_3$ | CN |
| C.1049 | $CH_3$ | cyclopropyl | $C_2H_5$ | CN |
| C.1050 | $CH_3$ | cyclopropyl | $C_3H_7$ | CN |
| C.1051 | $CH_3$ | cyclopropyl | $CH(CH_3)_2$ | CN |
| C.1052 | $CH_3$ | cyclopropyl | cyclopropyl | CN |
| C.1053 | $CH_3$ | cyclopropyl | $CF_3$ | CN |
| C.1054 | $CH_3$ | cyclopropyl | $OCH_3$ | CN |
| C.1055 | $CH_3$ | cyclopropyl | $C_6H_5$ | CN |
| C.1056 | $CH_3$ | cyclopropyl | 4-F—$C_6H_5$ | CN |
| C.1057 | $CH_3$ | $CF_3$ | H | CN |
| C.1058 | $CH_3$ | $CF_3$ | $CH_3$ | CN |
| C.1059 | $CH_3$ | $CF_3$ | $C_2H_5$ | CN |
| C.1060 | $CH_3$ | $CF_3$ | $C_3H_7$ | CN |
| C.1061 | $CH_3$ | $CF_3$ | $CH(CH_3)_2$ | CN |
| C.1062 | $CH_3$ | $CF_3$ | cyclopropyl | CN |
| C.1063 | $CH_3$ | $CF_3$ | $CF_3$ | CN |
| C.1064 | $CH_3$ | $CF_3$ | $OCH_3$ | CN |
| C.1065 | $CH_3$ | $CF_3$ | $C_6H_5$ | CN |
| C.1066 | $CH_3$ | $CF_3$ | 4-F—$C_6H_5$ | CN |
| C.1067 | $CH_3$ | Cl | H | CN |
| C.1068 | $CH_3$ | Cl | $CH_3$ | CN |
| C.1069 | $CH_3$ | Cl | $C_2H_5$ | CN |
| C.1070 | $CH_3$ | Cl | $C_3H_7$ | CN |
| C.1071 | $CH_3$ | Cl | $CH(CH_3)_2$ | CN |
| C.1072 | $CH_3$ | Cl | cyclopropyl | CN |
| C.1073 | $CH_3$ | Cl | $CF_3$ | CN |
| C.1074 | $CH_3$ | Cl | $OCH_3$ | CN |
| C.1075 | $CH_3$ | Cl | $C_6H_5$ | CN |
| C.1076 | $CH_3$ | Cl | 4-F—$C_6H_5$ | CN |
| C.1077 | $CH_3$ | F | H | CN |
| C.1078 | $CH_3$ | F | $CH_3$ | CN |
| C.1079 | $CH_3$ | F | $C_2H_5$ | CN |
| C.1080 | $CH_3$ | F | $C_3H_7$ | CN |
| C.1081 | $CH_3$ | F | $CH(CH_3)_2$ | CN |
| C.1082 | $CH_3$ | F | cyclopropyl | CN |
| C.1083 | $CH_3$ | F | $CF_3$ | CN |
| C.1084 | $CH_3$ | F | $OCH_3$ | CN |
| C.1085 | $CH_3$ | F | $C_6H_5$ | CN |
| C.1086 | $CH_3$ | F | 4-F—$C_6H_5$ | CN |
| C.1087 | $CH_3$ | $OCH_3$ | H | CN |
| C.1088 | $CH_3$ | $OCH_3$ | $CH_3$ | CN |
| C.1089 | $CH_3$ | $OCH_3$ | $C_2H_5$ | CN |
| C.1090 | $CH_3$ | $OCH_3$ | $C_3H_7$ | CN |
| C.1091 | $CH_3$ | $OCH_3$ | $CH(CH_3)_2$ | CN |
| C.1092 | $CH_3$ | $OCH_3$ | cyclopropyl | CN |
| C.1093 | $CH_3$ | $OCH_3$ | $CF_3$ | CN |
| C.1094 | $CH_3$ | $OCH_3$ | $OCH_3$ | CN |
| C.1095 | $CH_3$ | $OCH_3$ | $C_6H_5$ | CN |
| C.1096 | $CH_3$ | $OCH_3$ | 4-F—$C_6H_5$ | CN |
| C.1097 | $CH_3$ | H | H | Cl |
| C.1098 | $CH_3$ | H | $CH_3$ | Cl |
| C.1099 | $CH_3$ | H | $C_2H_5$ | Cl |
| C.1100 | $CH_3$ | H | $C_3H_7$ | Cl |
| C.1101 | $CH_3$ | H | $CH(CH_3)_2$ | Cl |
| C.1102 | $CH_3$ | H | cyclopropyl | Cl |
| C.1103 | $CH_3$ | H | $CF_3$ | Cl |
| C.1104 | $CH_3$ | H | $OCH_3$ | Cl |
| C.1105 | $CH_3$ | H | $C_6H_5$ | Cl |
| C.1106 | $CH_3$ | H | 4-F—$C_6H_5$ | Cl |
| C.1107 | $CH_3$ | $CH_3$ | H | Cl |
| C.1108 | $CH_3$ | $CH_3$ | $CH_3$ | Cl |
| C.1109 | $CH_3$ | $CH_3$ | $C_2H_5$ | Cl |
| C.1110 | $CH_3$ | $CH_3$ | $C_3H_7$ | Cl |
| C.1111 | $CH_3$ | $CH_3$ | $CH(CH_3)_2$ | Cl |
| C.1112 | $CH_3$ | $CH_3$ | cyclopropyl | Cl |
| C.1113 | $CH_3$ | $CH_3$ | $CF_3$ | Cl |
| C.1114 | $CH_3$ | $CH_3$ | $OCH_3$ | Cl |
| C.1115 | $CH_3$ | $CH_3$ | $C_6H_5$ | Cl |
| C.1116 | $CH_3$ | $CH_3$ | 4-F—$C_6H_5$ | Cl |
| C.1117 | $CH_3$ | $C_2H_5$ | H | Cl |
| C.1118 | $CH_3$ | $C_2H_5$ | $CH_3$ | Cl |
| C.1119 | $CH_3$ | $C_2H_5$ | $C_2H_5$ | Cl |
| C.1120 | $CH_3$ | $C_2H_5$ | $C_3H_7$ | Cl |
| C.1121 | $CH_3$ | $C_2H_5$ | $CH(CH_3)_2$ | Cl |
| C.1122 | $CH_3$ | $C_2H_5$ | cyclopropyl | Cl |
| C.1123 | $CH_3$ | $C_2H_5$ | $CF_3$ | Cl |
| C.1124 | $CH_3$ | $C_2H_5$ | $OCH_3$ | Cl |
| C.1125 | $CH_3$ | $C_2H_5$ | $C_6H_5$ | Cl |
| C.1126 | $CH_3$ | $C_2H_5$ | 4-F—$C_6H_5$ | Cl |
| C.1127 | $CH_3$ | cyclopropyl | H | Cl |
| C.1128 | $CH_3$ | cyclopropyl | $CH_3$ | Cl |
| C.1129 | $CH_3$ | cyclopropyl | $C_2H_5$ | Cl |
| C.1130 | $CH_3$ | cyclopropyl | $C_3H_7$ | Cl |
| C.1131 | $CH_3$ | cyclopropyl | $CH(CH_3)_2$ | Cl |
| C.1132 | $CH_3$ | cyclopropyl | cyclopropyl | Cl |
| C.1133 | $CH_3$ | cyclopropyl | $CF_3$ | Cl |
| C.1134 | $CH_3$ | cyclopropyl | $OCH_3$ | Cl |
| C.1135 | $CH_3$ | cyclopropyl | $C_6H_5$ | Cl |
| C.1136 | $CH_3$ | cyclopropyl | 4-F—$C_6H_5$ | Cl |
| C.1137 | $CH_3$ | $CF_3$ | H | Cl |
| C.1138 | $CH_3$ | $CF_3$ | $CH_3$ | Cl |
| C.1139 | $CH_3$ | $CF_3$ | $C_2H_5$ | Cl |
| C.1140 | $CH_3$ | $CF_3$ | $C_3H_7$ | Cl |
| C.1141 | $CH_3$ | $CF_3$ | $CH(CH_3)_2$ | Cl |
| C.1142 | $CH_3$ | $CF_3$ | cyclopropyl | Cl |
| C.1143 | $CH_3$ | $CF_3$ | $CF_3$ | Cl |
| C.1144 | $CH_3$ | $CF_3$ | $OCH_3$ | Cl |
| C.1145 | $CH_3$ | $CF_3$ | $C_6H_5$ | Cl |
| C.1146 | $CH_3$ | $CF_3$ | 4-F—$C_6H_5$ | Cl |
| C.1147 | $CH_3$ | Cl | H | Cl |
| C.1148 | $CH_3$ | Cl | $CH_3$ | Cl |
| C.1149 | $CH_3$ | Cl | $C_2H_5$ | Cl |
| C.1150 | $CH_3$ | Cl | $C_3H_7$ | Cl |
| C.1151 | $CH_3$ | Cl | $CH(CH_3)_2$ | Cl |
| C.1152 | $CH_3$ | Cl | cyclopropyl | Cl |
| C.1153 | $CH_3$ | Cl | $CF_3$ | Cl |
| C.1154 | $CH_3$ | Cl | $OCH_3$ | Cl |
| C.1155 | $CH_3$ | Cl | $C_6H_5$ | Cl |
| C.1156 | $CH_3$ | Cl | 4-F—$C_6H_5$ | Cl |
| C.1157 | $CH_3$ | F | H | Cl |
| C.1158 | $CH_3$ | F | $CH_3$ | Cl |

TABLE C-continued

| No. | R³ | Rˣ | Rʸ | Rᶻ |
|---|---|---|---|---|
| C.1159 | CH₃ | F | C₂H₅ | Cl |
| C.1160 | CH₃ | F | C₃H₇ | Cl |
| C.1161 | CH₃ | F | CH(CH₃)₂ | Cl |
| C.1162 | CH₃ | F | cyclopropyl | Cl |
| C.1163 | CH₃ | F | CF₃ | Cl |
| C.1164 | CH₃ | F | OCH₃ | Cl |
| C.1165 | CH₃ | F | C₆H₅ | Cl |
| C.1166 | CH₃ | F | 4-F—C₆H₅ | Cl |
| C.1167 | CH₃ | OCH₃ | H | Cl |
| C.1168 | CH₃ | OCH₃ | CH₃ | Cl |
| C.1169 | CH₃ | OCH₃ | C₂H₅ | Cl |
| C.1170 | CH₃ | OCH₃ | C₃H₇ | Cl |
| C.1171 | CH₃ | OCH₃ | CH(CH₃)₂ | Cl |
| C.1172 | CH₃ | OCH₃ | cyclopropyl | Cl |
| C.1173 | CH₃ | OCH₃ | CF₃ | Cl |
| C.1174 | CH₃ | OCH₃ | OCH₃ | Cl |
| C.1175 | CH₃ | OCH₃ | C₆H₅ | Cl |
| C.1176 | CH₃ | OCH₃ | 4-F—C₆H₅ | Cl |
| C.1177 | CH₃ | CH₃ | CH₂CH₂ | |
| C.1178 | CH₃ | CF₃ | CH₂CH₂ | |
| C.1179 | CF₃ | CH₃ | CH₂CH₂ | |
| C.1180 | CH₃ | C₂H₅ | CH₂CH₂ | |
| C.1181 | C₂H₅ | CH₃ | CH₂CH₂ | |
| C.1182 | Cl | CH₃ | CH₂CH₂ | |
| C.1183 | CH₃ | Cl | CH₂CH₂ | |
| C.1184 | CH₃ | CH₃ | CH₂CH₂CH₂ | |
| C.1185 | CH₃ | CF₃ | CH₂CH₂CH₂ | |
| C.1186 | CF₃ | CH₃ | CH₂CH₂CH₂ | |
| C.1187 | CH₃ | C₂H₅ | CH₂CH₂CH₂ | |
| C.1188 | C₂H₅ | CH₃ | CH₂CH₂CH₂ | |
| C.1189 | Cl | CH₃ | CH₂CH₂CH₂ | |
| C.1190 | CH₃ | Cl | CH₂CH₂CH₂ | |
| C.1191 | CH₃ | CH₃ | CH₂CH₂CH₂CH₂ | |
| C.1192 | CH₃ | CF₃ | CH₂CH₂CH₂CH₂ | |
| C.1193 | CF₃ | CH₃ | CH₂CH₂CH₂CH₂ | |
| C.1194 | CH₃ | C₂H₅ | CH₂CH₂CH₂CH₂ | |
| C.1195 | C₂H₅ | CH₃ | CH₂CH₂CH₂CH₂ | |
| C.1196 | Cl | CH₃ | CH₂CH₂CH₂CH₂ | |
| C.1197 | CH₃ | Cl | CH₂CH₂CH₂CH₂ | |
| C.1198 | CH₂CH₃ | CH₃ | H | H |
| C.1199 | CH₂CH₃ | CH₃ | CH₃ | H |
| C.1200 | CH₂CH₃ | CH₃ | C₂H₅ | H |
| C.1201 | CH₂CH₃ | CH₃ | C₃H₇ | H |
| C.1202 | CH₂CH₃ | CH₃ | C₄H₉ | H |
| C.1203 | CH₂CH₃ | CH₃ | CH(CH₃)₂ | H |
| C.1204 | CH₂CH₃ | CH₃ | cyclopropyl | H |
| C.1205 | CH₂CH₃ | CH₃ | CF₃ | H |
| C.1206 | CH₂CH₃ | CH₃ | OCH₃ | H |
| C.1207 | CH₂CH₃ | CH₃ | OC₂H₅ | H |
| C.1208 | CH₂CH₃ | CH₃ | CH₂—C₆H₅ | H |
| C.1209 | CH₂CH₃ | CH₃ | CH(CH₃)C₆H₅ | H |
| C.1210 | CH₂CH₃ | CH₃ | C₆H₅ | H |
| C.1211 | CH₂CH₃ | CH₃ | 4-F—C₆H₅ | H |
| C.1212 | CH₂CH₃ | CH₃ | 4-Cl-2-pyridyl | H |
| C.1213 | CH₂CH₃ | CH₃ | F | H |
| C.1214 | CH₂CH₃ | CH₃ | CN | H |
| C.1215 | CH₂CH₃ | C₂H₅ | H | H |
| C.1216 | CH₂CH₃ | C₂H₅ | CH₃ | H |
| C.1217 | CH₂CH₃ | C₂H₅ | C₂H₅ | H |
| C.1218 | CH₂CH₃ | C₂H₅ | C₃H₇ | H |
| C.1219 | CH₂CH₃ | C₂H₅ | C₄H₉ | H |
| C.1220 | CH₂CH₃ | C₂H₅ | CH(CH₃)₂ | H |
| C.1221 | CH₂CH₃ | C₂H₅ | cyclopropyl | H |
| C.1222 | CH₂CH₃ | C₂H₅ | CF₃ | H |
| C.1223 | CH₂CH₃ | C₂H₅ | OCH₃ | H |
| C.1224 | CH₂CH₃ | C₂H₅ | OC₂H₅ | H |
| C.1225 | CH₂CH₃ | C₂H₅ | CH₂—C₆H₅ | H |
| C.1226 | CH₂CH₃ | C₂H₅ | CH(CH₃)C₆H₅ | H |
| C.1227 | CH₂CH₃ | C₂H₅ | C₆H₅ | H |
| C.1228 | CH₂CH₃ | C₂H₅ | 4-F—C₆H₅ | H |
| C.1229 | CH₂CH₃ | C₂H₅ | 4-Cl-2-pyridyl | H |
| C.1230 | CH₂CH₃ | C₂H₅ | F | H |
| C.1231 | CH₂CH₃ | C₂H₅ | CN | H |
| C.1232 | CH₂CH₃ | CF₃ | H | H |
| C.1233 | CH₂CH₃ | CF₃ | CH₃ | H |
| C.1234 | CH₂CH₃ | CF₃ | C₂H₅ | H |
| C.1235 | CH₂CH₃ | CF₃ | C₃H₇ | H |
| C.1236 | CH₂CH₃ | CF₃ | C₄H₉ | H |
| C.1237 | CH₂CH₃ | CF₃ | CH(CH₃)₂ | H |
| C.1238 | CH₂CH₃ | CF₃ | cyclopropyl | H |
| C.1239 | CH₂CH₃ | CF₃ | CF₃ | H |
| C.1240 | CH₂CH₃ | CF₃ | OCH₃ | H |
| C.1241 | CH₂CH₃ | CF₃ | OC₂H₅ | H |
| C.1242 | CH₂CH₃ | CF₃ | CH₂—C₆H₅ | H |
| C.1243 | CH₂CH₃ | CF₃ | CH(CH₃)C₆H₅ | H |
| C.1244 | CH₂CH₃ | CF₃ | C₆H₅ | H |
| C.1245 | CH₂CH₃ | CF₃ | 4-F—C₆H₅ | H |
| C.1246 | CH₂CH₃ | CF₃ | 4-Cl-2-pyridyl | H |
| C.1247 | CH₂CH₃ | CF₃ | F | H |
| C.1248 | CH₂CH₃ | CF₃ | CN | H |
| C.1249 | CH₂CH₃ | Cl | H | H |
| C.1250 | CH₂CH₃ | Cl | CH₃ | H |
| C.1251 | CH₂CH₃ | Cl | C₂H₅ | H |
| C.1252 | CH₂CH₃ | Cl | C₃H₇ | H |
| C.1253 | CH₂CH₃ | Cl | C₄H₉ | H |
| C.1254 | CH₂CH₃ | Cl | CH(CH₃)₂ | H |
| C.1255 | CH₂CH₃ | Cl | cyclopropyl | H |
| C.1256 | CH₂CH₃ | Cl | CF₃ | H |
| C.1257 | CH₂CH₃ | Cl | OCH₃ | H |
| C.1258 | CH₂CH₃ | Cl | OC₂H₅ | H |
| C.1259 | CH₂CH₃ | Cl | CH₂—C₆H₅ | H |
| C.1260 | CH₂CH₃ | Cl | CH(CH₃)C₆H₅ | H |
| C.1261 | CH₂CH₃ | Cl | C₆H₅ | H |
| C.1262 | CH₂CH₃ | Cl | 4-F—C₆H₅ | H |
| C.1263 | CH₂CH₃ | Cl | 4-Cl-2-pyridyl | H |
| C.1264 | CH₂CH₃ | Cl | F | H |
| C.1265 | CH₂CH₃ | Cl | CN | H |
| C.1266 | CH₂CH₃ | OCH₃ | H | H |
| C.1267 | CH₂CH₃ | OCH₃ | CH₃ | H |
| C.1268 | CH₂CH₃ | OCH₃ | C₂H₅ | H |
| C.1269 | CH₂CH₃ | OCH₃ | C₃H₇ | H |
| C.1270 | CH₂CH₃ | OCH₃ | C₄H₉ | H |
| C.1271 | CH₂CH₃ | OCH₃ | CH(CH₃)₂ | H |
| C.1272 | CH₂CH₃ | OCH₃ | cyclopropyl | H |
| C.1273 | CH₂CH₃ | OCH₃ | CF₃ | H |
| C.1274 | CH₂CH₃ | OCH₃ | OCH₃ | H |
| C.1275 | CH₂CH₃ | OCH₃ | OC₂H₅ | H |
| C.1276 | CH₂CH₃ | OCH₃ | CH₂—C₆H₅ | H |
| C.1277 | CH₂CH₃ | OCH₃ | CH(CH₃)C₆H₅ | H |
| C.1278 | CH₂CH₃ | OCH₃ | C₆H₅ | H |
| C.1279 | CH₂CH₃ | OCH₃ | 4-F—C₆H₅ | H |
| C.1280 | CH₂CH₃ | OCH₃ | 4-Cl-2-pyridyl | H |
| C.1281 | CH₂CH₃ | OCH₃ | F | H |
| C.1282 | CH₂CH₃ | OCH₃ | CN | H |
| C.1283 | CH₂CH₃ | CH₃ | H | CH₃ |
| C.1284 | CH₂CH₃ | CH₃ | CH₃ | CH₃ |
| C.1285 | CH₂CH₃ | CH₃ | C₂H₅ | CH₃ |
| C.1286 | CH₂CH₃ | CH₃ | C₃H₇ | CH₃ |
| C.1287 | CH₂CH₃ | CH₃ | C₄H₉ | CH₃ |
| C.1288 | CH₂CH₃ | CH₃ | CH(CH₃)₂ | CH₃ |
| C.1289 | CH₂CH₃ | CH₃ | cyclopropyl | CH₃ |
| C.1290 | CH₂CH₃ | CH₃ | CF₃ | CH₃ |
| C.1291 | CH₂CH₃ | CH₃ | OCH₃ | CH₃ |
| C.1292 | CH₂CH₃ | CH₃ | OC₂H₅ | CH₃ |
| C.1293 | CH₂CH₃ | CH₃ | CH₂—C₆H₅ | CH₃ |
| C.1294 | CH₂CH₃ | CH₃ | CH(CH₃)C₆H₅ | CH₃ |
| C.1295 | CH₂CH₃ | CH₃ | C₆H₅ | CH₃ |
| C.1296 | CH₂CH₃ | CH₃ | 4-F—C₆H₅ | CH₃ |
| C.1297 | CH₂CH₃ | CH₃ | 4-Cl-2-pyridyl | CH₃ |
| C.1298 | CH₂CH₃ | CH₃ | F | CH₃ |
| C.1299 | CH₂CH₃ | CH₃ | CN | CH₃ |
| C.1300 | CH₂CH₃ | C₂H₅ | H | CH₃ |
| C.1301 | CH₂CH₃ | C₂H₅ | CH₃ | CH₃ |
| C.1302 | CH₂CH₃ | C₂H₅ | C₂H₅ | CH₃ |
| C.1303 | CH₂CH₃ | C₂H₅ | C₃H₇ | CH₃ |
| C.1304 | CH₂CH₃ | C₂H₅ | C₄H₉ | CH₃ |
| C.1305 | CH₂CH₃ | C₂H₅ | CH(CH₃)₂ | CH₃ |
| C.1306 | CH₂CH₃ | C₂H₅ | cyclopropyl | CH₃ |
| C.1307 | CH₂CH₃ | C₂H₅ | CF₃ | CH₃ |
| C.1308 | CH₂CH₃ | C₂H₅ | OCH₃ | CH₃ |
| C.1309 | CH₂CH₃ | C₂H₅ | OC₂H₅ | CH₃ |
| C.1310 | CH₂CH₃ | C₂H₅ | CH₂—C₆H₅ | CH₃ |
| C.1311 | CH₂CH₃ | C₂H₅ | CH(CH₃)C₆H₅ | CH₃ |
| C.1312 | CH₂CH₃ | C₂H₅ | C₆H₅ | CH₃ |

TABLE C-continued

| No. | $R^3$ | $R^x$ | $R^y$ | $R^z$ |
|---|---|---|---|---|
| C.1313 | $CH_2CH_3$ | $C_2H_5$ | $4\text{-}F\text{---}C_6H_5$ | $CH_3$ |
| C.1314 | $CH_2CH_3$ | $C_2H_5$ | 4-Cl-2-pyridyl | $CH_3$ |
| C.1315 | $CH_2CH_3$ | $C_2H_5$ | F | $CH_3$ |
| C.1316 | $CH_2CH_3$ | $C_2H_5$ | CN | $CH_3$ |
| C.1317 | $CH_2CH_3$ | $CF_3$ | H | $CH_3$ |
| C.1318 | $CH_2CH_3$ | $CF_3$ | $CH_3$ | $CH_3$ |
| C.1319 | $CH_2CH_3$ | $CF_3$ | $C_2H_5$ | $CH_3$ |
| C.1320 | $CH_2CH_3$ | $CF_3$ | $C_3H_7$ | $CH_3$ |
| C.1321 | $CH_2CH_3$ | $CF_3$ | $C_4H_9$ | $CH_3$ |
| C.1322 | $CH_2CH_3$ | $CF_3$ | $CH(CH_3)_2$ | $CH_3$ |
| C.1323 | $CH_2CH_3$ | $CF_3$ | cyclopropyl | $CH_3$ |
| C.1324 | $CH_2CH_3$ | $CF_3$ | $CF_3$ | $CH_3$ |
| C.1325 | $CH_2CH_3$ | $CF_3$ | $OCH_3$ | $CH_3$ |
| C.1326 | $CH_2CH_3$ | $CF_3$ | $OC_2H_5$ | $CH_3$ |
| C.1327 | $CH_2CH_3$ | $CF_3$ | $CH_2\text{---}C_6H_5$ | $CH_3$ |
| C.1328 | $CH_2CH_3$ | $CF_3$ | $CH(CH_3)C_6H_5$ | $CH_3$ |
| C.1329 | $CH_2CH_3$ | $CF_3$ | $C_6H_5$ | $CH_3$ |
| C.1330 | $CH_2CH_3$ | $CF_3$ | $4\text{-}F\text{---}C_6H_5$ | $CH_3$ |
| C.1331 | $CH_2CH_3$ | $CF_3$ | 4-Cl-2-pyridyl | $CH_3$ |
| C.1332 | $CH_2CH_3$ | $CF_3$ | F | $CH_3$ |
| C.1333 | $CH_2CH_3$ | $CF_3$ | CN | $CH_3$ |
| C.1334 | $CH_2CH_3$ | Cl | H | $CH_3$ |
| C.1335 | $CH_2CH_3$ | Cl | $CH_3$ | $CH_3$ |
| C.1336 | $CH_2CH_3$ | Cl | $C_2H_5$ | $CH_3$ |
| C.1337 | $CH_2CH_3$ | Cl | $C_3H_7$ | $CH_3$ |
| C.1338 | $CH_2CH_3$ | Cl | $C_4H_9$ | $CH_3$ |
| C.1339 | $CH_2CH_3$ | Cl | $CH(CH_3)_2$ | $CH_3$ |
| C.1340 | $CH_2CH_3$ | Cl | cyclopropyl | $CH_3$ |
| C.1341 | $CH_2CH_3$ | Cl | $CF_3$ | $CH_3$ |
| C.1342 | $CH_2CH_3$ | Cl | $OCH_3$ | $CH_3$ |
| C.1343 | $CH_2CH_3$ | Cl | $OC_2H_5$ | $CH_3$ |
| C.1344 | $CH_2CH_3$ | Cl | $CH_2\text{---}C_6H_5$ | $CH_3$ |
| C.1345 | $CH_2CH_3$ | Cl | $CH(CH_3)C_6H_5$ | $CH_3$ |
| C.1346 | $CH_2CH_3$ | Cl | $C_6H_5$ | $CH_3$ |
| C.1347 | $CH_2CH_3$ | Cl | $4\text{-}F\text{---}C_6H_5$ | $CH_3$ |
| C.1348 | $CH_2CH_3$ | Cl | 4-Cl-2-pyridyl | $CH_3$ |
| C.1349 | $CH_2CH_3$ | Cl | F | $CH_3$ |
| C.1350 | $CH_2CH_3$ | Cl | CN | $CH_3$ |
| C.1351 | $CH_2CH_3$ | $OCH_3$ | H | $CH_3$ |
| C.1352 | $CH_2CH_3$ | $OCH_3$ | $CH_3$ | $CH_3$ |
| C.1353 | $CH_2CH_3$ | $OCH_3$ | $C_2H_5$ | $CH_3$ |
| C.1354 | $CH_2CH_3$ | $OCH_3$ | $C_3H_7$ | $CH_3$ |
| C.1355 | $CH_2CH_3$ | $OCH_3$ | $C_4H_9$ | $CH_3$ |
| C.1356 | $CH_2CH_3$ | $OCH_3$ | $CH(CH_3)_2$ | $CH_3$ |
| C.1357 | $CH_2CH_3$ | $OCH_3$ | cyclopropyl | $CH_3$ |
| C.1358 | $CH_2CH_3$ | $OCH_3$ | $CF_3$ | $CH_3$ |
| C.1359 | $CH_2CH_3$ | $OCH_3$ | $OCH_3$ | $CH_3$ |
| C.1360 | $CH_2CH_3$ | $OCH_3$ | $OC_2H_5$ | $CH_3$ |
| C.1361 | $CH_2CH_3$ | $OCH_3$ | $CH_2\text{---}C_6H_5$ | $CH_3$ |
| C.1362 | $CH_2CH_3$ | $OCH_3$ | $CH(CH_3)C_6H_5$ | $CH_3$ |
| C.1363 | $CH_2CH_3$ | $OCH_3$ | $C_6H_5$ | $CH_3$ |
| C.1364 | $CH_2CH_3$ | $OCH_3$ | $4\text{-}F\text{---}C_6H_5$ | $CH_3$ |
| C.1365 | $CH_2CH_3$ | $OCH_3$ | 4-Cl-2-pyridyl | $CH_3$ |
| C.1366 | $CH_2CH_3$ | $OCH_3$ | F | $CH_3$ |
| C.1367 | $CH_2CH_3$ | $OCH_3$ | CN | $CH_3$ |

It is known that inhibitors of mitochondrial respiration of fungi can be employed as fungicides, eg. Antimycin (cf. "Inhibitors of Mitochondrial Function", Eds.: Rieske et al.; Pergamon Press, Oxford 1981, p. 110). However, the practical use of antimycin is impeded by various disadvantages, eg. the difficult and complicated preparation and the insufficient stability under realistic conditions, eg. in crop protection.

Mitochondrial respiration is essential for the metabolism. In the mitochondria, energy is stored, with the aid of respiration, in the form of adenosine triphosphate (ATP). Inhibition of mitochondrial respiration finally results in inhibition of ATP formation.

For example, the compounds I according to the invention inhibit the mitochondrial respiration of harmful fungi. In fungi which have been treated with the compounds I according to the invention, the ATP metabolism, or energy-dependent metabolic processes, cease, which results in a standstill of fungal growth and thus in the death of the fungi.

The mitochondrial respiration of animal pests is inhibited in a similar manner.

The compounds I are therefore suitable for controlling animal pests, in particular from the classes of the insects, arachnids and nematodes, and harmful fungi.

The compounds I are distinguished by an outstanding activity against a broad spectrum of phytopathogenic fungi, in particular from the classes of the Ascomycetes, Deuteromycetes, Phycomycetes and Basidiomycetes. Some of them act systemically and can be employed as foliar- and soil-acting fungicides.

They are especially important for controlling a large number of fungi on a variety of crop plants such as wheat, rye, barley, oats, rice, maize, grass, bananas, cotton, soybeans, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, Uncinula necator on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines, Pseudocercosporella species in hops and cucumbers, Alternaria species on vegetables and fruit and Mycosphaerella species in bananas.

Moreover, the compounds I are suitable for controlling harmful fungi in the protection of materials (eg. wood, paper, paint dispersions, fibers or tissues) and in the protection of stored products.

The compounds I are applied by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the specific intended use; in any case, it should guarantee fine and uniform distribution of the compound according to the invention. The formulations are prepared in a known manner, eg. by extending the active ingredient with solvents and/or carriers, if desired using emulsifiers and dispersants, it being possible to use other organic solvents as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates), and dispersants such as lignin-sulfite waste liquors and methyl-cellulose.

The fungicidal compositions generally comprise from 0.1 to 95, preferably from 0.5 to 90, % by weight of active ingredient.

Depending on the nature of the desired effect, the rates of application in crop protection are from 0.01 to 2.0 kg of active ingredient per ha.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the desired effect. Normal rates of application in the protection of materials are, for example, 0.001 g to 2 kg, preferably 0.005 g to 1 kg, of active ingredient per cubic meter of material treated.

In the use form as fungicides, the compositions according to the invention can also exist together with other active ingredients, eg. with herbicides, insecticides, growth regulators, fungicides, or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl 3,3-dimethyl acrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-2-triazine, O,O-diethylphthalimidophosphonothioate, 5-amino-1-[bis(dimethylamino)phosphinyl]-3-phenyl-1,2, 4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)-benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenyl-sulfodiamide, 5-ethoxy-3-trichloromethyl-1,2,3-thiadiazole, 2-thiocyanato-methylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methyl-furan-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2, 5-dimethylfuran-3-carboxamide, 2-methylbenzanilide, 2-iodobenzanilide, N-formyl-N-morpholine-2,2,2-trichloroethyl acetal, piperazine-1,4-diylbis(2,2,2-trichloro-ethyl)formamide, 1-(3,4-dichloroanilino)-1-formylamino-2, 2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-yl-ethyl]-1H-1, 2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3, 3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino-[α-(o-tolyloxy)-o-tolyl]acetate, methyl E-2-{2-[6-[(2-cyanophenoxy)pyrimidin-4-yloxy]phenyl}-3-methoxyacrylate, N-methyl-E-methoxyimino-[α-(2-phenoxyphenyl]acetamide, N-methyl-E-methoxyimino-[α-(2,5-dimethylphenoxy)-o-tolyl]acetamide, anilinopyrimidines such as N-(4,6-dimethylpyrimidin-2-yl)-aniline, N-[4-methyl-6-(1-propynyl)pyrimidin-2-yl] aniline, N-[4-methyl-6-cyclopropylpyrimidin-2-yl]aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acryloylmorpholine, and a variety of fungicides, such as dodecylguanidine acetate, 3-[3-(3,5-dimethyl-2-oxycyclohexyl)-2-hydroxyethyl]-glutarimide, hexachlorobenzene, methyl-N-(2,6-dimethylphenyl)-N-(2-furoyl)-DL-alaninate, DL-N-(2, 6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)-alanine methyl ester, 5-methyl-5-vinyl-3-(3, 5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarb-oximide, 2-cyano-[N-(ethylaminocarbonyl)-2-methoximino]-acetamide, 1-[2-(2, 4-dichlorophenyl)-pentyl]-1H-1,2,4-triazole, 2,4-difluoro-α-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole.

The compounds of the formula I are furthermore suitable for effectively controlling pests from the classes of the insects, arachnids and nematodes. They can be employed as pesticides in crop protection and in the hygiene, stored-product and veterinary sector.

The harmful insects include, from the order of the lepi-dopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lamb-* dina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani, Zeiraphera canadensis.

From the order of the beetles (Coleoptera), for example, Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.

From the order of the dipterans (Diptera), for example, Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.

From the order of the thrips (Thysanoptera), for example, Frankliniella fusca, Frankliniella occidentalis, Frankliniella tritici, Scirtothrips citri, Thrips oryzae, Thrips palmi, Thrips tabaci.

From the order of the hymenopterans (Hymenoptera), for example, Athalia rosae, Atta cephalotes, Atta sexdens, Atta texana, Hoplocampa minuta, Hoplocampa testudinea, Monomorium pharaonis, Solenopsis geminata, Solenopsis invicta.

From the order of the heteropterans (Heteroptera), for example, Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.

From the order of the homopterans (Homoptera), for example, Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.

From the order of the termites (Isoptera), for example, Calotermes flavicollis, Leucotermes flavipes, Reticulitermes lucifugus, Termes natalensis.

From the order of the orthopterans (Orthoptera), for example, Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.

From the class of the Arachnoidea, for example, arachnids (Acarina) such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.

From the class of the nematodes, for example, root knot nematodes, eg. Meloidogyne hapla, Meloidogyne incognita, Meloidogyne javanica, cyst-forming nematodes, eg. Globodera rostochiensis, Heterodera avenae, Heterodera glycines, Heterodera schachtii, Heterodera trifolii, stem eelworms and foliar nematodes, eg. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.

The active ingredients can be used as such, in the form of their formulations or the use forms prepared therefrom, for example in the form of ready-to-spray solutions, powders, suspensions or dispersions, emulsions, oil dispersions, pastes, dusts, materials for spreading or granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can be varied within substantial ranges.

In general, they are from 0.0001 to 10%, preferably from 0.01 to 1%.

The active ingredients can also be used successfully in the ultra-low-volume method (ULV), it being possible to apply formulations with over 95% by weight of active ingredient, or even the active ingredient without additives.

Under field conditions, the rate of application of active ingredient for controlling pests is 0.1 to 2.0, preferably 0.2 to 1.0, kg/ha.

Substances which are suitable for the preparation of ready-to-spray solutions, emulsions, pastes or oil dispersions are mineral oil fractions of medium to high boiling point such as kerosene or diesel oil, furthermore coal tar oil and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, n-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active ingredient, wetting agent, tackifier, dispersant or emulsifier and, if desired, solvent or oil, which are suitable for dilution with water.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, materials for spreading and dusts can be prepared by mixing or concomitantly grinding the active substances with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

Examples of the formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a preparation of the active ingredient with good adhesion (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-mono-ethanolamide, 2 parts by weight of calcium dodecylbenzene-sulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenyl and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII.20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients onto solid carriers. Examples of solid carriers are mineral earths such as silicas, silica gels, silicates, talcs, kaolin, attaclay, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nut shell meal, cellulose powders, and other solid carriers.

Various types of oils, or herbicides, fungicides, other pesticides, or bactericides, can be added to the active ingredients, if appropriate also only just prior to use (tank mix). These agents can be admixed with the agents according to the invention in a weight ratio of 1:10 to 10:1.

SYNTHESIS EXAMPLES

The protocols given in the synthesis examples which follow were used for obtaining further compounds I by altering the starting compounds as required. The resulting compounds are listed in the tables which follow together with physical data.

The chemical shifts (in ppm) of the $^1$H NMR spectra were recorded against tetramethylsilane (br=broad signal, s=singlet, d=doublet, m=multiplet).

1. Preparation of the Intermediates 1.a Synthesis of 2-fluorobenzaldehyde cyanohydrin

First, 171 g of 2-fluorobenzaldehyde are added dropwise at room temperature to a stirred suspension of 179 g of potassium cyanide in 500 ml of diethyl ether, and then, in the course of 5 minutes and with ice-cooling, a solution of 148 g of ammonium chloride in 600 ml of water. After the mixture has been stirred for 2 hours at room temperature (approx. 25° C.), the phases are separated, and the ether phase is washed once with dilute NaCl solution and three times with H$_2$O, dried and concentrated. This gives 191 g (91%) of the title compound as an oil.

$^1$H NMR (CDCl$_3$): 4.20 (s, br, 1H, OH); 5.75 (s, 1H, CHOH); 7.05–7.75 (m, 4H, phenyl H).

1.b Synthesis of methyl 2-fluoromandelimidate hydrochloride

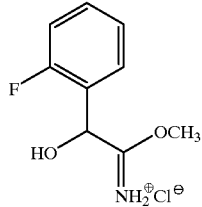

235 g of the cyanohydrin of 1.a are dissolved in 1000 ml of diethyl ether and 100 g of methanol. 126 g of a 55 percent strength solution of HCl in ether (≙69 g HCl) are added dropwise to this solution with ice-cooling in the course of 15 minutes. After the mixture has been left to stand for 20 hours at room temperature (approx. 25° C.), the precipitate is filtered off and dried in a stream of nitrogen. Yield: 108 g of the title compound.

$^1$NMR [D$_6$ dimethyl sulfoxide (D$_6$ DMSO)]: 3.05 (s, 3H, OCH$_3$); 5.12 (s, 1H, CHOH); 6.25 (s, br, 1H, CHOH); 7.10–7.60 (m, 4H, phenyl H).

1.c Synthesis of methyl 2-fluoromandelate

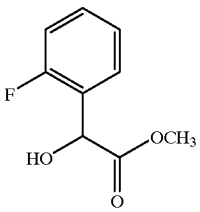

The product of 1.b (108 g) is refluxed with stirring for half an hour in 450 ml of H$_2$O. When cold, the mixture is extracted three times with ether, and the ether phase is dried and concentrated. This gives 77 g of the title compound.

$^1$H NMR (D$_6$ DMSO): 3.62 (s, 3H, OCH$_3$); 5.40 (s, 1H, CHOH); 6.30 (s, br, 1H, CHOH); 7.10–7.40 (m, 4H, phenyl H).

1.d Synthesis of methyl 2-fluorophenylglyoxylate

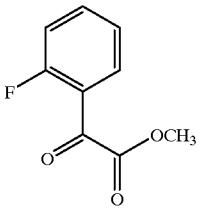

3.2 g of KBr, 8.7 g of Na$_2$HPO$_4$, 7.6 g of NaH$_2$PO$_4$×2H$_2$O, 2.8 g of 2,2,6,6-tetramethylpiperidine N-oxide and 600 ml of H$_2$O are added to 77.1 g of the product of 1.c in 700 ml of CH$_2$Cl$_2$. 343 g of a 12.5 percent strength NaOCl solution are added dropwise at 20° C. in the course of ½ hour to this mixture, with stirring. Stirring is continued for 1 hour. The organic phase is separated off and the aqueous phase is re-extracted with CH$_2$Cl$_2$. The combined organic phases are washed three times with H$_2$O, dried and concentrated. This gives 72.3 g of the title compound.

$^1$H NMR (CDCl$_3$): 3.97 (s, 3H, OCH$_3$), 7.08 (dd, 1H, phenyl H), 7.16 (dd, 1H, phenyl H), 7.33 (dd, 1H, phenyl H), 7.93 ppm (dd, 1H, phenyl H). cl 1.e Synthesis of N-methyl-2-fluorophenylglyoxylamide

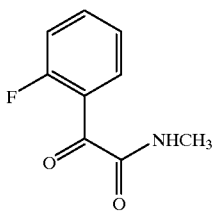

17.1 g (0.22 mol=1.1 eq.) of methylamine solution (40% strength in water) were added at approx. 25° C. to a solution of 36 g (0.2 mol) of the product of 1.d in 150 ml of tetrahydrofuran. After the mixture had been stirred for 3 hours, the solvent was removed under reduced pressure. The resulting residue crystallized. This gave 30.0 g of the title compound (m.p.: 98–100° C.).

$^1$H NMR (CDCl$_3$): 3.01 (d, 3H, NCH$_3$); 6.98 (d, 1H, NH); 7.05–7.18 (m, 2H, phenyl H); 7.60 (dd, 1H, phenyl H); 7.94 (t, 1H, phenyl H).

1.f Synthesis of butane-2,3-dione O-methyloxime

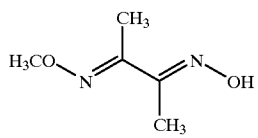

43.8 g of pyridine are added to 18.7 g of (E)-diacetyl-monoxime in 100 ml of methanol, and 17 g of o-methylhydroxylamine hydrochloride, dissolved in 50 ml of methanol, are subsequently added dropwise with stirring. After 3 hours, the mixture is evaporated to dryness, the residue is taken up in ether and washed with dilute hydrochloric acid, and the ether phase is subsequently dried and concentrated. This gives 24 g of the title compound.

$^1$H NMR (CDCl$_3$): 2.01+2.09 (2×s, 6H, CH$_3$); 3.98 (s, 3H, OCH$_3$); 8.59 (s, 1H, OH).

1.g Synthesis of 3-methylpent-3-en-2-one oxime

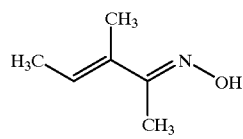

80 g (1 mol) of pyridine and 35 g (0.5 mol) of hydroxylamine hydrochloride were added to a solution of 50 g (0.5 mol) of 3-methylpent-3-en-2-one in 500 ml of methanol. After the reaction mixture had been stirred for 12 hours at room temperature (approx. 25° C.), it was freed from solvent under reduced pressure. The residue was taken up in tert-butyl methyl ether. The organic phase was washed with water and dilute hydrochloric acid, dried and concentrated and evaporated under reduced pressure. This gave 48.0 g of the title compound as white crystals (m.p.: 70–72° C).

$^1$H NMR (CDCl$_3$): 1.78 (d, 3H, CH$_3$); 1.85 (s, 3H, CH$_3$); 2.04 (s, 3H, CH$_3$); 6.01 (q, 3H,=CH); 9.98 (s, 1H, OH).

1.h Synthesis of methyl 2-oxo-[2-(1-meta-tolylethylideneaminooxy)phenyl]acetate

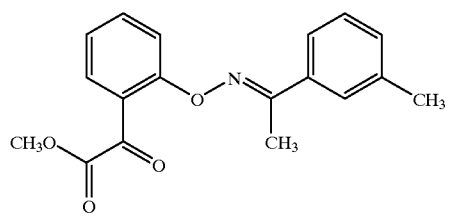

3.0 g of potassium tert-butanoxide are added at 20° C. to a mixture of 4.0 g of 3-methylacetophenone oxime in 20 ml of N,N-dimethylacetamide (DMA), the mixture is stirred for ½ hour, and a mixture of 5.9 g of methyl 2-fluorophenylglyoxalate in 20 ml of DMA is subsequently added dropwise at 15° C. After 3 hours at 20° C., a sufficient amount of methyl tert-butyl ether and aqueous NH$_4$Cl solution are added, the phases are separated, and the organic phase is washed three times with NH$_4$Cl solution and then dried and concentrated. After column chromatography on silica gel, 4.1 g of the title compound are obtained.

$^1$H NMR (CDCl$_3$): 2.40+2.41 (2×s, 6H, CH$_3$); 3.85 (s, 3H, OCH$_3$); 7.14 (m, 1H, phenyl H); 7.22–7.63 (m, 6H, phenyl H); 7.80 (dd, 1H, phenyl H).

1.i Synthesis of methyl [2-(2-methoxyimino-1-methylpropylideneaminooxy)phenyl]oxoacetate

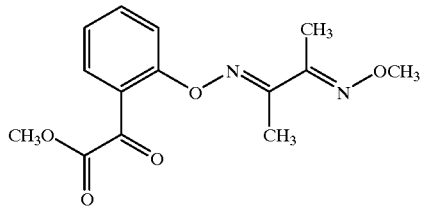

2.0 g of potassium tert-butoxide are added to 2.3 g of the product of 1.f in 15 ml of DMA, the mixture is stirred for ½ hour, and 3 g of the methyl 2-fluorophenylglyoxalate of 1.d, dissolved in 6 ml of DMA (dimethylformamide), are subsequently added dropwise at 20° C., during which process the temperature is held at 20° C. by means of ice-cooling. Stirring is then continued for 2 hours. For work-up, the reaction mixture is transferred into NH$_4$Cl solution and the aqueous phase is extracted repeatedly with ether. The combined organic phases are washed with ammonium chloride solution, dried and concentrated. This gives 3.9 g of the title compound.

$^1$H NMR (CDCl$_3$): 2.09+2.2 (2×s, 6H, CH$_3$); 3.88+4.01 (2×s, 6H, OCH$_3$); 7.50 (dd, 2H, phenyl H); 7.82 (d, 1H, phenyl H).

1.j Synthesis of N-methyl-2-oxo[2-(2-methoxyimino-1-methylpropylideneaminooxy)phenyl]acetamide

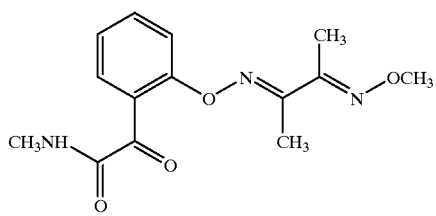

A mixture of 1.4 g (10.5 mol) of the product of 1.f, 1.2 g (11 mol) of potassium tert-butoxide and 1.8 g (10 mmol) of the product of 1.e in 30 ml of dimethylacetamide was stirred for 1 hour at 60° C. The resulting reaction mixture was poured into ice-water. The aqueous mixture was extracted twice with CH$_2$Cl$_2$. The combined organic phases were dried with Na$_2$SO$_4$ and subsequently concentrated under reduced pressure. This gave 1.3 g of the title compound as a brown oil.

$^1$H NMR (CDC$_3$): 2.02+2.20 (2×s, 6H, CH$_3$); 2.91 (d, 3H, NCH$_3$); 3.98 (s, 3H, OCH$_3$); 6.89 (d, 1H, NCH); 7.09 (d, 1H, phenyl H); 7.31 (t, 1H, phenyl H); 7.49 (t, 1H, phenyl H); 7.65 (d, 1H, phenyl H).

1.k Synthesis of methyl 2-oxo-[2-(1-ethoxyethylideneaminooxy)phenyl]acetate

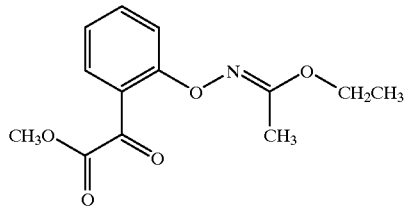

24.7 g (0.22 mol) of potassium tert-butoxide were added to a solution of 22.7 g of 1-ethoxyethylamine oxime in 300 ml of toluene and the mixture was subsequently stirred for 2 hours. The resulting mixture was concentrated at 400 C under reduced pressure, and the residue obtained was taken up in 500 ml of dimethylformamide. A solution of 40.1 g (0.22 mol) of [lacuna] in 250 ml of dimethylformamide was added dropwise to the resulting solution at 15° C. After 3 hours, the reaction mixture obtained was treated with ice-water and extracted three times with tert-butyl methyl ether. The combined organic phases were dried over $Na_2SO_4$ and concentrated under reduced pressure. The oil which remained was purified by column chromatography [on silica gel with cyclohexane/ethyl acetate (10:1)]. This gave 30 g of the title compound as an oil.

$^1$H NMR ($CDCl_3$): 1.28 (t, 3H, $CH_3$); 2.08 (s, 3H, $CH_3$); 3.83+3.88 (2×s, 6H, $OCH_3$); 4.18 (q, 2H, $OCH_2$); 7.05 (t, 1H, phenyl H); 7.38 (d, 1H, phenyl H); 7.54 (t, 1H, phenyl H); 7.76 (d, 1H, phenyl H).

1.l Synthesis of methyl 2-oxo-[2-(3-methylpent-3-en-2-ylideneiminooxy)phenyl]acetate

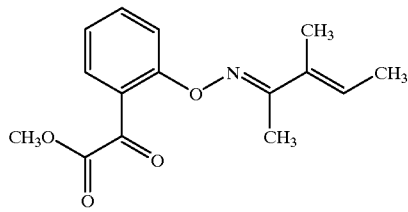

A mixture of 3.0 g (20 mmol) of the product of 1.g, 2.2 g (20 mmol) of potassium tert-butoxide and 20 ml of methanol was stirred for 10 minutes and then evaporated to dryness under reduced pressure at approx. 25° C. The mixture was taken up in 20 ml of dimethylformamide, a solution of 3.5 g (20 mmol) of the product of 1.d and 10 ml of dimethylformamide was added, and the resulting mixture was stirred for 2 hours at 50° C. The reaction mixture was treated with water and extracted with tert-butyl methyl ether. The combined organic phases were dried and concentrated under reduced pressure. The residue (4.0 g of oil) was purified by column chromatography [silica gel, cyclohexane/ethyl acetate (10→5/1)]. This gave 2.0 g of the title compound as an oil.

$^1$H NMR ($CDCl_3$): 1.82 (d, 3H, $CH_3$); 1.90+2.04 (2×s, 6H, $CH_3$); 3.85 (s, 3H, $OCH_3$); 6.14 (q, 1H,=CH); 7.10 (t, 1H, phenyl H); 7.52 (m, 2H, phenyl H); 7.80 (d, 1H, phenyl H).

2. Preparation of the Compounds I

2.a Synthesis of methyl methoxyimino-[2-(1-meta-tolylethylideneaminooxy)phenyl]acetate

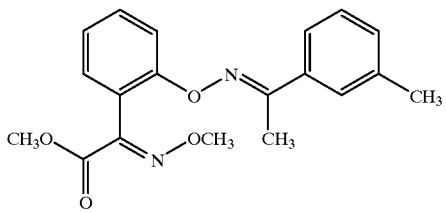

0.8 g of the keto ester of 1.h together with 0.24 g of O-methylhydroxylamine hydrochloride and 0.23 g of pyridine are stirred for 1 hour at 50° C. in 7 ml of $CH_3OH$. The methanol is then removed in vacuo and the residue is taken up in ethyl acetate, washed with dilute HCl and then with water, dried and concentrated. Crude yield 6.3 g which slowly crystallize. After purification by column chromatography, 2.2 g of the title compound are isolated from the second fraction; m.p. 90° C.

$^1$H NMR ($CDCl_3$): 2.32+2.34 (2×s, 6H, $CH_3$); 3.82+4.09 (2×s, 6H), $OCH_3$); 7.10 (t, 1H, phenyl H); 7.21–7.61 (m, 7H, phenyl H).

2.b Synthesis of 2-methoxyimino-N-methyl-2-[2-(1-meta-tolylethylideneamino-oxy)phenyl]acetamide 2.9 ml of 40 percent strength aqueous methylamine solution are added, a little at a time, at reflux temperature to 0.5 g of the oxime ether of 2.a in 4 ml of tetrahydrofuran. Stirring of the mixture is continued overnight, and the mixture is then concentrated under reduced pressure, taken up in ethyl acetate, washed with NaCl solution, dried and evaporated. This gives 0.4 g of the title compound; pale yellow crystals, m.p. 109–111° C.

$^1$H NMR ($CDCl_3$): 2.35+2.40 (2×s, 6H, $CH_3$); 2.92 (d, 3H, $NCH_3$); 4.00 (s, 3H, $OCH_3$); 6.68 (d, 1H, NH); 7.10 (t, 1H, phenyl H); 7.22–7.62 (m, 7H, phenyl H).

2.c Synthesis of methyl methoxyimino-[2-(2-methoxyimino-1-methylpropylideneaminooxy)phenyl]acetate

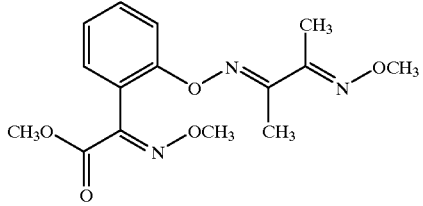

3 g of the crude product of 1.i in 20 ml of methanol are reacted with 0.83 g of O-methylhydroxylamine at room temperature (approx. 25° C.). After 3 hours, the solvent is stripped off in vacuo and the residue is subjected to column chromatography on silica gel with cyclohexane/ethyl acetate 15:1 as the eluent. 1.3 g of of the title compound of m.p. 93–94° C. were isolated as the second fraction.

$^1$H NMR ($D_6$-DMSO): 2.01+2.04 (2×s, 6H, $CH_3$); 3.71 (s, 3H, $OCH_3$); 3.95 (s, 6H, $OCH_3$); 7.12 (m, 1H, phenyl H); 7.31 (d, 1H, phenyl H); 7.43 (d, 2H, phenyl H).

2.d Synthesis of N-methyl-methoxyimino-[2-(2-methoxyimino-1-methylpropylideneaminooxy)phenyl]acetamide

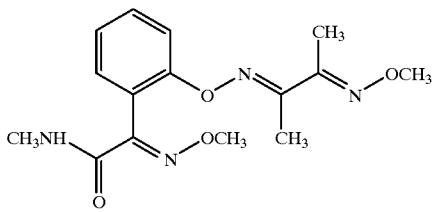

Process A:

The product of 2.c (0.6 g) was stirred overnight at room temperature (approx. 25° C.) in 10 ml of tetrahydrofuran together with 3.6 g of 40 percent strength aqueous methylamine solution. After the solvent had been stripped off under reduced pressure, water had been added, and the resulting crystal-line residue had been isolated and dried, 0.3 g of the title compound was obtained (m.p. 122–123° C.).

$^1$H NMR ($CDCl_3$): 2.05+2.12 (2×s, 6H, $CH_3$); 2.90 (d, 3H, $NCH_3$); 3.92+3.8 (2×s, 6H, $OCH_3$); 6.70 (m, 1H, NH); 7.07 (t, 1H, phenyl H); 7.22 (d, 1H, phenyl H); 7.38 (t, 1H, phenyl H); 7.49 (d, 1H, phenyl H).

Process B:

A solution of 1.1 g (4 mmol) of the product of 1.i in 30 ml of methanol was treated with 0.4 g (4.2 mmol) of O-methyl-hydroxylamine hydrochloride and 0.5 g (6 mmol) of pyridine. After 2 hours at 50° C., the solvent and the base were removed under reduced pressure. The residue was taken up in ethyl acetate, and the resulting solution was washed in each case twice with water and dilute hydrochloric acid. The organic phase was dried over $Na_2SO_4$ and concentrated under reduced pressure. This gave 1.1 g of the title compound as a yellow oil.

2.e Synthesis of methyl 3-methoxy-[2-(2-methoxyimino-1-methyl-propylideneaminooxy)phenyl]acrylate

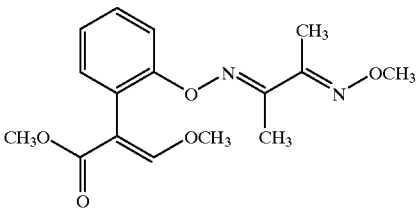

e) The crude product of Preparation Example 1.i, specifically 2.4 g of this, dissolved in 10 ml of dimethylformamide (DMF), is added dropwise to a mixture of 5.6 g of methoxymethyltriphenylphosphonium chloride and 2.5 g of 30 percent strength sodium methylate solution (in methanol) in 20 ml of DMF. After 3 hours, 30 ml of $H_2O$ are added dropwise with ice-cooling, and the resulting precipitate is filtered off with suction. After chromatography over $SiO_2$ with cyclohexane/ethyl acetate, 1.8 g of the title compound are obtained from the second fraction as pale yellow solid (m.p. 101° C.).

$^1$H NMR ($CDCl_3$): 2.09+2.11 (2×s, 6H, $CH_3$); 3.65+3,82 (2×s, 6H, $OCH_3$); 7.01 (t, 1H, phenyl H); 7.22 (m, 2H, phenyl H); 7.45 (d, 1H, phenyl H); 7.49 (s, 1H, CH).

2.f Synthesis of methyl 3-methoxy-[2-(1-ethoxyethylideneaminooxy)phenyl]acrylate

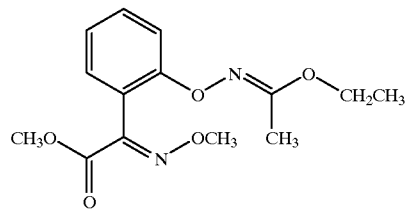

A solution of 2.7 g (0.01 mol) of the product of 1.k and 10 ml of dimethylformamide was added dropwise to a solution of 6.9 g (0.02 mol) of methoxymethyltriphenylphosphonium chloride, 3.1 g (0.017 mol) of sodium methoxide (30% strength in methanol) and 30 ml of dimethylformamide. After 3 hours, the reaction mixture was transferred into ice-water and extracted with tert-butyl methyl ether. The combined organic phases are dried over $Na_2SO_4$ and concentrated under reduced pressure. The resulting residue was purified by column chromatography [silica gel, toluene/ethyl acetate (10/1)]. This gave 1.9 g of the title compound as an oil.

$^1$H NMR ($CDCl_3$): 1.26 (t, 3H, $CH_3$); 2.00 (s, 3H, $CH_3$); 3.65 (s, 3H, $OCH_3$); 3.80 (s, 3H, $OCH_3$); 4.18 (q, 2H, $OCH_2$); 6.95 (t, 1H, phenyl H); 7.20 (d, 1H, phenyl H); 7.30 (t, 1H, phenyl H); 7.43 (d, 1H, phenyl H); 7.50 (s, 1H, =CH).

2.g Synthesis of methyl 2-methoxyimino-[2-(1-ethoxyethylideneaminooxy)phenyl]acetate

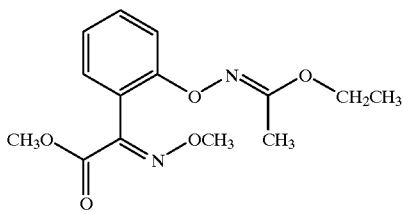

A mixture of 1.0 g (4.0 mmol) of the product of 1.k and 5 ml of methanol was treated with 0.25 g of O-methylhydroxylamine and stirred for approximately 24 hours at approximately 25° C. The resulting reaction mixture was concentrated under reduced pressure, and the residue obtained was taken up in $CH_2Cl_2$. The organic phase was washed with water, dried and concentrated under reduced pressure. This gave 1.0 g of the title compound [2:1 isomer mixture].

$^1$H NMR (CDCl$_3$): 1.26 (t, 3H, CH$_3$); 2.01+2.05 (2×s, 6H, CH$_3$); 3.86+4.04 (2×s, 6H, OCH$_3$); 4.10 (q, 2H, OCH$_2$); 6.94–7.50 (m, 4H, phenyl H).

2.h Synthesis of methyl 2-methoxyimino-[2-phenylmethylideneaminooxyphenyl]acetate

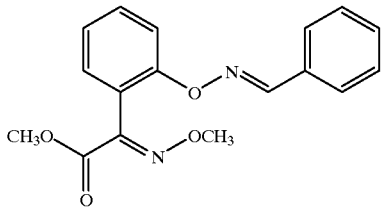

A solution of 1.0 g (3.4 mmol) of the product of 1.k and 5 ml of methanol was treated with 1.8 g (17 mmol) of benzaldehyde and 0.33 g of methanesulfonic acid, and the resulting mixture was stirred for 1 hour. The resulting solution was concentrated under reduced pressure and the residue which remained was taken up in $CH_2Cl_2$. The organic phase was washed with water, dried and concentrated. The residue obtained thus was purified by column chromatography [toluene/ethyl acetate (10:1)]. This gave 400 mg of the title compound as an oil.

$^1$H NMR (CDCl$_3$): 3.95 (s, 3H, OCH$_3$); 4.02 (s, 3H, OCH$_3$); 7.30–7.68 (m, 9H, phenyl H); 8.05 (s, 1H, =CH).

2.i Synthesis of methyl 2-[2-(3-methylpent-3-en-2-ylideneiminooxy)phenyl]but-2-enoate

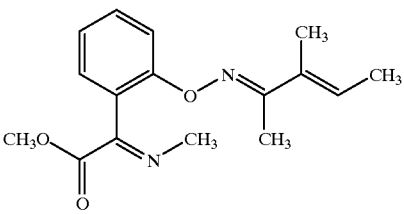

A mixture of 4.7 g (14.5 mmol) of ethyltriphenylphosphonium chloride in 20 ml of dimethylformamide was treated with 2.2 g (12 mmol) of sodium methoxide solution (30% strength in methanol) at approximately 25° C. A solution of 2.0 g of the product of 1.1 in 10 ml of dimethylformamide was subsequently added dropwise to the resulting mixture, and stirring was continued for 2 hours. The reaction mixture was then treated with water and extracted with tert-butyl methyl ether. The combined organic phases were dried and concentrated under reduced pressure. The residue which remained was purified by column chromatography [cyclohexane/ethyl acetate (10/1)]. This gave 700 mg of the title compound as a solid (m.p.: 90–93° C.).

$^1$H NMR (CDCl$_3$): 1.72 (d, 3H, CH$_3$); 1.80 (d, 3H, CH$_3$); 1.89 (s, 3H, CH$_3$); 2.03 (s, 3H, CH$_3$); 3.68 (s, 3H, OCH$_3$); 6,03 (pseudo q, 1H, =CH); 6.98–7.35 (m, 5H, phenyl H, =CH); 7.50 (d, 1H, phenyl H).

TABLE I(1)

I(i)

| No. | R$^1$ | R$^3$ | R$^4$ | Physical data |
|---|---|---|---|---|
| I(1).1 | Ia | CH$_3$ | 3-CH$_3$—C$_6$H$_4$ | 90° C. |
| I(1).2 | Ib | CH$_3$ | 3-CH$_3$—C$_6$H$_4$ | 109–111° C. |
| I(1).3 | Ia | CH$_3$ | 4-CH$_3$—C$_6$H$_4$ | 99° C. |
| I(1).4 | Ib | CH$_3$ | 4-CH$_3$—C$_6$H$_4$ | 109° C. |
| I(1).5 | Id | —CH$_2$—(CH$_2$)$_3$—CH$_2$— | | oil |
| I(1).6 | Ia | CH$_3$ | OC$_2$H$_5$ | $^1$H: 1.32(t, 3H); 2.06(s, 3H); 3.92(s, 3H); 4.05(s, 3H); 4.08 (q, 2H), 6.95–7.42(m, 4H) |
| I(1).7 | Id | CH$_3$ | OC$_2$H$_5$ | $^1$H: 1.28(t, 3H); 2.03(s, 3H); 3.76(s, 3H); 3.84(s, 3H); 4.08 (q, 2H); 6.98(t, 1H); 7.08 (d, 1H); 7.21(t, 1H); 7.42 (d, 1H); 7.50(s, 1H). |
| I(1).8 | Ia | | cyclopentenyl, CH$_3$ | 128° C. |
| I(1).9 | Ib | | cyclopentenyl, CH$_3$ | 135–137° C. |

TABLE I(2)

I(iii)

![Structure I(iii)]

| No. | R¹ | R³ | R⁵ | R⁶ | Physical data |
|---|---|---|---|---|---|
| I(2).1 | Ia | CH₃ | 4-F-C₆H₅ | CH₃ | 112° C. |
| I(2).2 | Ia | CH₃ | CH₃ | CH₃ | 93° C. |
| I(2).3 | Ib | CH₃ | CH₃ | CH₃ | 122–123° C. |
| I(2).4 | Id | CH₃ | 4-F-C₆H₅ | CH₃ | 141° C. |
| I(2).5 | Ib | CH₃ | 4-F-C₆H₅ | CH₃ | 139° C. |
| I(2).6 | Id | CH₃ | CH₃ | CH(CH₃)₂ | 103° C. |
| I(2).7 | Id | CH₃ | CH₃ | CH₃ | 101° C. |
| I(2).8 | Ib | CH₃ | CH₃ | CH(CH₃)₂ | 97° C. |
| I(2).9 | Ia | CH₃ | CH₃ | C₂H₅ | 106–109° C. |
| I(2).10 | Ib | CH₃ | CH₃ | C₂H₅ | 119–123° C. |
| I(2).11 | Ia | C₂H₅ | CH₃ | CH₃ | 92–97° C. |
| I(2).12 | Ib | C₂H₅ | CH₃ | CH₃ | 97–100° C. |
| I(2).13 | Ia | CH₃ | CH₃ | CH(CH₃)₂ | 74° C. |
| I(2).14 | Id | C₂H₅ | CH₃ | CH₃ | 1711, 1647, 1542, 1288, 1266, 1132 |
| I(2).15 | Id | CH₃ | CH₃ | C₂H₅ | 78–80° C. |
| I(2).16 | Ia | CH₃ | CH₃ | CH₂C≡CH | 51–53° C. |
| I(2).17 | Id | CH₃ | CH₃ | CH₂C≡CH | 59–63° C. |
| I(2).18 | Ib | CH₃ | CH₃ | CH₂C≡CH | 146–149° C. |
| I(2).19 | Ib | CH₃ | C₂H₅ | CH₃ | 113° C. |
| I(2).20 | Id | CH₃ | C₂H₅ | CH₃ | 1713, 1638, 1541, 1258, 1128, 1051. |
| I(2).21 | Ia | CH₃ | C₂H₅ | CH₃ | 1732, 1453, 1224, 1207, 1073, 1050. |
| I(2).22 | Ib | C₂H₅ | CH₃ | C₂H₅ | 101–103° C. |
| I(2).23 | Id | C₂H₅ | CH₃ | C₂H₅ | 88–92° C. |
| I(2).24 | Ia | C₂H₅ | CH₃ | C₂H₅ | 102° C. |
| I(2).25 | Ib | C₂H₅ | CH₃ | CH(CH₃)₂ | 92–94° C. |
| I(2).26 | Id | C₂H₅ | CH₃ | CH(CH₃)₂ | 74–78° C. |
| I(2).27 | Ia | C₂H₅ | CH₃ | CH(CH₃)₂ | 93–96° C. |
| I(2).28 | Ib | C₂H₅ | CH₃ | CH₂C≡CH | 95–100° C. |
| I(2).29 | Id | C₂H₅ | CH₃ | CH₂C≡CH | 1711, 1637, 1542, 1252, 1218, 1129. |
| I(2).30 | Ia | C₂H₅ | CH₃ | CH₂C≡CH | 1731, 1480, 1453, 1227, 1207, 1072. |
| I(2).31 | Ib | C₆H₅ | CH₃ | CH₃ | 122–125° C. |
| I(2).32 | Id | C₆H₅ | CH₃ | CH₃ | 116–120° C. |
| I(2).33 | Ia | C₆H₅ | CH₃ | CH₃ | 107–113° C. |
| I(2).34 | Ia | CH₃ | OCH(CH₃)₂ | CH₃ | 78° C. |
| I(2).35 | Ib | CH₃ | CH₂CH₃ | CH₂C≡CH | 100–103° C. |
| I(2).36 | Ia | CH₃ | CH₂CH₃ | CH₂C≡CH | 94–97° C. |
| I(2).37 | Id | CH₃ | CH₂CH₃ | CH₂C≡CH | oil |
| I(2).38 | Ia | CH₃ | CH₂CH₃ | CH₂CH₃ | 91–95° C. |
| I(2).39 | Ib | CH₃ | CH₂CH₃ | CH₂CH₃ | 91–93° C. |
| I(2).40 | Id | CH₃ | CH₂CH₃ | CH₂CH₃ | oil |
| I(2).41 | Ie | CH₃ | CH₂CH₃ | CH₂CH₃ | oil |
| I(2).42 | Ia | CH₃ | CH₂OCH₃ | CH₃ | oil |
| I(2).43 | Ib | CH₃ | CH₂OCH₃ | CH₃ | 95–100° C. |

TABLE I(3)

I(v)

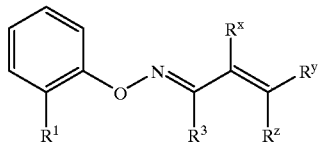
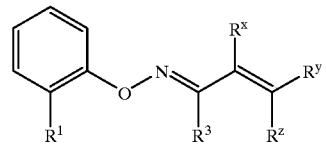

| No. | R¹ | R³ | Rˣ | Rʸ | Rᶻ | Physical data |
|---|---|---|---|---|---|---|
| I(3).1 | Ia | CH₃ | H | C₆H₅ | H | 102° C. |
| I(3).2 | Ib | CH₃ | H | C₆H₅ | H | 155° C. |
| I(3).3 | Ia | CH₃ | H | 4-F-C₆H₅ | H | 109° C. |
| I(3).4 | Ib | CH₃ | H | 4-F-C₆H₅ | H | 72–75° C. |

TABLE I(3)-continued

I(v)

| No. | $R^1$ | $R^3$ | $R^x$ | $R^y$ | $R^z$ | Physical data |
|---|---|---|---|---|---|---|
| I(3).5 | Ia | $CH_3$ | H | 4-Cl-$C_6H_5$ | H | 141° C. |
| I(3).6 | Ib | $CH_3$ | H | 4-Cl-$C_6H_5$ | H | 147° C. |
| I(3).7 | Ia | $CH_3$ | H | $CH_3$ | $CH_3$ | 58–60° C. |
| I(3).8 | Ib | $CH_3$ | H | $CH_3$ | $CH_3$ | 85–88° C. |
| I(3).9 | Ib | $CH_3$ | $CH_3$ | $CH_3$ | H | 83–84° C. |
| I(3).10 | Ib | $CH_3$ | $CH_3$ | $CH(CH_3)_2$ | H | 69–71° C. |
| I(3).11 | Ia | $CH_3$ | $CH_3$ | $CH_3$ | H | 81–83° C. |
| I(3).12 | Ia | $CH_3$ | $CH_3$ | $CH(CH_3)_2$ | H | 90–92° C. |
| I(3).13 | Id | $CH_3$ | $CH_3$ | $CH_3$ | H | 90–93° C. |
| I(3).14 | Id | $CH_3$ | $CH_3$ | $CH(CH_3)_2$ | H | 78–80° C. |
| I(3).15 | Ie | $CH_3$ | $CH_3$ | $CH_3$ | H | 69–72° C. |
| I(3).16 | Ie | $CH_3$ | $CH_3$ | $CH(CH_3)_2$ | H | 56–59° C. |
| I(3).17 | Ia | $CH_3$ | H | H | $C_6H_5$ | 88° C. |
| I(3).18 | Ia | $CH_3$ | $CH_3$ | $C_2H_5$ | H | 83–86° C. |
| I(3).19 | Ib | $CH_3$ | $CH_3$ | $C_2H_5$ | H | 81–86° C. |
| I(3).20 | Id | $CH_3$ | $CH_3$ | $C_2H_5$ | H | 77–79° C. |
| I(3).21 | Ie | $CH_3$ | $CH_3$ | $C_2H_5$ | H | oil |
| I(3).22 | Ia | $CH_3$ | $CH_3$ | $C_3H_7$ | H | 80–82° C. |
| I(3).23 | Ib | $CH_3$ | $CH_3$ | $C_3H_7$ | H | 99–100° C. |
| I(3).24 | Id | $CH_3$ | $CH_3$ | $C_3H_7$ | H | 74–76° C. |
| I(3).25 | Ie | $CH_3$ | $CH_3$ | $C_3H_7$ | H | 54–56° C. |
| I(3).26 | Ib | $CH_3$ | $CH_3$ | 4-F-$C_6H_4$ | H | 140–142° C. |
| I(3).27 | Ia | $CH_3$ | $CH_3$ | $C_6H_5$ | H | 115–117° C. |
| I(3).28 | Ia | $CH_3$ | $CH_3$ | 4-F-$C_6H_4$ | H | 103–105° C. |
| I(3).29 | Id | $CH_3$ | $CH_3$ | $C_6H_5$ | H | 108° C. |
| I(3).30 | Id | $CH_3$ | $CH_3$ | 4-F-$C_6H_4$ | H | 108° C. |
| I(3).31 | Ie | $CH_3$ | $CH_3$ | $C_6H_5$ | H | 81–83° C. |
| I(3).32 | Ie | $CH_3$ | $CH_3$ | 4-F-$C_6H_4$ | H | 82–84° C. |

TABLE VI (VI)

| No. | $R^2_m$ | $R^3$ | $R^4$ | $^1$H NMR ($CDCl_3$, ppm) | * |
|---|---|---|---|---|---|
| VI.1 | H | $CH_3$ | 3-$CH_3$—$C_6H_4$ | 2.42(3H, s), 2.44(3H, s), 3.85(3H, s), 7.1–7.9(8H, four multiplets) | E |
| VI.2 | H | $CH_3$ | $C(CH_3)$=$NOCH_3$ | 2.1(3H, s), 2.2(3H, s), 3.75(3H, s), 4.0(3H, s), 7.1–7,9 (4H, four multiplets) | E, E |

*= Configuration of the double bond

Examples of the action against harmful fungi:

1. Action of the compounds as mitochondrial respiration inhibitors

To determine the effect of the compounds according to the invention on mitochondrial respiration, it is first necessary to isolate the mitochondria from the test organisms. In the case of the yeast *Saccharomyces cerevisiae*, a 30 to 40% cell suspension of the fungus is disrupted, to this end, in an aqueous solution of 0.6 M Mannitol+0.01 M tris[hydroxymethyl]aminomethane+0.002 M disodium ethylenediaminetetraacetate (pH 6.8) using a glass bead mill, and the extract is fractionated by means of differential centrifugation at 1000×g and 12000×g. The mitochondria are in the precipitate of the 12000×g centrifugation.

Using similar methods, it is also possible to isolate mitochondria from other fungi, eg. from the phytopathogenic fungus *Drechslera sorokiniana* (synonym *Helminthosphorium sativum*), from the dermatophyte Trichophyton mentagrophytes, which is pathogenic to humans, and from other organisms, eg. from the common housefly (*Musca domestica*) as an insect, or from the spider mite *Tetranychus urticae*.

The effect of the compounds on the respiration chain is determined by adding a solution of the test compound in dimethyl sulfoxide to a suspension of mitochondria in an aqueous solution of 0.01 M tris[hydroxymethyl]aminomethane+0.65 M sorbitol+0.01 M $KH_2PO_4$+0.01 M KCl+0.0004 M disodium ethylenediamine-tetraacetate+0.3% bovine serum albumin+0.0007 M KCN+6×$10^{-6}$ ubiquinone–50+0.01 M sodium succinate+0.15% cytochrome c (pH 7.5), and the reduction rate of the cytochrome c is determined photometrically on the basis of the increased absorption at 546 nm. A batch with a corresponding amount of pure DMSO is used as control. The inhibitory value for the active ingredient at the concentration shown in each case is then calculated as follows.

$$\% \text{ inhibition} = 100 \cdot \frac{\left(\frac{\Delta E}{\Delta t}\right)_o - \left(\frac{\Delta E}{\Delta t}\right)_x}{\left(\frac{\Delta E}{\Delta t}\right)_o}$$

where $\Delta E$ is the difference in absorption, $\Delta t$ the difference in time, $\left(\frac{\Delta E}{\Delta t}\right)_o$ the reaction rate of the control and $\left(\frac{\Delta E}{\Delta t}\right)_x$ the reaction rate of the sample $x$.

In the table which follows, the action of a series of compounds according to the invention as respiration inhibitors on the mitochondria of the yeast *Saccharomyces cerevisiae*, the phyto-pathogenic fungus *Drechslera sorokiniana* and the common housefly *Musca domestics*.

In each case, the inhibition of mytochondrial respiration is given as $I_{50}$ value (this being the concentration of test substance where a 50% inhibition is observed) and as F value, this being a relative value defined as follows:

$$F = \frac{I_{50}(\text{test substance})}{I_{50}(\text{reference substance})}$$

The reference substance is the so-called enol ether stilbene, of the following formula:

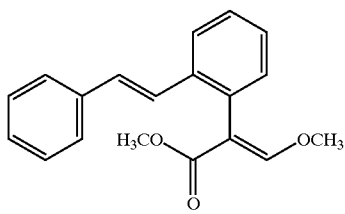

Table II:
Inhibition of mitochondrial respiration by compounds of the formula I of Tables I(1)–I(3)

TABLE II

Inhibition of mitochondrial respiration by compounds of the formula I of Tables I(1)–I(3)

| No. | Saccharom. cerevisiae $I_{50}$ (Mol/l) | F |
|---|---|---|
| I(1).1 | $2.7 \cdot 10^{-8}$ | 0.96 |
| I(1).2 | $3.2 \cdot 10^{-7}$ | 11 |
| I(2).7 | $3.3 \cdot 10^{-9}$ | 0.14 |
| I(2).2 | $1.2 \cdot 10^{-8}$ | 0.43 |
| I(2).3 | $2.7 \cdot 10^{-7}$ | 9.6 |

The fungicidal activity of the compounds of the general formula I was demonstrated by the following experiments:

The active ingredients were formulated as a 20% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Emulphor® EL (Emulane® EL, emulsifier based on ethoxylated fatty alcohols) and diluted with water to give the desired concentration.

Activity against *Erysiphe graminis* var. *tritici*

Leaves of wheat seedlings (variety "Kanzler") were first treated with the aqueous preparation of the active ingredients (strength 250 ppm). After approximately 24 hours, the plants were dusted with spores of powdery mildew of wheat (*Erysiphe graminis* var. *tritici*). The treated plants were subsequently incubated for 7 days at 20–22° C. and a relative atmospheric humidity of 75–80%. The extent of fungal development was subsequently determined.

In this test, the disease level of plants which had been treated with the compounds according to the invention was 15% and less, the disease level of the plants which had been treated with a known active ingredient (Compound No. 195, Table 3, EP-A 463 488) was 40% and the disease level of the untreated plants was 70%.

In a similar test (wheat seedlings cv. "Kanzler", rate of application 63 ppm), in which the plants were first infected and incubated and subsequently treated with the active ingredients, the disease level of the plants which had been treated with the compounds according to the invention was 5% and less, the disease level of the plants which had been treated with a known active ingredient (Compound No. 195, Table 3, EP-A 463 488) was 25% and the disease level of the untreated plants was 60%.

In a similar test (wheat seedlings cv. "Frühgold", rate of application 250 ppm), in which the plants were first treated with the active ingredients and subsequently infected and incubated, the disease level of the plants which had been treated with the compounds according to the invention was 15% and less and the disease level of the untreated plants was 75%.

Activity against *Plasmopara viticola* (Rebenperonospora)

Grapevines in pots (variety: "Müller Thurgau") were sprayed to run-off point with the preparation of active ingredient (rate of application: 63 ppm). After 8 days, the plants were sprayed with a zoospore suspension of the fungus *Plasmopara viticola* and kept for 5 days at 20–30° C. and high atmospheric humidity. Then, prior to assessment, the plants were kept for 16 hours at high atmospheric humidity. Scoring was carried out visually.

In this test, the disease level of the plants which had been treated with the active ingredients according to the invention was 15% and less, while the disease level of the untreated (control) plants was 70%.

Examples of the activity against animal pests

The insecticidal activity of the compounds of the general formula I against insects, arachnids and nematodes was demonstrated by the following greenhouse experiments:

The active ingredients were formulated a) as a 0.1% strength solution in acetone or b) as a 10% emulsion in a mixture of 70% by weight of cyclohexanol, 20% by weight of Nekanil® LN (Lutensol® AP6, wetting agent having emulsifying and dispersant action based on ethoxylated alkylphenols) and 10% by weight of Emulphor® EL emulsifier based on ethoxylated fatty alcohols)

and diluted to give the desired concentraton, using acetone in the case of a) and water in the case of b).

After the experiments had been concluded, in each case the lowest concentration at which the compounds still caused an 80–100% inhibition or mortality in comparison with untreated controls was determined (limit or minimum concentration).

*Aphis fabae* (blackbean aphid), contact action

Severely infested dwarf beans (*Vicia faba*) were treated with the aqueous preparation of active ingredient. After 24 hours, the mortality rate was determined.

In this test, a limit concentration of 200 ppm was shown by compound I(2).b 9.

*Heliothis virescens* (tobacco budworm), contact/stomach action

Tobacco plants approximately 10 cm high were treated with the aqueous preparation of active ingredient. After the plants had dried, they were populated with in each case 10 3rd instar larvae. Mortality and antifeeding effect were assessed after 48 hours.

In this test, a limit concentration of 40 ppm was shown by compound I(2).b 17.

*Nephotettix cincticeps* (green rice leafhopper), contact action

Circular paper filters were treated with the aqueous preparation of active ingredient and subsequently populated with 5 adult leafhoppers. After 24 hours, the mortality was assessed.

In this test, limit concentrations of 0.2 mg and less were shown by compounds I(1).4, I(2).7, I(2).19, I(2).20, I(2).21, I(2).22, I(2).25, I(2).26, I(2).27, I(2).28 and I(2).29.

*Prodenia litura* (Egyptian cotton leafworm), contact/stomach action

Five L3 instar caterpillars (10–12 mm) which had not suffered noticeable damage in the contact experiment were placed on standard culture media (3.1 l water, 80 g agar, 137 g brewers' yeast, 515 g cornflour, 130 g wheat germ and customary additives and vitamins (20 g Wesson salt, 5 g Nipagin, 5 g sorbose, 10 g cellulose, 18 g ascorbic acid, 1 g Lutavit® blend (vitamin), 5 ml alcoholic biotin solution)) which had previously been wetted with the aqueous preparation of active ingredient. The caterpillars were observed until the adults had hatched in a control experiment without active ingredient.

In this test, limit concentrations of 0.2 mg and less were shown by compounds I(2).2, I(2).16 and I(2).17.

*Tetranychus telarius* (greenhouse red spider mite), contact action

Severely infested dwarf beans, in pots, which showed the second consecutive pair of leaves were treated with aqueous preparations of active ingredient. After 5 days in the greenhouse, the result of the control measures was determined by means of a stereomicroscope.

In this test, limit concentrations of 200 ppm and less were shown by compounds I(2).2, I(2).6, I(2).7, I(2).8, I(2).9, (2).13, I(2).14, I(2).15, I(2).16, I(2).17, I(2).19, I(2).20 and I(2).21.

We claim:

1. A 2-iminooxyphenylacetic acid of the formula I $$\text{(I)}$$

where the substituents and the index have the following meanings:

$R^1$ is $C(CO_2CH_3)$=$NOCH_3$ (Ia), $C(CONHCH_3)$=$NOCH_3$ (Ib), $C(CONH_2)$=$NOCH_3$ (Ic), $C(CO_2CH_3)$=$CHOCH_3$ (Id) or $C(CO_2CH_3)$=$CCH_3$ (Ie);

$R^2$ is cyano, nitro, halogen, $C_1$–$C_4$-alkyl, $C_1$–$C_4$-haloalkyl or $C_1$–$C_4$-alkoxy;

m is 0, 1 or 2, it being possible for the radicals $R^2$ to be different when m is 2;

$R^3$ is hydrogen, cyano, hydroxyl, halogen,
  $C_1$–$C_6$-alkyl, $C_1$–$C_6$-haloalkyl, $C_1$–$C_6$-alkoxy-$C_1$–$C_6$-alkyl, $C_1$–$C_6$-alkoxy, $C_1$–$C_6$-haloalkoxy, $C_1$–$C_6$-alkylthio, $C_3$–$C_6$-cycloalkyl, $C_3$–$C_6$-cycloalkyl-$C_1$–$C_6$-alkyl, $C_2$–$C_6$-alkenyl, aryl, aryloxy-$C_1$–$C_6$-alkyl, aryl-$C_1$–$C_4$-alkyl or benzyloxy, where the aromatic rings in these radicals are unsubstituted or carry one to three of the following groups: cyano, nitro, halogen, $C_1$–$C_6$-alkyl, $C_1$–$C_6$-alkoxy, $C_1$–$C_6$-haloalkoxy, or $C(CH_3)$=$N$—$Y$—$R^a$ where $R^a$ is $C_1$–$C_6$-alkyl and Y is oxygen or nitro, where the nitrogen atom carries a hydrogen atom or a $C_1$–$C_6$-alkyl group;

$R^4$ is hydrogen, cyano,
  unsubstituted or substituted alkyl, alkenyl, alkynyl, cycloalkyl, heterocyclyl, aryl and hetaryl;
  unsubstituted or substituted alkoxy, alkenyloxy, alkynyloxy, cycloalkoxy, heterocyclyloxy, aryloxy and hetaryloxy; unsubstituted or substituted arylthio and hetarylthio;
  —$Q_p$—$C(R^5)$=$N$—$Y^1$—$R^6$ or —$O_p$—$O$—$N$=$CR^7R^8$, where Q is $CH_2$, $CH(CH_3)$, $CH(CH_2CH_3)$ or 1,1-cyclopropyl;

p is 0 or 1;

$Y^1$ is oxygen or nitrogen, where the nitrogen atom carries a hydrogen atom or a $C_1$–$C_4$-alkyl group;

$R^5$ is one of the groups mentioned for $R^3$, or unsubstituted or substituted cycloalkoxy, heterocyclyloxy, aryloxy, hetaryloxy, arylthio and hetarylthio;

$R^6$ is unsubstituted or substituted $C_{1-C10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl; unsubstituted or substituted aryl, hetaryl, arylcarbonyl, hetarylcarbonyl, arylsulfonyl or hetarylsulfonyl;

$R^7$, $R^8$ are methyl, ethyl, phenyl and benzyl, where the aromatic rings are unsubstituted or carry one to three of the following groups: cyano, nitro, halogen, $C_1$–$C_6$-alkyl, $C_1$–$C_6$-haloalkyl, $C_1$–$C_6$-alkoxy and $C_1$–$C_6$-haloalkoxy;

$R^3$ and $R^4$ together with the carbon atom to which they are bonded are a four- to eight-membered ring which, besides carbon atoms, may contain one or two oxygen and/or sulfur atoms and/or NH and/or N($C_1$–$C_4$-alkyl) groups and whose carbon atoms can have attached to them one of the following groups: halogen, $C_1$–$C_6$-alkyl or $C_1$–$C_4$-alkoxyimino;

$R^3$ and $R^4$ not simultaneously being bonded to the carbon atom via hetero atoms;

or a salt thereof.

2. The compound of the formula I defined in claim 1, where $R^4$ has the following meanings:

alkyl, alkenyl, alkynyl, alkoxy, alkenyloxy or alkynyloxy, where the hydrocarbon groups are unsubstituted, partially or fully halogenated and/or carry one to three of the following radicals:

cyano, nitro, hydroxyl, mercapto, amino, carboxyl, aminocarbonyl, aminothiocarbonyl,
$C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyloxy, benzyloxy, aryl, aryloxy, hetaryl and hetaryloxy, where the aromatic rings are unsubstituted or substituted by customary groups; cycloalkyl, cycloalkoxy, heterocyclyl or heterocyclyloxy, where the cyclic groups are unsubstituted, partially or fully halogenated and/or carry one to three of the following radicals:

cyano, nitro, hydroxyl, mercapto, amino, carboxyl, aminocarbonyl, aminothiocarbonyl,
$C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy, where the aromatic rings are unsubstituted or substituted by customary groups;

aryl, hetaryl, aryloxy or hetaryloxy, where the aromatic rings are unsubstituted, partially or fully halogenated and/or carry one to three of the following radicals:

cyano, nitro, hydroxyl, mercapto, amino, carboxyl, aminocarbonyl, aminothiocarbonyl,
$C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy, where the aromatic rings are unsubstituted or substituted by customary groups, C(=NOR$^i$)—A$_n$—R$^{ii}$ or NR$^{iii}$—CO—D—R$^{iv}$;

A is oxygen, sulfur or nitrogen, where the nitrogen atom carries a hydrogen atom or a $C_1$–$C_6$-alkyl group;

n is 0 or 1;

R$^i$ is hydrogen, $C_1$–$C_6$-alkyl, $C_3$–$C_6$-alkenyl or $C_3$–$C_6$-alkynyl;

R$^{ii}$ is hydrogen or $C_1$–$C_6$-alkyl;

D is a direct bond, oxygen or NR$^b$, where R$^b$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl;

R$^{iii}$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

R$^{iv}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl.

3. A composition which is suitable for controlling pests or harmful fungi, comprising a solid or liquid carrier and a compound of the formula I as defined in claim 1.

4. A method of controlling harmful fungi, which comprises treating the fungi, or the materials, plants, the soil or seed to be protected against fungal infection, with an effective amount of a compound of the formula I as defined in claim 1.

5. A method of controlling pests, which comprises treating the pests, or the materials, plants, the soil or seed to be protected against them, with an effective amount of a compound of the formula I as defined in claim 1.

6. A process for the preparation of a compound I as defined in claim 1 where R$^1$ is C(CO$_2$CH$_3$)=NOCH$_3$ (Ia), C(CO$_2$CH$_3$)=CHOCH$_3$ (Id) or C(CO$_2$CH$_3$)=CCH$_3$ (Ie), which comprises converting a benzoic ester of the formula II

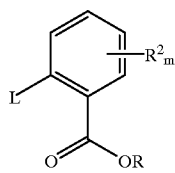

(II)

where L is a nucleophilically exchangeable leaving group and R is a $C_1$–$C_4$-alkyl group, in the presence of a base, with an oxime of the formula III (III)

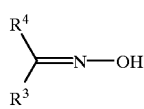

to give the corresponding compound of the formula IV

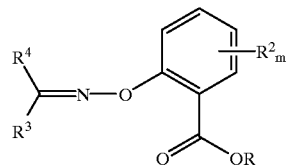

(IV)

hydrolyzing IV to give the corresponding carboxylic acid IVa

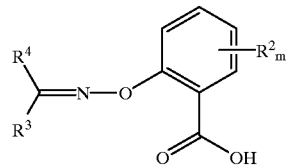

(IVa)

and subsequently first reacting IVa to the chloride Va

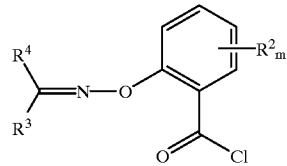

(Va)

and then to the cyanide Vb

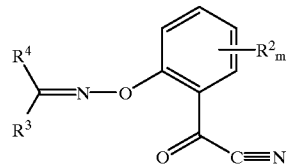

(Vb)

converting Vb, via a Pinner reaction, into the corresponding α-keto ester VI

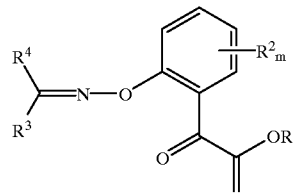

(VI)

and subsequently converting VI either
a) with O-methylhydroxylamine or a salt thereof (VIIa)

H$_3$C—O—NH$_2$H$_3$C—O—NH$_3$$^⊕$Z$^⊖$  (VIIa)

where Z$^-$ is a halide ion, to give the corresponding compound Ia (R=C(CO$_2$CH$_3$)=NOCH$_3$), b) with a Wittig, or Wittig-Horner reagent, of the formula VIIb

109

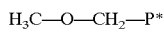  (VIIb)

where P* is a phosphonate or a phosphonium halide radical, to give the corresponding compound Id (R=C(CO$_2$CH$_3$)=CHOCH$_3$), or c) with a Wittig, or Wittig-Horner reagent, of the formula VIIc

  (VIIc)

to give the corresponding compound Ie (R=C(CO$_2$CH$_3$)=CHCH$_3$).

7. A process for the preparation of a compound I as defined in claim 1, where R$^1$ is C(CONHCH$_3$)=NOCH$_3$ (Ib) or C(CONH$_2$)=NOCH$_3$ (Ic), which comprises converting a compound of the formula Ia

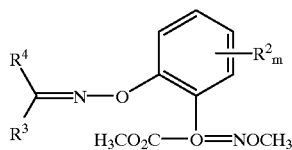  (Ia)

with methylamine or a salt thereof (XIII)

H$_3$C—NH$_2$H$_3$C—NH$_3^\oplus$Z$^\ominus$  (XIII)

where Z$^-$ is a halide ion, to give the corresponding compound Ib (R=C(CONHCH$_3$)=NOCH$_3$), or with ammonia or an ammonium salt to give the corresponding compound Ic (R=C(CONH$_2$)=NOCH$_3$).

8. An intermediate of the formula Vb

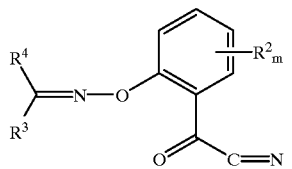  (Vb)

where the substituents and the index have the following meanings:

R$^2$ is cyano, nitro, halogen, C$_1$–C$_4$-alkyl, C$_1$–C$_4$-haloalkyl or C$_1$–C$_4$-alkoxy;

m is 0, 1 or 2, it being possible for the radicals R$^2$ to be different when m is 2;

R$^3$ is hydrogen, cyano, hydroxyl, halogen, C$_1$–C$_6$-alkyl, C$_1$–C$_6$-haloalkyl, C$_1$–C$_6$-alkoxy-C$_1$–C$_6$-alkyl, C$_1$–C$_6$-alkoxy, C$_1$–C$_6$-haloalkoxy, C$_1$–C$_6$-alkylthio, C$_3$–C$_6$-cyclopropyl, C$_3$–C$_6$-cycloalkyl-C$_1$–C$_6$-alkyl, C$_2$–C$_6$-alkenyl, aryl, aryloxy-C$_1$–C$_6$-alkyl, aryl-C$_1$–C$_4$-alkyl or benzyloxy, where the aromatic rings in these radicals are unsubstituted or carry one to three of the following groups: cyano, nitro, halogen, C$_1$–C$_6$-alkyl, C$_1$–C$_6$-alkoxy, C$_1$–C$_6$-haloalkoxy, or C(CH$_3$)=N—Y—R$^a$ where R$^a$ is C$_1$–C$_6$-alkyl and Y is oxygen or nitro, where the nitrogen atom carries a hydrogen atom or a C$_1$–C$_6$-alkyl group;

R$^4$ is hydrogen, cyano, unsubstituted or substituted alkyl, alkenyl, alkynyl, cycloalkyl, heterocyclyl, aryl and hetaryl;

110 unsubstituted or substituted alkoxy, alkenyloxy, alkynyloxy, cycloalkoxy, heterocyclyloxy, aryloxy and hetaryloxy;

unsubstituted or substituted arylthio and hetarylthio;

—O$_p$—C(R$^5$)=N—Y$^1$—R$^6$ or —O$_p$—O—N=CR$^7$R$^8$ where

O is CH$_2$, CH(CH$_3$), CH(CH$_2$CH$_3$) or 1,1-cyclopropyl;

p is 0 or 1;

Y$_1$ is oxygen or nitrogen, where the nitrogen atom carries a hydrogen atom or a C$_1$–C$_4$-alkyl group;

R$^5$ is one of the groups mentioned for R$^3$, or unsubstituted or substituted cycloalkoxy, heterocyclyloxy, aryloxy, hetaryloxy, arylthio and hetarylthio;

R$^6$ is unsubstituted or substituted C$_1$–C$_{10}$-alkyl, C$_3$–C$_6$-cycloalkyl, C$_2$–C$_{10}$-alkenyl, C$_2$–C$_{10}$-alkynyl, C$_1$–C$_{10}$-alkylcarbonyl, C$_2$–C$_{10}$-alkenylcarbonyl, C$_2$–C$_{10}$-alkynylcarbonyl or C$_1$–C$_{10}$-alkylsulfonyl; unsubstituted or substituted aryl, hetaryl, arylcarbonyl, hetarylcarbonyl, arylsulfonyl or hetarylsulfonyl;

R$^7$, R$^8$ are methyl, ethyl, phenyl and benzyl, where the aromatic rings are unsubstituted or carry one to three of the following groups: cyano, nitro, halogen, C$_1$–C$_6$-alkyl, C$_1$–C$_6$-haloalkyl, C$_1$–C$_6$-alkoxy and C$_1$–C$_6$-haloalkoxy;

R$^3$ and R$^4$ together with the carbon atom to which they are bonded are a four- to eight-membered ring which, besides carbon atoms, may contain one or two oxygen and/or sulfur atoms and/or NH and/or N(C$_1$–C$_4$-alkyl) groups and whose carbon atoms can have attached to them one of the following groups: halogen, C$_1$–C$_6$-alkyl or C$_1$–C$_4$-alkoxyimino;

R$^3$ and R$^4$ not simultaneously being bonded to the carbon atom via hetero atoms.

9. An intermediate of the formula X

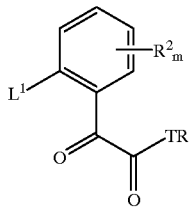  (X)

where

R$^2$ is cyano, nitro, halogen, C$_1$–C$_4$-alkyl, C$_1$–C$_4$-haloalkyl or C$_1$–C$_4$-alkoxy;

m is 0, 1 or 2, it being possible for the radicals R$^2$ to be different when m is 2;

T is an oxygen or nitrogen, where the nitrogen atom carries a hydrogen atom or a C$_1$–C$_6$-alkyl group;

R is a C$_1$–C$_4$-alkyl group, and

L$^1$ is a radical —O—N=CR$^3$R$^4$, where

R$^3$ is hydrogen, cyano, hydroxyl, halogen,
C$_1$–C$_6$-alkyl, C$_1$–C$_6$-haloalkyl, C$_1$–C$_6$-alkoxy-C$_1$–C$_6$-alkyl, C$_1$–C$_6$-alkoxy, C$_1$–C$_6$-haloalkoxy, C$_1$–C$_6$-alkylthio, C$_3$–C$_6$-cycloalkyl, C$_3$–C$_6$-cycloalkyl-C$_1$–C$_6$-alkyl, C$_2$–C$_6$-alkenyl,
aryl, aryloxy-C$_1$–C$_6$-alkyl, aryl-C$_1$–C$_4$-alkyl or benzyloxy, where the aromatic rings in these radicals are unsubstituted or carry one to three of the following groups: cyano, nitro, halogen, C$_1$–C$_6$-alkyl, C$_1$–C$_6$-alkoxy, C$_1$–C$_6$-haloalkoxy, or C(CH$_3$)=N—Y—R$^a$ where $R^a$ is $C_1$–$C_6$-alkyl and Y is oxygen or nitro, where the nitrogen atom carries a hydrogen atom or a $C_1$–$C_6$-alkyl group;

$R^4$ is hydrogen, cyano, unsubstituted or substituted alkyl, alkenyl, alkynyl, cycloalkyl, heterocyclyl, aryl and hetaryl; unsubstituted or substituted alkoxy, alkenyloxy, alkynyloxy, cycloalkoxy, heterocyclyloxy, aryloxy and hetaryloxy;

unsubstituted or substituted arylthio and hetarylthio;

—$O_p$—$C(R^5)$=N—$Y^1$—$R^6$ or —$O_p$—O—N=$CR^7R^8$ where

O is $CH_2$, $CH(CH_3)$, $CH(CH_2CH_3)$ or 1,1-cyclopropyl;

p is 0 or 1;

$Y^1$ is oxygen or nitrogen, where the nitrogen atom carries a hydrogen atom or a $C_1$–$C_4$-alkyl group;

$R^5$ is one of the groups mentioned for $R^3$, or unsubstituted or substituted cycloalkoxy, heterocyclyloxy, aryloxy, hetaryloxy, arylthio and hetarylthio;

$R^6$ is unsubstituted or substituted $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl;

unsubstituted or substituted aryl, hetaryl, arylcarbonyl, hetarylcarbonyl, arylsulfonyl or hetarylsulfonyl;

$R^7$, $R^8$ are methyl, ethyl, phenyl and benzyl, where the aromatic rings are unsubstituted or carry one to three of the following groups: cyano, nitro, halogen, $C_1$–$C_6$-alkyl, $C_1$–$C_6$-haloalkyl, $C_1$–$C_6$-alkoxy and $C_1$–$C_6$-haloalkoxy;

$R^3$ and $R^4$ together with the carbon atom to which they are bonded are a four- to eight-membered ring which, besides carbon atoms, may contain one or two oxygen and/or sulfur atoms and/or NH and/or N($C_1$–$C_4$-alkyl) groups and whose carbon atoms can have attached to them one of the following groups: halogen, $C_1$–$C_6$-alkyl or $C_1$–$C_4$-alkoxyimino;

$R^3$ and $R^4$ not simultaneously being bonded to the carbon atom via hetero atoms.

10. The compound of the formula I as defined in claim 1, wherein $R^3$ is hydrogen or cyano, $C_1$–$C_6$-alkyl, $C_1$–$C_6$-haloalkyl, $C_3$–$C_6$-cycloalkyl, $C_3$–$C_6$-cycloalkyl-$C_1$–$C_6$-alkyl, aryl, aryloxy-$C_1$–$C_4$-alkyl and aryl-$C_1$–$C_4$-alkyl, where the aromatic rings in these radicals are unsubstituted or carry one to three of the following groups: cyano, nitro, halogen, $C_1$–$C_6$-alkyl, $C_1$–$C_6$-alkoxy, $C_1$–$C_6$-haloalkoxy, or $C(CH_3)$=N—Y—$R^a$, $R^4$ is unsubstituted or substituted aryl, hetaryl, aryloxy, hetaryloxy, arylthio and hetarylthio;

—$Q_p$—$C(R^5)$=N—$Y^1$—$R^6$ or —$Q_p$—O—N=$CR^7R^8$, $R^3$ and $R^4$ together with the carbon atom to which they are bonded are a four- to eight-membered ring which, besides carbon atoms, may contain one or two oxygen and/or sulfur atoms and/or NH and/or N($C_1$–$C_4$-alkyl) groups and whose carbon atoms can have attached to them one of the following groups: halogen, $C_1$–$C_6$-alkyl or $C_1$–$C_4$-alkoxyimino;

$R^3$ and $R^4$ not simultaneously being bonded to the carbon atom via hetero atoms.

11. The compound of the formula I as defined in claim 1, wherein $R^3$ is hydrogen, cyano, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_3$–$C_6$-cycloalkyl, $C_3$–$C_6$-cycloalkyl-$C_1$–$C_6$-alkyl, aryl, aryloxy-$C_1$–$C_4$-alkyl, aryl-$C_1$–$C_4$-alkyl or benzyloxy, where the aromatic rings in these radicals are unsubstituted or carry one to three of the following groups: cyano, nitro, halogen, $C_1$–$C_6$-alkyl, $C_1$–$C_6$-alkoxy, $C_1$–$C_6$-haloalkoxy, and $C(CH_3)$=N—Y—$R^a$, $R^4$ is unsubstituted or substituted aryl and hetaryl;

—$Q_p$—$C(R^5)$=N—$Y^1$—$R^6$ or —$Q_p$—O—N=$CR^7R^8$, $R^3$ and $R^4$ not simultaneously being bonded to the carbon atom via hetero atoms.

12. The compound of the formula I as defined in claim 1, wherein $R^3$ is $C_1$–$C_6$-alkyl, $C_1$–$C_6$-haloalkyl, $C_1$–$C_6$-alkoxy, $C_1$–$C_6$-haloalkoxy, cyclopropyl or $C(CH_3)$=NO—$C_1$–$C_6$-alkyl, and $R^4$ is aryl, hetaryl or benzyl, where the aromatic rings in these radicals are unsubstituted or carry one to three of the following groups: cyano, nitro, halogen, $C_1$–$C_6$-alkyl, $C_1$–$C_6$-haloalkyl, $C_1$–$C_6$-alkoxy, $C_1$–$C_6$-haloalkoxy, and $C(=NOR^i)$—$A_n$—$R^{ii}$, where A is oxygen, sulfur or nitrogen, where the nitrogen atom carries a hydrogen atom or a $C_1$–$C_6$-alkyl group;

n is 0 or 1;

$R^i$ is hydrogen, $C_1$–$C_6$-alkyl, $C_3$–$C_6$-alkenyl or $C_3$–$C_6$-alkynyl;

$R^{ii}$ is hydrogen or $C_1$–$C_6$-alkyl; or $R^4$ is $CR^5$=N—$Y^1$—$R^6$.

13. The compound of the formula I as defined in claim 1, wherein $R^3$ is $C_1$–$C_6$-alkyl, $C_1$–$C_6$-haloalkyl, $C_1$–$C_6$-alkoxy, $C_1$–$C_6$-haloalkoxy, cyclopropyl or $C(CH_3)$=NO—$C_1$–$C_6$-alkyl, and $R^4$ is $C_1$–$C_6$-alkyl, $C_2$–$C_6$-alkenyl, $C_2$–$C_6$-alkynyl or cyclopropyl, where these radicals are unsubstituted, partially or fully halogenated and/or carry one to three of the following groups: aryl and hetaryl, where the aromatic rings are unsubstituted or carry one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy.

14. The compound of the formula I as defined in claim 1, wherein $R^3$ is $C_1$–$C_6$-alkyl, $C_1$–$C_6$-haloalkyl, cyclopropyl or $C(CH_3)$=NO—$C_1$–$C_6$-alkyl, and $R^4$ is $C_1$–$C_6$-alkoxy, which is unsubstituted, partially or fully halogenated and/or carries one to three of the following groups: aryl and hetaryl, where the aromatic rings are unsubstituted or carry one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy.

15. The compound of the formula I as defined in claim 1, wherein $R^3$ is $C_1$–$C_6$-alkyl, $C_1$–$C_6$-haloalkyl, $C_1$–$C_6$-alkoxy, $C_1$–$C_6$-haloalkoxy, cyclopropyl or $C(CH_3)$=NO—$C_1$–$C_6$-alkyl, and $R^4$ is $C_1$–$C_6$-alkyl, $C_2$–$C_6$-alkenyl, $C_2$–$C_6$-alkynyl or cyclopropyl, where these radicals are unsubstituted, partially or fully halogenated and/or carry one to three of the following groups: aryl and hetaryl, where the aromatic rings are unsubstituted or carry one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy, or $R^4$ is aryl, hetaryl or benzyl, where the aromatic rings are unsubstituted, partially or fully halogenated and/or carry one to three of the following groups: cyano, nitro, $C_1$–$C_6$-alkyl, $C_1$–$C_6$-haloalkyl, $C_1$–$C_6$-alkoxy, $C_1$–$C_6$-haloalkoxy, and $C(=NOR^i)$—$A_n$—$R^{ii}$, where A is oxygen, sulfur or nitrogen, where the nitrogen atom carries a hydrogen atom or a $C_1$–$C_6$-alkyl group;

n is 0 or 1;

$R^i$ is hydrogen, $C_1$–$C_6$-alkyl, $C_3$–$C_6$-alkenyl or $C_3$–$C_6$-alkynyl;

$R^{ii}$ is hydrogen or $C_1$–$C_6$-alkyl; or $R^4$ is $CR^5=N$—$Y^1$—$R^6$.

16. The compound of the formula I as defined in claim 1, wherein $R^3$ is $C_1$–$C_6$-alkyl, $C_1$–$C_6$-haloalkoxy, cyclopropyl or $C(CH_3)=NO$—$C_1$–$C_6$-alkyl, and $R^4$ is $C_1$–$C_6$-alkoxy, which is unsubstituted, partially or fully halogenated and/or carries one to three of the following groups: aryl and hetaryl, where the aromatic rings are unsubstituted or carry one to three of the following substituents: cyano, halogen, $C_1$–$C_6$-alkyl, $C_1$–$C_6$-haloalkyl, $C_1$–$C_6$-alkoxy and $C_1$–$C_6$-haloalkoxy, or $R^4$ is aryloxy or hetaryloxy, where the aromatic rings are unsubstituted, partially or fully halogenated and/or carries one to three of the following groups: cyano, nitro, $C_1$–$C_6$-alkyl, $C_1$–$C_6$-haloalkyl, $C_1$–$C_6$-alkoxy, $C_1$–$C_6$-haloalkoxy, and $C(=NOR^i)$—$A_n$—$R^{ii}$, where A is oxygen, sulfur or nitrogen, where the nitrogen atom carries a hydrogen atom or a $C_1$–$C_6$-alkyl group;

n is 0 or 1;

$R^i$ is hydrogen, $C_1$–$C_6$-alkyl, $C_3$–$C_6$-alkenyl or $C_3$–$C_6$-alkynyl;

$R^{ii}$ is hydrogen or $C_1$–$C_6$-alkyl; or $R^4$ is $CR^5=N$—$Y^1$—$R^6$.

* * * * *

UNITED STATES PATENT AND TRADEMARK OFFICE
CERTIFICATE OF CORRECTION

PATENT NO. : 5,994,359
DATED : November 30, 1999
INVENTOR(S) : GROTE et al.

It is certified that error appears in the above-identified patent and that said Letters Patent is hereby corrected as shown below:

Col. 105, claim 1, line 57, "$-O_p-O-$" should be -- $-Q_p-O-$ --.

Col. 105, claim 1, line 66, "$C_1-C_{10}$-alkyl" should be --$C_1-C_{10}$-alkyl--.

Col. 108, claim 6, line 62, formula (VIIa) should appear as follows:
--$H_3C-O-NH_2$    $H_3C-O-NH_3^{\oplus}Z^{\ominus}$    (VIIa)--.

Col. 109, claim 7, line 28, formula (XIII) should appear as follows:
--$H_3C-NH_2$    $H_3C-NH_3^{\oplus}Z^{\ominus}$    (XIII)--.

Col. 109, claim 8, line 40, in formula (Vb), "C=N" should be --C≡N--.

Col. 110, claim 8, line 5, "$O_p$" should be --$Q_p$--, both occurrences.

Col. 110, claim 8, line 7, "O" should be --Q--.

Col. 111, claim 9, line 11, "$O_p$" should be --$Q_p$--, both occurrences.

Col. 111, claim 9, line 13, "O" should be --Q--.

Signed and Sealed this

Twenty-fourth Day of April, 2001

Attest:

NICHOLAS P. GODICI

*Attesting Officer*    Acting Director of the United States Patent and Trademark Office